US009169499B2

(12) United States Patent
Paul et al.

(10) Patent No.: US 9,169,499 B2
(45) Date of Patent: Oct. 27, 2015

(54) FLUX TO ACETOLACTATE-DERIVED PRODUCTS IN LACTIC ACID BACTERIA

(75) Inventors: Brian James Paul, Wilmington, DE (US); Wonchul Suh, Hockessin, DE (US)

(73) Assignee: BUTAMAX ADVANCED BIOFUELS LLC DE (US)

( * ) Notice: Subject to any disclaimer, the term of this patent is extended or adjusted under 35 U.S.C. 154(b) by 594 days.

(21) Appl. No.: 12/893,065

(22) Filed: Sep. 29, 2010

(65) Prior Publication Data

US 2011/0136192 A1    Jun. 9, 2011

Related U.S. Application Data

(60) Provisional application No. 61/246,717, filed on Sep. 29, 2009.

(51) Int. Cl.

| C12N 1/20 | (2006.01) |
|---|---|
| C12N 15/00 | (2006.01) |
| C12N 9/04 | (2006.01) |
| C12N 9/88 | (2006.01) |
| C12P 7/16 | (2006.01) |
| C12N 9/10 | (2006.01) |
| C12N 15/74 | (2006.01) |

(52) U.S. Cl.
CPC ................ *C12P 7/16* (2013.01); *C12N 9/0006* (2013.01); *C12N 9/1029* (2013.01); *C12N 9/88* (2013.01); *C12N 15/746* (2013.01); *C12Y 101/01027* (2013.01); *C12Y 203/01054* (2013.01); *C12Y 401/01005* (2013.01); *Y02E 50/10* (2013.01)

(58) Field of Classification Search
CPC ...... C12N 9/0006; C12N 9/88; C12N 15/746; C12P 7/16
See application file for complete search history.

(56) References Cited

U.S. PATENT DOCUMENTS

| 4,683,202 | A | 7/1987 | Mullis | |
|---|---|---|---|---|
| 6,645,754 | B1 * | 11/2003 | Nilsson | .......... 435/252.9 |
| 8,129,162 | B2 | 3/2012 | Li et al. | |
| 2007/0031918 | A1 | 2/2007 | Dunson | |
| 2007/0092957 | A1 | 4/2007 | Donaldson | |
| 2008/0261230 | A1 | 10/2008 | Liao | |
| 2009/0016337 | A1 | 1/2009 | Jorgensen et al. | |
| 2009/0269823 | A1 | 10/2009 | Bramucci | |
| 2009/0305363 | A1 | 12/2009 | Anthony | |
| 2010/0019751 | A1 | 1/2010 | Chen | |
| 2010/0081182 | A1 | 4/2010 | Paul | |
| 2010/0081183 | A1 | 4/2010 | Paul | |
| 2010/0112655 | A1 | 5/2010 | Paul | |
| 2010/0120105 | A1 | 5/2010 | Anthony et al. | |
| 2010/0197519 | A1 | 8/2010 | Li et al. | |
| 2010/0221802 | A1 | 9/2010 | Grady et al. | |
| 2011/0195505 | A1 | 8/2011 | Euler et al. | |

FOREIGN PATENT DOCUMENTS

| FR | 2 777 905 A1 | 4/1998 |
|---|---|---|
| FR | 2777905 | 10/1999 |

OTHER PUBLICATIONS

Stewart et al. Biotechnology and Genetic Engineering Reviews, 14:67-143, 1997.*
Aarnikunnas. Metabolic engineering of lactic acid bacteria and characterization of novel enzymes for the production of industrially important compounds. Academic Dissertation. University of Helsinki. 2006.*
UniProt Database. retrived from the internet via: http://www.uniprot.org/ on Mar. 7, 2013.*
De Vos et al. Making More of Milk Sugar by Engineering Lactic Acid Bacteria. 1998. Int. Dairy J. 8:227-233.*
Felipe et al. Cofactor Engineering: a Novel Approach to Metabolic Engineering in *Lactococcus lactis* by Controlled Expression of NADH Oxidase. J Bacteriol. Aug. 1998; 180(15): 3804-3808.*
U.S. Appl. No. 61/246,844, filed Sep. 29, 2009 in the name of Nagarajan et al. now U.S. Appl. No. 12/893,077, filed Sep. 29, 2010.
Alegre et al., "Transformation of *Lactobacillus plantarum* by electroporation with in vitro modified plasmid DNA", FEMS Microbiology Letters, vol. 241 (2004) pp. 73-77.
Altschul et al., "Basic Local Alignment Search Tool", M. Mol. Biol., (1990) vol. 215, pp. 403-410.
Arthur et al., "Contribution of VanY D,D-carboxypeptidase to Glycopeptide Resistance in *Enterococcus faecalis* by hydrolysis of peptidoglycan precursors", Antimicrobial Agents and Chemotherapy, Sep. 1994, pp. 1899-1903.
Atsumi et al., "Metabolic engineering for advanced biofuels production from *Escherichia coli*", Current Opinion in Biotechnology (2008) vol. 19, pp. 414-419.
Bringel et al., "Optimized transformation by electroporation of *Lactobacillus plantarum* strains with plasmid vectors", Appl. Microbiol. Biotechnol. (1990) vol. 33, pp. 664-670.
Chang et al., "Construction and Characterization of Amplifiable Multicopy DNA Cloning Vehicles Derived from the P15A Cryptic Miniplasmid", J. Bacteriology, Jun. 1978, vol. 134, No. 3, pp. 1141-1156.
Cruz-Rodz et al., "High efficiency introduction of plasmid DNA into glycine treated *Enterococcus faecalis* by electroporation", Mol. Gen. Genet. (1990) vol. 224, pp. 152-154.
de Vos et al., "Making more of milk sugar by engineering lactic acid bacteria", Int. Dairy Journal 8 (1998) pp. 227-233.
Durre, "New insights and novel developments in clostridial acetone/butanol/isopropanol fermentation", Appl. Microbiol. Biotechnol. (1998) vol. 49, pp. 639-648.
Eichenbaum et al., "Use of the Lactococcal nisA promoter to regulate gene expression in gram-positive bacteria: comparison of induction level and promoter strength", Applied and Environmental Microbiology, vol. 64, No. 8, Aug. 1998, pp. 2763-2769.
Ferain et al., "Lactobacillus plantarum ldhL gene: overexpression and deletion", J. Bacteriology, Feb. 1994, vol. 176, No. 3, pp. 596-601.
Fujimoto et al., "pAM401-based shuttle vectors that enable overexpression of promoterless genes and one-step purification of tag fusion proteins directly from *Enterococcus faecalis*", Applied and Environmental Microbiology, Mar. 2001, vol. 67, No. 3, pp. 1262-1267.
Godon et al., "Branched-chain amino acid biosynthesis genes in Lactococcus lactic subsp. lactis", Journal of Bacteriology, Oct. 1992, vol. 174, No. 20, pp. 6580-6589.

(Continued)

*Primary Examiner* — Yong Pak

(57) ABSTRACT

An engineering method was developed to allow genetic modification and isolation of lactic acid bacteria cells that lack lactate dehydrogenase and acetolactate decarboxylase activities. In cells with these modifications and an isobutanol biosynthetic pathway, improved production of isobutanol was observed.

11 Claims, 2 Drawing Sheets

(56) References Cited

OTHER PUBLICATIONS

Gollop, et al., "Physiological implications of the substrate specificites of acetohydroxy acid synthases from varied organisms", Jounral of Bacteriology, Jun. 1990, vol. 172, No. 6, pp. 3444-3449.
Groot et al., "Technologies for butanol recovery integrated with fermentations", Process Biochemistry, vol. 27 (1992) pp. 61-75.
Hols et al., "Conversion of *Lactococcus lactis* from homolactic to homoalanine fermentation through metabolic engineering", Nature Biotechnology, vol. 17 Jun. 1999, pp. 588-592.
Holtzclaw et al., "Degradative acetolactate synthase of *Bacillus subtilis*: purification and properties", Journal of Bacteriology, Mar. 1975, vol. 121, No. 3, pp. 917-922.
Horinouchi et al., "Nucleotide sequence and functional map of pE194, a plasmid that specifies inducible resistance to macrolide, lincosamide, and streptogramin type B antibiotics", Journal of Bacteriology, vol. 150, No. 2, May 1982, pp. 804-814.
Higgins et al., "Clustal V: improved software for multiple sequence alignment", CABIOS, vol. 8, No. 2 (1992) pp. 189-191.
Higgins et al., "Fast and sensitive multiple sequence alignments on a microcomputer", CABIOS Communications, vol. 5, No. 2 (1989) pp. 151-153.
Johnson et al., "DNA sequences at the ends of transposon Tn5 required for transposition", Nature, vol. 304, Jul. 21, 1983, pp. 280-282.
Kleerebezem et al., "Controlled gene expression systems for lactic acid bacteria: transferable nisin-inducible expression cassettes for *Lactococcus, Leuconostoc* and *Lactobacillus* spp.", Applied and Environmental Microbiology, vol. 63, No. 11, Nov. 1997, pp. 4581-4584.
Liu et al., "Metabolic engineering of a *Lactobacillus plantarum* double ldh knockout strain for enhanced ethanol production", Journal of Industrial Microbiology Biotechnology (2006) vol. 33, pp. 1-7.
Monnet et al., "Diacetyl and -Acetolactate Overproduction by *Lactococcus lactis* subsp. lactic Biovar Diacetylactis Mutants That Are Deficient in -Acetolactate Decarboxylase and Have a Low Lactate Dehydrogenase Activity", Applied and Environmental Microbiology, Dec. 2000, vol. 66, No. 12, pp. 5518-5520.
Nagarajan et al., "Secretion of Streptavidin from *Bacillus subtilis*", Applied and Environmental Microbiology, Nov. 1993, vol. 59, No. 11, pp. 3894-3898.
O'Sullivan et al., "High- and low-copy-Number *Lactococcus* shuttle cloning vectors with features for clone screening", Gene, 137 (1993) pp. 227-231.
Renault et al., "Plasmid vectors for gram-positive bacteria switching from high to low copy number", Gene 183 (1996) pp. 175-182.
Rud et al., "A synthetic promoter library for constitutive gene expression in *Lactobacillus plantarum*", Microbiology (2006), 152, pp. 1011-1019.
Sharpe et al., "Use of Transposon Promoter-Probe Vectors in the Metabolic Engineering of the Obligate Methanotroph *Methylomonas* sp. Strain 16a for Enhanced C40 Carotenoid Synthesis", Applied and Environmental Microbiology, Mar. 2007, vol. 73, No. 6, pp. 1721-1728.
Shrago et al., "Conjugal plasmid transfer (pAMβ1) in *Lactobacillus plantarum*", Applied and Environmental Microbiology, vol. 52, No. 3., Sep. 1986, pp. 574-576.
Tabor et al., "A bacteriophage T7 RNA polymerase/promoter system for controlled exclusive expression of specific genes", Proceedings of the National Academy of Sciences USA, vol. 82 (1985) pp. 1074-1078.
Tanimoto et al., "Analysis of the conjugal transfer system of the pheromone-independent highly transferable enterococcus plasmid pMG1: identification of a tra Gene (traA) up-regulated during conjugation", Journal of Bacteriology, vol. 184, No. 20, Oct. 2002, pp. 5800-5804.
Thompson et al., "Clustal W: improving the sensitivity of progressive multiple sequence alignment through sequence weighting, position-specific gap penalties and weight matrix choice", Nucleic Acids Research, 1994, vol. 22, No. 22, pp. 4673-4680.
Van Kranenburg et al., "Functional anaylsis of three plasmids from *Lactobacillus pantarum*", Applied and Environmental Microbiology, vol. 71, No. 3, Mar. 2005, p. 1223-1230.
Vasantha et al., "Genes for Alkaline Protease and Neutral Protease from *Bacillus amyloliquefaciens* Contain a Large Open Reading Frame Between the Regions Coding for Signal Sequence and Mature Protein", Journal of Bacteriology, Sep. 1984, vol. 159, No. 3, pp. 811-819.
Walker et al., "Isothermal in vitro amplification of DNA by a restriction enzyme/DNA polymerase system", Proceedings of the National Academy of Sciences USA, vol. 89, Jan. 1992, pp. 392-396.
Wyckoff et al., "Characterization and sequence analysis of a stable cryptic plasmid from enterococcus faecium 226 and development of a stable cloning vector", Applied and Environmental Microbiology, vol. 62, No. 4, Apr. 1996, pp. 1481-1486.
Yansura et al., "Use of the *Escherichia coli* lac repressor and operator to control gene expression in *Bacillus subtilis*", Proceedings of the National Academy of Sciences USA, vol. 81, Jan. 1984, pp. 439-443.
Yuan et al., "Regulation of groE Expression in *Bacillus subtilis*: the Involvement of the $\sigma^4$-Like Promoter and the Roles of the Inverted Repeat Sequence (CIRCE)", Journal of Bacteriology, Oct. 1995, vol. 177, No. 19, pp. 5427-5433.
Sambrook, J., Fritsch, E. F. and Maniatis, T. Molecular Cloning: A Laboratory Manual, $2^{nd}$ ed., Cold Spring Harbor Laboratory: Cold Spring Harbor, NY (1989), particularly 9.50-9.51, 11.7-11.8 and Table 11.1.
Pearson, Comput. Methods Genome Res., [Proc. Int. Symp.] (1994), Meeting Date 1992, 111-20. Editor(s): Suhai, Sandor. Plenum: New York, NY.
Oliveira et al., "Modeling lactococcus lactis using a genome-scale flux model", BMC Microbiology, Biomed Central, London, GB, vol. 5, No. 1, Jun. 27, 2005, p. 39.
Biswas et al., "High-efficiency gene inactivation and replacement system for gram-positive bacteria", Journal of Bacteriology, Jun. 1993, vol. 175, No. 11, pp. 3628-3635.
De Vos, "Safe and sustainable systems for food-grade fermentations by genetically modified lactic acid bacteria", International Dairy Journal, Elsevier Applied Science, Barking, GB, vol. 9, No. 1, Jan. 1, 1999, pp. 3-10.
International Search Report and Written Opinion of corresponding PCT/US2010/050705 mailed Feb. 17, 2011.
Ausubel, et al., "Current Protocols in Molecular Biology," 1:1.8.1-1.8.10, John Wiley & Sons, Inc. (1997).
Hugenholtz, J. *FEMS Microbiology Review*, 12(1-3): 165-178 (1993).
GenBank Accession No. NC004567.1; Lactobacillus platarum WCFS1, complete genome; last modification date Mar. 4, 2010; printed on Mar. 9, 2010. www.ncbi.nlm.nih.gov/nuccore/28376974.

* cited by examiner

FLUX TO ACETOLACTATE-DERIVED PRODUCTS IN LACTIC ACID BACTERIA

CROSS-REFERENCE TO RELATED APPLICATIONS

This application claims the benefit of priority to U.S. Provisional Patent Application No. 61/246,717, filed on Sep. 29, 2009, the entirety of which is herein incorporated by reference.

FIELD OF THE INVENTION

The invention relates to the field of industrial microbiology and the metabolism of lactic acid bacteria. More specifically, engineered genetic modifications were made to reduce or eliminate enzyme activity of endogenously expressed acetolactate decarboxylase and lactate dehydrogenase genes to increase availability of acetolactate as a substrate for biosynthesis of desired products, including isobutanol.

BACKGROUND OF THE INVENTION

Metabolic flux in biosynthetic pathways endogenous to lactic acid bacteria has been altered for production of products that use pyruvate as a starting substrate. In lactic acid bacteria the major pyruvate metabolic pathway is conversion to lactate through activity of lactate dehydrogenase (LDH). Metabolic engineering to redirect pyruvate from lactate to other products in lactic acid bacteria has had unpredictable results. Production of alanine in LDH-deficient *Lactococcus lactis* expressing alanine dehydrogenase was shown by Hols et al. (Nature Biotech. 17:588-592 (1999)). However, production of ethanol in LDH-deficient *Lactobacillus plantarum* expressing pyruvate decarboxylase was very limited, with carbon flow not significantly improved toward ethanol and lactate still produced (Liu et al. (2006) J. Ind. Micro. Biotech. 33:1-7).

In lactic acid bacteria pyruvate is also converted in a pathway to acetolactate, which is then converted to acetoin by acetolactate decarboxylase, and then to 2,3-butanediol. Additional pathways convert acetolactate to diacetyl, valine or leucine. Monnet et al. (Applied and Environmental Microbiology 66:5518-5520 (2000)) have through chemical mutagenesis eliminated acetolactate decarboxylase activity and reduced LDH activity to increase acetolactate, acetoin, and diacetyl production. Disclosed in US Patent Application Publication No. 20100112655 is engineering high flux from pyruvate to 2,3-butanediol in lactic acid bacteria by expressing heterologous butanediol dehydrogenase activity and substantially eliminating lactate dehydrogenase activity.

Disclosed in co-pending US Patent Application Publication No. 2010-0081183 is engineering lactic acid bacteria for high dihydroxy-acid dehydratase (DHAD) activity by expressing a heterologous DHAD and substantially eliminating lactate dehydrogenase activity. DHAD is one of the enzymes in a biosynthetic pathway for synthesis of isobutanol that is disclosed in co-pending US Patent Pub No. US20070092957 A1. Disclosed therein is engineering of recombinant microorganisms for production of isobutanol. Isobutanol is useful as a fuel additive, whose availability may reduce the demand for petrochemical fuels.

Disclosed in de Vos et al. (Int. Dairy J. 8:227-233 (1998)) is that it has appeared impossible to combine inactivation of aldB, encoding acetolactate decarboxylase, with inactivation of ldh, encoding lactate dehydrogenase, in rapidly growing cells of lactic acid bacteria.

There remains a need for altering metabolic flux in lactic acid bacteria away from lactate and away from the acetoin to 2,3-butanediol pathway, and into other biosynthetic pathways downstream of acetolactate, such as for production of isobutanol.

SUMMARY OF THE INVENTION

Disclosed herein are lactic acid bacteria cells that are genetically modified to eliminate lactate dehydrogenase activity and reduce or eliminate acetolactate decarboxylase activity as expressed endogenously by genes encoding lactate dehydrogenase (ldh) and acetolactate decarboxylase (aldB). The cells lack detectable dehydrogenase and acetolactate decarboxylase enzyme activity. These cells may be used to produce isobutanol and other products having acetolactate as an intermediate.

Accordingly, a recombinant lactic acid bacteria cell comprising at least one engineered genetic modification that reduces or eliminates enzyme activity of endogenously expressed acetolactate decarboxylase and at least one engineered genetic modification that eliminates enzyme activity of endogenously expressed lactate dehydrogenase is provided.

In another embodiment the recombinant lactic acid bacteria cell may further comprise at least one genetic modification that reduces pyruvate formate lyase activity. Further genetic modifications may also be included, such as additional biosynthetic pathways and/or additional modifications that provide for utilization of various substrates or production of other products.

In another embodiment, a method for producing a recombinant lactic acid bacteria cell is provided, said method comprises:
  a) providing a lactic acid bacteria cell;
  b) modifying by genetic engineering at least one endogenous gene encoding lactate dehydrogenase in the cell of (a) to eliminate enzyme activity of endogenously expressed lactate dehydrogenase;
  c) expressing acetolactate decarboxylase activity from a plasmid in the cell of (b) to create a cell with non-chromosomally expressed acetolactate decarboxylase;
  d) modifying by genetic engineering an endogenous gene encoding acetolactate decarboxylase in the cell of (c) to eliminate enzyme activity of endogenously expressed acetolactate decarboxylase; and
  e) curing the plasmid expressing acetolactate decarboxylase activity from the cell of (d);
  whereby a recombinant lactic acid bacteria cell lacking enzyme activity of endogenously expressed lactate dehydrogenase and acetolactate decarboxylase is produced.

In yet another embodiment the invention provides a method for producing isobutanol comprising:
  (a) providing a lactic acid bacteria cell comprising:
    i) at least one genetic modification that eliminates enzyme activity of endogenously expressed acetolactate decarboxylase and at least one genetic modification that eliminates enzyme activity of endogenously expressed lactate dehydrogenase; and
    ii) an isobutanol biosynthetic pathway; and
  (b) culturing the cell of (a) under conditions wherein isobutanol is produced.

In yet another embodiment the invention provides an integration vector for lactic acid bacteria comprising:
  a) a Tn-5 transposase coding region operably linked to a promoter that is active in LAB cells;

b) Tn5IE and TN5OE elements bounding a selection marker active in lactic acid bacteria cells and a DNA segment targeted for integration;

c) a selection marker active in *E. coli* cells;

d) an origin of replication for *E. coli* cells;

e) an origin of replication for lactic acid bacteria cells that is temperature sensitive;

wherein the Tn5IE and TN5OE elements direct random integration of the DNA segment of b).

In yet another embodiment the invention provides a method for randomly integrating a DNA segment into the LAB cell genome comprising:

a) providing a vector comprising:

i) a Tn-5 transposase coding region operably linked to a promoter that is active in lactic acid bacteria cells;

(ii) Tn5IE and TN5OE elements bounding a selection marker that is active in *E. coli* and lactic acid bacteria cells;

(iii) a second selection marker active in lactic acid bacteria cells;

(iv) an origin of replication for *E. coli* cells;

(v) an origin of replication for lactic acid bacteria cells that is conditionally active;

b) placing a DNA segment for integration between the elements of step a (ii) creating an integration construction;

c) transforming the integration construction into a lactic acid bacteria cell whereby transformed cells are produced;

d) growing and selecting the transformed cells of step (c) in permissive conditions using the selection marker of step a (ii) to produce selected transformants; and e) growing the selected transformants of step (d) in non-permissive conditions;

wherein the vector is cured from the lactic acid bacteria cells and the DNA segment for integration is randomly integrated into the genome of said lactic acid bacteria cell.

BRIEF DESCRIPTION OF THE FIGURES AND SEQUENCES

The various embodiments of the invention can be more fully understood from the following detailed description, the figures, and the accompanying sequence descriptions, which form a part of this application.

Figure 1:
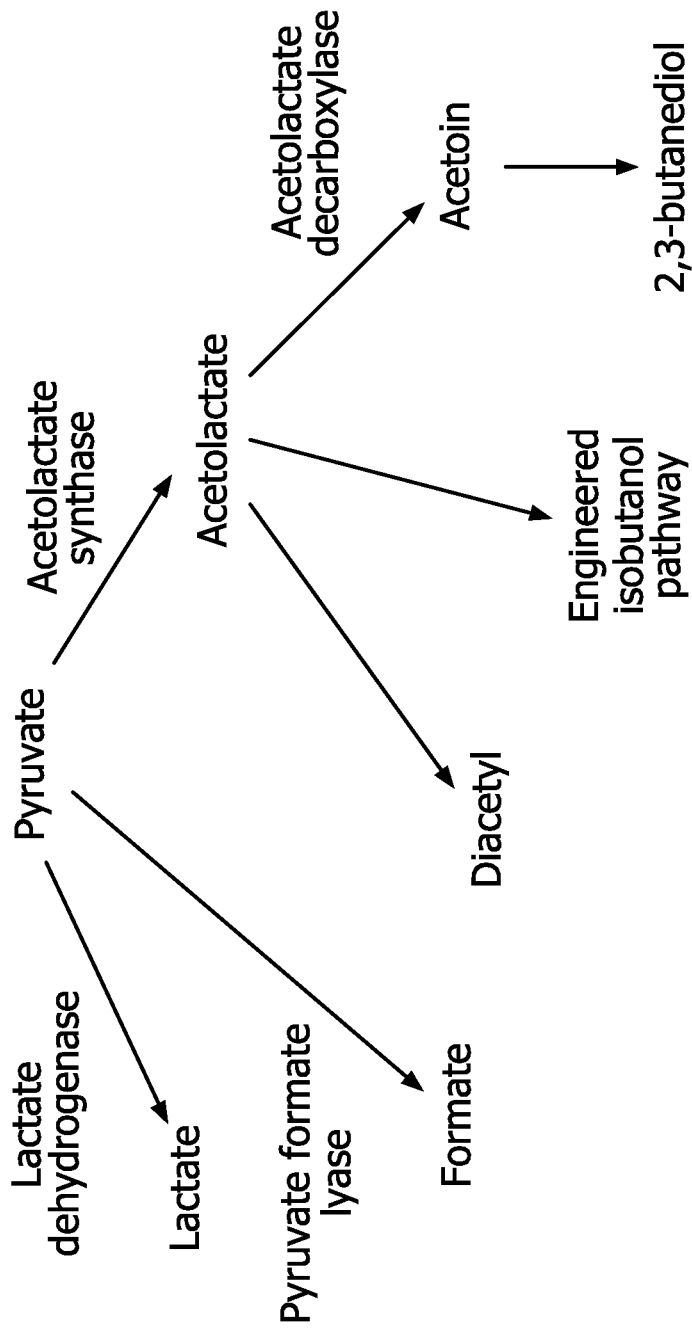
FIG. 1 shows a diagram of biosynthetic pathways initiating with pyruvate in lactic acid bacteria.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (2009) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

SEQ ID NOs of lactate dehydrogenase coding regions and proteins

| Organism and gene name | SEQ ID NO: nucleic acid | SEQ ID NO: amino acid |
|---|---|---|
| *Lactobacillus plantarum* ldhD | 1 | 2 |
| *Lactobacillus plantarum* ldhL1 | 3 | 4 |
| *Lactobacillus plantarum* ldhL2 | 5 | 6 |
| *Lactococcus lactis* ldhL | 7 | 8 |
| *Leuconostoc mesenteroides* ldhD | 9 | 10 |
| *Streptococcus thermophilus* ldhL | 11 | 12 |
| *Pediococcus pentosaceus* ldhD | 13 | 14 |
| *Pediococcus pentosaceus* ldhL | 15 | 16 |
| *Lactobacillus acidophilus* ldhL1 | 17 | 18 |
| *Lactobacillus acidophilus* ldhL2 | 19 | 20 |
| *Lactobacillus acidophilus* ldhD | 21 | 22 |

TABLE 2

SEQ ID NOs of acetolactate decarboxylase coding regions and proteins

| Organism and gene name | SEQ ID NO: nucleic acid | SEQ ID NO: amino acid |
|---|---|---|
| aldB from *Lactobacillus plantarum* | 23 | 24 |
| aldB from *Lactobacillus rhamnosus* | 25 | 26 |
| aldB from *Pediococcus pentosaceus* | 27 | 28 |
| aldB from *Leuconostoc mesenteroides* | 29 | 30 |
| aldB from *Oenococcus oeni* | 31 | 32 |
| aldB from *Enterococcus faecalis* | 33 | 34 |
| aldB from *Streptococcus mutans* | 35 | 36 |
| aldB from *Lactococcus lactis* | 37 | 38 |

TABLE 3

SEQ ID NOs of pyruvate formate lyase and pyruvate formate lyase activating enzyme coding regions and proteins

| Organism and gene name | SEQ ID NO: nucleic acid | SEQ ID NO: amino acid |
|---|---|---|
| PflB1 from *Lactobacillus plantarum* | 39 | 40 |
| PflB2 from *Lactobacillus plantarum* | 41 | 42 |
| PflA1 from *Lactobacillus plantarum* | 43 | 44 |
| PflA2 from *Lactobacillus plantarum* | 45 | 46 |
| Pfl from *Lactococcus lactis* | 47 | 48 |
| PflA from *Lactococcus lactis* | 49 | 50 |
| Pfl from *Streptococcus thermophilus* | 51 | 52 |
| PflA from *Streptococcus thermophilus* | 53 | 54 |

TABLE 4

SEQ ID NOs of expression coding regions and proteins

| Description | SEQ ID NO: nucleic acid | SEQ ID NO: amino acid |
|---|---|---|
| ALS from *Bacillus subtilis* | 55 | 56 |
| ALS from *Bacillus subtilis* coding region optimized for *Lactobacillus plantarum* | 57 | 56* |
| ALS from *Klebsiella pneumoniae* (budB) | 58 | 59 |
| ALS from *Lactococcus lactis* | 60 | 61 |
| ALS from *Staphylococcus aureus* | 62 | 63 |
| ALS from *Listeria monocytogenes* | 64 | 65 |
| ALS from *Streptococcus mutans* | 66 | 67 |
| ALS from *Streptococcus thermophilus* | 68 | 69 |
| ALS from *Vibrio angustum* | 70 | 71 |
| ALS from *Bacillus cereus* | 72 | 73 |
| KARI: ilvC gene of *Lactococcus lactis* | 74 | 75 |
| KARI from *Vibrio cholerae* | 76 | 77 |
| KARI from *Pseudomonas aeruginosa* I | 78 | 79 |

TABLE 4-continued

SEQ ID NOs of expression coding regions and proteins

| Description | SEQ ID NO: nucleic acid | SEQ ID NO: amino acid |
|---|---|---|
| KARI from *Pseudomonas fluorescens* | 80 | 81 |
| DHAD from *Lactococcus lactis* ilvD | 82 | 83 |
| DHAD from *Streptococcus mutans* ilvD | 84 | 85 |
| branched chain keto acid decarboxylase from *Lactococcus lactis* kivD | 86 | 87 |
| *Lactococcus lactis* kivD opt for *L. plantarum* | 88 | 87* |
| secondary alcohol dehydrogenase from *Achromobacter xylosoxidans* sadB | 91 | 92 |
| *A. xylosoxidans* sadB opt for *L. plantarum* | 157 | 92* |
| Tn5 transposase | 93 | 94 |

*same protein sequence encoded by native and optimized sequence

SEQ ID NOs:95 and 96 are transposase recognition sites Tn5IE and Tn5OE.

SEQ ID NO:97 is the sequence of plasmid pFP996. SEQ ID NOs:89, 90, 98-113, 117, 118, 120-122, 124-129, 131-136, 139-142, 144-147, 149-151, 153, 154, 156, 159-169, 171-175, 178-182, and 184-190 are PCR and sequencing primers.

SEQ ID NO:114 is a ribosome binding site (RBS).

SEQ ID NO:115 is the sequence of plasmid pDM20-ilvD (*L. lactis*).

SEQ ID NO:116 is the sequence of plasmid pDM1.

SEQ ID NO:119 is the sequence of a PCR fragment including a RBS and ilvD coding region from *Lactococcus lactis*.

SEQ ID NO:123 is a right homologous arm DNA fragment containing the 5' portion of the suf operon (sufC and part of sufD).

SEQ ID NO:130 is a left homologous arm DNA fragment containing the native suf promoter and sequences upstream into the feoBA operon.

SEQ ID NO:137 is the sequence of plasmid pTN6.

SEQ ID NO:138 is the sequence of a Tn5IE-loxP-cm-Pspac-loxP cassette.

SEQ ID NO:143 is the Pnpr promoter.

SEQ ID NO:148 is a Pnpr-tnp fusion DNA fragment.

SEQ ID NO:152 is a PgroE promoter sequence.

SEQ ID NO:155 is a PCR fragment containing the kivD(o) coding region together with a RBS.

SEQ ID NO:157 is the sadB coding region optimized for expression in *L. plantarum*.

SEQ ID NO:158 a DNA fragment containing an RBS and sadB(o) coding region.

SEQ ID NO:170 is a PrrnC1 promoter.

SEQ ID NO:176 is the sequence of plasmid pDM5.

SEQ ID NO:177 is a lacI-PgroE/lacO fragment.

SEQ ID NO:183 is the sequence of plasmid pDM5-PldhL1-ilvC(*L. lactis*).

DETAILED DESCRIPTION

The present invention relates to recombinant lactic acid bacteria (LAB) cells that are modified by genetic engineering to reduce or eliminate enzyme activity of an endogenously expressed enzymes encoded by genes encoding acetolactate decarboxylase (aldB) and lactate dehydrogenase (ldh). The cells have reduced or no acetolactate decarboxylase and no lactate dehydrogenase activity due to reduced or eliminated expression from these modified genes. The present invention also relates to the method of obtaining LAB cells which lack acetolactate decarboxylase and lactate dehydrogenase activities with engineered genetic modifications in aldB and ldh, which requires expressing one of the activities non-chromosomally while the chromosomal gene is modified. The non-chromosomal gene is then eliminated.

In these cells there is increased flux from pyruvate to acetolactate but away from acetoin. These cells may be used to produce isobutanol and other products having acetolactate as an intermediate. Isobutanol is useful as a fuel or fuel additive for replacing fossil fuels.

The following abbreviations and definitions will be used for the interpretation of the specification and the claims.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "isobutanol biosynthetic pathway" refers to an enzyme pathway to produce isobutanol from pyruvate.

The term "lactate dehydrogenase" refers to a polypeptide (or polypeptides) having an enzyme activity that catalyzes the conversion of pyruvate to lactate. Lactate dehydrogenases are known as EC 1.1.1.27 (L-lactate dehydrogenase) or EC 1.1.1.28 (D-lactate dehydrogenase).

The term "acetolactate decarboxylase" refers to a polypeptide (or polypeptides) having an enzyme activity that catalyzes the conversion of acetolactate to acetoin. Acetolactate decarboxylases are known as EC 4.1.1.5.

The term "pyruvate formate lyase", also called "formate C-acetyltransferase", refers to a polypeptide having enzyme activity that catalyzes the conversion of pyruvate to formate. Pyruvate formate lyases are known as EC 2.3.1.54.

The term "pyruvate formate lyase activating enzyme", also called "formate C-acetyltransferase activating enzyme", refers to a polypeptide that is required for activity of pyruvate formate lyase. Formate C-acetyltransferase activating enzymes are known as EC 1.97.1.4.

The term "a facultative anaerobe" refers to a microorganism that can grow in both aerobic and anaerobic environments.

The term "carbon substrate" or "fermentable carbon substrate" refers to a carbon source capable of being metabolized by host organisms of the present invention and particularly carbon sources selected from the group consisting of monosaccharides, oligosaccharides, polysaccharides, and one-carbon substrates or mixtures thereof.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign gene" or "heterologous gene" refers to a gene not normally found in the host organism, but that is introduced into the host organism by gene transfer. "Heterologous gene" includes a native coding region, or portion thereof, that is reintroduced into the source organism in a form that is different from the corresponding native gene. For example, a heterologous gene may include a native coding region that is a portion of a chimeric gene including non-native regulatory regions that is reintroduced into the native host. Also a foreign gene can comprise native genes inserted into a non-native organism, or chimeric genes. A "transgene" is a gene that has been introduced into the genome by a transformation procedure.

As used herein the term "coding region" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA). Expression may also refer to translation of mRNA into a polypeptide.

As used herein the term "transformation" refers to the transfer of a nucleic acid molecule into a host cell, which may be maintained as a plasmid or integrated into the genome. Host cells containing the transformed nucleic acid molecules are referred to as "transgenic" or "recombinant" or "transformed" cells.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein the term "codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a coding region for improved expression in a host cell, it is desirable to design the coding region such that its frequency of codon usage approaches the frequency of preferred codon usage of the host cell.

The term "codon-optimized" as it refers to coding regions of nucleic acid molecules for transformation of various hosts, refers to the alteration of codons in the coding regions of the nucleic acid molecules to reflect the typical codon usage of the host organism without altering the polypeptide encoded by the DNA.

As used herein, an "isolated nucleic acid fragment" or "isolated nucleic acid molecule" will be used interchangeably and will mean a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid fragment is "hybridizable" to another nucleic acid fragment, such as a cDNA, genomic DNA, or RNA molecule, when a single-stranded form of the nucleic acid fragment can anneal to the other nucleic acid fragment under the appropriate conditions of temperature and solution ionic strength. Hybridization and washing conditions are well known and exemplified in Sambrook, J., Fritsch, E. F. and Maniatis, T. Molecular Cloning: A Laboratory Manual, $2^{nd}$ ed., Cold Spring Harbor Laboratory: Cold Spring Harbor, N.Y. (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments (such as homologous sequences from distantly related organisms), to highly similar fragments (such as genes that duplicate functional enzymes from closely related organisms). Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. An additional set of stringent conditions include hybridization at 0.1×SSC, 0.1% SDS, 65° C. and washes with 2×SSC, 0.1% SDS followed by 0.1×SSC, 0.1% SDS, for example.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least about 30 nucleotides. Furthermore, the skilled artisan will recognize that the temperature and wash solution salt concentration may be adjusted as necessary according to factors such as length of the probe.

A "substantial portion" of an amino acid or nucleotide sequence is that portion comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Altschul, S. F., et al., J. Mol. Biol., 215:403-410 (1993)). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches the complete amino acid and nucleotide sequence encoding particular proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "complementary" is used to describe the relationship between nucleotide bases that are capable of hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: 1.) Computational Molecular Biology (Lesk, A. M., Ed.) Oxford University: NY (1988); 2.) Biocomputing: Informatics and Genome Projects (Smith, D. W., Ed.) Academic: NY (1993); 3.) Computer Analysis of Sequence Data, Part I (Griffin, A. M., and Griffin, H. G., Eds.) Humania: NJ (1994); 4.) Sequence Analysis in Molecular Biology (von Heinje, G., Ed.) Academic (1987); and 5.) Sequence Analysis Primer (Gribskov, M. and Devereux, J., Eds.) Stockton: NY (1991).

Preferred methods to determine identity are designed to give the best match between the sequences tested. Methods to determine identity and similarity are codified in publicly available computer programs.

Sequence alignments and percent identity calculations may be performed using the MegAlign™ program of the LASERGENE bioinformatics computing suite (DNASTAR Inc., Madison, Wis.). Multiple alignment of the sequences is performed using the "Clustal method of alignment" which encompasses several varieties of the algorithm including the "Clustal V method of alignment" corresponding to the alignment method labeled Clustal V (described by Higgins and Sharp, CABIOS. 5:151-153 (1989); Higgins, D. G. et al., Comput. Appl. Biosci., 8:189-191 (1992)) and found in the MegAlign™ program of the LASERGENE bioinformatics computing suite (DNASTAR Inc.). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program. Additionally the "Clustal W method of alignment" is available and corresponds to the alignment method labeled Clustal W (described by Higgins and Sharp, CABIOS. 5:151-153 (1989);

Higgins, D. G. et al., *Comput. Appl. Biosci.* 8:189-191 (1992), Thompson, J. D., Higgins, D. G., and Gibson T. J. (1994) *Nuc. Acid Res.* 22: 4673 4680) and found in the MegAlign™ v6.1 program of the LASERGENE bioinformatics computing suite (DNASTAR Inc.). Default parameters for multiple alignment (GAP PENALTY=10, GAP LENGTH PENALTY=0.2, Delay Divergen Seqs(%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

The term "sequence analysis software" refers to any computer algorithm or software program that is useful for the analysis of nucleotide or amino acid sequences. "Sequence analysis software" may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mich.); and 5.) the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Press, Cold Spring Harbor, N.Y. (1984); and by Ausubel, F. M. et al., *Current Protocols in Molecular Biology*, published by Greene Publishing Assoc. and Wiley-Interscience (1987).

Improved Production of Isobutanol in Lactic Acid Bacteria

The present invention provides for greatly improved isobutanol production in lactic acid bacteria (LAB) cells having genetic modifications, e.g., deletions, in certain genes, said modifications provide for the elimination of lactate dehydrogenase and reduction or elimination of acetolactate enzyme activity in these cells.

The primary flux of pyruvate in LAB cells, which is to lactic acid, is altered by decreased expression of lactate dehydrogenase (Ldh) activity. With reduced Ldh activity, there may be increased flux of pyruvate to production of acetolactate via acetolactate synthase, and from acetolactate to acetoin (see FIG. 1). Acetolactate decarboxylase catalyzes conversion of acetolactate to acetoin. Decreased lactate dehydrogenase activity in an acetolactate decarboxylase null LAB cell has been found to result in increases in acetolactate and in acetoin after about 20 hours of growth (Monnet et al. Appl and Envrt. Microbiology 66:5518-5520 (2000). Thus efficient conversion of acetolactate to acetoin occurred even in the absence of acetolactate decarboxylase activity. Modifications to the LAB cells made in Monnet et al (ibid.) were made by chemical mutagenesis followed by screening for reduced enzyme activities. Thus the nature of the alterations to the genome are unknown, in contrast to when engineered genetic modifications are made.

In the present invention a method was developed to engineer genetic modifications to eliminate the enzyme activity encoded by lactate dehydrogenase and acetolactate decarboxylase genes in LAB cells. Elimination of enzyme activity according to the invention means elimination of appreciable or detectable levels in functional activity. These modifications could not be obtained using standard engineering methods. It was found, as described herein that in a LAB cell with these modifications in the presence of an isobutanol biosynthetic pathway, isobutanol production was increased 6-fold over isobutanol production in a cell with ldh gene deletions but no aldB deletion. Thus the isobutanol pathway was able to effectively divert flux from production of acetoin from acetolactate.

Engineered genetic modifications to eliminate enzyme activity resulting from modifications to genes encoding lactate dehydrogenase and acetolactate decarboxylase may be made as described below in any LAB, which may also be engineered for the presence of an isobutanol biosynthetic pathway. The LAB which may be host cells in the present disclosure include, but are not limited to, *Lactococcus, Lactobacillus, Leuconostoc, Oenococcus, Pediococcus*, and *Streptococcus*.

Eliminating Lactate Dehydrogenase Enzyme Activity

In the present invention genetic modifications are engineered in LAB to eliminate the enzyme activity from expression of endogenous lactate dehydrogenase genes that are naturally expressed under growth conditions used during fermentation for product production. LAB may have one or more genes, typically one, two or three genes, encoding lactate dehydrogenase. For example, *Lactobacillus plantarum* has three genes encoding lactate dehydrogenase which are named ldhL2 (protein SEQ ID NO:6, coding region SEQ ID NO:5), ldhD (protein SEQ ID NO:2, coding region SEQ ID NO:1), and ldhL1 (protein SEQ ID NO:4, coding region SEQ ID NO:3). *Lactococcus lactis* has one gene encoding lactate dehydrogenase which is named ldhL (protein SEQ ID NO:8, coding region SEQ ID NO:7), and *Pediococcus pentosaceus* has two genes named ldhD (protein SEQ ID NO:14, coding region SEQ ID NO:13) and ldhL (protein SEQ ID NO:16, coding region SEQ ID NO:15).

Genetic modification is made in at least one gene encoding lactate dehydrogenase to eliminate its activity. When more than one lactate dehydrogenase gene is expressed (is active) under the growth conditions to be used for production, a genetic modification may be made in each of these active genes to affect their expression such that enzyme activity is eliminated. For example, in *L. plantarum* ldhL1 and ldhD genes are modified. It is not necessary to modify the third gene, ldhL2, for growth in typical conditions because this gene appears to be inactive in these conditions. Typically, expression of one or more genes encoding lactate dehydrogenase is disrupted to eliminate the expressed enzyme activity. Examples of LAB lactate dehydrogenase genes that may be targeted for disruption are represented by the coding regions of SEQ ID NOs:1, 3, 5, 7, 9, 11, 13, 15, 17, 19, and 21 listed in Table 1. Other target genes, such as those encoding lactate dehydrogenase proteins having at least about 80-85%, 85%-90%, 90%-95%, or at least about 96%, 97%, 98%, or 99% sequence identity to a lactate dehydrogenase of SEQ ID NO:2, 4, 6, 8, 10, 12, 14, 16, 18, 20, or 22 listed in Table 1 may be identified in the literature and using bioinformatics approaches, as is well known to the skilled person, since lactate dehydrogenases are well known. Typically BLAST (described above) searching of publicly available databases with known lactate dehydrogenase amino acid sequences, such as those provided herein, is used to identify lactate dehydrogenases, and their encoding sequences, that may be targets for disruption to eliminate expressed lactate dehydrogenase activity. Identities are based on the Clustal W method of alignment using the default parameters of GAP PENALTY=10, GAP LENGTH PENALTY=0.1, and Gonnet 250 series of protein weight matrix.

Additionally, the sequences described herein or those recited in the art may be used to identify other homologs in nature. For example each of the lactate dehydrogenase encoding nucleic acid fragments described herein may be used to isolate genes encoding homologous proteins. Isolation of homologous genes using sequence-dependent protocols is well known in the art. Examples of sequence-dependent protocols include, but are not limited to: 1) methods of nucleic acid hybridization; 2) methods of DNA and RNA amplification, as exemplified by various uses of nucleic acid amplification technologies [e.g., polymerase chain reaction (PCR), Mullis et al., U.S. Pat. No. 4,683,202; ligase chain reaction (LCR), Tabor, S. et al., *Proc. Acad. Sci.* USA 82:1074 (1985); or strand displacement amplification (SDA), Walker, et al., *Proc. Natl. Acad. Sci. U.S.A.,* 89:392 (1992)]; and 3) methods of library construction and screening by complementation.

In the present LAB cells at least one engineered genetic modification is made that affects expression of the target gene encoding lactate dehydrogenase such that enzyme activity is eliminated. Any genetic modification method known by one skilled in the art for eliminating expression of a gene may be used to eliminate expressed enzyme activity. Methods include, but are not limited to, deletion of the entire or a portion of the lactate dehydrogenase encoding gene, inserting a DNA fragment into the lactate dehydrogenase encoding gene (in either the promoter or coding region) so that the encoded protein cannot be expressed or expression does not occur to a level sufficient for the production of enzyme activity, introducing a mutation into the lactate dehydrogenase coding region which adds a stop codon or frame shift such that a functional protein is not expressed, and introducing one or more mutations into the lactate dehydrogenase coding region to alter amino acids so that a non-functional protein is expressed. In addition lactate dehydrogenase expression may be blocked by expression of an antisense RNA or an interfering RNA, and constructs may be introduced that result in cosuppression. All of these methods may be readily practiced by one skilled in the art making use of the known lactate dehydrogenase encoding sequences such as those of SEQ ID NOs:1, 3, 5, 7, 9, 11, 13, 15, 17, 19, and 21.

For some methods genomic DNA sequences that surround a lactate dehydrogenase encoding sequence are useful, such as for homologous recombination-based methods. These sequences may be available from genome sequencing projects such as for *Lactobacillus plantarum*, which is available through the National Center for Biotechnology Information (NCBI) database, with Genbank™ identification gi|28376974|ref|NC_004567.1|[28376974]. Adjacent genomic DNA sequences may also be obtained by sequencing outward from a lactate dehydrogenase coding sequence using primers within the coding sequence, as well known to one skilled in the art.

A particularly suitable method for eliminating enzyme activity of a lactate dehydrogenase, as exemplified herein in Example 1, is using homologous recombination mediated by lactate dehydrogenase coding region flanking DNA sequences to delete the entire gene that encodes lactate dehydrogenase. The flanking sequences are cloned adjacent to each other so that a double crossover event using these flanking sequences deletes the lactate dehydrogenase coding region.

Eliminating Acetolactate Decarboxylase Enzyme Activity

In the present invention a genetic modification is engineered in LAB cells to reduce or eliminate enzyme activity of endogenously expressed acetolactate decarboxylase gene. Genes encoding acetolactate decarboxylase in LAB cells are typically called aldB. However alternative names of ald and aldC have sometimes been used. Thus ald and aldC are interchangeable with aldB herein as referring to a gene encoding acetolactate decarboxylase, as are any other names referring to the same gene.

Examples of acetolactate decarboxylase genes from LAB that may be targeted for modification are represented by the coding regions of SEQ ID NOs:23, 25, 27, 29, 31, 33, 35, and 37 listed in Table 2. Other target genes, such as those encoding an acetolactate decarboxylase protein having at least about 80-85%, 85%-90%, 90%-95%, or at least about 96%, 97%, 98% or 99% sequence identity to an acetolactate decarboxylase of SEQ ID NO:24, 26, 28, 30, 32, 34, 36, or 38 listed in Table 2 may be identified in the literature and using bioinformatics approaches, as is well known to the skilled person, since acetolactate decarboxylases are well known. Typically BLAST (described above) searching of publicly available databases with known acetolactate decarboxylase amino acid sequences, such as those provided herein, is used to identify acetolactate decarboxylases, and their encoding sequences, that may be targets for modification to eliminate enzyme activity of acetolactate decarboxylase. Identities are based on the Clustal W method of alignment using the default parameters of GAP PENALTY=10, GAP LENGTH PENALTY=0.1, and Gonnet 250 series of protein weight matrix.

Additionally, the acetolactate decarboxylase encoding sequences described herein or those recited in the art may be used to identify other homologs in nature as described above. In the present LAB cells at least one engineered genetic modification is made that affects expression of the target gene encoding acetolactate decarboxylase such that the enzyme activity of acetolactate decarboxylase is reduced or eliminated. Modifications are made as described for modifying the lactate dehydrogenase gene, using the method for combining ldh and aldB modifications as described below.

Transient Expression Allows ldh and ald Gene Knockouts

Similarly to what others had reported previously (de Vos et al. (1998) Int. Dairy J. 8:227-233), applicants were unable to recover a strain following genetic modification to eliminate aldB expression in LAB cells with genetic modifications engineered to eliminate expression of ldh genes as described in Example 4 herein. Both ldh genes that are active in typical growth conditions in *Lactobacillus plantarum*, ldhD and ldhL, had been modified to eliminate their expression.

In the present invention, acetolactate decarboxylase activity is expressed from a plasmid in a cell with ldh gene expression eliminated (as described above), during engineering of the chromosomal aldB gene. In the presence of the non-chromosomally expressed (from a plasmid) acetolactate decarboxylase activity, a genetic modification is engineered in the endogenous aldB gene to reduce or eliminate its expression. Then the plasmid is cured from the cell creating a cell with modifications that results in elimination of the enzyme activity resulting from expression of ldh and reduction or elimination of the enzyme activity resulting from expression of aldB genes. Through this method, cells with engineered modifications such that they are lacking lactate dehydrogenase activity and lack or have reduced acetolactate decarboxylase activity may be recovered.

Alternatively, lactate dehydrogenase activity may be expressed from a plasmid in a cell with aldB gene expression eliminated, during engineering of a chromosomal ldh gene. If more than one ldh gene is active, expression of one ldh gene may be eliminated prior to expressing lactate dehydrogenase activity from a plasmid. Then expression of the second ldh gene is eliminated. Then the plasmid is cured from the cell creating a cell with modifications that affects expression of ldh and aldB genes such that enzyme activity is eliminated. Through this method, engineered cells lacking lactate dehydrogenase activity and acetolactate decarboxylase activity may be recovered.

Alternatively, lactate dehydrogenase activity may be expressed from a plasmid in a cell with ldh gene expression eliminated, during engineering of a chromosomal aldB gene. Then the plasmid is cured from the cell creating a cell with modifications that eliminate expression of ldh and reduce or eliminate expression of aldB genes. Through this method, engineered cells lacking lactate dehydrogenase activity and acetolactate decarboxylase activity may be recovered.

Acetolactate decarboxylase or lactate dehydrogenase activity may be expressed from a plasmid as is well known to one skilled in the art. Any of the sequences encoding acetolactate decarboxylase that are provided herein as SEQ ID NOs: 23, 25, 27, 29, 31, 33, 35, 37, or any acetolactate decarboxylase coding regions additionally identified through bioinformatics or experimental methods as described above, may be operably linked to a promoter for expression in LAB from a chimeric gene. Additionally, suitable acetolactate decarboxylase enzymes are classified as EC number 4.1.1.5. Alternatively, any of the sequences encoding lactate dehydrogenase that are provided herein as SEQ ID NOs:1, 3, 5, 7, 9, 11, 13, 15, 17, 19, 21, or any lactate dehydrogenase coding regions additionally identified through bioinformatics or experimental methods as described above, may be operably linked to a promoter for expression in LAB from a chimeric gene. Additionally, suitable lactate dehydrogenase enzymes are classified as EC number EC 1.1.1.27 (L-lactate dehydrogenase) or EC 1.1.1.28 (D-lactate dehydrogenase). A ribosome binding site and a termination control region may be included in the chimeric expression gene. The chimeric gene is typically constructed in an expression vector or plasmid containing a selectable marker and sequences allowing autonomous replication in LAB cells. In addition, a native ldh or aldB gene with a native promoter that is active in LAB cells may be used for expression from a plasmid.

Initiation control regions or promoters which are useful to drive expression of an acetolactate decarboxylase or lactate dehydrogenase coding region in LAB cells are familiar to those skilled in the art. Some examples include the amy, apr, npr and rrnC1 promoters; nisA promoter (useful for expression Gram-positive bacteria (Eichenbaum et al. *Appl. Environ. Microbiol.* 64(8):2763-2769 (1998)); and the synthetic P11 promoter (useful for expression in *Lactobacillus plantarum*, Rud et al., *Microbiology* 152:1011-1019 (2006)). In addition, the ldhL1, and fabZ1 promoters of *L plantarum* are useful for expression of chimeric genes in LAB. The fabZ1 promoter directs transcription of an operon with the first gene, fabZ1, encoding (3R)-hydroxymyristoyl-[acyl carrier protein] dehydratase.

Termination control regions may also be derived from various genes, typically from genes native to the preferred hosts. Optionally, a termination site may be unnecessary, however, it is most preferred if included.

Vectors or plasmids useful in LAB cells include those having two origins of replication and two selectable markers which allow for replication and selection in both *Escherichia coli* and LAB. An example is pFP996, the sequence of which is provided as SEQ ID NO:97, which is useful in *L. plantarum* and other LAB. Many plasmids and vectors used in the transformation of *Bacillus subtilis* and *Streptococcus* may be used generally for LAB. Non-limiting examples of suitable vectors include pAMβ1 and derivatives thereof (Renault et al., *Gene* 183:175-182 (1996); and O'Sullivan et al., *Gene* 137:227-231 (1993)); pMBB1 and pHW800, a derivative of pMBB1 (Wyckoff et al. *Appl. Environ. Microbiol.* 62:1481-1486 (1996)); pMG1, a conjugative plasmid (Tanimoto et al., *J. Bacteriol.* 184:5800-5804 (2002)); pNZ9520 (Kleerebezem et al., *Appl. Environ. Microbiol.* 63:4581-4584 (1997)); pAM401 (Fujimoto et al., *Appl. Environ. Microbiol.* 67:1262-1267 (2001)); and pAT392 (Arthur et al., *Antimicrob. Agents Chemother.* 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. *Appl. Environ. Microbiol.* 2005 March; 71(3): 1223-1230).

Vectors or plasmids may be introduced into a host cell using methods known in the art, such as electroporation (Cruz-Rodz et al. Molecular Genetics and Genomics 224: 1252-154 (1990), Bringel, et al. *Appl. Microbiol. Biotechnol.* 33: 664-670 (1990), Alegre et al., *FEMS Microbiology letters* 241:73-77 (2004)), and conjugation (Shrago et al., *Appl. Environ. Microbiol.* 52:574-576 (1986)).

Following recovery of cells with ldh and aldB modifications, the cells are cured of the expression plasmid. Curing of the plasmid may be accomplished by any method known to one skilled in the art. Typically a temperature sensitive origin of replication is used, where growth of plasmid-harboring cells at the restrictive temperature causes the plasmid to be lost. Another method, for example, is to place a negative selection marker on the plasmid to be cured, where growth in the presence of the selective agent causes the plasmid to be lost.

Reducing Pyruvate Formate Lyase Activity

In addition to the modifications described above of ldh and aldB genes in the present cells, they may optionally have at least one modification that reduces endogenous pyruvate formate lyase activity. Pyruvate formate lyase activity converts pyruvate to formate (see FIG. 1). Activity of pyruvate formate lyase in the cell may be reduced or eliminated. Preferably the activity is eliminated.

For expression of pyruvate formate lyase activity a gene encoding pyruvate formate lyase (pfl) and a gene encoding pyruvate formate lyase activating enzyme are required. To reduce pyruvate formate lyase activity a modification may be made in either or both of these genes. There may be one or more genes encoding each of pyruvate formate lyase and pyruvate formate lyase activating enzyme in a particular strain of LAB. For example, *Lactobacillus plantarum* WCFS1 contains two pfl genes (pflB1: coding region SEQ ID NO:39, protein SEQ ID NO:40; and pflB2: coding region SEQ ID NO:41, protein SEQ ID NO:42) and two pfl activating enzyme genes (pflA1: coding region SEQ ID NO:43, protein SEQ ID NO:44; and pflA2: coding region SEQ ID NO:45, protein SEQ ID NO:46), *Lactobacillus plantarum* PN0512 only contains one pfl gene (pflB2) and one pfl activating enzyme gene (pflA2). Expression is reduced for all pfl encoding genes that are active in a production host cell under the desired production conditions and/or for all pfl activating enzyme encoding genes that are active in a production host cell under the desired production conditions.

Examples of pfl genes that may be modified to reduce pyruvate formate lyase activity are represented by the coding regions of SEQ ID NOs:39, 41, 47, and 51. Other target genes for modification include those encoding pyruvate formate lyase proteins having SEQ ID NOs:40, 42, 48, and 52 and those encoding a protein having at least about 80-85%, 85%-90%, 90%-95%, or at least about 96%, 97%, 98%, or 99% sequence identity to one of these proteins, which may be identified in the literature and using bioinformatics approaches, as is well known to the skilled person as described above for lactate dehydrogenase proteins. Additionally, the sequences described herein or those recited in the art may be used to identify other homologs in nature as described above.

Examples of pfl activating enzyme genes that may be modified to reduce pyruvate formate lyase activity are represented by the coding regions of SEQ ID NOs:43, 45, 49, and 53. Other target genes for modification include those encoding pyruvate formate lyase activating enzyme proteins having SEQ ID NOs:44, 46, 50, 54 and those encoding a protein having at least about 80-85%, 85%-90%, 90%-95%, or at least about 96%, 97%, 98%, or 99% sequence identity to one of these proteins, which may be identified in the literature and using bioinformatics approaches, as is well known to the skilled person as described above for lactate dehydrogenase proteins. Additionally, the sequences described herein or those recited in the art may be used to identify other homologs in nature as described above.

Any genetic modification method known by one skilled in the art for reducing the expression of a protein may be used to alter pyruvate formate lyase activity. Methods to reduce or eliminate expression of the pyruvate formate lyase and/or pyruvate formate lyase activating enzyme genes include, but are not limited to, deletion of the entire or a portion of the gene, inserting a DNA fragment into the gene (in either the promoter or coding region) so that the encoded protein cannot be expressed or has reduced expression, introducing a mutation into the coding region which adds a stop codon or frame shift such that a functional protein is not expressed, and introducing one or more mutations into the coding region to alter amino acids so that a non-functional or reduced-functional protein is expressed. In addition expression from the target gene may be partially or substantially blocked by expression of an antisense RNA or an interfering RNA, and constructs may be introduced that result in cosuppression.

Isobutanol Production

Figure 2:
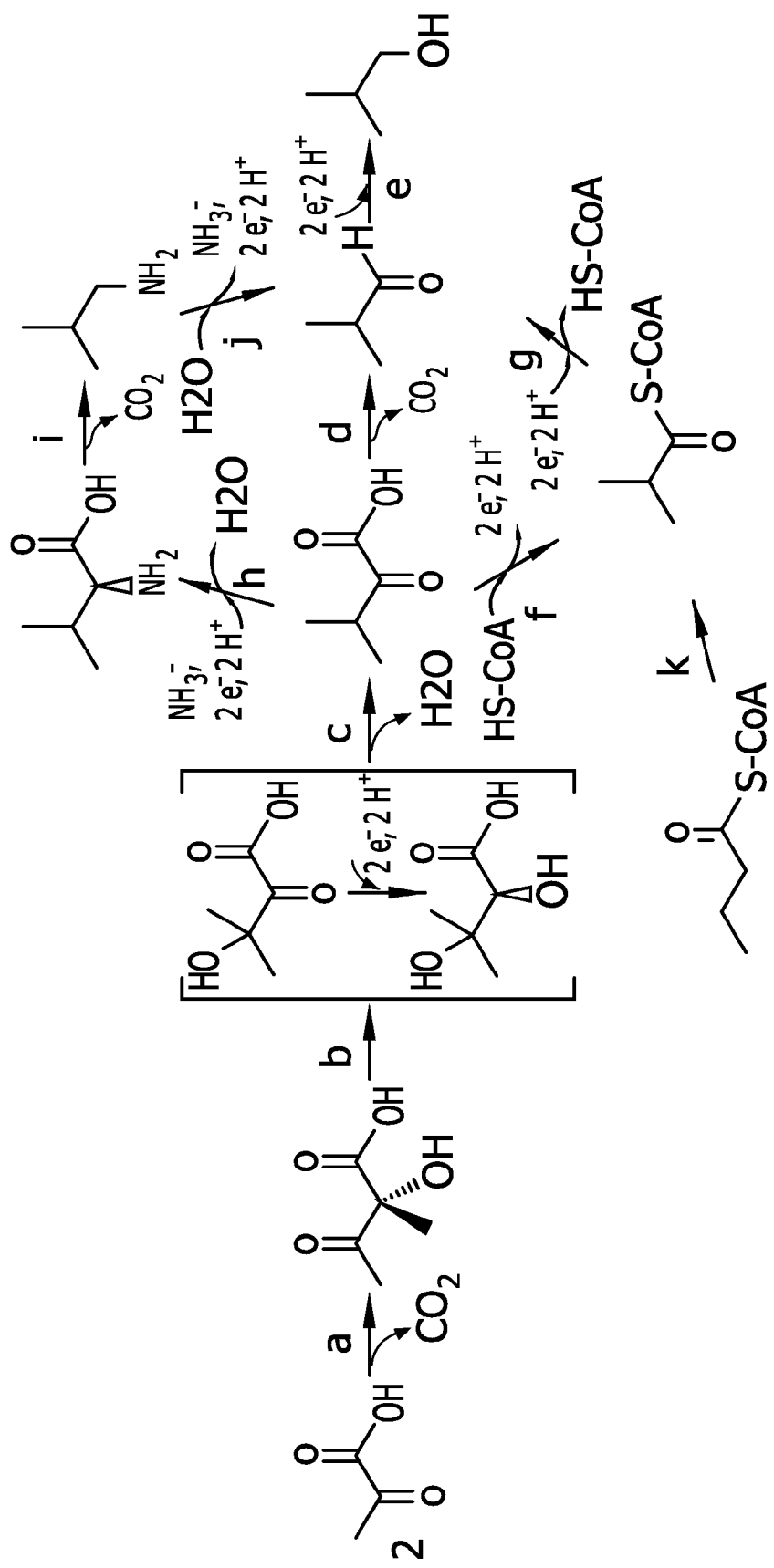
FIG. 2 shows biosynthetic pathways for biosynthesis of isobutanol.

In one embodiment of the present invention, a LAB cell with engineered modifications to the ldh and aldB genes as described above, and optionally reducing pyruvate formate lyase activity, produces isobutanol. Biosynthetic pathways for synthesis of isobutanol are disclosed in co-pending US Patent Pub No. US20070092957 A1, which is herein incorporated by reference. A diagram of the disclosed isobutanol biosynthetic pathways is provided in FIG. 2. Production of isobutanol in a genetically engineered LAB cell disclosed herein is increased by eliminating the enzyme activity expressed by ldh and aldB genes, and increased further by eliminating expression of pfl and/or pflA genes. In addition, an LAB host cell may be engineered for increased expression of Fe—S cluster forming proteins to improve the activity of the Fe—S cluster requiring dihydroxy-acid dehydratase enzyme of the isobutanol pathway as disclosed in co-pending US Patent Application Publication No. 20100081182, which is herein incorporated by reference. For example, expression of the endogenous suf operon encoding Fe—S cluster forming proteins may be increased as described in Example 2 herein.

As described in US Patent Pub No. US20070092957 A1, steps in an example isobutanol biosynthetic pathway include conversion of:

Pyruvate to acetolactate (FIG. 2 pathway step a) as catalyzed for example by acetolactate synthase (ALS) known by the EC number 2.2.1.6 9;

Acetolactate to 2,3-dihydroxyisovalerate (FIG. 2 pathway step b) as catalyzed for example by acetohydroxy acid isomeroreductase, also called ketol-acid reductoisomerase (KARI) known by the EC number 1.1.1.86;

2,3-dihydroxyisovalerate to α-ketoisovalerate (FIG. 2 pathway step c) as catalyzed for example by acetohydroxy acid dehydratase, also called dihydroxy-acid dehydratase (DHAD) known by the EC number 4.2.1.9;

α-ketoisovalerate to isobutyraldehyde (FIG. 2 pathway step d) as catalyzed for example by branched-chain α-keto acid decarboxylase known by the EC number 4.1.1.72; and Isobutyraldehyde to isobutanol (FIG. 2 pathway step e) as catalyzed for example by branched-chain alcohol dehydrogenase known by the EC number 1.1.1.265, but may also be classified under other alcohol dehydrogenases (specifically, EC 1.1.1.1 or 1.1.1.2).

The substrate to product conversions, and enzymes involved in these reactions, for steps f, g, h, I, j, and k of alternative pathways are described in US Patent Pub No. US20070092957 A1.

Genes that may be used for expression of these enzymes, as well as those for two additional isobutanol pathways, are described in US Patent Pub No. US20070092957 A1, and additional genes that may be used can be identified in the literature and using bioinformatics approaches, as is well known to the skilled person as described above. Additionally, sequences provided therein may be used to isolate genes encoding homologous proteins using sequence-dependent protocols is well known in the art, as described above.

For example, some representative ALS enzymes that may be used include those encoded by alsS of *Bacillus* and budB of *Klebsiella* (Gollop et al., *J. Bacteriol.* 172(6):3444-3449 (1990); Holtzclaw et al., *J. Bacteriol.* 121(3):917-922 (1975)). ALS from *Bacillus subtilis* (DNA: SEQ ID NO:55; protein: SEQ ID NO:56), from *Klebsiella pneumoniae* (DNA: SEQ ID NO:58; protein:SEQ ID NO:59), and from *Lactococcus lactis* (DNA: SEQ ID NO:60; protein: SEQ ID NO:61) are provided herein. Additional Als coding regions and encoded proteins that may be used include those from *Staphylococcus aureus* (DNA: SEQ ID NO:62; protein:SEQ ID NO:63), *Listeria monocytogenes* (DNA: SEQ ID NO:64; protein:SEQ ID NO:65), *Streptococcus mutans* (DNA: SEQ ID NO:66; protein:SEQ ID NO:67), *Streptococcus thermophilus* (DNA: SEQ ID NO:68; protein:SEQ ID NO:69), *Vibrio angustum* (DNA: SEQ ID NO:70; protein:SEQ ID NO:71), and *Bacillus cereus* (DNA: SEQ ID NO:72; protein: SEQ ID NO:73). Any Als gene that encodes an acetolactate synthase having at least about 80-85%, 85%-90%, 90%-95%, or at least about 96%, 97%, or 98% sequence identity to any one of those with SEQ ID NOs:56, 59, 61, 63, 65, 67, 69, 71, or 73 that converts pyruvate to acetolactate may be used. Identities are based on the Clustal W method of alignment using the default parameters of GAP PENALTY=10, GAP LENGTH PENALTY=0.1, and Gonnet 250 series of protein weight matrix.

Additionally, US Patent Application Publication No. 2009-0305363 provides a phylogenetic tree depicting acetolactate synthases that are the 100 closest neighbors of the *B. subtilis* AlsS sequence, any of which may be used. Additional Als sequences that may be used in the present strains may be identified in the literature and in bioinformatics databases as is well known to the skilled person. Identification of coding and/or protein sequences using bioinformatics is typically through BLAST (described above) searching of publicly available databases with known Als encoding sequences or encoded amino acid sequences, such as those provided herein. Identities are based on the Clustal W method of alignment as specified above. Additionally, the sequences listed herein or those recited in the art may be used to identify other homologs in nature as described above.

For example, KARI enzymes that may be used may be from the ilvC gene of *Lactococcus lactis* (DNA: SEQ ID NO:74; protein SEQ ID NO:75), *Vibrio cholerae* (DNA: SEQ ID NO:76; protein SEQ ID NO:77), *Pseudomonas aeruginosa* PAO1, (DNA: SEQ ID NO:78; protein SEQ ID NO:79), or *Pseudomonas fluorescens* PF5 (DNA: SEQ ID NO:80; protein SEQ ID NO:81). The later three are disclosed in US Patent Application Publication No, 20080261230, which is incorporated herein by reference. Additional KARI enzymes are described in U.S. Application No. 61/246,844, US Application Publication Nos. 2008026123, 2009016337, and 2010019751.

For example, DHAD enzymes that may be used may be from the ilvD gene of *Lactococcus lactis* (DNA: SEQ ID NO:82; protein SEQ ID NO:83) or *Streptococcus mutans* (DNA: SEQ ID NO:84; protein SEQ ID NO:85), and in addition sequences of DHAD coding regions and encoded proteins that may be used are provided in US Patent Application Publication No. 20100081183, which is incorporated herein by reference. This reference also includes descriptions for obtaining additional DHAD sequences that may be used.

For example, branched chain keto acid decarboxylase enzymes that may be used include one from the kivD gene of *Lactococcus lactis* (DNA: SEQ ID NO:86; protein SEQ ID NO:87) and others that may be identified by one skilled in the art using bioinformatics as described above.

For example, branched-chain alcohol dehydrogenases that may be used are known by the EC number 1.1.1.265, but may also be classified under other alcohol dehydrogenases (specifically, EC 1.1.1.1 or 1.1.1.2). These enzymes utilize NADH (reduced nicotinamide adenine dinucleotide) and/or NADPH as electron donors and sequences of branched-chain alcohol dehydrogenase enzymes and their coding regions that may be used are provided in US20070092957 A1.

In addition, useful for the last step of converting isobutyraldehyde to isobutanol is a new butanol dehydrogenase isolated from an environmental isolate of a bacterium identified as *Achromobacter xylosoxidans* (DNA: SEQ ID NO:91, protein SEQ ID NO:92) that is disclosed in US Patent Application Publication No. 20090269823, which is herein incorporated by reference Improved activity of DHAD in LAB cells that are substantially free of lactate dehydrogenase activity was disclosed in US Patent Application Publication No. 20100081183, which is herein incorporated by reference. Additionally, increased expression of iron-sulfur cluster forming proteins to improve activity of DHAD was disclosed in US Patent Application Publication No. 20100081183, which is herein incorporated by reference.

Described in US Pub No. US20070092957 A1 is construction of chimeric genes and genetic engineering of LAB, exemplified by *Lactobacillus plantarum*, for isobutanol production using disclosed biosynthetic pathways. Chimeric genes for pathway enzyme expression may be present in a cell on a replicating plasmid or integrated into the cell genome, as well known to one skilled in the art and described in Examples herein. A new method for integration developed herein is described below and used in Example 3.

Additional Products

The present engineered LAB cells may be used for production of other products made from acetolactate that do not require acetolactate decarboxylase activity, to provide improved production. These products may include, but are not limited to valine, isoleucine, leucine, pantothenic acid (vitamin B5), 2-methyl-1-butanol, 3-methyl-1-butanol (isoamyl alcohol), and diacetyl. For production of these or other products the present LAB cells have in addition a biosynthetic pathway for the desired product, which may be endogenous, engineered, or a combination of both, For example, a biosynthetic pathway for valine includes steps of acetolactate conversion to 2,3-dihydroxy-isovalerate by acetohydroxyacid reductoisomerase (ilvC), conversion of 2,3-dihydroxy-isovalerate to α-ketoisovalerate (also called 2-keto-isovalerate) by dihydroxy-acid dehydratase (ilvD), and conversion of α-ketoisovalerate to valine by branched-chain amino acid aminotransferase (ilvE). Biosynthesis of leucine includes the same steps to α-ketoisovalerate, followed by conversion of α-ketoisovalerate to leucine by enzymes encoded by leuA (2-isopropylmalate synthase), leuCD (isopropylmalate isomerase), leuB (3-isopropylmalate dehydrogenase), and tyrB/ilvE (aromatic amino acid transaminase). Biosynthesis of pantothenate includes the same steps to α-ketoisovalerate, followed by conversion of α-ketoisovalerate to pantothenate by enzymes encoded by panB (3-methyl-2-oxobutanoate hydroxymethyltransferase), panE (2-dehydropantoate reductase), and panC (pantoate-beta-alanine ligase). Engineering expression of enzymes for enhanced production of pantothenic acid in microorganisms is described in U.S. Pat. No. 6,177,264.

2-methyl-1-butanol and 3-methyl-1-butanol may be produced by converting 2-ketoacids from amino acid biosynthetic pathways using 2-ketoacid decarboxylases and alcohol dehyddrogenases (Atsumi and Liao (2008) Current Opinion in Biotechnology 19:414-419).

In combination with the elimination of ldh and aldB expression, increased expression of at least one gene in any of these pathways may be used to increase the production of the product of the pathway. Though some LAB naturally have the branched chain amino acid pathways for valine, isoleucine and leucine such as *Lactococcus lactis*, others such as *Lactobacillus plantarum* do not. LAB without an endogenous pathway producing the desired product, or precursor to a desired product, require engineering for expression of the missing pathway enzymes. One skilled in the art can readily assess which enzymes are present and missing for a desired pathway.

Diacetyl is produced from acetolactate spontaneously in the presence of oxygen, requiring no enzyme activity.

Tn5-Mediated Transposition in LAB

For long term maintenance and stability of foreign gene expression, such as for genes expressing enzymes of a desired biosynthetic pathway, it may be desired to integrate the expression gene into the cell genome. A vector was prepared herein to make use of the Tn5 transposition system in LAB cells, It was found that random integration into the genome of LAB cells was achieved using the Tn5 transposition vector developed herein. For integration, the vector includes a Tn5 transposase coding region (SEQ ID NO:93; encoded protein SEQ ID NO:94) operably linked to and expressed from a promoter that is active in LAB cells, examples of which are listed above, and transposase recognition sequences Tn5IE and Tn5OE (SEQ ID NOS:95 and 96). Any sequence that encodes a protein having at least about 90%, 95%, or 99% sequence identity with SEQ ID NO:94 and having Tn5 transposase activity may be used in the vector. Between Tn5IE and Tn5OE are a chloramphenicol resistance gene flanked by Cre recombinase sites, and a multiple cloning site (MCS). Any selection marker active in E. coli and LAB cells may substitute for the chloramphenicol resistance gene, examples of which are tetracycline resistance, spectinomycin resistance, and erythromycin resistance markers. The Cre recombinase sites are optional. In addition the vector has a second marker gene, which is used for screening for transposition and loss of the Tn5 transposition vector. The second marker may be any marker active in LAB cells, including any of those listed above. The vector also has origins of replication for E. coli and LAB, the LAB origin being conditionally active, such as temperature sensitive. DNA segments placed between the Tn5IE and Tn5OE elements, typically in the MCS, may be randomly integrated into the genome of LAB cells using this vector. The described vector with a DNA segment between the Tn5IE and Tn5OE elements is an integration construction. For example, the vector has a temperature sensitive origin of replication for lactic acid bacteria cells and the chloramphenicol resistance marker is used to select transformants. The transformants are grown in permissive conditions (temperature typically of 30° C.) for approximately 10 generations during which integration occurs. Transformants are then grown in nonpermissive conditions (temperature typically of 37° C.) for approximately 20 generations to cure the plasmid, and chloramphenicol resistant colonies are screened for erythromycin sensitivity (loss of second marker) to confirm loss of the plasmid. The chloramphenicol resistance marker may be excised by expression of Cre recombinase in the cell, typically from a chimeric gene on a plasmid as is well known in the art.

Growth for Production

Recombinant LAB cells disclosed herein may be used for fermentation production of isobutanol or other products as follows. The recombinant cells are grown in fermentation media which contains suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt.

Although it is contemplated that all of the above mentioned carbon substrates and mixtures thereof are suitable in the present invention, preferred carbon substrates are glucose, fructose, and sucrose. Sucrose may be derived from renewable sugar sources such as sugar cane, sugar beets, cassava, sweet sorghum, and mixtures thereof. Glucose and dextrose may be derived from renewable grain sources through saccharification of starch based feedstocks including grains such as corn, wheat, rye, barley, oats, and mixtures thereof. In addition, fermentable sugars may be derived from renewable cellulosic or lignocellulosic biomass through processes of pretreatment and saccharification, as described, for example, in U.S. Patent Application Publication No. 2007/0031918A1, which is herein incorporated by reference. Biomass refers to any cellulosic or lignocellulosic material and includes materials comprising cellulose, and optionally further comprising hemicellulose, lignin, starch, oligosaccharides and/or monosaccharides. Biomass may also comprise additional components, such as protein and/or lipid. Biomass may be derived from a single source, or biomass can comprise a mixture derived from more than one source; for example, biomass may comprise a mixture of corn cobs and corn stover, or a mixture of grass and leaves. Biomass includes, but is not limited to, bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, grasses, wheat, wheat straw, barley, barley straw, hay, rice straw, switchgrass, waste paper, sugar cane bagasse, sorghum, soy, components obtained from milling of grains, trees, branches, roots, leaves, wood chips, sawdust, shrubs and bushes, vegetables, fruits, flowers, animal manure, and mixtures thereof.

In addition to an appropriate carbon source, fermentation media must contain suitable minerals, salts, cofactors, buffers and other components, known to those skilled in the art, suitable for the growth of the cultures and promotion of the enzymatic pathway necessary for isobutanol production.

Typically cells are grown at a temperature in the range of about 25° C. to about 40° C. in an appropriate medium. Suitable growth media are common commercially prepared media such as Bacto Lactobacilli MRS broth or Agar (Difco), Luria Bertani (LB) broth, Sabouraud Dextrose (SD) broth or Yeast Medium (YM) broth. Other defined or synthetic growth media may also be used, and the appropriate medium for growth of the particular bacterial strain will be known by one skilled in the art of microbiology or fermentation science. The use of agents known to modulate catabolite repression directly or indirectly, e.g., cyclic adenosine 2':3'-monophosphate, may also be incorporated into the fermentation medium.

Suitable pH ranges for the fermentation are between pH 3.0 to pH 9.0, where pH 6.0 to pH 8.0 is preferred as the initial condition.

Fermentations may be performed under aerobic or anaerobic conditions, where anaerobic or microaerobic conditions are preferred.

It is contemplated that the production of isobutanol, or other product, may be practiced using either batch, fed-batch or continuous processes and that any known mode of fermentation would be suitable. Additionally, it is contemplated that cells may be immobilized on a substrate as whole cell catalysts and subjected to fermentation conditions for isobutanol production.

Methods for Isobutanol Isolation from the Fermentation Medium

Bioproduced isobutanol may be isolated from the fermentation medium using methods known in the art for ABE fermentations (see for example, Durre, *Appl. Microbiol. Biotechnol.* 49:639-648 (1998), Groot et al., *Process. Biochem.* 27:61-75 (1992), and references therein). For example, solids may be removed from the fermentation medium by centrifugation, filtration, decantation, or the like. Then, the isobutanol may be isolated from the fermentation medium using methods such as distillation, azeotropic distillation, liquid-liquid extraction, adsorption, gas stripping, membrane evaporation, or pervaporation.

EXAMPLES

The meaning of abbreviations is as follows: "s" means second(s), "min" means minute(s), "h" means hour(s), "psi" means pounds per square inch, "nm" means nanometers, "d" means day(s), "μl" means microliter(s), "ml" means milliliter(s), "L" means liter(s), "mm" means millimeter(s), "nm" means nanometers, "mM" means millimolar, "M" means molar, "mmol" means millimole(s), "μmol" means micromole(s)", "g" means gram(s), "μg" means microgram(s) and "ng" means nanogram(s), "PCR" means polymerase chain reaction, "OD" means optical density, "$OD_{600}$" means the optical density measured at a wavelength of 600 nm, "kDa" means kilodaltons, "g" means the gravitation constant, "bp" means base pair(s), "kbp" means kilobase pair(s), "% w/v" means weight/volume percent, % v/v" means volume/volume percent, "wt %" means percent by weight, "HPLC" means high performance liquid chromatography, and "GC" means gas chromatography. The term "molar selectivity" is the number of moles of product produced per mole of sugar substrate consumed and is reported as a percent. "SLPM" stands for Standard Liters per Minute (of air), "dO" is dissolved oxygen, $q_p$ is "specific productivity" measured in grams isobutanol per gram of cells over time.

General Methods

Recombination plasmids were constructed using standard molecular biology methods known in the art. All restriction and modifying enzymes and Phusion High-Fidelity PCR Master Mix were purchased from New England Biolabs (Ipswich, Mass.). DNA fragments were purified with Qiaquick PCR Purification Kit (Qiagen Inc., Valencia, Calif.). Plasmid DNA was prepared with QIAprep Spin Miniprep Kit (Qiagen Inc., Valencia, Calif.). *L. plantarum* PN0512 genomic DNA was prepared with MasterPure DNA Purification Kit (Epicentre, Madison, Wis.). Oligonucleotides were synthesized by Sigma-Genosys (Woodlands, Tex.) or Invitrogen Corp (Carlsbad, Calif.).

Transformation

*Lactobacillus plantarum* PN0512 was transformed by the following procedure: 5 ml of Lactobacilli MRS medium (Accumedia, Neogen Corporation, Lansing, Mich.) containing 1% glycine (Sigma-Aldrich, St. Louis, Mo.) was inoculated with PN0512 cells and grown overnight at 30° C. 100 ml MRS medium with 1% glycine was inoculated with overnight culture to an OD600 of 0.1 and grown to an OD600 of 0.7 at 30° C. Cells were harvested at 3700×g for 8 min at 4° C., washed with 100 ml cold 1 mM $MgCl_2$ (Sigma-Aldrich, St. Louis, Mo.), centrifuged at 3700×g for 8 min at 4° C., washed with 100 ml cold 30% PEG-1000 (Sigma-Aldrich, St. Louis, Mo.), recentrifuged at 3700×g for 20 min at 4° C., then resuspended in 1 ml cold 30% PEG-1000. 60 μl cells were mixed with ~100 ng plasmid DNA in a cold 1 mm gap gap electroporation cuvette and electroporated in a BioRad Gene Pulser (Hercules, Calif.) at 1.7 kV, 25 μF, and 400Ω. Cells were resuspended in 1 ml MRS medium containing 500 mM sucrose (Sigma-Aldrich, St. Louis, Mo.) and 100 mM $MgCl_2$, incubated at 30° C. for 2 hrs, plated on MRS medium plates containing 1 or 2 μg/ml of erythromycin (Sigma-Aldrich, St. Louis, Mo.), then placed in an anaerobic box containing a Pack-Anaero sachet (Mitsubishi Gas Chemical Co., Tokyo, Japan) and incubated at 30° C.

Example 1

Construction of the ilvD Integration Vector and PN0512ΔldhDΔldhL1::ilvDL1⁺ Integration Strain This example describes integration of the *Lactococcus lactis* ilvD gene into the chromosome of *L. plantarum* strain PN0512 ΔldhDΔldhL1 for expression of DHAD. The construction of *L. plantarum* PN0512 ΔldhDΔldhL1 was described in Example 1 of co-pending U.S. patent application Ser. No. 61/100,786, which is herein incorporated by reference. This strain is deleted for the two genes that encode the major lactate dehydrogenases: ldhD and ldhL1. The double deletion was made in *Lactobacillus plantarum* PN0512 (ATCC strain #PTA-7727).

Gene knockouts were constructed using a process based on a two-step homologous recombination procedure to yield unmarked gene deletions (Ferain et al., 1994, *J. Bact.* 176: 596). The procedure utilized a shuttle vector, pFP996 (SEQ ID NO:97). pFP996 is a shuttle vector for gram-positive bacteria. It can replicate in both *E. coli* and gram-positive bacteria. It contains the origins of replication from pBR322 (nucleotides #2628 to 5323) and pE194 (nucleotides #43 to 2627). pE194 is a small plasmid isolated originally from a gram positive bacterium, *Staphylococcus aureus* (Horinouchi and Weisblum J. Bacteriol. (1982) 150(2):804-814). In pFP996, the multiple cloning sites (nucleotides #1 to 50) contain restriction sites for EcoRI, BglII, XhoI, SmaI, ClaI, KpnI, and HindIII. There are two antibiotic resistance markers; one is for resistance to ampicillin and the other for resistance to erythromycin. For selection purposes, ampicillin was used for transformation in *E. coli* and erythromycin was used for selection in *L. plantarum*.

Two segments of DNA, each containing 900 to 1200 bp of sequence either upstream or downstream of the intended deletion, were cloned into the plasmid to provide the regions of homology for the two genetic cross-overs. Cells were grown for an extended number of generations (30-50) to allow for the cross-over events to occur. The initial cross-over (single cross-over) integrated the plasmid into the chromosome by homologous recombination through one of the two homology regions on the plasmid. The second cross-over (double cross-over) event yielded either the wild type sequence or the intended gene deletion. A cross-over between the sequences that led to the initial integration event would yield the wild type sequence, while a cross-over between the other regions of homology would yield the desired deletion. The second cross-over event was screened for by antibiotic sensitivity. Single and double cross-over events were analyzed by PCR and DNA sequencing.

ΔldhD

The knockout cassette to delete the ldhD gene was created by amplifying from PN0512 genomic DNA an upstream flanking region with primers Top D F1 (SEQ ID NO:98) containing an EcoRI site and Top D R1 (SEQ ID NO:99). The downstream homology region including part of the coding sequence of ldhD was amplified with primers Bot D F2 (SEQ ID NO:100) and Bot D R2 (SEQ ID NO:101) containing an XhoI site. The two homology regions were joined by PCR SOE as follows. The 0.9 kbp upstream and downstream PCR products were gel-purified. The PCR products were mixed in equal amounts in a PCR reaction and re-amplified with primers Top D F1 and Bot D R2. The final 1.8 kbp PCR product was gel-purified and TOPO cloned into pCR4BluntII-TOPO (Invitrogen) to create vector pCRBluntII::ldhD. To create the integration vector carrying the internal deletion of the ldhD gene, pFP996 was digested with EcoRI and XhoI and the 5311-bp fragment gel-purified. Vector pCRBluntII::ldhD was digested with EcoRI and XhoI and the 1.8 kbp fragment gel-purified. The ldhD knockout cassette and vector were ligated using T4 DNA ligase, resulting in vector pFP996:: ldhD ko.

Electrocompetent *Lactobacillus plantarum* PN0512 cells were prepared, transformed with pFP996::ldhD ko, and plated on MRS containing 1 μg/ml of erythromycin. To obtain the single-crossover event (sco), transformants were passaged for approximately 50 generations in MRS medium at 37° C. After growth, aliquots were plated for single colonies on MRS containing 1 μg/ml of erythromycin. The erythromycin-resistant colonies were screened by PCR amplification with primers ldhD Seq F1 (SEQ ID NO:102) and D check R (SEQ ID NO:103) to distinguish between wildtype and clones carrying the sco event. To obtain clones with a double crossover, the sco strains were passaged for approximately 30 generations in MRS medium with 20 mM D, L-lactate (Sigma, St. Louis, Mo.) at 37° C. and then plated for single colonies on MRS with lactate. Colonies were picked and patched onto MRS with lactate and MRS with lactate containing 1 μg/ml of erythromycin to find colonies sensitive to erythromycin. Sensitive colonies were screened by PCR amplification using primer D check R (SEQ ID NO:103) and D check F3 (SEQ ID NO:104). Wildtype colonies gave a 3.2 kbp product and deletion clones, called PN0512ΔldhD, gave a 2.3 kbp PCR product.

ΔldhDΔldhL1

A deletion of the ldhL1 gene was made in the PN0512ΔldhD strain background in order to make a double ΔldhL1ΔldhD deletion strain. The knockout cassette to delete the ldhL1 gene was amplified from PN0512 genomic DNA. The ldhL1 left homologous arm was amplified using primers oBP31 (SEQ ID NO:105) containing a BglII restriction site and oBP32 (SEQ ID NO:106) containing an XhoI restriction site. The ldhL1 right homologous arm was amplified using primers oBP33 (SEQ ID NO:107) containing an XhoI restriction site and oBP34 (SEQ ID NO:108) containing an XmaI restriction site. The ldhL1 left homologous arm was cloned into the BglII/XhoI sites and the ldhL1 right homologous arm was cloned into the XhoI/XmaI sites of pFP996pyrFΔerm, a derivative of pFP996. pFP996pyrFΔerm contains the pyrF sequence (SEQ ID NO:109) encoding orotidine-5'-phosphate decarboxylase from *Lactobacillus plantarum* PN0512 in place of the erythromycin coding region in pFP996. The plasmid-borne pyrF gene, in conjunction with the chemical 5-fluoroorotic acid in a ΔpyrF strain, can be used as an effective counter-selection method in order to isolate the second homologous crossover. The XmaI fragment containing the ldhL1 homologous arms was isolated following XmaI digestion and cloned into the XmaI restriction site of pFP996, yielding a 900 bp left homologous region and a 1200 bp right homologous region resulting in vector pFP996-ldhL1-arms.

PN0512ΔldhD was transformed with pFP996-ldhL1-arms and grown at 30° C. in Lactobacilli MRS medium with lactate (20 mM) and erythromycin (1 μg/ml) for approximately 10 generations. Transformants were then grown under non-selective conditions at 37° C. for about 50 generations by serial inoculations in MRS+lactate before cultures were plated on MRS containing lactate and erythromycin (1 μg/ml). Isolates were screened by colony PCR for a single crossover using chromosomal specific primer oBP49 (SEQ ID NO:110) and plasmid specific primer oBP42 (SEQ ID NO:111). Single crossover integrants were grown at 37° C. for approximately 40 generations by serial inoculations under non-selective conditions in MRS with lactate before cultures were plated on MRS medium with lactate. Isolates were patched to MRS with lactate plates, grown at 37° C., and then patched onto MRS plates with lactate and erythromycin (1 μg/ml). Erythromycin sensitive isolates were screened by colony PCR for the presence of a wild-type or deletion second crossover using chromosomal specific primers oBP49 (SEQ ID NO:110) and oBP56 (SEQ ID NO:112). A wild-type sequence yielded a 3505 bp product and a deletion sequence yielded a 2545 bp product. The deletions were confirmed by sequencing the PCR product and absence of plasmid was tested by colony PCR with primers oBP42 (SEQ ID NO:111) and oBP57 (SEQ ID NO:113).

The *Lactobacillus plantarum* PN0512 double ldhDldhL1 deletion strain was designated PNP0001. The ΔldhD deletion included 83 bp upstream of where the ldhD start codon was through amino acid 279 of 332. The ΔldhL1 deletion included the fMet through the final amino acid.

The chromosomal integration of a single copy of the *L. lactis* ilvD coding region expressed from the ldhL1 promoter was constructed by the same two-step homologous recombination procedure to yield an unmarked integration as described above using the pFP996 shuttle vector except that the second crossover event yielded the wild type sequence or the intended integration rather than the deletion. Two segments of DNA containing sequences upstream and downstream of the intended integration site were cloned into the plasmid to provide the regions of homology for two genetic crossovers.

Two DNA segments (homologous arms) were designed to provide regions of homology for the two genetic cross-overs such that integration would place the ilvD coding region downstream of the ldhL1 promoter in strain PN0512ΔldhDΔldhL1. The left and right homologous arms cloned into the plasmid were each approximately 1200 base pairs. The left homologous arm was amplified from *L. plantarum* PN0512 genomic DNA with primers oBP31 (SEQ ID NO:105), containing a BglII restriction site, and oBP32 (SEQ ID NO106), containing an XhoI restriction site using Phusion High-Fidelity PCR Master Mix. The right homologous arm was amplified from *L. plantarum* PN0512 genomic DNA with primers oBP33 (SEQ ID NO:107), containing an XhoI restriction site and oBP34 (SEQ ID NO:108), containing an XmaI restriction site using Phusion High-Fidelity PCR Master Mix. The left homologous arm was digested with BglII and XhoI and the right homologous arm was digested with XhoI and XmaI. The two homologous arms were ligated with T4 DNA Ligase into the corresponding restriction sites of pFP996, after digestion with the appropriate restriction enzymes, to generate the vector pFP996-ldhL1arms.

A DNA fragment containing the ilvD coding region from *Lactococcus lactis* (SEQ ID NO:82) and a ribosome binding sequence (RBS; SEQ ID NO:114) was amplified from pDM20-ilvD (*L. lactis*) (SEQ ID NO:115). Construction of pDM20-ilvD (*L. lactis*) was described in U.S. Patent Appln No. 61/100,809, which is herein incorporated by reference. This plasmid is pDM20 containing the ilvD coding region derived by PCR from *L. lactis* subsp *lactis* NCD02118 (NCIMB 702118) (Godon et al., J. Bacteriol. (1992) 174: 6580-6589) and a ribosome binding sequence (SEQ ID NO:114) added in the 5" PCR primer. pDM20 is modified pDM1 (SEQ ID NO:116) which contains a minimal pLF1 replicon (~0.7 Kbp) and pemK-pem1 toxin-antitoxin (TA) from *Lactobacillus plantarum* ATCC14917 plasmid pLF1, a P15A replicon from pACYC184, chloramphenicol resistance marker for selection in both *E. coli* and *L. plantarum*, and P30 synthetic promoter (Rud et al., *Microbiology* (2006) 152: 1011-1019). Vector pDM1 was modified by deleting nucleotides 3281-3646 spanning the lacZ region which were replaced with a multi cloning site. Primers oBP120 (SEQ ID NO:117), containing an XhoI site, and oBP182 (SEQ ID NO:118), containing DrdI, PstI, HindIII, and BamHI sites, were used to amplify the P30 promoter from pDM1 with Phusion High-Fidelity PCR Master Mix. The resulting PCR product and pDM1 vector were digested with XhoI and DrdI, which drops out lacZ and P30. The PCR product and the large fragment of the pDM1 digestion were ligated to yield vector pDM20 in which the P30 promoter was reinserted, bounded by XhoI and DrdI restriction sites.

The DNA fragment containing the ilvD coding region and RBS (SEQ ID NO:119) was obtained by PCR using pDM20-ilvD (*L. lactis*) as the template with primers oBP246 (SEQ ID NO:120), containing an XhoI restriction site, and oBP237 (SEQ ID NO:121), containing an XhoI restriction site, using Phusion High-Fidelity PCR Master Mix. The resulting PCR product and pFP996-ldhL1 arms were ligated with T4 DNA Ligase after digestion with XhoI. Clones were screened by PCR for the insert in the same orientation as the ldhL1 promoter in the left homologous arm using vector specific primer oBP57 (SEQ ID NO:113) and ilvD-specific primer oBP237 (SEQ ID NO:121). A clone that had the correctly oriented insert was named pFP996-ldhL1arms-ilvDL1.

Integration of the *L. lactis* ilvD coding region was obtained by transforming *L. plantarum* PN0512ΔldhDΔldhL1 with pFP996-ldhL1arms-ilvDL1. 5 ml of Lactobacilli MRS medium (Accumedia, Neogen Corporation, Lansing, Mich.) containing 0.5% glycine (Sigma-Aldrich, St. Louis, Mo.) was inoculated with PN0512ΔldhDΔldhL1 and grown overnight at 30° C. 100 ml MRS medium with 0.5% glycine was inoculated with overnight culture to an OD600 of 0.1 and grown to an OD600 of 0.7 at 30° C. Cells were harvested at 3700×g for 8 min at 4° C., washed with 100 ml cold 1 mM $MgCl_2$ (Sigma-Aldrich, St. Louis, Mo.), centrifuged at 3700×g for 8 min at 4° C., washed with 100 ml cold 30% PEG-1000 (Sigma-Aldrich, St. Louis, Mo.), recentrifuged at 3700×g for 20 min at 4° C., then resuspended in 1 ml cold 30% PEG-1000. 60 µl of cells were mixed with ~100 ng of plasmid DNA in a cold 1 mm gap electroporation cuvette and electroporated in a BioRad Gene Pulser (Hercules, Calif.) at 1.7 kV, 25 µF, and 400Ω. Cells were resuspended in 1 ml MRS medium containing 500 mM sucrose (Sigma-Aldrich, St. Louis, Mo.) and 100 mM $MgCl_2$, incubated at 30° C. for 2 hrs, and then plated on MRS medium plates containing 2 µg/ml of erythromycin (Sigma-Aldrich, St. Louis, Mo.).

Transformants were screened by PCR using ilvD specific primers oBP237 (SEQ ID NO:121) and oBP246 (SEQ ID NO:120). Transformants were grown at 30° C. in Lactobacilli MRS medium with erythromycin (1 µg/ml) for approximately 8 generations and then at 37° C. for approximately 40 generations by serial inoculations in Lactobacilli MRS medium. The cultures were plated on Lactobacilli MRS medium with erythromycin (0.5 µg/ml). The isolates were screened by colony PCR for a single crossover with chromosomal specific primer oBP49 (SEQ ID NO:110) and plasmid specific primer oBP42 (SEQ ID NO:111).

Single crossover integrants were grown at 37° C. for approximately 43 generations by serial inoculations in Lactobacilli MRS medium. The cultures were plated on MRS medium. Colonies were patched to MRS plates and grown at 37° C. The isolates were then patched onto MRS medium with erythromycin (0.5 µg/ml). Erythromycin sensitive isolates were screened by (colony) PCR for the presence of a wild-type or integration second crossover using chromosomal specific primers oBP49 (SEQ ID NO:110) and oBP56 (SEQ ID NO:112). A wild-type sequence yielded a 2600 bp product and an integration sequence yielded a 4300 bp product. The integration was confirmed by sequencing the PCR product and an identified integration strain was designated PN0512ΔldhDΔldhL1::ilvDL1+.

Example 2

Construction of a suf Operon Promoter Integration Vector and PN0512ΔldhDΔldhL1::ilvDL1+ suf:: P5P4+ Integration Strain This Example describes integration of two promoters into the chromosome of *L. plantarum* PN0512ΔldhDΔldhL1::ilvDL1+. The promoters were integrated upstream of the suf operon, whose gene products are responsible for Fe—S cluster assembly. The promoter integration results in a strain with increased expression of the endogenous Fe—S cluster machinery.

The suf operon chromosomal promoter integration was constructed by a two-step homologous recombination procedure to yield an unmarked integration using the shuttle vector pFP996 (SEQ ID NO:97) as described above.

The suf operon promoter integration vector was constructed in three steps. In the first step, a right homologous arm fragment containing the 5' portion of the suf operon (sufC and part of sufD) was cloned into pFP996. In the second step, the synthetic promoters P5 and P4 [Rud et al., *Microbiology* (2006) 152:1011] were cloned into the pFP996-right arm clone upstream of the right arm. In the final step, a left homologous arm fragment containing the native suf promoter and sequences upstream into the feoBA operon was cloned into the pFP996-P5P4-right arm clone upstream of the P5P4 promoters.

The right homologous arm DNA fragment (SEQ ID NO:123) was PCR amplified from *L. plantarum* PN0512 genomic DNA with primers AA199 (SEQ ID NO:124), containing an XmaI restriction site, and AA200 (SEQ ID NO:125), containing a KpnI restriction site, using Phusion High-Fidelity PCR Master Mix. The right homologous arm PCR fragment and pFP996 were ligated with T4 DNA Ligase after digestion with XmaI and KpnI to generate pFP996-sufCD. A DNA fragment containing promoters P5 and P4 was generated by performing PCR with two partially complementary primer sequences. Primer $AA_2O_3$ (SEQ ID NO:126), containing an XhoI site, the P5 promoter sequence, and part of the P4 promoter sequence, was combined with primer AA204 (SEQ ID NO:127), containing an XmaI site and the P4 promoter sequence, and PCR was performed with Phusion High-Fidelity PCR Master Mix. The resulting PCR product was then amplified with primers AA206 (SEQ ID NO:128) and AA207 (SEQ ID NO:129) with Phusion High-Fidelity PCR Master Mix. The P5P4 PCR product and pFP996-sufCD were ligated after digestion with XhoI and XmaI to generate pFP996-P5P4-sufCD. The left homologous arm DNA fragment (SEQ ID NO:130) was amplified from *L. plantarum* PN0512 genomic DNA with primers AA201 (SEQ ID NO:131), containing an EcoRI restriction site, and AA202 (SEQ ID NO:132), containing an XhoI restriction site, using Phusion High-Fidelity PCR Master Mix. The left homologous arm and pFP996-P5P4-sufCD were ligated with T4 DNA Ligase after digestion with EcoRI and XhoI to generate pFP996-feoBA-P5P4-sufCD. The vector was confirmed by sequencing. The vector had a five base pair deletion (TTGTT), encompassing part of the −35 hexamer in the upstream P5 promoter.

Integration of the synthetic promoters (P5P4) upstream of the suf operon was obtained by transforming L. plantarum PN0512ΔldhDΔldhL1::ilvDLl$^+$ with pFP996-feoBA-P5P4-sufCD as described above. Transformants were grown at 30° C. in Lactobacilli MRS medium with erythromycin (2 μg/ml) for approximately 20 generations. The cultures were plated on Lactobacilli MRS medium with erythromycin (0.5 μg/ml). Isolates were screened by colony PCR for a single crossover with chromosomal specific primer AA209 (SEQ ID NO:133) and plasmid specific primer AA210 (SEQ ID NO:134). Single crossover integrants were grown at 37° C. for approximately 30 generations by serial inoculations in Lactobacilli MRS medium. The cultures were plated on MRS medium. Isolates were screened for erythromycin sensitivity. Isolates were screened by (colony) PCR for the presence of a wild-type or integration second crossover using P5 specific primer AA211 (SEQ ID NO:135) and chromosomal specific primer oBP126 (SEQ ID NO:136). An identified integration strain was designated PN0512ΔldhDΔldhL1::ilvDLl$^+$ suf::P5P4$^+$.

Example 3

Construction of the Tn5-Transposon Vector (pTN6) and its Use for Integration of PgroE-kivD(o)-sadB(o) Cassette Tn5 is a bacterial transposon which has been well characterized in E. coli (Johnson & Reznikoff, Nature (1983) 304: 280-282). A Tn5-mediated transposition system for lactic acid bacteria (LAB), however, has not been reported so far. In this Example, use of a Tn5-transposon vector as a delivery system for random gene integration into the chromosome of LAB was developed. The developed Tn5-transposon vector (pTN6) (SEQ ID NO:137) is an E. coli-L. plantarum shuttle vector. Plasmid pTN6 contains a transposase gene (tnp), transposase recognition nucleotide sequences Tn5IE (19 base pairs inside end) and Tn5OE (19 base pairs outside end), two antibiotic resistance markers; one for resistance to chloramphenicol and the other for resistance to erythromycin, P15A replication origin for E. coli, pE194 replication origin for L. plantarum which is temperature sensitive (Horinouchi and Weisblum J. Bacteriol. (1982) 150:804-814), and two loxP nucleotide sequences (34 base pairs). The chloramphenicol resistance gene is flanked by loxP sites for later excision by Cre recombinase. Multiple cloning sites (MSC) that contain restriction sites for BamHI, NotI, ScaI, and SpeI are located between the loxP and Tn5OE sites. The chloramphenicol resistance gene, two loxP sites, and MCS are flanked by Tn5IE and Tn5OE.

To construct the Tn5-transposon vector pTN6, first, the 1,048 bp Tn5IE-loxP-cm-loxP cassette containing Tn5IE, loxP, chloramphenicol resistant gene (cm), and loxP was synthesized by Genscript Corp (Piscataway, N.J.) (SEQ ID NO:138). The Tn5IE-loxP-cm-Pspac-loxP cassette was cloned in the pUC57 vector (Genscript Corp, Piscataway, N.J.), producing plasmid pUC57-Tn5IE-loxP-cm-loxP. The chloramphenicol resistance gene is expressed under the control of the spac promoter (Yansura & Henner, (1984) Proc Natl Acad Sci USA. 81:439-443) for selection in both E. coli and L. plantarum. Plasmid pUC57-Tn5IE-loxP-cm-loxP was digested with NsiI and SacI, and the 1,044 bp Tn5IE-loxP-cm-loxP fragment was gel-purified. Plasmid pFP996 (SEQ ID NO:97) was digested with NsiI and SacI, and the 4,417 bp pFP996 fragment containing the pBR322 and pE194 replication origins was gel-purified. The Tn5IE-loxP-cm-loxP fragment was ligated with the 4,417 bp pFP996 fragment to generate pTnCm.

Second, the pBR322 replication origin on pTnCm was replaced by the P15A replication origin. Plasmid pTnCm was digested with AatII and SalI, and the 2,524 bp pTnCm fragment containing the pE194 replication origin and Tn5IE-loxP-cm-loxP cassette was gel-purified. The 913 bp p15A replication origin was PCR-amplified from pACYC184 [Chang and Cohen, J. Bacteriol. (1978)134:1141-1156] with primers T-P15A(SalITn5OE) (SEQ ID NO:139) that contains a SalI restriction site and 19 bp Tn5OE nucleotide sequence, and B-P15A(AatII) (SEQ ID NO:140) that contains an AatII restriction site by using Phusion High-Fidelity PCR Master Mix (New England Biolabs, Ipswich, Mass.). The P15A fragment, after digestion with SalI and AatII restriction enzymes, was ligated with the 2,524 bp pTnCm fragment to generate pTN5.

Third, the erythromycin resistance gene (erm) was cloned into the HindIII site on pTN5. The 1,132 bp erythromycin resistant gene (erm) DNA fragment was generated from vector pFP996 (SEQ ID NO:97) by PCR amplification with primers T-erm(HindIII) (SEQ ID NO:141) containing an NsiI restriction site and B-erm(HindIII) (SEQ ID NO:142) containing an NsiI restriction site by using Phusion High-Fidelity PCR Master Mix, and cloned into the HindIII restriction site on pTN5, producing pTN5-erm.

Finally, a tnp gene sequence encoding transposase was fused to the npr (neutral protease from Bacillus amyloliquefaciens) promoter [Nagarajan et al., J. Bacteriol (1984) 159: 811-819] bp SOE (splicing by overlap extension) PCR, and cloned into the NsiI site on pTN5-erm. A DNA fragment containing the Pnpr promoter (SEQ ID NO:143) was PCR-amplified from pBE83 [Nagarajan et al., Appl Environ Microbiol (1993) 59:3894-3898] with primer set T-Pnpr(NsiI) (SEQ ID NO:144) containing an NsiI restriction site and B-Pnpr(tnp) (SEQ ID NO:145) containing a 17 bp overlapping sequence by using Phusion High-Fidelity PCR Master Mix. A tnp coding region (SEQ ID NO:93) was PCR-amplified from pUTmTn5-(Sharpe et al., Appl Environ Microbiol (2007) 73:1721-1728) with primer set T-tnp(Pnpr) (SEQ ID NO:146) containing a 21 bp overlapping sequence and B-tnp (NsiI) (SEQ ID NO:147) containing an NsiI restriction site by using Phusion High-Fidelity PCR Master Mix. The PCR products of the two reactions were mixed and amplified using outer primers (T-Pnpr(NsiI) and B-tnp(NsiI)), resulting in the production of a Pnpr-tnp fusion DNA fragment (SEQ ID NO:148). Plasmid pTN5-erm was digested with NsiI and treated with Calf Intestinal Phosphatase (New England Biolabs, MA) to prevent self-ligation. The digested pTN5-erm vector was ligated with the Pnpr-tnp fragment digested with NsiI. The ligation mixture was transformed into E. coli Top10 cells (Invitrogen Corp, Carlsbad, Calif.) by electroporation. Transformants were selected on LB plates containing 25 μg/mL chloramphenicol at 37° C. Transformants then were screened by colony PCR with outer primers of the Pnpr-tnp cassette, and confirmed by DNA sequencing with primers pTnCm(711) (SEQ ID NO:149), pTnCm(1422) (SEQ ID NO: 150), and pTnCm(3025) (SEQ ID NO:151). The resulting plasmid was named pTN6.

This Tn5-transposon vector pTN6 was used as a random gene delivery system for integration of a PgroE-kivD(o)-sadB(o) cassette into the chromosome of the PN0512ΔldhDΔldhL1::ilvDLl$^+$ suf::P5P4$^+$strain. A DNA fragment containing a PgroE promoter (Yuan and Wong, *J. Bacteriol* (1995) 177:5427-5433) (SEQ ID NO:152) was PCR-amplified from genomic DNA of *Bacillus subtilis* with primer set T-groE (SalIKpnI) (SEQ ID NO:153) containing SalI and KpnI restriction sites and B-groE (BamHI) (SEQ ID NO:154) containing a BamHI restriction site by using Phusion High-Fidelity PCR Master Mix. The resulting 154 bp PgroE promoter fragment, after digesting with SalI and BamHI restriction enzymes, was cloned into SalI and BamHI sites of plasmid pTN6, generating pTN6-PgroE. The coding region of the kivD gene encoding the branched-chain keto acid decarboxylase from *Lactococcus lactis* was codon optimized for expression in *L. plantarum*. The optimized coding region sequence called kivD(o) (SEQ ID NO:88) with a RBS was synthesized by Genscript Corp (Piscataway, N.J.). The kivD(o) coding region together with a RBS (SEQ ID NO:155) was cloned in the pUC57 vector, producing plasmid pUC57-kivD(o). Plasmid pUC57-kivD(o) was digested with BamHI and NotI, and the 1,647 bp RBS-kivD(o) fragment was gel-purified. The RBS-kivD(o) fragment was cloned into BamHI and NotI restriction sites on pTN6-PgroE, producing pTN6-PgroE-kivD(o). The correct clone was confirmed by colony PCR with primers T-groE(SalIKpnI) and kivD(o)R (SEQ ID NO:153 and 156), producing a 1,822 bp fragment of the expected size. Then, the sadB gene coding region for branched-chain alcohol dehydrogenase from *Achromobacter xylosoxidans*, that was described in U.S. patent application Ser. No. 12/430,356, was cloned downstream of the kivD(o) coding region of pTN6-PgroE-kivD(o). The *A. xylosoxidans* sadB coding region was codon optimized for expression in *L. plantarum*. The new coding region called sadB(o) (SEQ ID NO:157) with a RBS was synthesized by Genscript Corp (Piscataway, N.J.), and cloned in the pUC57 vector, producing plasmid pUC57-sadB(o). A 1,089 bp DNA fragment (SEQ ID NO:158) containing the RBS and sadB(o) coding region was PCR-amplified from pUC57-sadB(o) with primer set T-sadB(o)(NotI) (SEQ ID NO:159) containing a NotI restriction site and B-sadB(o)(NotI) (SEQ ID NO:160) containing a NotI restriction site by using Phusion High-Fidelity PCR Master Mix. The RBS-sadB(o) gene fragment, after digesting with NotI, was cloned into NotI restriction site of pTN6-PgroE-kivD(o), producing pTN6-PgroE-kivD(o)-sadB(o). The correct clone was confirmed by DNA sequencing with kivD(o)1529 (SEQ ID NO:161) and B-spac(cm) (SEQ ID NO:162) primers. In this construction sadB(o) and kivD(o) coding regions are expressed in an operon from PgroE promoter.

The resulting plasmid pTN6-PgroE-kivD(o)-sadB(o) was transformed into PN0512ΔldhDΔldhL1::ilvDL1+ suf::P5P4+ by electroporation as described in General Methods. Transformants were selected on Lactobacilli MRS medium supplemented with 7.5 μg/ml chloramphenicol. The chloramphenicol resistant colonies were grown in Lactobacilli MRS medium with 7.5 μg/ml chloramphenicol at the permissive temperature of 30° C. for approximately 10 generations. The culture was inoculated at 1/100 dilution in fresh MRS medium and grown at 37° C. for approximately 20 generations by serial inoculation in Lactobacilli MRS medium. The cultures were plated on Lactobacilli MRS with 7.5 μg/ml chloramphenicol. The isolates were screened by re-streaking colonies on Lactobacilli MRS plates containing 1.5 μg/ml erythromycin for erythromycin sensitive colonies that were presumed to contain a chromosomally integrated PgroE-kivD(o)-sadB(o) cassette along with the transposon. The transposon-mediated integrants were confirmed by colony PCR with the kivD(o) sequence specific primer KivD(o)1529 and sadB (o) sequence specific primer B-sadB(o)(NotI), to produce the expected sized PCR product (1,220 bp).

To excise the chloramphenicol resistance marker that is flanked by loxP sites from the chromosome, a helper plasmid pFP352 (SEQ ID NO:163) expressing a Cre recombinase was transformed into the transposon-mediated integrant, according to the protocol as described in General Methods, and grown on *Lactobacillus* MRS plate containing 1.5 μg/ml erythromycin at 30° C. The cre recombinase excises the chloramphenicol marker from the chromosome by a recombiniation event between the loxP sites. The erythromycin resistant transformants were inoculated in MRS medium and grown at 37° C. for approximately 10 generations. The cultures were plated on Lactobacilli MRS without antibiotic and grown at 30° C. The isolates were screened for both erythromycin and chloramphenicol sensitive colonies by testing growth of colonies on Lactobacilli MRS plates containing 1.5 μg/ml erythromycin and Lactobacilli MRS plates containing chloramphenicol (7.5 μg/ml), separately, to verify loss of pFP352 and the chloramphenicol marker removal. Finally, the integrant was confirmed by genomic DNA sequencing with primer B-groE(BamHI). Genomic DNA was prepared using MasterPure DNA Purification® kit (Enpicentre, Inc., Madison, Wis.). The DNA sequencing result indicated that the PgroE-kivD(o)-sadB(o) cassette was Inserted within the coding region of the glgB gene encoding glycogen branching enzyme that catalyzes the transfer of a segment of a 1,4-alpha-D-glucan chain to a primary hydroxy group in a similar glucan chain. The resulting integrant was named PN0512ΔldhDΔldhL1::ilvD(Ll) suf::P5P4+ glgB::Tn5-PgroE-kivD(o)-sadB(o).

Example 4

Construction of an aldB Deletion Vector and Initial Deletion Attempt

An attempt to delete the aldB gene, encoding acetolactate decarboxylase, in strain PN0512ΔldhDΔldhL1::ilvD(Ll) suf::P5P4+ glgB::Tn5-PgroE-kivD(o)-sadB(o) is described.

A two-step homologous recombination procedure was used to try to create an unmarked deletion. The homologous recombination procedure utilized the shuttle vector, pFP996 (SEQ ID NO:97), described above. Two segments of DNA containing sequences upstream and downstream of the intended deletion were cloned into the plasmid to provide the regions of homology for two genetic crossovers. An initial single crossover integrates the plasmid into the chromosome. A second crossover event can then yield either the wild type sequence or the intended gene deletion.

The homologous DNA arms were designed such that the deletion would encompass the region encoding the first 23 amino acids of the AIdB protein (nucleotides 1-68 of the aldB coding sequence). The left and right homologous arms cloned into the plasmid were 1186 and 700 base pairs, respectively. The homologous arms were separated by the sequence GGTACCT, which replaced the 68 nucleotide aldB sequence deletion. The left homologous arm was amplified from *L. plantarum* PN0512 genomic DNA with primers oBP23 (SEQ ID NO:122), containing an XhoI restriction site, and oBP24 (SEQ ID NO:164), containing a KpnI restriction site using Phusion High-Fidelity PCR Master Mix. The right homologous arm was amplified from *L. plantarum* PN0512 genomic DNA with primers oBP335 (SEQ ID NO:165), containing a KpnI restriction site and oBP336 (SEQ ID NO:166), containing a BsrGI restriction site using Phusion High-Fidelity PCR Master Mix. The left homologous arm DNA fragment was digested with XhoI and KpnI and the right homologous arm DNA fragment was digested with KpnI and BsrGI. The two homologous arms were ligated with T4 DNA Ligase into the corresponding restriction sites of pFP996, after digestion with the appropriate restriction enzymes, to generate the vector pFP996aldBdel23arms.

The single cross-over was obtained by transforming Lactobacillus plantarum PN0512ΔldhDΔldhL1::ilvD(Ll) suf::P5P4+ glgB::Tn5-PgroE-kivD(o)-sadB(o) with pFP996aldBdel23arms. 100 ml of Lactobacilli MRS medium (Accumedia, Neogen Corporation, Lansing, Mich.) containing 0.5% glycine (Sigma-Aldrich, St. Louis, Mo.) was inoculated with PN0512ΔldhDΔldhL1::ilvD(Ll) suf::P5P4+ glgB::Tn5-PgroE-kivD(o)-sadB(o) and grown at 30° C. to an OD600 of 0.7. Cells were harvested at 3700×g for 8 min at 4° C., washed with 100 ml cold 1 mM MgCl$_2$ (Sigma-Aldrich, St. Louis, Mo.), centrifuged at 3700×g for 8 min at 4° C., washed with 100 ml cold 30% PEG-1000 (Sigma-Aldrich, St. Louis, Mo.), recentrifuged at 3700×g for 20 min at 4° C., then resuspended in 1 ml cold 30% PEG-1000. 60 μl of cells were mixed with ~100 ng of plasmid DNA in a cold 1 mm gap electroporation cuvette and electroporated in a BioRad Gene Pulser (Hercules, Calif.) at 1.7 kV, 25 μF, and 400Ω. Cells were resuspended in 1 ml MRS medium containing 500 mM sucrose (Sigma-Aldrich, St. Louis, Mo.) and 100 mM MgCl$_2$, incubated at 30° C. for 2 hrs, and then plated on MRS medium plates containing 1 μg/ml of erythromycin (Sigma-Aldrich, St. Louis, Mo.).

Transformants were screened by PCR using plasmid specific primers oBP42 (SEQ ID NO:111) and oBP57 (SEQ ID NO:113). Transformants were grown at 30° C. in Lactobacilli MRS medium with erythromycin (1 μg/ml) for approximately 10 generations and then at 37° C. for approximately 35 generations by serial inoculations in Lactobacilli MRS medium. The cultures were plated on Lactobacilli MRS medium with erythromycin (1 μg/ml). The isolates obtained were screened by colony PCR for a single crossover with chromosomal specific primer oBP47 (SEQ ID NO:167) and plasmid specific primer oBP42 (SEQ ID NO:111), and chromosomal specific primer oBP54 (SEQ ID NO:168) and plasmid specific primer oBP337 (SEQ ID NO:169).

Single crossover integrants were grown at 37° C. for approximately 41 generations by serial inoculations in Lactobacilli MRS medium without glucose. The cultures were plated on MRS medium without glucose and grown at 37° C. Colonies were patched to MRS plates without glucose and grown at 37° C. 96 isolates were screened by (colony) PCR for the presence of a deletion second crossover using chromosomal specific primer oBP54 (SEQ ID NO:168) and deletion specific primer oBP337 (SEQ ID NO:169). None of the isolates tested contained the deletion.

Example 5

Construction of the pTN5-PrrnC1-aldB(L. lactis) Vector

The purpose of this Example is to describe cloning of the aldB coding region (SEQ ID NO:37) for acetolactate decarboxylase from Lactococcus lactis subsp lactis NCDO2118 [Godon et al., J. Bacteriol. (1992) 174:6580-6589] into the E. coli-L. plantarum shuttle vector pTN5. The construction of the pTN5 vector was described in Example 3.

The DNA fragment containing a PrrnC1 promoter (SEQ ID NO:170) was PCR-amplified from genomic DNA of Lactococcus lactis subsp lactis NCDO2118 with primer set T-rrnC1(SalIKpnI) (SEQ ID NO:171) containing SalI and KpnI restriction sites and B-rrnC1(BamHI) (SEQ ID NO:172) containing a BamHI restriction site by using Phusion High-Fidelity PCR Master Mix. The resulting 149 bp PrrnC1 promoter fragment, after digesting with SalI and BamHI restriction enzymes, was cloned into SalI and BamHI sites of plasmid pTN5, generating pTN5-PrrnC1. A DNA fragment containing a RBS and aldB coding region was PCR-amplified from genomic DNA of Lactococcus lactis subsp lactis NCDO2118 with primer set T-aldBLI(BamHI) (SEQ ID NO:173) containing a BamHI restriction site and B-aldBLI(NotISpeI) (SEQ ID NO:174) containing NotI and SpeI restriction sites. The resulting 735 bp aldB(L. lactis) coding region and RBS fragment was digested with BamHI and NotI, and then cloned into BamHI and NotI sites on pTN5-PrrnC1, generating pTN5-PrrnC1-aldB(L. lactis). The correct clone was confirmed by restriction enzyme mapping with BamHI and NotI, showing expected size (3,569 bp and 735 bp) DNA fragments.

Example 6 aldB Deletion in the Presence of Plasmid-Expressed Acetolactate Decarboxylase

In this Example, the second crossover to cause deletion of aldB was attempted in cells expressing an aldB gene on a plasmid.

A single cross-over integrant from Example 5 was transformed with the plasmid pTN5-PrrnC1-aldB(L. lactis) by electroporation. The electro-competent cells were prepared as described above in Example 4. Transformants were selected following incubation at 30° C. for 5 days on Lactobacillus MRS agar plates containing chloramphenicol (7.5 μg/ml) and erythromycin (1 μg/ml). The chloramphenicol and erythromycin resistant transformants were grown at 30° C. for approximately 20 generations by serial inoculations in Lactobacilli MRS medium with chloramphenicol (7.5 μg/ml), and then the cultures were plated on Lactobacillus MRS agar plates containing chloramphenicol (7.5 μg/ml). The resulting colonies were patched onto Lactobacillus MRS agar plates containing erythromycin (1 μg/ml) to test erythromycin sensitivity. 42 out of 130 colonies showed erythromycin sensitivity. Then, the 42 erythromycin sensitive colonies were screened for deletion of the region encoding the first 23 amino acids of the AldB protein (nucleotides 1-68 of the aldB coding sequence) by colony PCR analysis with the chromosomal specific primers OBP47 and OBP54 (expected size: ~3.3 kbp), and chromosomal specific primers OBP54 and OBP337 (expected size: ~1.9 kbp). The colony PCR analysis showed that 22 out of 42 erythromycin sensitive colonies had Δ23aa aldB.

To cure the plasmid pTN5-PrrnC1-aldB(L. lactis) the Δ23aa aldB deletion mutant strain was grown at 37° C. for approximately 20 generations by serial inoculations in Lactobacilli MRS medium. The cultures were plated on Lactobacillus MRS agar plates. The plasmid removal of the Δ23aa aldB deletion mutant strain was confirmed by no growth of the strain on an MRS agar plate containing chloramphenicol (7.5 μg/ml). After removing the plasmid pTN5-PrrnC1-aldB (L. lactis), the deletion of the nucleotides 1-68 of the aldB coding sequence, corresponding to the first 23 amino acids of the AldB protein, was confirmed by DNA sequencing with AA213 primer (SEQ ID NO:175) showing that the endogenous aldB gene was successfully deleted in the presence of plasmid expression of AldB. The resulting A23aa aldB mutation strain was named PN0512ΔldhDΔldhL1::ilvD(Ll) suf::P5P4+ glgB::Tn5-PgroE-kivD(o)-sadB(o) Δ23aa aldB.

Example 7

Construction of the pDM5-PldhL1-ilvC(*L. lactis*) Vector

The purpose of this example is to describe cloning of the ilvC coding region (SEQ ID NO:74) for keto-acid reductoisomerase from *Lactococcus lactis* subsp *lactis* NCDO2118 (NCIMB 702118) [Godon et al., J. Bacteriol. (1992) 174: 6580-6589] into the pDM5 vector.

Plasmid pDM5 (SEQ ID NO:176) was constructed by replacing the P30 promoter on pDM1 with the *B. subtilis* groE promoter (PgroE) fused to a lacO operator sequence and a lacI repressor gene. Plasmid pDM1 is described in Example 1. Plasmid pHTO1 (Mo Bi Tec, Goettingen, Germany) was digested with SacI, treated with Klenow fragment to make blunt ends, digested with BamHI, and then the 1,548 bp lacI-PgroE/lacO fragment (SEQ ID NO:177) was gel-purified. The lacI-PgroE/lacO fragment was cloned into KpnI (blunt end by Klenow fragment) and BamHI sites of pDM1 in place of the P30 promoter, generating pDM5.

A DNA fragment, PldhL1-ilvC(*L. lactis*), containing a ldhL1 (L-lactate dehydrogenase from *Lactobacillus plantarum* PN0512) promoter (PldhL1) and ilvC coding region from *Lactococcus lactis* subsp *lactis* NCDO2118 was generated by SOE (splicing by overlap extension) PCR. The DNA fragment containing a PldhL1 promoter was PCR-amplified from the genomic DNA of *Lactobacillus plantarum* PN0512 with primer set T-ldhL1(NotI) (SEQ ID NO:178) containing a NotI restriction site and B-ldhLI(CLl) (SEQ ID NO:179) containing a 19 bp overlapping sequence by using Phusion High-Fidelity PCR Master Mix. An ilvC coding region was PCR-amplified from the genomic DNA of *Lactococcus lactis* subsp *lactis* NCDO2118 with primer set T-CLI(ldh) (SEQ ID NO:180) containing a 17 bp overlapping sequence and B-CLI (PvuI) (SEQ ID NO:181) containing a PvuI restriction site by using Phusion High-Fidelity PCR Master Mix. The PCR products of the two fragments were mixed and amplified using outer primers T-ldhL1(NotI) and B-CLI(PvuI), resulting in the production of a PldhL1-ilvC(*L. lactis*) fusion DNA fragment. Plasmid pDM5 was digested with NotI and PvuI restriction enzymes, and ligated with the PldhL1-ilvC(*L. lactis*) cassette after digesting with NotI and PvuI restriction enzymes. The ligation mixture was transformed into *E. coli* Top10 cells (Invitrogen Corp, Carlsbad, Calif.) by electroporation. Transformants were selected on LB plates containing 25 μg/mL chloramphenicol at 37° C. Transformants then were screened by colony PCR with outer primers of the PldhL1-ilvC(*L. lactis*) cassette, and confirmed by DNA sequencing with T-ldhL1(NotI) (SEQ ID NO:178) and pDM (R)new (SEQ ID NO:182). The resulting plasmid was named pDM5-PldhL1-ilvC(*L. lactis*) (SEQ ID NO:183).

Example 8

Production of Isobutanol Using PN0512ΔldhDΔldhL1::ilvD(Ll) suf::P5P4+ glgB::Tn5-PgroE-kivD(o)-sadB(o) Δ23aa aldB Containing Vector pDM5-PldhL1-ilvC(*L. lactis*)

The purpose of this example is to demonstrate the increased production of isobutanol in the recombinant *Lactobacillus plantarum* aldB-strain background, compared to an aldB+ strain background.

To construct the recombinant *Lactobacillus plantarum* expressing the genes of the isobutanol biosynthetic pathway, competent cells of the two integrants PN0512ΔldhDΔldhL1::ilvD(Ll) suf::P5P4+ glgB::Tn5-PgroE-kivD(o)-sadB(o) and PN0512ΔldhDΔldhL1::ilvD(Ll) suf::P5P4+ glgB::Tn5-PgroE-kivD(o)-sadB(o) Δ23aa aldB– were prepared as described above, and transformed with plasmid pDM5-PldhL1-ilvC(*L. lactis*), yielding PN0512ΔdhDΔldhL1::ilvD(Ll) suf::P5P4+ glgB::Tn5-PgroE-kivD(o)-sadB(o)/pDM5-PldhL1-ilvC(*L. lactis*), named DWS2269, and PN0512ΔldhDΔldhL1::ilvD(Ll) suf::P5P4+ glgB::Tn5-PgroE-kivD(o)-sadB(o) Δ23aa aldB-/pDM5-PldhL1-ilvC(*L. lactis*), named DWS2279. The first enzyme acetolactate synthase for the isobutanol pathway was provided by native expression from the endogenous gene.

The two strains DWS2269 and DWS2279 were inoculated in Lactobacilli MRS (100 mM 3-Morpholinopropanesulfonic acid (MOPS) pH7.0) medium containing 7.5 μg/ml chloramphenicol in 10 ml culture tubes and grown aerobically at 30° C. overnight. Overnight cultures were inoculated with an initial OD600=0.4 into 40 ml MRS medium (100 mM MOPS pH7.0) containing 7.5 μg/ml chloramphenicol, 40 μM ferric citrate, 0.5 mM cysteine in 120 ml serum bottles, and grown with 100 rpm shaking anaerobically at 37° C. for 96 hours. Samples of the cultures were centrifuged at 3700×g for 10 minutes at 4° C. and the supernatants filtered through a 0.2 μm filter (Pall Life Sciences, Ann Arbor, Mich.). The filtered supernatants were analyzed by HPLC (1200 Series, Agilent Technologies, Santa Clara, Calif.) with a SHODEX Sugar column, detected by UV210 and refractive index, mobile phase 10 mM $H_2SO_4$. Results in Table 5 show the production of isobutanol, acetoin, and ethanol for strains DWS2269 and DWS2279 grown in MRS medium (100 mM MOPS pH7.0) at 37° C. anaerobically. The amount of isobutanol produced by DWS2279 that contains the aldB– mutation was 8 mM, which is approximately 6-fold higher than the isobutanol level (1.3 mM) produced by DWS2269 that contains wild type aldB+.

TABLE 5

Production of isobutanol, acetoin, and ethanol by DWS2269 (aldB+) and DWS2279 (aldB–) grown in grown in MRS medium (100 mM MOPS pH 7.0) at 37° C. anaerobically.

| Strain | Ethanol (mM) | Acetoin (mM) | Isobutanol (mM) |
|---|---|---|---|
| DWS2269 = PN0512ΔldhDΔldhL1::ilvD(Ll) suf::P5P4+ glgB::Tn5-PgroE-kivD(o)-sadB(o)/pDM5-PldhL1-ilvC(*L. lactis*) | 25.9 | 25.4 | 1.3 |
| DWS2279 = PN0512ΔldhDΔldhL1::ilvD(Ll) suf::P5P4+ glgB::Tn5-PgroE-kivD(o)-sadB(o) Δ23aa aldB–/pDM5-PldhL1-ilvC(*L. lactis*) | 79.0 | 4.0 | 8.0 |

Example 9

Construction of the *Lactobacillus plantarum* PN0512ΔldhDΔldhL1::ilvD(Ll) suf::P5P4+ glgB::Tn5-PgroE-kivD(o)-sadB(o) Δ23aa aldB ΔpflB2A2::alsS(o) Strain The purpose of this example is to describe the construction of a *Lactobacillus plantarum* strain in the PN0512ΔldhDΔldhL1::ilvD(Ll) suf::P5P4+ glgB::Tn5-PgroE-kivD(o)-sadB(o) Δ23aa aldB strain background that is deleted for the genes pflB2, encoding formate C-acetyltransferase (pyruvate formate lyase), and pflA2, encoding the formate C-acetyltransferase activating enzyme, and thus does not contain formate C-acetyltransferase activity. A gene (alsS), codon optimized for expression in *Lactobacillus plantarum*, encoding the *Bacillus subtilis* acetolactate synthase enzyme was integrated in place of the pflB2A2 genes of *Lactobacillus plantarum* PN0512.

The pflB2A2 gene knockout and alsS gene integration were engineered using the two-step homologous recombination procedure described above. The knockout deleted the C-terminal 351 amino acids (nucleotides 1204 through 2256 of the coding sequence) of PflB2 and the entire coding sequence of pflA2. The deleted sequence was replaced with a stop codon, in frame with the truncated pflB2, followed by a ribosome binding sequence and the coding region of the *Bacillus subtilis* alsS gene codon optimized for expression in *Lactobacillus plantarum*.

The knockout/integration vector was constructed in plasmid pFP996 (SEQ ID NO:97) as follows. The homologous arms to delete the pflB2A2 genes were amplified from *L. plantarum* PN0512 genomic DNA. The pflB2A2 left homologous arm was amplified using primers oBP309 (SEQ ID NO:184) containing an XhoI restriction site and oBP310 (SEQ ID NO:185) containing a stop codon (complement of TAA) and XmaI restriction site. The pflB2A2 right homologous arm was amplified using primers oBP271 (SEQ ID NO:186) containing a KpnI restriction site and oBP272 (SEQ ID NO:187) containing a BsrGI restriction site. The pflB2A2 left homologous arm was cloned into the XhoI/XmaI sites and the pflB2A2 right homologous arm was cloned into the KpnI/BsrGI sites of pFP996 to create pFP996-pflB2A2arms. The *Bacillus subtilis* alsS coding region codon optimized for expression in *Lactobacillus plantarum* (SEQ ID NO:57; synthesized by Genscript Corp, Piscataway, N.J.) was amplified using primers oBP282 (SEQ ID NO:188) containing an XmaI restriction site and oBP283 (SEQ ID NO:189) containing a KpnI restriction site. The codon optimized alsS coding region was cloned into the XmaI/KpnI sites of pFP996-pflB2A2arms to create pFP996-pflB2A2arms-als(o).

PN0512ΔldhDΔldhL1::ilvD(Ll) suf::P5P4$^+$ glgB::Tn5-PgroE-kivD(o)-sadB(o) L23aa aldB (prepared in Example 6) was transformed with pFP996-pflB2A2arms-als(o) as above, except competent cells were prepared in the absence of glycine, and transformants were selected on MRS plates containing 1 μg/ml erythromycin. Transformants were streaked on MRS plates containing erythromycin (1 μg/ml) and then re-streaked on MRS plates. Isolates were screened by colony PCR for a single crossover using chromosomal specific primer oBP278 (SEQ ID NO:190) and als(o) specific primer oBP283 (SEQ ID NO:189). A single crossover integrant was grown at 37° C. for approximately 25 generations by serial inoculations in MRS medium without glucose before cultures were plated on MRS medium without glucose. Erythromycin sensitive isolates were screened by colony PCR for the presence of a wild-type or deletion/integration second crossover using als(o) specific primer oBP282 (SEQ ID NO:188) and chromosomal specific primer oBP280 (SEQ ID NO:89). The resulting deletion/integration strain PN0512ΔldhDΔldhL1::ilvD(Ll) suf::P5P4$^+$ glgB::Tn5-PgroE-kivD(o)-sadB(o) Δ23aa aldB ΔpflB2A2::alsS(o) was confirmed by sequencing the PCR product amplified with chromosomal specific primers oBP279 (SEQ ID NO:90) and oBP280 (SEQ ID NO:89).

Example 10

Production of Isobutanol Using PN0512ΔldhDΔldhL1::ilvD(Ll) suf::P5P4$^+$ glgB::Tn5-PgroE-kivD(o)-sadB(o) Δ23aa aldB ΔpflB2A2::alsS(o) Containing a Vector gDM5-PldhL1-ilvC(*L. lactis*)

The purpose of this example is to demonstrate the increased production of isobutanol in the *Lactobacillus plantarum* PN0512ΔldhDΔldhL1::ilvD(Ll) suf::P5P4$^+$ glgB::Tn5-PgroE-kivD(o)-sadB(o) Δ23aa aldB ΔpflB2A2::alsS(o) strain background, compared to the parental strain PN0512ΔldhDΔldhL1::ilvD(Ll) suf::P5P4$^+$ glgB::Tn5-PgroE-kivD(o)-sadB(o) Δ23aa aldB strain background.

To construct a recombinant *Lactobacillus plantarum* expressing the genes of the isobutanol biosynthetic pathway, competent cells of the integrant PN0512ΔldhDΔldhL1::ilvD(Ll) suf::P5P4$^+$ glgB::Tn5-PgroE-kivD(o)-sadB(o) Δ23aa aldB ΔpflB2A2::alsS(o) were prepared as described in Example 1, and transformed with plasmid pDM5-PldhL1-ilvC(*L. lactis*) (construction described in Example 7), yielding PN0512ΔldhDΔldhL1::ilvD(Ll) suf::P5P4$^+$ glgB::Tn5-PgroE-kivD(o)-sadB(o) Δ23aa aldB ΔpflB2A2::alsS(o)/pDM5-PldhL1-ilvC(*L. lactis*), which was named DWS2307.

Production of isobutanol with strain DWS2307 was tested using the same medium, growth conditions, and sample preparation as described in Example 8. Strain DWS2279 (Example 8) was grown as the control. The filtered supernatants were analyzed by HPLC (1200 Series, Agilent Technologies, Santa Clara, Calif.) with a SHODEX Sugar column, detected by UV210 and refractive index, mobile phase 10 mM H$_2$SO$_4$. Results in Table 6 show the production of isobutanol, formate, acetoin, and ethanol for DWS2307, compared to DWS2279. The amount of isobutanol produced by DWS2307 that contains the ΔpflB2A2− mutation was 19.1 mM, which is approximately 2.4-fold higher than the isobutanol level (8 mM) produced by DWS2279 that contains wild type pflB2A2+. DWS2307 that is deleted for the genes pflB2 and pflA2 and thus does not contain formate C-acetyltransferase activity, showed no production of formate.

TABLE 6

Production of isobutanol, formate, acetoin, and ethanol by DWS2279 (pflB2A2+) and DWS2307 (ΔpflB2A2−) grown in grown in MRS medium (100 mM MOPS pH 7.0) at 37° C. anaerobically.

| Strain | Ethanol (mM) | Formate (mM) | Acetoin (mM) | Isobutanol (mM) |
|---|---|---|---|---|
| DWS2279 = PN0512ΔldhDΔldhL1::ilvD(Ll) suf::P5P4$^+$ glgB::Tn5-PgroE-kivD(o)-sadB(o) Δ23aa aldB−/pDM5-PldhL1-ilvC(*L. lactis*) | 79.0 | 30.0 | 4.0 | 8.0 |
| DWS2307 = PN0512ΔldhDΔldhL1::ilvD(Ll) suf::P5P4$^+$ glgB::Tn5-PgroE-kivD(o)-sadB(o) Δ23aa aldB− ΔpflAB::alsS(*B. subtilis*)/pDM5-PldhL1-ilvC(*L. lactis*) | 39.0 | 0.0 | 4.0 | 19.1 |

What is claimed is:

1. A recombinant *Lactobacillus* cell comprising at least one engineered genetic modification that eliminates enzyme activity of endogenously expressed acetolactate decarboxylase, wherein the at least one engineered genetic modification is a deletion of at least a portion of an endogenous gene encoding acetolactate decarboxylase, and at least one engineered genetic modification that eliminates enzyme activity of endogenously expressed lactate dehydrogenase, wherein the at least one engineered genetic modification is a deletion of at least a portion of an endogenous gene encoding lactate dehydrogenase.

2. The recombinant *Lactobacillus* cell of claim 1 wherein said gene encoding acetolactate decarboxylase is selected from the group consisting of aldB, aldC, and ald.

3. The recombinant *Lactobacillus* cell of claim 2 wherein the gene encoding acetolactate decarboxylase encodes a protein having an amino acid sequence that has at least about 95% identity to a sequence selected from the group consisting of SEQ ID NOs: 24, 26, 28, 30, 32, 34, 36, and 38.

4. The recombinant *Lactobacillus* cell of claim 1 wherein said gene encodes lactate dehydrogenase and is selected from the group consisting of ldhL, ldhD, ldhL1, and ldhL2.

5. The recombinant *Lactobacillus* cell of claim 4 wherein the gene encoding lactate dehydrogenase encodes a protein having an amino acid sequence that has at least about 95% identity to a sequence selected from the group consisting of SEQ ID NOs: 2, 4, 6, 8, 10, 12, 14, 16, 18, 20, and 22.

6. The recombinant *Lactobacillus* cell of claim 1 further comprising at least one genetic modification that eliminates pyruvate formate lyase activity, wherein the at least one genetic modification is a deletion of at least a portion of an endogenous gene encoding pyruvate formate lyase.

7. The recombinant *Lactobacillus* cell of claim 1 further comprising at least one genetic modification that eliminates pyruvate formate lyase activating enzyme activity, wherein the at least one genetic modification is a deletion of at least a portion of an endogenous gene encoding pyruvate formate lyase activating enzyme.

8. The recombinant *Lactobacillus* cell of claim 6 or 7 wherein the said gene encoding pyruvate formate lyase is selected from the group consisting of pfl, pflB1 and pflB2 and said gene encoding formate C-acetyltransferase activating enzyme is selected from the group consisting of pflA, pflA1 and pflA2.

9. The recombinant *Lactobacillus* cell of claim 1 comprising an isobutanol biosynthetic pathway, wherein the isobutanol biosynthetic pathway comprises heterologous polynucleotides encoding polypeptides that catalyze the following substrate to product conversions:
   a) pyruvate to acetolactate;
   b) acetolactate to 2,3-dihydroxyisovalerate;
   c) 2,3-dihydroxyisovalerate to α-ketoisovalerate;
   d) α-ketoisovalerate to isobutyraldehyde; and
   e) isobutyraldehyde to isobutanol,
wherein
   i) the substrate to product conversion of step (a) is performed by an acetolactate synthase enzyme;
   ii) the substrate to product conversion of step (b) is performed by a ketol-acid reductoisomerase enzyme;
   iii) the substrate to product conversion of step (c) is performed by a dihydroxy-acid dehydratase enzyme;
   iv) the substrate to product conversion of step (d) is performed by a branched-chain α-keto acid decarboxylase; and v) the substrate to product conversion of step (e) is performed by an alcohol dehydrogenase enzyme.

10. A method for producing isobutanol comprising:
(a) providing the *Lactobacillus* cell of claim 9; and
(b) culturing the cell of (a) under conditions wherein isobutanol is produced.

11. The method of claim 10 wherein the *Lactobacillus* cell of (a) further comprises at least one genetic modification that eliminates pyruvate formate lyase activity, wherein the at least one genetic modification is a deletion of at least a portion of an endogenous gene encoding pyruvate formate lyase.

* * * * *

SEQUENCE LISTING

<160> NUMBER OF SEQ ID NOS: 190

<210> SEQ ID NO 1
<211> LENGTH: 999
<212> TYPE: DNA
<213> ORGANISM: Lactobacillus plantarum

<400> SEQUENCE: 1

| | | | | | |
|---|---|---|---|---|---|
| atgaaaatta | ttgcatatgc | tgtacgtgat | gacgaacgtc | cattcttcga | tacttggatg | 60 |
| aaagaaaacc | cagatgttga | agttaaatta | gttccagaat | tacttactga | agacaacgtt | 120 |
| gacttagcta | aaggcttcga | cggtgccgat | gtataccaac | aaaaggacta | tactgctgaa | 180 |
| gtattgaaca | agttagccga | cgaaggggtt | aagaacatct | ctcttcgtaa | cgttggtgtt | 240 |
| gataacttgg | acgttcctac | tgttaaagca | cgtggcttaa | acatttctaa | cgtacctgca | 300 |
| tactcaccaa | atgcgattgc | tgaattatca | gtaacgcaat | tgatgcaatt | attacgtcaa | 360 |
| accccattgt | tcaataagaa | gttagctaag | caagacttcc | gttgggcacc | agatattgcc | 420 |
| aaggaattaa | acaccatgac | tgttggtgtt | atcggtactg | gtcggattgg | ccgtgctgcc | 480 |
| atcgatattt | tcaaaggctt | cggcgctaag | gttatcggtt | acgatgttta | ccggaatgct | 540 |
| gaacttgaaa | aggaaggcat | gtacgttgac | accttggacg | aattatacgc | ccaagctgat | 600 |
| gttatcacgt | tacacgttcc | tgcattgaag | gataactacc | acatgttgaa | tgcggatgcc | 660 |
| ttcagcaaga | tgaaagatgg | cgcctacatc | ttgaactttg | ctcgtgggac | actcatcgat | 720 |
| tcagaagact | tgatcaaagc | cttagacagt | ggcaaagttg | ccggtgccgc | tcttgatacg | 780 |
| tatgaatacg | aaactaagat | cttcaacaaa | gaccttgaag | gtcaaacgat | tgatgacaag | 840 |
| gtcttcatga | acttgttcaa | ccgcgacaat | gttttgatta | caccacatac | ggctttctac | 900 |
| actgaaactg | ccgttcacaa | catggtgcac | gtttcaatga | acagtaacaa | acaattcatc | 960 |
| gaaactggta | aagctgatac | gcaagttaag | tttgactaa | | | 999 |

<210> SEQ ID NO 2
<211> LENGTH: 332
<212> TYPE: PRT
<213> ORGANISM: Lactobacillus plantarum

<400> SEQUENCE: 2

Met Lys Ile Ile Ala Tyr Ala Val Arg Asp Asp Glu Arg Pro Phe Phe
1               5                   10                  15

Asp Thr Trp Met Lys Glu Asn Pro Asp Val Glu Val Lys Leu Val Pro
            20                  25                  30

Glu Leu Leu Thr Glu Asp Asn Val Asp Leu Ala Lys Gly Phe Asp Gly
        35                  40                  45

Ala Asp Val Tyr Gln Gln Lys Asp Tyr Thr Ala Glu Val Leu Asn Lys
    50                  55                  60

Leu Ala Asp Glu Gly Val Lys Asn Ile Ser Leu Arg Asn Val Gly Val
65                  70                  75                  80

Asp Asn Leu Asp Val Pro Thr Val Lys Ala Arg Gly Leu Asn Ile Ser
                85                  90                  95

Asn Val Pro Ala Tyr Ser Pro Asn Ala Ile Ala Glu Leu Ser Val Thr
            100                 105                 110

Gln Leu Met Gln Leu Leu Arg Gln Thr Pro Leu Phe Asn Lys Lys Leu
        115                 120                 125

Ala Lys Gln Asp Phe Arg Trp Ala Pro Asp Ile Ala Lys Glu Leu Asn
    130                 135                 140

```
Thr Met Thr Val Gly Val Ile Gly Thr Gly Arg Ile Gly Arg Ala Ala
145                 150                 155                 160

Ile Asp Ile Phe Lys Gly Phe Gly Ala Lys Val Ile Gly Tyr Asp Val
                165                 170                 175

Tyr Arg Asn Ala Glu Leu Glu Lys Glu Gly Met Tyr Val Asp Thr Leu
            180                 185                 190

Asp Glu Leu Tyr Ala Gln Ala Asp Val Ile Thr Leu His Val Pro Ala
        195                 200                 205

Leu Lys Asp Asn Tyr His Met Leu Asn Ala Asp Ala Phe Ser Lys Met
    210                 215                 220

Lys Asp Gly Ala Tyr Ile Leu Asn Phe Ala Arg Gly Thr Leu Ile Asp
225                 230                 235                 240

Ser Glu Asp Leu Ile Lys Ala Leu Asp Ser Gly Lys Val Ala Gly Ala
                245                 250                 255

Ala Leu Asp Thr Tyr Glu Tyr Glu Thr Lys Ile Phe Asn Lys Asp Leu
            260                 265                 270

Glu Gly Gln Thr Ile Asp Asp Lys Val Phe Met Asn Leu Phe Asn Arg
        275                 280                 285

Asp Asn Val Leu Ile Thr Pro His Thr Ala Phe Tyr Thr Glu Thr Ala
    290                 295                 300

Val His Asn Met Val His Val Ser Met Asn Ser Asn Lys Gln Phe Ile
305                 310                 315                 320

Glu Thr Gly Lys Ala Asp Thr Gln Val Lys Phe Asp
                325                 330
```

<210> SEQ ID NO 3
<211> LENGTH: 963
<212> TYPE: DNA
<213> ORGANISM: Lactobacillus plantarum

<400> SEQUENCE: 3

```
ttgtcaagca tgccaaatca tcaaaaagtt gtgttagtcg gcgacggcgc tgttggttct      60
agttacgctt ttgccatggc acaacaagga attgctgaag aatttgtaat tgtcgatgtt     120
gttaaagatc ggacaaaggg tgacgcccct gatcttgaag acgcccaagc attcaccgct     180
cccaagaaga tttactcagg cgaatattca gattgtaagg acgctgactt agttgttatt     240
acagccggtg cgcctcaaaa gcctggtgaa tcacgtttag acttagttaa caagaattta     300
aatatcctat catccattgt caaaccagtt gttgactccg gctttgacgg catcttctta     360
gttgctgcta accctgttga catcttaact tacgctactt ggaaattctc aggttttcca     420
aaggatcgtg tcattggttc agggacttcc ttagactctt cacgtttacg cgttgcgtta     480
ggcaaacaat tcaatgttga tcctcgttcc gttgatgctt acatcatggg tgaacacggt     540
gattctgaat tgctgctta ctcaactgca accatcggga cacgtccagt tcgcgatgtc     600
gctaaggaac aaggcgtttc tgacgaagat ttagccaagt tagaagacgg tgttcgtaac     660
aaagcttacg acatcatcaa cttgaagggt gccacgttct acggtatcgg gactgcttta     720
atgcggattt ccaaagccat tttacgtgat gaaaatgccg ttttaccagt aggtgcctac     780
atggacggcc aatacggctt aaacgacatt tatatcggga ctccggctgt gattggtgga     840
actggtttga acaaatcat cgaatcacca ctttcagctg acgaactcaa gaagatgcaa     900
gattccgccg caactttgaa aaagtgctt aacgacggtt tagctgaatt agaaaataaa     960
taa                                                                   963
```

<210> SEQ ID NO 4
<211> LENGTH: 320
<212> TYPE: PRT
<213> ORGANISM: Lactobacillus plantarum

<400> SEQUENCE: 4

Met Ser Ser Met Pro Asn His Gln Lys Val Val Leu Val Gly Asp Gly
1               5                   10                  15

Ala Val Gly Ser Ser Tyr Ala Phe Ala Met Ala Gln Gln Gly Ile Ala
            20                  25                  30

Glu Glu Phe Val Ile Val Asp Val Val Lys Asp Arg Thr Lys Gly Asp
        35                  40                  45

Ala Leu Asp Leu Glu Asp Ala Gln Ala Phe Thr Ala Pro Lys Lys Ile
    50                  55                  60

Tyr Ser Gly Glu Tyr Ser Asp Cys Lys Asp Ala Asp Leu Val Val Ile
65                  70                  75                  80

Thr Ala Gly Ala Pro Gln Lys Pro Gly Glu Ser Arg Leu Asp Leu Val
                85                  90                  95

Asn Lys Asn Leu Asn Ile Leu Ser Ser Ile Val Lys Pro Val Val Asp
            100                 105                 110

Ser Gly Phe Asp Gly Ile Phe Leu Val Ala Ala Asn Pro Val Asp Ile
        115                 120                 125

Leu Thr Tyr Ala Thr Trp Lys Phe Ser Gly Phe Pro Lys Asp Arg Val
    130                 135                 140

Ile Gly Ser Gly Thr Ser Leu Asp Ser Ser Arg Leu Arg Val Ala Leu
145                 150                 155                 160

Gly Lys Gln Phe Asn Val Asp Pro Arg Ser Val Asp Ala Tyr Ile Met
                165                 170                 175

Gly Glu His Gly Asp Ser Glu Phe Ala Ala Tyr Ser Thr Ala Thr Ile
            180                 185                 190

Gly Thr Arg Pro Val Arg Asp Val Ala Lys Glu Gln Gly Val Ser Asp
        195                 200                 205

Glu Asp Leu Ala Lys Leu Glu Asp Gly Val Arg Asn Lys Ala Tyr Asp
    210                 215                 220

Ile Ile Asn Leu Lys Gly Ala Thr Phe Tyr Gly Ile Gly Thr Ala Leu
225                 230                 235                 240

Met Arg Ile Ser Lys Ala Ile Leu Arg Asp Glu Asn Ala Val Leu Pro
                245                 250                 255

Val Gly Ala Tyr Met Asp Gly Gln Tyr Gly Leu Asn Asp Ile Tyr Ile
            260                 265                 270

Gly Thr Pro Ala Val Ile Gly Thr Gly Leu Lys Gln Ile Ile Glu
        275                 280                 285

Ser Pro Leu Ser Ala Asp Glu Leu Lys Lys Met Gln Asp Ser Ala Ala
    290                 295                 300

Thr Leu Lys Lys Val Leu Asn Asp Gly Leu Ala Glu Leu Glu Asn Lys
305                 310                 315                 320

<210> SEQ ID NO 5
<211> LENGTH: 930
<212> TYPE: DNA
<213> ORGANISM: Lactobacillus plantarum

<400> SEQUENCE: 5
atggataaga agcaacgcaa agtcgtaatt gttggtgatg ctcggtgggg ttcatcattt      60
gccttttcat tggtccaaaa ttgcgcccta gatgaactcg ttatcgttga cttggttaaa     120

```
acgcacgcag aggggggacgt taaggatttg aagatgttg ccgcctttac gaatgcgacc    180
aacattcata ccggtgaata tgcggatgcg cgtgatgctg acatcgttgt cattacggct    240
ggtgtgcctc gtaagcctgg tgagagtcgt ttagatttga ttaaccgcaa tacgaagatt    300
ctggaatcca tcgtcaaacc agtggttgcg agtggtttta atggttgctt cgttatctca    360
agtaatcccg tcgatatttt gacttcgatg acgcaacgtt tatccggttt tccacggcat    420
cgggtcattg gtaccgggac ttccttggat acggcgcggt tacgggtcgc cttggctcag    480
aagttgaatg ttgccaccac tgcagttgat gctgcggtac ttggagaaca tggtgatagt    540
tccatcgtta attttgatga aattatgatc aatgctcagc ccttaaagac ggtcacaacg    600
gtcgatgatc agttcaaagc tgaaatcgag caagctgttc gtggtaaagg tggtcaaatc    660
attagtcaga aggggccac gttctatggg gtcgccgtta gtttgatgca aatctgccga    720
gcaattttga cgatgaaaa tgctgagttg attgtctccg ccgctttgtc tggtcaatat    780
ggcattaacg atttgtactt ggggtcaccc gccattatta accgcaacgg gctccaaaaa    840
gtgatcgaag ctgagctatc agatgatgag cgtgcccgga tgcaacattt cgcagccaag    900
atgctgacca tgatgaatgt ggcatcataa                                     930
```

<210> SEQ ID NO 6
<211> LENGTH: 309
<212> TYPE: PRT
<213> ORGANISM: Lactobacillus plantarum

<400> SEQUENCE: 6

Met Asp Lys Lys Gln Arg Lys Val Val Ile Val Gly Asp Gly Ser Val
1               5                   10                  15

Gly Ser Ser Phe Ala Phe Ser Leu Val Gln Asn Cys Ala Leu Asp Glu
            20                  25                  30

Leu Val Ile Val Asp Leu Val Lys Thr His Ala Glu Gly Asp Val Lys
        35                  40                  45

Asp Leu Glu Asp Val Ala Ala Phe Thr Asn Ala Thr Asn Ile His Thr
    50                  55                  60

Gly Glu Tyr Ala Asp Ala Arg Asp Ala Asp Ile Val Val Ile Thr Ala
65                  70                  75                  80

Gly Val Pro Arg Lys Pro Gly Glu Ser Arg Leu Asp Leu Ile Asn Arg
                85                  90                  95

Asn Thr Lys Ile Leu Glu Ser Ile Val Lys Pro Val Val Ala Ser Gly
            100                 105                 110

Phe Asn Gly Cys Phe Val Ile Ser Ser Asn Pro Val Asp Ile Leu Thr
        115                 120                 125

Ser Met Thr Gln Arg Leu Ser Gly Phe Pro Arg His Arg Val Ile Gly
    130                 135                 140

Thr Gly Thr Ser Leu Asp Thr Ala Arg Leu Arg Val Ala Leu Ala Gln
145                 150                 155                 160

Lys Leu Asn Val Ala Thr Thr Ala Val Asp Ala Ala Val Leu Gly Glu
                165                 170                 175

His Gly Asp Ser Ser Ile Val Asn Phe Asp Glu Ile Met Ile Asn Ala
            180                 185                 190

Gln Pro Leu Lys Thr Val Thr Thr Val Asp Asp Gln Phe Lys Ala Glu
        195                 200                 205

Ile Glu Gln Ala Val Arg Gly Lys Gly Gly Gln Ile Ile Ser Gln Lys
    210                 215                 220

Gly Ala Thr Phe Tyr Gly Val Ala Val Ser Leu Met Gln Ile Cys Arg

```
225                 230                 235                 240
Ala Ile Leu Asn Asp Glu Asn Ala Glu Leu Ile Val Ser Ala Ala Leu
                245                 250                 255

Ser Gly Gln Tyr Gly Ile Asn Asp Leu Tyr Leu Gly Ser Pro Ala Ile
            260                 265                 270

Ile Asn Arg Asn Gly Leu Gln Lys Val Ile Glu Ala Glu Leu Ser Asp
        275                 280                 285

Asp Glu Arg Ala Arg Met Gln His Phe Ala Ala Lys Met Leu Thr Met
    290                 295                 300

Met Asn Val Ala Ser
305

<210> SEQ ID NO 7
<211> LENGTH: 978
<212> TYPE: DNA
<213> ORGANISM: Lactococcus lactis

<400> SEQUENCE: 7
atggctgata acaacgtaa aaaagttatc cttgtaggtg acggtgctgt aggttcatca      60
tacgcttttg ctcttgtaaa ccaagggatt gcacaagaat taggaattgt tgaccttttt     120
aaagaaaaaa ctcaaggaga tgcagaagac ctttctcatg ccttggcatt tacttcacct    180
aaaaagattt actctgcaga ctactctgat gcaagcgacg ctgacctcgt agtcttgact    240
tctggtgctc acaaaaaacc aggtgaaact cgtcttgacc ttgttgaaaa aaatcttcgt    300
atcactaaag atgttgtcac taaaattgtt gcttcaggtt tcaaaggaat cttccttgtt    360
gctgctaacc cagttgatat cttgacatac gctacttgga aattctcagg tttccctaaa    420
aaccgcgttg taggttcagg tacttcactt gatactgcac gtttccgtca agcattggca    480
gaaaaagttg atgttgacgc tcgttcaatc cacgcataca tcatgggtga acacggtgac    540
tcagaatttg ccgtttggtc acacgctaac gttgctggtg ttaaattgga caatggttc    600 caagaaaatg actaccttaa cgaagctgaa atcgttgaat tgtttgaatc tgtacgtgat    660
gctgcttact caatcatcgc taaaaaaggt gcaacattct atggtgtcgc tgtagctctt    720
gctcgtatta ctaaagcaat tcttgatgat gaacatgcag tacttccagt atcagtattc    780
caagatggac aatatggcgt aagcgactgc taccttggtc aaccagctgt agttggtgct    840
gaaggtgttg ttaacccaat ccacattcca ttgaatgatg ctgaaatgca aaaaatggaa    900
gcttctggtg ctcaattgaa agcaatcatt gacgaagctt tgctaaaga gaatttgct    960 tctgcagtta aaaactaa                                                   978

<210> SEQ ID NO 8
<211> LENGTH: 325
<212> TYPE: PRT
<213> ORGANISM: Lactococcus lactis

<400> SEQUENCE: 8

Met Ala Asp Lys Gln Arg Lys Lys Val Ile Leu Val Gly Asp Gly Ala
1               5                   10                  15

Val Gly Ser Ser Tyr Ala Phe Ala Leu Val Asn Gln Gly Ile Ala Gln
            20                  25                  30

Glu Leu Gly Ile Val Asp Leu Phe Lys Glu Lys Thr Gln Gly Asp Ala
        35                  40                  45

Glu Asp Leu Ser His Ala Leu Ala Phe Thr Ser Pro Lys Lys Ile Tyr
    50                  55                  60
```

Ser Ala Asp Tyr Ser Asp Ala Ser Asp Ala Asp Leu Val Val Leu Thr
 65                  70                  75                  80

Ser Gly Ala Pro Gln Lys Pro Gly Glu Thr Arg Leu Asp Leu Val Glu
                 85                  90                  95

Lys Asn Leu Arg Ile Thr Lys Asp Val Val Thr Lys Ile Val Ala Ser
            100                 105                 110

Gly Phe Lys Gly Ile Phe Leu Val Ala Ala Asn Pro Val Asp Ile Leu
        115                 120                 125

Thr Tyr Ala Thr Trp Lys Phe Ser Gly Phe Pro Lys Asn Arg Val Val
130                 135                 140

Gly Ser Gly Thr Ser Leu Asp Thr Ala Arg Phe Arg Gln Ala Leu Ala
145                 150                 155                 160

Glu Lys Val Asp Val Asp Ala Arg Ser Ile His Ala Tyr Ile Met Gly
                165                 170                 175

Glu His Gly Asp Ser Glu Phe Ala Val Trp Ser His Ala Asn Val Ala
            180                 185                 190

Gly Val Lys Leu Glu Gln Trp Phe Gln Glu Asn Asp Tyr Leu Asn Glu
        195                 200                 205

Ala Glu Ile Val Glu Leu Phe Glu Ser Val Arg Asp Ala Ala Tyr Ser
210                 215                 220

Ile Ile Ala Lys Lys Gly Ala Thr Phe Tyr Gly Val Ala Val Ala Leu
225                 230                 235                 240

Ala Arg Ile Thr Lys Ala Ile Leu Asp Asp Glu His Ala Val Leu Pro
                245                 250                 255

Val Ser Val Phe Gln Asp Gly Gln Tyr Gly Val Ser Asp Cys Tyr Leu
            260                 265                 270

Gly Gln Pro Ala Val Val Gly Ala Glu Gly Val Val Asn Pro Ile His
        275                 280                 285

Ile Pro Leu Asn Asp Ala Glu Met Gln Lys Met Glu Ala Ser Gly Ala
290                 295                 300

Gln Leu Lys Ala Ile Ile Asp Glu Ala Phe Ala Lys Glu Glu Phe Ala
305                 310                 315                 320

Ser Ala Val Lys Asn
                325

<210> SEQ ID NO 9
<211> LENGTH: 996
<212> TYPE: DNA
<213> ORGANISM: Leuconostoc mesenteroides

<400> SEQUENCE: 9
atgaagattt ttgcttacgg cattcgtgat gatgaaaagc catcacttga agaatggaaa      60
gcggctaacc cagagattga agtggactac acacaagaat tattgacacc tgaaacagct     120
aagttggctg agggatcaga ttcagctgtt gtttatcaac aattggacta tacacgtgaa     180
acattgacag ctttagctaa cgttggtgtt actaacttgt cattgcgtaa cgttggtaca     240
gataacattg attttgatgc agcacgtgaa tttaacttta catttcaaa tgttcctgtt      300 tattcaccaa tgctattgc agaacactca atgattcaat tatctcgttt gctacgtcgc      360
acgaaagcat ggatgccaa attgctaag cacgacttgc gttgggcacc aacaattgga       420
cgtgaaatgc gtatgcaaac agttggtgtt attggtacag gtcatattgg ccgtgttgct     480
attaacattt tgaaaggctt tggggccaag gttattgctt atgacaagta cccaaatgct     540
gaattacaag cagaaggttt gtacgttgac acattagacg aattatatgc acaagctgat     600

-continued

```
gcaatttcat tgtatgttcc tggtgtacct gaaaaccatc atctaatcaa tgcagatgct    660
attgctaaga tgaaggatgg tgtggttatc atgaacgctg cgcgtggtaa tttgatggac    720
attgacgcta ttattgatgg tttgaattct ggtaagattt cagacttcgg tatggacgtt    780
tatgaaaatg aagttggctt gttcaatgaa gattggtctg gtaaagaatt cccagatgct    840
aagattgctg acttgattgc acgcgaaaat gtattggtta cgccacacac ggctttctat    900
acaactaaag ctgttctaga aatggttcac caatcatttg atgcagcagt tgctttcgcc    960
aagggtgaga agccagctat tgctgttgaa tattaa                              996
```

```
<210> SEQ ID NO 10
<211> LENGTH: 331
<212> TYPE: PRT
<213> ORGANISM: Leuconostoc mesenteroides

<400> SEQUENCE: 10
```

| | | | | | | | | | | | | | | |
|---|---|---|---|---|---|---|---|---|---|---|---|---|---|---|
| Met | Lys | Ile | Phe | Ala | Tyr | Gly | Ile | Arg | Asp | Asp | Glu | Lys | Pro | Ser | Leu |
| 1 | | | | 5 | | | | | 10 | | | | | 15 | |
| Glu | Glu | Trp | Lys | Ala | Ala | Asn | Pro | Glu | Ile | Glu | Val | Asp | Tyr | Thr | Gln |
| | | | 20 | | | | | 25 | | | | | 30 | | |
| Glu | Leu | Leu | Thr | Pro | Glu | Thr | Ala | Lys | Leu | Ala | Glu | Gly | Ser | Asp | Ser |
| | | 35 | | | | | 40 | | | | | 45 | | | |
| Ala | Val | Val | Tyr | Gln | Gln | Leu | Asp | Tyr | Thr | Arg | Glu | Thr | Leu | Thr | Ala |
| | 50 | | | | | 55 | | | | | 60 | | | | |
| Leu | Ala | Asn | Val | Gly | Val | Thr | Asn | Leu | Ser | Leu | Arg | Asn | Val | Gly | Thr |
| 65 | | | | | 70 | | | | | 75 | | | | | 80 |
| Asp | Asn | Ile | Asp | Phe | Asp | Ala | Ala | Arg | Glu | Phe | Asn | Phe | Asn | Ile | Ser |
| | | | | 85 | | | | | 90 | | | | | 95 | |
| Asn | Val | Pro | Val | Tyr | Ser | Pro | Asn | Ala | Ile | Ala | Glu | His | Ser | Met | Ile |
| | | | 100 | | | | | 105 | | | | | 110 | | |
| Gln | Leu | Ser | Arg | Leu | Leu | Arg | Arg | Thr | Lys | Ala | Leu | Asp | Ala | Lys | Ile |
| | | 115 | | | | | 120 | | | | | 125 | | | |
| Ala | Lys | His | Asp | Leu | Arg | Trp | Ala | Pro | Thr | Ile | Gly | Arg | Glu | Met | Arg |
| | 130 | | | | | 135 | | | | | 140 | | | | |
| Met | Gln | Thr | Val | Gly | Val | Ile | Gly | Thr | Gly | His | Ile | Gly | Arg | Val | Ala |
| 145 | | | | | 150 | | | | | 155 | | | | | 160 |
| Ile | Asn | Ile | Leu | Lys | Gly | Phe | Gly | Ala | Lys | Val | Ile | Ala | Tyr | Asp | Lys |
| | | | | 165 | | | | | 170 | | | | | 175 | |
| Tyr | Pro | Asn | Ala | Glu | Leu | Gln | Ala | Glu | Gly | Leu | Tyr | Val | Asp | Thr | Leu |
| | | | 180 | | | | | 185 | | | | | 190 | | |
| Asp | Glu | Leu | Tyr | Ala | Gln | Ala | Asp | Ala | Ile | Ser | Leu | Tyr | Val | Pro | Gly |
| | | 195 | | | | | 200 | | | | | 205 | | | |
| Val | Pro | Glu | Asn | His | His | Leu | Ile | Asn | Ala | Asp | Ala | Ile | Ala | Lys | Met |
| | 210 | | | | | 215 | | | | | 220 | | | | |
| Lys | Asp | Gly | Val | Val | Ile | Met | Asn | Ala | Ala | Arg | Gly | Asn | Leu | Met | Asp |
| 225 | | | | | 230 | | | | | 235 | | | | | 240 |
| Ile | Asp | Ala | Ile | Ile | Asp | Gly | Leu | Asn | Ser | Gly | Lys | Ile | Ser | Asp | Phe |
| | | | | 245 | | | | | 250 | | | | | 255 | |
| Gly | Met | Asp | Val | Tyr | Glu | Asn | Glu | Val | Gly | Leu | Phe | Asn | Glu | Asp | Trp |
| | | | 260 | | | | | 265 | | | | | 270 | | |
| Ser | Gly | Lys | Glu | Phe | Pro | Asp | Ala | Lys | Ile | Ala | Asp | Leu | Ile | Ala | Arg |
| | | 275 | | | | | 280 | | | | | 285 | | | |
| Glu | Asn | Val | Leu | Val | Thr | Pro | His | Thr | Ala | Phe | Tyr | Thr | Thr | Lys | Ala |
| | 290 | | | | | 295 | | | | | 300 | | | | |

Val Leu Glu Met Val His Gln Ser Phe Asp Ala Ala Val Ala Phe Ala
305                 310                 315                 320

Lys Gly Glu Lys Pro Ala Ile Ala Val Glu Tyr
                325                 330

<210> SEQ ID NO 11
<211> LENGTH: 987
<212> TYPE: DNA
<213> ORGANISM: Streptococcus thermophilus

<400> SEQUENCE: 11
atgactgcaa ctaaactaca caaaaaagtc atccttgttg gtgacggtgc cgtaggttca      60
tcttacgctt tcgcacttgt aaaccaaggt atcgctcaag actaggtat catcgaaatt     120 ccacaattat ttgaaaaagc cgttggtgat gcgcttgacc ttagccacgc acttcctttc     180
acttcaccta aaaaatcta tgcagctaaa tatgaagact gtgcggatgc tgaccttgta     240
gttatcactg ctggtgctcc tcaaaaacca ggtgagactc gtcttgatct tgttggtaaa     300
aaccttgcaa tcaacaaatc aatcgttact caagttgttg aatcaggatt caacggtatt     360
ttccttgtag ctgctaaccc agtagacgta ttgacttact ctacatggaa gttctcagga     420
ttccctaaag aacgcgttat cggttcaggt acttcacttg actcagctcg tttccgtcaa     480
gcacttgctg aaaaacttaa tgtcgatgct cgttcagttc acgcttacat catgggtgaa     540
cacggcgact cagagtttgc ggtttggtca cacgctaaca tcgccggtgt aaaccttgaa     600
gagttcctta agacgaaga aacgttcaa gaagctgaat tagttgaatt gttcgaaggt     660
gttcgtgatg cagcttacac aattatcaac aaaaaaggtg ctacatacta cggtatcgca     720
gtagcccttg ctcgtatcac taaagctatc cttgacgatg aaaatgcagt acttccattg     780
tctgtattcc aagaaggtca atatggtgta acaacatct ttatcggtca acctgctatt     840
gtaggcgcac acggtatcgt acgtccagta acatcccat gaacgatgc tgaacaacaa     900 aagatgaagg cttctgccga tgaattgcaa gctatcattg atgaagcatg gaaaaaccct     960
gaattccaag aagcttcaaa aaactaa                                        987

<210> SEQ ID NO 12
<211> LENGTH: 328
<212> TYPE: PRT
<213> ORGANISM: Streptococcus thermophilus

<400> SEQUENCE: 12

Met Thr Ala Thr Lys Leu His Lys Lys Val Ile Leu Val Gly Asp Gly
1               5                   10                  15

Ala Val Gly Ser Ser Tyr Ala Phe Ala Leu Val Asn Gln Gly Ile Ala
            20                  25                  30

Gln Glu Leu Gly Ile Ile Glu Ile Pro Gln Leu Phe Lys Ala Val
        35                  40                  45

Gly Asp Ala Leu Asp Leu Ser His Ala Leu Pro Phe Thr Ser Pro Lys
    50                  55                  60

Lys Ile Tyr Ala Ala Lys Tyr Glu Asp Cys Ala Asp Ala Asp Leu Val
65                  70                  75                  80

Val Ile Thr Ala Gly Ala Pro Gln Lys Pro Gly Glu Thr Arg Leu Asp
                85                  90                  95

Leu Val Gly Lys Asn Leu Ala Ile Asn Lys Ser Ile Val Thr Gln Val
            100                 105                 110

Val Glu Ser Gly Phe Asn Gly Ile Phe Leu Val Ala Ala Asn Pro Val
        115                 120                 125

```
Asp Val Leu Thr Tyr Ser Thr Trp Lys Phe Ser Gly Phe Pro Lys Glu
        130                 135                 140

Arg Val Ile Gly Ser Gly Thr Ser Leu Asp Ser Ala Arg Phe Arg Gln
145                 150                 155                 160

Ala Leu Ala Glu Lys Leu Asn Val Asp Ala Arg Ser Val His Ala Tyr
                165                 170                 175

Ile Met Gly Glu His Gly Asp Ser Glu Phe Ala Val Trp Ser His Ala
            180                 185                 190

Asn Ile Ala Gly Val Asn Leu Glu Glu Phe Leu Lys Asp Glu Glu Asn
        195                 200                 205

Val Gln Glu Ala Glu Leu Val Glu Leu Phe Glu Gly Val Arg Asp Ala
210                 215                 220

Ala Tyr Thr Ile Ile Asn Lys Lys Gly Ala Thr Tyr Tyr Gly Ile Ala
225                 230                 235                 240

Val Ala Leu Ala Arg Ile Thr Lys Ala Ile Leu Asp Asp Glu Asn Ala
                245                 250                 255

Val Leu Pro Leu Ser Val Phe Gln Glu Gly Gln Tyr Gly Val Asn Asn
            260                 265                 270

Ile Phe Ile Gly Gln Pro Ala Ile Val Gly Ala His Gly Ile Val Arg
        275                 280                 285

Pro Val Asn Ile Pro Leu Asn Asp Ala Glu Gln Lys Met Lys Ala
290                 295                 300

Ser Ala Asp Glu Leu Gln Ala Ile Ile Asp Glu Ala Trp Lys Asn Pro
305                 310                 315                 320

Glu Phe Gln Glu Ala Ser Lys Asn
                325

<210> SEQ ID NO 13
<211> LENGTH: 996
<212> TYPE: DNA
<213> ORGANISM: Pediococcus pentosaceus

<400> SEQUENCE: 13
atgaaaatta ttgcttatgg cattcgagat gacgaaaaac cttacctaga agaatgggtt      60
aaagataata aaattgaagt aaaggctgtt agcgaattgt tggactccaa cacgattgaa     120
caagctaagg ttatgacgg agttgttgca tatcaacaga aaccttatac agatgatttg      180
ttcgataaaa tgaatgaatt cgggattcat gccttttcgc ttcgtaacgt tggtgttgat     240
aatgttccag ttgaggcttt aaagcgaaat aatattaaga ttaccaatgt tccagcgtac     300
tctccaatgg cgattgcaga actttcagta acccaactcc tagctttaat tcgtcgaatt     360
ccagaatttg atgctaagat ggctcgtggt gatttcagat gggaaccaga tattgctcta     420
gaacttaacc aaatgacagt aggagttatt ggtaccggaa gaattgggcg tgcggccatt     480
aatatcttta aggctttgg agctaaagtg attgcttatg atgttttccg aaattcagaa      540
cttgaaaaag aaggaatcta tgttgactcg cttgaagaac tttatcgtca gtagatgtt      600 attccttac atgttcccgc tttaaaagat aactaccata tgttaaatga tgaagcgttc      660
gcacagatgc atgatggggt atttgttcta aattttgctc gcggtagctt gattgacacg     720
aaggcattac ttaaggcttt agatagtggt aaggtggctg gtgcggcact agataccat     780 gaagacgaag taggtatttt tgatgtggat caccaaaatg acccaatcaa tgatcccgta     840
tttaatgatt tatacagtag acgtaatgta aaaatcacac acatgcggc ttttatact      900 aagccagcag ttaaaaatat ggtacaaatt gctcttgaaa ataataaagc actaattgaa     960
```
aaaggtgctg caagaaatga agttaagttt gactaa                    996

<210> SEQ ID NO 14
<211> LENGTH: 331
<212> TYPE: PRT
<213> ORGANISM: Pediococcus pentosaceus

<400> SEQUENCE: 14

Met Lys Ile Ile Ala Tyr Gly Ile Arg Asp Asp Glu Lys Pro Tyr Leu
1               5                   10                  15

Glu Glu Trp Val Lys Asp Asn Lys Ile Glu Val Lys Ala Val Ser Glu
            20                  25                  30

Leu Leu Asp Ser Asn Thr Ile Glu Gln Ala Lys Gly Tyr Asp Gly Val
        35                  40                  45

Val Ala Tyr Gln Gln Lys Pro Tyr Thr Asp Asp Leu Phe Asp Lys Met
50                  55                  60

Asn Glu Phe Gly Ile His Ala Phe Ser Leu Arg Asn Val Gly Val Asp
65                  70                  75                  80

Asn Val Pro Val Glu Ala Leu Lys Arg Asn Asn Ile Lys Ile Thr Asn
                85                  90                  95

Val Pro Ala Tyr Ser Pro Met Ala Ile Ala Glu Leu Ser Val Thr Gln
            100                 105                 110

Leu Leu Ala Leu Ile Arg Arg Ile Pro Glu Phe Asp Ala Lys Met Ala
        115                 120                 125

Arg Gly Asp Phe Arg Trp Glu Pro Asp Ile Ala Leu Glu Leu Asn Gln
130                 135                 140

Met Thr Val Gly Val Ile Gly Thr Gly Arg Ile Gly Arg Ala Ala Ile
145                 150                 155                 160

Asn Ile Phe Lys Gly Phe Gly Ala Lys Val Ile Ala Tyr Asp Val Phe
                165                 170                 175

Arg Asn Ser Glu Leu Glu Lys Glu Gly Ile Tyr Val Asp Ser Leu Glu
            180                 185                 190

Glu Leu Tyr Arg Gln Val Asp Val Ile Thr Leu His Val Pro Ala Leu
        195                 200                 205

Lys Asp Asn Tyr His Met Leu Asn Asp Glu Ala Phe Ala Gln Met His
210                 215                 220

Asp Gly Val Phe Val Leu Asn Phe Ala Arg Gly Ser Leu Ile Asp Thr
225                 230                 235                 240

Lys Ala Leu Leu Lys Ala Leu Asp Ser Gly Lys Val Ala Gly Ala Ala
                245                 250                 255

Leu Asp Thr Tyr Glu Asp Glu Val Gly Ile Phe Asp Val Asp His Gln
            260                 265                 270

Asn Asp Pro Ile Asn Asp Pro Val Phe Asn Asp Leu Tyr Ser Arg Arg
        275                 280                 285

Asn Val Lys Ile Thr Pro His Ala Ala Phe Tyr Thr Lys Pro Ala Val
290                 295                 300

Lys Asn Met Val Gln Ile Ala Leu Glu Asn Asn Lys Ala Leu Ile Glu
305                 310                 315                 320

Lys Gly Ala Ala Arg Asn Glu Val Lys Phe Asp
                325                 330

<210> SEQ ID NO 15
<211> LENGTH: 1110
<212> TYPE: DNA
<213> ORGANISM: Pediococcus pentosaceus

<400> SEQUENCE: 15

```
atgacaatga ttaatggtta tgaacaaagt gatcgtgaag aaaaaattga cattttaaat      60
ttggagtctt tggaagaaag agccgaaaag attattccaa ctggtgggtt tggatatatc     120
tctggtggtt ctgaagatga atggactctc cgacaaaatc gaactgcatt ccagcatcga     180
caaatcgcgc ccaaagcttt gagtggaatt gaaaaaccag aactaaatac agaaatcttt     240
ggaattccat tgaatactcc agtgatgatg gcgccagctg cagctcaagg cttagcacat     300
tcacaaggtg aaaaagatac agctagaggt cttgccgcag taggaggctt aatggcacaa     360
agcacatatt catcagtttc tattgctgat acggcagctg ctggtgaagg tgctcctcaa     420
tttttccagc tttacatgag taaggactgg aattttaatg agagcttgct agatgaggct     480
aaaaaagctc atgttaaagc aattattttg accgtagatg ccactgttga tggttatcga     540
gaagctgata ttaaaaataa gtttgcattt ccacttccaa tggctaactt aactaagttt     600
tccgagggtg atggtcaagg aaaggaatt gaagaaatct acgcttctgc agctcaaaat      660
ataagaccgg aagatgttag aagaattgct gattacacac aattaccgt aattgttaaa      720
ggaattcaaa ctcctgagga tgctattcga gcaattgatg ctggggcagc cggcattat      780
gtatcaaacc atggaggtcg tcagctaaac gggggacctg atcttttga tgttttggaa      840
gatatcgcta cctccgttaa taagcaggtg ccaattatct tgatagtgg tgtacgtcgt      900
ggttcagatg tatttaaagc tttggctagt ggcgcagaca tcgtggcttt gggtcgtcca     960
gtaatttatg gattagcttt aggtggtgcc aaagggttc aatctgtatt tgaacatata    1020
gaccatgaac ttgaaattgt gatgcaacta gcaggtacta aaaccattga tgatattaaa    1080
aataacccac tactaaacat caaatattaa                                    1110
```

<210> SEQ ID NO 16
<211> LENGTH: 369
<212> TYPE: PRT
<213> ORGANISM: Pediococcus pentosaceus

<400> SEQUENCE: 16

```
Met Thr Met Ile Asn Gly Tyr Glu Gln Ser Asp Arg Glu Glu Lys Ile
  1               5                  10                  15

Asp Ile Leu Asn Leu Glu Ser Leu Glu Glu Arg Ala Glu Lys Ile Ile
             20                  25                  30

Pro Thr Gly Gly Phe Gly Tyr Ile Ser Gly Gly Ser Glu Asp Glu Trp
         35                  40                  45

Thr Leu Arg Gln Asn Arg Thr Ala Phe Gln His Arg Gln Ile Ala Pro
     50                  55                  60

Lys Ala Leu Ser Gly Ile Glu Lys Pro Glu Leu Asn Thr Glu Ile Phe
 65                  70                  75                  80

Gly Ile Pro Leu Asn Thr Pro Val Met Met Ala Pro Ala Ala Ala Gln
                 85                  90                  95

Gly Leu Ala His Ser Gln Gly Glu Lys Asp Thr Ala Arg Gly Leu Ala
            100                 105                 110

Ala Val Gly Gly Leu Met Ala Gln Ser Thr Tyr Ser Ser Val Ser Ile
        115                 120                 125

Ala Asp Thr Ala Ala Ala Gly Glu Gly Ala Pro Gln Phe Phe Gln Leu
    130                 135                 140

Tyr Met Ser Lys Asp Trp Asn Phe Asn Glu Ser Leu Leu Asp Glu Ala
145                 150                 155                 160
```

```
                Lys Lys Ala His Val Lys Ala Ile Ile Leu Thr Val Asp Ala Thr Val
                            165                 170                 175

Asp Gly Tyr Arg Glu Ala Asp Ile Lys Asn Lys Phe Ala Phe Pro Leu
                            180                 185                 190

Pro Met Ala Asn Leu Thr Lys Phe Ser Glu Gly Asp Gly Gln Gly Lys
                            195                 200                 205

Gly Ile Glu Glu Ile Tyr Ala Ser Ala Ala Gln Asn Ile Arg Pro Glu
                            210                 215                 220

Asp Val Arg Arg Ile Ala Asp Tyr Thr Gln Leu Pro Val Ile Val Lys
                225                 230                 235                 240

Gly Ile Gln Thr Pro Glu Asp Ala Ile Arg Ala Ile Asp Ala Gly Ala
                            245                 250                 255

Ala Gly Ile Tyr Val Ser Asn His Gly Gly Arg Gln Leu Asn Gly Gly
                            260                 265                 270

Pro Gly Ser Phe Asp Val Leu Glu Asp Ile Ala Thr Ser Val Asn Lys
                            275                 280                 285

Gln Val Pro Ile Ile Phe Asp Ser Gly Val Arg Arg Gly Ser Asp Val
                            290                 295                 300

Phe Lys Ala Leu Ala Ser Gly Ala Asp Ile Val Ala Leu Gly Arg Pro
                305                 310                 315                 320

Val Ile Tyr Gly Leu Ala Leu Gly Gly Ala Lys Gly Val Gln Ser Val
                            325                 330                 335

Phe Glu His Ile Asp His Glu Leu Glu Ile Val Met Gln Leu Ala Gly
                            340                 345                 350

Thr Lys Thr Ile Asp Asp Ile Lys Asn Asn Pro Leu Leu Asn Ile Lys
                            355                 360                 365

Tyr

<210> SEQ ID NO 17
<211> LENGTH: 972
<212> TYPE: DNA
<213> ORGANISM: Lactobacillus acidophilus

<400> SEQUENCE: 17
atggcaagag ttgaaaaacc tcgtaaagtt attttagttg gtgacggtgc tgtaggttct        60
acctttgcat tttcaatggt gcaacaaggt attgctgaag aattaggtat cattgatatt       120
gctaaggaac acgttgaagg tgacgcaatc gacttagcag atgctactcc atggactttc       180
ccaaagaaca tttacgcagc tgactacgct gactgcaagg acgcagactt agtagttatt       240
actgctggtg ctccacaaaa gccaggtgaa actcgtcttg accttgttaa caagaacttg       300
aagattttat catcaatcgt tgaaccagtt gttgaatcag ctttgaagg tatcttctta       360 gtagttgcta acccagttga catcttgact cacgcaactt ggaagatttc aggcttccct       420
aaggatcgcg ttattggttc aggtacttca cttgatactg gtcgtcttca aaaggttatc       480
ggtaagatgg aacacgttga cccacgttca gttaatgcat acatgcttgg tgaacacggt       540
gatactgaat tcccagtatg gagctacaac aatgttggtg gcgtaaaggt tagcgactgg       600
gttaaggctc acggtatgga tgaatctaag cttgaagaaa tccacaagga agttgctgac       660
atggcttacg acattatcaa caagaagggt gctactttct acggtatcgg tacagcttca       720
gcaatgatcg ctaaggctat cttgaacgat gaacaccgtg tacttccact ctcagttgca       780
atggatggtc aatacggttt acacgacctt cacattggta ctcctgcagt tgttggccgt       840
aacggtcttg aacaaattat tgaaatgcct ttaaccgctg atgaacaagc taagatggaa       900
```

```
gcttctgcta agcaattaaa ggaagttatg gacaaagcct ttgaagaaac tggcgttaag    960
gttcgtcaat aa                                                        972
```

<210> SEQ ID NO 18
<211> LENGTH: 323
<212> TYPE: PRT
<213> ORGANISM: Lactobacillus acidophilus

<400> SEQUENCE: 18

```
Met Ala Arg Val Glu Lys Pro Arg Lys Val Ile Leu Val Gly Asp Gly
1               5                   10                  15

Ala Val Gly Ser Thr Phe Ala Phe Ser Met Val Gln Gln Gly Ile Ala
            20                  25                  30

Glu Glu Leu Gly Ile Ile Asp Ile Ala Lys Glu His Val Glu Gly Asp
        35                  40                  45

Ala Ile Asp Leu Ala Asp Ala Thr Pro Trp Thr Phe Pro Lys Asn Ile
    50                  55                  60

Tyr Ala Ala Asp Tyr Ala Asp Cys Lys Asp Ala Asp Leu Val Val Ile
65                  70                  75                  80

Thr Ala Gly Ala Pro Gln Lys Pro Gly Glu Thr Arg Leu Asp Leu Val
                85                  90                  95

Asn Lys Asn Leu Lys Ile Leu Ser Ser Ile Val Glu Pro Val Val Glu
            100                 105                 110

Ser Gly Phe Glu Gly Ile Phe Leu Val Val Ala Asn Pro Val Asp Ile
        115                 120                 125

Leu Thr His Ala Thr Trp Lys Ile Ser Gly Phe Pro Lys Asp Arg Val
130                 135                 140

Ile Gly Ser Gly Thr Ser Leu Asp Thr Gly Arg Leu Gln Lys Val Ile
145                 150                 155                 160

Gly Lys Met Glu His Val Asp Pro Arg Ser Val Asn Ala Tyr Met Leu
                165                 170                 175

Gly Glu His Gly Asp Thr Glu Phe Pro Val Trp Ser Tyr Asn Asn Val
            180                 185                 190

Gly Gly Val Lys Val Ser Asp Trp Val Lys Ala His Gly Met Asp Glu
        195                 200                 205

Ser Lys Leu Glu Glu Ile His Lys Glu Val Ala Asp Met Ala Tyr Asp
    210                 215                 220

Ile Ile Asn Lys Lys Gly Ala Thr Phe Tyr Gly Ile Gly Thr Ala Ser
225                 230                 235                 240

Ala Met Ile Ala Lys Ala Ile Leu Asn Asp Glu His Arg Val Leu Pro
                245                 250                 255

Leu Ser Val Ala Met Asp Gly Gln Tyr Gly Leu His Asp Leu His Ile
            260                 265                 270

Gly Thr Pro Ala Val Val Gly Arg Asn Gly Leu Glu Gln Ile Ile Glu
        275                 280                 285

Met Pro Leu Thr Ala Asp Glu Gln Ala Lys Met Glu Ala Ser Ala Lys
    290                 295                 300

Gln Leu Lys Glu Val Met Asp Lys Ala Phe Glu Glu Thr Gly Val Lys
305                 310                 315                 320

Val Arg Gln
```

<210> SEQ ID NO 19
<211> LENGTH: 927
<212> TYPE: DNA
<213> ORGANISM: Lactobacillus acidophilus

<400> SEQUENCE: 19

```
atgagtagaa aagtgtttct tgtaggtgat ggtgctgttg gttcaacttt tgcaaatgac      60
ttattgcaaa atacaactgt tgatgaatta gcgattttg atgttgctaa agatcgtcca     120
gttggtgatt caatggattt ggaagatatt actccattta caggtcaaac taatattcat     180
ccagcagaat atagtgatgc taaagatgca gatgtgtgtg taattactgc tggtgttcct     240
cgtaaacctg gtgaaactag acttgactta gttaataaga atgtaaagat tttaaagact     300
attgttgatc cggttgttga atccggtttt aagggtgtat tgttgtttc agctaacccg     360
gttgatattt taccacatt gactcaaaaa atatccggtt ttccaaaaga tcgtgtaatt     420
ggtactggta cttcacttga ttcaatgcgt cttcgcgttg aattggcaaa gaaacttaat     480
gttccagtag ctaaggttaa ctcaatggtt cttggtgaac acggtgatac tagttttgaa     540
aactttgacg aatcaactgt tgacaataag ccacttcgcg attactcaga aatcaatgat     600
aatgttttaa gtgaaattga gtcagacgtc cgtaaaaagg gtggaaagat catcactaac     660
aaaggagcta cattctatgg tgttgctatg atgcttactc aaattgttag tgctatttta     720
gataatcgtt caatttgttt gccattatca gccccaatta atggtgaata tggcattaag     780
catgatcttt acttaggtac tccaactata attaacggta atggtattga aaaagttatt     840
gaaactaaac tttcagatgt agaaaaagct aagatgatca attctgcaga taagatgcaa     900
gaagttttat caggtgttga aatgtaa                                         927
```

<210> SEQ ID NO 20  
<211> LENGTH: 308  
<212> TYPE: PRT  
<213> ORGANISM: Lactobacillus acidophilus

<400> SEQUENCE: 20

```
Met Ser Arg Lys Val Phe Leu Val Gly Asp Gly Ala Val Gly Ser Thr
1               5                   10                  15

Phe Ala Asn Asp Leu Leu Gln Asn Thr Thr Val Asp Glu Leu Ala Ile
            20                  25                  30

Phe Asp Val Ala Lys Asp Arg Pro Val Gly Asp Ser Met Asp Leu Glu
        35                  40                  45

Asp Ile Thr Pro Phe Thr Gly Gln Thr Asn Ile His Pro Ala Glu Tyr
    50                  55                  60

Ser Asp Ala Lys Asp Ala Asp Val Cys Val Ile Thr Ala Gly Val Pro
65                  70                  75                  80

Arg Lys Pro Gly Glu Thr Arg Leu Asp Leu Val Asn Lys Asn Val Lys
                85                  90                  95

Ile Leu Lys Thr Ile Val Asp Pro Val Val Glu Ser Gly Phe Lys Gly
            100                 105                 110

Val Phe Val Ser Ala Asn Pro Val Asp Ile Leu Thr Thr Leu Thr
        115                 120                 125

Gln Lys Ile Ser Gly Phe Pro Lys Asp Arg Val Ile Gly Thr Gly Thr
    130                 135                 140

Ser Leu Asp Ser Met Arg Leu Arg Val Glu Leu Ala Lys Lys Leu Asn
145                 150                 155                 160

Val Pro Val Ala Lys Val Asn Ser Met Val Leu Gly Glu His Gly Asp
                165                 170                 175

Thr Ser Phe Glu Asn Phe Asp Glu Ser Thr Val Asp Asn Lys Pro Leu
            180                 185                 190
```

Arg Asp Tyr Ser Glu Ile Asn Asp Asn Val Leu Ser Glu Ile Glu Ser
            195                 200                 205

Asp Val Arg Lys Lys Gly Lys Ile Ile Thr Asn Lys Gly Ala Thr
        210                 215                 220

Phe Tyr Gly Val Ala Met Met Leu Thr Gln Ile Val Ser Ala Ile Leu
225                 230                 235                 240

Asp Asn Arg Ser Ile Cys Leu Pro Leu Ser Ala Pro Ile Asn Gly Glu
                245                 250                 255

Tyr Gly Ile Lys His Asp Leu Tyr Leu Gly Thr Pro Thr Ile Ile Asn
                260                 265                 270

Gly Asn Gly Ile Glu Lys Val Ile Glu Thr Lys Leu Ser Asp Val Glu
            275                 280                 285

Lys Ala Lys Met Ile Asn Ser Ala Asp Lys Met Gln Glu Val Leu Ser
        290                 295                 300

Gly Val Glu Met
305

<210> SEQ ID NO 21
<211> LENGTH: 1050
<212> TYPE: DNA
<213> ORGANISM: Lactobacillus acidophilus

<400> SEQUENCE: 21
atggtcatac taataaattt tacggaggtt aaatttatga caaagatttt tgcttacgct      60
attcgtaaag acgaagaacc attcttaaac gaatggaagg aagctcacaa agatatcgat     120
gttgattaca ctgataaact tttgactcct gaaactgcaa agcttgctga aggtgcagac     180
ggtgttgttg tttaccaaca attagactac actcctgaaa cccttcaagc attggcagat     240
gctggcgtaa ctaagatgtc attacgtaac gttggtgtcg ataacatcga catggacaag     300
gccaaagaat taggctttga atcactaat gttcctgttt actcaccaga cgctattgct     360
gaacatgctg ctattcaagc tgcacgtgta ttacgtcaag acaagcgcat ggacgaaaag     420
atggctaaac gtgatttacg ttgggcacca actatcggcc gtgaagttcg tgaccaagtt     480
gtcggtgttg ttggtactgg tcacattggt caagtattta tgaagattat ggaaggcttt     540
ggcgcaaaag ttattgctta cgatatcttc aagaaccctg aacttgaaaa gaagggttac     600
tacgttgatt cacttgatga cttgtacaag caagctgatg taattcact tcacgtacca     660 gacgttccag ctaacgtaca catgattaac gatgaatcaa tcgccaaaat gaaggatggc     720
gttgtaatcg taaactgctc acgtggtcca cttgttgaca ctgatgcagt aattcgtggt     780
ttagactcag gcaagatctt cggcttcgtt atggatactt acgaaggcga agttggtgta     840
tttaacaagg actgggaagg taaagaattc ccagacgaac gcttggcaga cttaattgat     900
cgtccaaacg tattggtaac cccacacact gccttctaca ctactcacgc tgtacgtaac     960
atggttgtta aggcatttga caacaacttg gaattaatca agggcgaaaa accagattct    1020
ccagttgctt tggacaagaa caagttctaa                                     1050

<210> SEQ ID NO 22
<211> LENGTH: 349
<212> TYPE: PRT
<213> ORGANISM: Lactobacillus acidophilus

<400> SEQUENCE: 22

Met Val Ile Leu Ile Asn Phe Thr Glu Val Lys Phe Met Thr Lys Ile
1               5                   10                  15

```
Phe Ala Tyr Ala Ile Arg Lys Asp Glu Glu Pro Phe Leu Asn Glu Trp
                20                  25                  30
Lys Glu Ala His Lys Asp Ile Asp Val Asp Tyr Thr Asp Lys Leu Leu
            35                  40                  45
Thr Pro Glu Thr Ala Lys Leu Ala Glu Gly Ala Asp Gly Val Val Val
        50                  55                  60
Tyr Gln Gln Leu Asp Tyr Thr Pro Glu Thr Leu Gln Ala Leu Ala Asp
65                  70                  75                  80
Ala Gly Val Thr Lys Met Ser Leu Arg Asn Val Gly Val Asp Asn Ile
                85                  90                  95
Asp Met Asp Lys Ala Lys Glu Leu Gly Phe Glu Ile Thr Asn Val Pro
            100                 105                 110
Val Tyr Ser Pro Asp Ala Ile Ala Glu His Ala Ala Ile Gln Ala Ala
        115                 120                 125
Arg Val Leu Arg Gln Asp Lys Arg Met Asp Glu Lys Met Ala Lys Arg
    130                 135                 140
Asp Leu Arg Trp Ala Pro Thr Ile Gly Arg Glu Val Arg Asp Gln Val
145                 150                 155                 160
Val Gly Val Val Gly Thr Gly His Ile Gly Gln Val Phe Met Lys Ile
                165                 170                 175
Met Glu Gly Phe Gly Ala Lys Val Ile Ala Tyr Asp Ile Phe Lys Asn
            180                 185                 190
Pro Glu Leu Glu Lys Lys Gly Tyr Tyr Val Asp Ser Leu Asp Asp Leu
        195                 200                 205
Tyr Lys Gln Ala Asp Val Ile Ser Leu His Val Pro Asp Val Pro Ala
    210                 215                 220
Asn Val His Met Ile Asn Asp Glu Ser Ile Ala Lys Met Lys Asp Gly
225                 230                 235                 240
Val Val Ile Val Asn Cys Ser Arg Gly Pro Leu Val Asp Thr Asp Ala
                245                 250                 255
Val Ile Arg Gly Leu Asp Ser Gly Lys Ile Phe Gly Phe Val Met Asp
            260                 265                 270
Thr Tyr Glu Gly Glu Val Gly Val Phe Asn Lys Asp Trp Glu Gly Lys
        275                 280                 285
Glu Phe Pro Asp Glu Arg Leu Ala Asp Leu Ile Asp Arg Pro Asn Val
    290                 295                 300
Leu Val Thr Pro His Thr Ala Phe Tyr Thr Thr His Ala Val Arg Asn
305                 310                 315                 320
Met Val Val Lys Ala Phe Asp Asn Asn Leu Glu Leu Ile Lys Gly Glu
                325                 330                 335
Lys Pro Asp Ser Pro Val Ala Leu Asp Lys Asn Lys Phe
            340                 345

<210> SEQ ID NO 23
<211> LENGTH: 708
<212> TYPE: DNA
<213> ORGANISM: Lactobacillus plantarum

<400> SEQUENCE: 23
atggacacaa caacaatttt tcaacacggc acattaggct tacttgttcc cggattattt      60
gacgggacga ttcggctggt gaactcttta acccatggtg atacgggtat tgggacgtta     120
aacggtctca atggtgaagt gattattcta gaaggtcacg cctatcaagc acgtgaggat     180
ggtcaaattc gggaaattca gcccgaagag acgttaccat ttgcatcggt gcactttgaa     240
```

-continued

```
aagcctgata ttagtgcgca attagctgca atcacacaaa ctgatttcga gcaacaagtg    300
gttcatgact atcgtttgac caacgtgttt gcggctattc gcgtcgatgg gacctttgca    360
aaagtcaaga cgcgagtcgc gcctcgtcag gagccaccgt acaaaacatt agtcgcggca    420
acggcaacac aaccggaatt caccggtgaa catgttgacg gaacgattat tggctactac    480
gcaccgcatt tgttccaagg cgctacggtc ggtggctttc acttacactt tctaagtaaa    540
gaccatcaat taggtggaca cttgctgggg tttgaagtcg aacaagcgac gctgaaagtt    600
caacattttg ctgactttca tgtgcacttg ccaatcgaca atgaagcgta cttacaagaa    660
caatttgata atgaaaccat tgatcatgcc attaataaag ctgaacgt               708
```

<210> SEQ ID NO 24
<211> LENGTH: 236
<212> TYPE: PRT
<213> ORGANISM: Lactobacillus plantarum

<400> SEQUENCE: 24

Met Asp Thr Thr Thr Ile Phe Gln His Gly Thr Leu Gly Leu Leu Val
1               5                   10                  15

Pro Gly Leu Phe Asp Gly Thr Ile Thr Ala Gly Glu Leu Leu Thr His
            20                  25                  30

Gly Asp Thr Gly Ile Gly Thr Leu Asn Gly Leu Asn Gly Glu Val Ile
        35                  40                  45

Ile Leu Gly Gly His Ala Tyr Gln Ala Arg Glu Asp Gly Gln Ile Arg
    50                  55                  60

Glu Ile Gln Pro Glu Glu Thr Leu Pro Phe Ala Ser Val His Phe Glu
65                  70                  75                  80

Lys Pro Asp Ile Ser Ala Gln Leu Ala Ala Ile Thr Gln Thr Asp Phe
                85                  90                  95

Glu Gln Gln Val Val His Asp Tyr Arg Leu Thr Asn Val Phe Ala Ala
            100                 105                 110

Ile Arg Val Asp Gly Thr Phe Ala Lys Val Lys Thr Arg Val Ala Pro
        115                 120                 125

Arg Gln Glu Pro Pro Tyr Lys Thr Leu Val Ala Ala Thr Ala Thr Gln
    130                 135                 140

Pro Glu Phe Thr Gly Glu His Val Asp Gly Thr Ile Ile Gly Tyr Tyr
145                 150                 155                 160

Ala Pro His Leu Phe Gln Gly Ala Thr Val Gly Gly Phe His Leu His
                165                 170                 175

Phe Leu Ser Lys Asp His Gln Leu Gly Gly His Leu Leu Gly Phe Glu
            180                 185                 190

Val Glu Gln Ala Thr Leu Lys Val Gln His Phe Ala Asp Phe His Val
        195                 200                 205

His Leu Pro Ile Asp Asn Glu Ala Tyr Leu Gln Glu Gln Phe Asp Asn
    210                 215                 220

Glu Thr Ile Asp His Ala Ile Asn Lys Ala Glu Arg
225                 230                 235

<210> SEQ ID NO 25
<211> LENGTH: 708
<212> TYPE: DNA
<213> ORGANISM: Lactobacillus rhamnosus

<400> SEQUENCE: 25

```
ttgaatacgg atcggttgta tcaacatgga acattagcca tgctggttcc ggggcttttt    60
```

```
gcggggacgc agacagttgg ggaattattg cagcaaggtg atactggcat ggaactttg      120 actgggcttg atggtgagct aattattcag gctggtaagg tttatcaagt gaatgcccaa     180
ggcaaagttc gagaagtgca agaagacgag aaggttcctt ttgctaacgt tcactatcaa     240
cacgacgttg cagctggtaa gcttcagggg cttgatttgg cagggtttca caaagcgact     300
cttgagcggc tgcagaccgg taatttattt gcggcagttc gtgtagaagg cacgtttacg     360
caaattcata cacgggcggt gctgccgcaa cagccacctt atccgacctt gaccgaaacg     420
gcttcgggtc aaaaagaatt tcatgccgag aatatcaagg gcactttaat tgggtacttt     480
tcaccggatc tctatgcagg tgcggtttca cctggtttcc atgtccattt tctggctgct     540
gatcatagta tgggtgggca tattcttggc ttcgaattgg atagtggcga actgttttta     600
caaaagttta gcgacttcca gttgcatttg ccaacagatg atcagccttt cttgaagcaa     660
caatttgata caacaagttt ggttgctgat attcttaaag ctgagagt                 708
```

<210> SEQ ID NO 26
<211> LENGTH: 236
<212> TYPE: PRT
<213> ORGANISM: Lactobacillus rhamnosus

<400> SEQUENCE: 26

```
Met Asn Thr Asp Arg Leu Tyr Gln His Gly Thr Leu Ala Met Leu Val
1               5                   10                  15

Pro Gly Leu Phe Ala Gly Thr Gln Thr Val Gly Glu Leu Leu Gln Gln
            20                  25                  30

Gly Asp Thr Gly Ile Gly Thr Leu Thr Gly Leu Asp Gly Glu Leu Ile
        35                  40                  45

Ile Gln Ala Gly Lys Val Tyr Gln Val Asn Ala Gln Gly Lys Val Arg
    50                  55                  60

Glu Val Gln Glu Asp Glu Lys Val Pro Phe Ala Asn Val His Tyr Gln
65                  70                  75                  80

His Asp Val Ala Ala Gly Lys Leu Gln Gly Leu Asp Leu Ala Gly Phe
                85                  90                  95

His Lys Ala Thr Leu Glu Arg Leu Gln Thr Gly Asn Leu Phe Ala Ala
            100                 105                 110

Val Arg Val Glu Gly Thr Phe Thr Gln Ile His Thr Arg Ala Val Leu
        115                 120                 125

Pro Gln Gln Pro Pro Tyr Pro Thr Leu Thr Glu Thr Ala Ser Gly Gln
    130                 135                 140

Lys Glu Phe His Ala Glu Asn Ile Lys Gly Thr Leu Ile Gly Tyr Phe
145                 150                 155                 160

Ser Pro Asp Leu Tyr Ala Gly Ala Val Ser Pro Gly Phe His Val His
                165                 170                 175

Phe Leu Ala Ala Asp His Ser Met Gly Gly His Ile Leu Gly Phe Glu
            180                 185                 190

Leu Asp Ser Gly Glu Leu Phe Leu Gln Lys Phe Ser Asp Phe Gln Leu
        195                 200                 205

His Leu Pro Thr Asp Asp Gln Pro Phe Leu Lys Gln Gln Phe Asp Thr
    210                 215                 220

Thr Ser Leu Val Ala Asp Ile Leu Lys Ala Glu Ser
225                 230                 235
```

<210> SEQ ID NO 27
<211> LENGTH: 702
<212> TYPE: DNA

<213> ORGANISM: Pediococcus pentosaceus

<400> SEQUENCE: 27

```
atggcaaaat tatttcaaca tgggacgctc gcaatgctag tagatggact ttttggtggg      60
acgcttgcgg tttccgattt actgaagcac ggtgactttg aatcggaac  tgctgaaggc     120
cttaatggcg aattaattat tttagatgga gccccttacc aagcgctagc agacggtaca    180
attagggtta ttggtgatga tgaactatta ccgtttgcta acgttaattc agcggatttt    240
gaaggacgag cagtgttatc tgacattgag atgaaagatg tggatgcgac acttgctaaa    300
gaattgtcat atcaaaatac atttgttgct attaaaatta gtggaacttt ccgtacagtt    360
caaactcggg tggtaaagca acaagaacgt ccttatccaa cccttagtga acagcatct     420
aaacaacaag ttttaatgc  tgaagatgtt agaggaacag tagttggcta ctacacccca    480
gatcttttcc atggtgcggg agtagcgggg atgcatcttc attttattga cgatcaacac    540
gaattcggag tcatttact  agactttaag gcggatcaag ttaaactttc ttggcaacta    600
ttagacggtt tagacctcaa tttaccaatt caagacgcag aatttatggc acatgaggct    660
agcgacgcgg aaaaaattca acaatcaatt tctgagtctg aa                        702
```

<210> SEQ ID NO 28
<211> LENGTH: 234
<212> TYPE: PRT
<213> ORGANISM: Pediococcus pentosaceus

<400> SEQUENCE: 28

```
Met Ala Lys Leu Phe Gln His Gly Thr Leu Ala Met Leu Val Asp Gly
1               5                   10                  15

Leu Phe Gly Gly Thr Leu Ala Val Ser Asp Leu Leu Lys His Gly Asp
            20                  25                  30

Phe Gly Ile Gly Thr Ala Glu Gly Leu Asn Gly Glu Leu Ile Ile Leu
        35                  40                  45

Asp Gly Ala Pro Tyr Gln Ala Leu Ala Asp Gly Thr Ile Arg Val Ile
    50                  55                  60

Gly Asp Asp Glu Leu Leu Pro Phe Ala Asn Val Asn Ser Ala Asp Phe
65                  70                  75                  80

Glu Gly Arg Ala Val Leu Ser Asp Ile Glu Met Lys Asp Val Asp Ala
                85                  90                  95

Thr Leu Ala Lys Glu Leu Ser Tyr Gln Asn Thr Phe Val Ala Ile Lys
            100                 105                 110

Ile Ser Gly Thr Phe Arg Thr Val Gln Thr Arg Val Val Lys Gln Gln
        115                 120                 125

Glu Arg Pro Tyr Pro Thr Leu Ser Glu Thr Ala Ser Lys Gln Gln Val
    130                 135                 140

Phe Asn Ala Glu Asp Val Arg Gly Thr Val Val Gly Tyr Tyr Thr Pro
145                 150                 155                 160

Asp Leu Phe His Gly Ala Gly Val Ala Gly Met His Leu His Phe Ile
                165                 170                 175

Asp Asp Gln His Glu Phe Gly Gly His Leu Leu Asp Phe Lys Ala Asp
            180                 185                 190

Gln Val Lys Leu Ser Trp Gln Leu Leu Asp Gly Leu Asp Leu Asn Leu
        195                 200                 205

Pro Ile Gln Asp Ala Glu Phe Met Ala His Glu Ala Ser Asp Ala Glu
    210                 215                 220

Lys Ile Gln Gln Ser Ile Ser Glu Ser Glu
```

<210> SEQ ID NO 29
<211> LENGTH: 717
<212> TYPE: DNA
<213> ORGANISM: Leuconostoc mesenteroides

<400> SEQUENCE: 29

```
atgacaacaa tatatcaaca tggtacatta gcacaattag tagcgcgcca aatgtcaggg        60
acaataacag tcgctgaaat gttggaacat ggggacactg gcattggtac ttttgagggc       120
ctcaatggtg aagctatttt tctaaacggg aagcctatc aagctgatag tacaggaaaa        180
gttcaccaca ttactgataa acaaactaca ttaccttttg catcaatcca ttttgatcaa       240
ccggaggcaa gccaaaaatt accttttaaa aaaataaaat atagtaattt gactcagaac       300
ttgaaagatg agcagttatt taacgttttc tctgccttaa aactgcatgg tgagtttgcc       360
cacgttcacg ttcgtattgt aacaaaacaa gagaagccat atccaagttt gttacaagta       420
gctgaacagc agcctgaatt caaagcagac aacataactg gtacattagt tggatattat       480
gcaccaaaag ttttggcgg tccaaccgca gcagggtggc atttacactt tttgtcagat       540
gatttaacct tgctgggca cgtttttgga ttttgaagcaa cagatgtcga tggtacttta       600
gaagttttg ataacttttt gcaacatcta cctattaata atgctgactt tagaagcatg       660
aatcaggata tagctggttt ggataaagcc attgaggcca gtgaaggcgg aaaaaat         717
```

<210> SEQ ID NO 30
<211> LENGTH: 239
<212> TYPE: PRT
<213> ORGANISM: Leuconostoc mesenteroides

<400> SEQUENCE: 30

```
Met Thr Thr Ile Tyr Gln His Gly Thr Leu Ala Gln Leu Val Ala Arg
1               5                   10                  15

Gln Met Ser Gly Thr Ile Thr Val Ala Glu Met Leu Glu His Gly Asp
            20                  25                  30

Thr Gly Ile Gly Thr Phe Glu Gly Leu Tyr Gly Glu Ala Ile Phe Leu
        35                  40                  45

Asn Gly Glu Ala Tyr Gln Ala Asp Ser Thr Gly Lys Val His His Ile
    50                  55                  60

Thr Asp Lys Gln Thr Thr Leu Pro Phe Ala Ser Ile His Phe Asp Gln
65                  70                  75                  80

Pro Glu Ala Ser Gln Lys Leu Pro Phe Lys Lys Ile Lys Tyr Ser Asn
                85                  90                  95

Leu Thr Gln Asn Leu Lys Asp Lys Gln Leu Phe Asn Val Phe Ser Ala
            100                 105                 110

Leu Lys Leu His Gly Glu Phe Ala His Val His Val Arg Ile Val Thr
        115                 120                 125

Lys Gln Glu Lys Pro Tyr Pro Ser Leu Leu Gln Val Ala Glu Gln Gln
    130                 135                 140

Pro Glu Phe Lys Ala Asp Asn Ile Thr Gly Thr Leu Val Gly Tyr Tyr
145                 150                 155                 160

Ala Pro Lys Val Phe Gly Gly Pro Thr Ala Ala Gly Trp His Leu His
                165                 170                 175

Phe Leu Ser Asp Asp Leu Thr Phe Ala Gly His Val Leu Asp Phe Glu
            180                 185                 190

Ala Thr Asp Val Asp Gly Thr Leu Glu Val Phe Asp Asn Phe Leu Gln
```

His Leu Pro Ile Asn Asn Ala Asp Phe Arg Ser Met Asn Gln Asp Ile
     210             215                 220

Ala Gly Leu Asp Lys Ala Ile Glu Ala Ser Glu Gly Gly Lys Asn
225             230                 235

<210> SEQ ID NO 31
<211> LENGTH: 810
<212> TYPE: DNA
<213> ORGANISM: Oenococcus oeni

<400> SEQUENCE: 31
ttgggatcaa ggaccggttt tggtcgatat tccagtcgat tattcgcacg ataccgaact    60
ttattcggaa ttgatcgaag gaggtatgga ttaaaaatga agatttaac aaaagcttat    120 caacatggca ctttggctca aattatggat ggccaatatg atgggacaat actgcttaaa   180
gatcttctcg aacacggcga tttcggtatt ggtacaacaa ccggaatcgg ggtcgaatta   240
atagttttgg atggggtggc ttatggaatc cccagcagcg gaaaagtcca aaaaatggac   300
atcgagcacg aaaaagcacc ctttgcaaat attaactact tcgatcaaaa gttgaagagc   360
gaaagcctaa ttaatcttga ttccgatagt tttcaaaaaa aggttgaaga gaatataaa    420 cttaaaaatg tctttgccgc aattagagta cacggagaat ttacaaatgt tttggcgcga   480
tcagccgata acaagaaaa accatacccg ccatttcaa aggtcgcggc agcgcaacat    540
gaattccatg ctgattcact gacggcaacg atggttggct attattcagc agcgatgtat   600
gaagggacaa ccgcggccgg ctttcacctt cacattctct ccgatgatcg tcaattcgga   660
gggcacctat tagattttaa aatcaaaaaa gccgacctcc aggttcagat ttttcaggat   720
ttccagttgc atctaccaat tgaaaatccc gattttcgcc gacgcgaatt agacttggaa   780
actttaaaaa aagcgattga aaagacagaa                                    810

<210> SEQ ID NO 32
<211> LENGTH: 270
<212> TYPE: PRT
<213> ORGANISM: Oenococcus oeni

<400> SEQUENCE: 32

Met Gly Ser Arg Thr Gly Phe Gly Arg Tyr Ser Ser Arg Leu Phe Ala
1               5                   10                  15

Arg Tyr Arg Thr Leu Phe Gly Ile Asp Arg Arg Tyr Gly Leu Lys
            20                  25                  30

Met Lys Asp Leu Thr Lys Ala Tyr Gln His Gly Thr Leu Ala Gln Ile
            35                  40                  45

Met Asp Gly Gln Tyr Asp Gly Thr Ile Leu Leu Lys Asp Leu Leu Glu
        50                  55                  60

His Gly Asp Phe Gly Ile Gly Thr Thr Thr Gly Ile Gly Val Glu Leu
65              70                  75                  80

Ile Val Leu Asp Gly Val Ala Tyr Gly Ile Pro Ser Ser Gly Lys Val
                85                  90                  95

Gln Lys Met Asp Ile Glu His Glu Lys Ala Pro Phe Ala Asn Ile Asn
            100                 105                 110

Tyr Phe Asp Gln Lys Leu Lys Ser Glu Ser Leu Ile Asn Leu Asp Ser
        115                 120                 125

Asp Ser Phe Gln Lys Lys Val Glu Glu Glu Tyr Lys Leu Lys Asn Val
    130                 135                 140

```
Phe Ala Ala Ile Arg Val His Gly Glu Phe Thr Asn Val Leu Ala Arg
145                 150                 155                 160

Ser Ala Asp Lys Gln Glu Lys Pro Tyr Pro Phe Ser Lys Val Ala
            165                 170                 175

Ala Ala Gln His Glu Phe His Ala Asp Ser Leu Thr Ala Thr Met Val
            180                 185                 190

Gly Tyr Tyr Ser Ala Ala Met Tyr Glu Gly Thr Thr Ala Ala Gly Phe
            195                 200                 205

His Leu His Ile Leu Ser Asp Asp Arg Gln Phe Gly Gly His Leu Leu
            210                 215                 220

Asp Phe Lys Ile Lys Lys Ala Asp Leu Gln Val Gln Ile Phe Gln Asp
225                 230                 235                 240

Phe Gln Leu His Leu Pro Ile Glu Asn Pro Asp Phe Arg Arg Arg Glu
            245                 250                 255

Leu Asp Leu Glu Thr Leu Lys Lys Ala Ile Glu Lys Thr Glu
            260                 265                 270

<210> SEQ ID NO 33
<211> LENGTH: 702
<212> TYPE: DNA
<213> ORGANISM: Enterococcus faecalis

<400> SEQUENCE: 33
atgagcgaac aatatgttta tcaacatggt acgctaggcg gtttaatgga agtttgatg      60 gcaggaacgg cagaaattgg tacgttactc acgcaaggtg attttggaat tgggacatta     120
gaaggctcaa atggcgaaat tatttattg gacggtacat tgtatcatgc aaatcaaact     180
ggcgaaatta ctattctaga aggcgaagaa ttaacgccat atgccgcagt tactcgtttt     240
caagaagatg gcgcattccc tgtatcaacg gaaaccgatg aaaatattaa agcacaaatt     300
ttagaaaaaa ttagtcctaa tttttttgcg gcaattaaaa ttagcggtct ttttgcgaag     360
atgcatgtcc gtgtggcacc taaacaagaa aaaccgtatc caccatttgt agaagcagca     420
cgcaatcaac ctgaatttac agcggagaat attcaggaa cagttgtagg gttctttaca     480
cctaaattat tcatggtgc ctctgccgca gggtttcatt tgcactttat cagtgaggat     540
caccaatttg gtgggcacat tcttgatttt ggcattaaac aagggactgt tcgtggatg      600 gaaacagcag aattgcgaca gcattttcca gttcatgatg ctgattatcg gaataaagaa     660
attgatattg caaaagcttt gtccgcaatt gaagaagcgg aa                        702

<210> SEQ ID NO 34
<211> LENGTH: 234
<212> TYPE: PRT
<213> ORGANISM: Enterococcus faecalis

<400> SEQUENCE: 34

Met Ser Glu Gln Tyr Val Tyr Gln His Gly Thr Leu Gly Gly Leu Met
1               5                   10                  15

Glu Ser Leu Met Ala Gly Thr Ala Glu Ile Gly Thr Leu Leu Thr Gln
            20                  25                  30

Gly Asp Phe Gly Ile Gly Thr Leu Glu Gly Ser Asn Gly Glu Ile Ile
        35                  40                  45

Leu Leu Asp Gly Thr Leu Tyr His Ala Asn Gln Thr Gly Glu Ile Thr
    50                  55                  60

Ile Leu Glu Gly Glu Glu Leu Thr Pro Tyr Ala Ala Val Thr Arg Phe
65                  70                  75                  80
```

Gln Glu Asp Gly Ala Phe Pro Val Ser Thr Glu Asp Glu Asn Ile
                85                  90                  95

Lys Ala Gln Ile Leu Glu Lys Ile Ser Pro Asn Phe Phe Ala Ala Ile
        100                 105                 110

Lys Ile Ser Gly Leu Phe Ala Lys Met His Val Arg Val Ala Pro Lys
        115                 120                 125

Gln Glu Lys Pro Tyr Pro Pro Phe Val Glu Ala Ala Arg Asn Gln Pro
        130                 135                 140

Glu Phe Thr Ala Glu Asn Ile Gln Gly Thr Val Gly Phe Phe Thr
145                 150                 155                 160

Pro Lys Leu Phe His Gly Ala Ser Ala Ala Gly Phe His Leu His Phe
                165                 170                 175

Ile Ser Glu Asp His Gln Phe Gly Gly His Ile Leu Asp Phe Gly Ile
                180                 185                 190

Lys Gln Gly Thr Val Ser Trp Met Glu Thr Ala Glu Leu Arg Gln His
        195                 200                 205

Phe Pro Val His Asp Ala Asp Tyr Arg Asn Lys Glu Ile Asp Ile Ala
        210                 215                 220

Lys Ala Leu Ser Ala Ile Glu Glu Ala Glu
225                 230

<210> SEQ ID NO 35
<211> LENGTH: 714
<212> TYPE: DNA
<213> ORGANISM: Streptococcus mutans

<400> SEQUENCE: 35
atggaaacca acaaattatt tcaatataat accttaggag cgcttatggc aggtctctat      60
gatggttctt taactgtggg tgagctgtta gaatatggag atttaggttt aggaacactt     120
gattccattg atggtgaatt aattgtccta gatggtaaag cttatcaggc taaaggatct     180
ggtgataaac agaagttgt tgaagtgcct gatgatatga agtgccctta tgcagctgtc     240
attcatcatg aagcagaggt tattttaag cagcgttttg aaatgacaga taaagaattg     300
caagaacgta ttgagtctta ctatgatggg gagaatctct ttcgttcgat taaaattcac     360
ggaacctttg ctaaaatgca tgtacgtatg attccgcgtt cgacccctga tgagaaattt     420
gcagaagtgg caaacatca gccagaatac agagccgaaa atattaccgg tactattgtt     480
ggtatttgga cgcctgaaat ttttcatggt gtcagtgtgg ctggttatca tttgcacttt     540
atttctgatg atcatacttt tggtggccat gttatggact atgttatttc agaagggcag     600
gttgaagtgg gtgctgttga tcagttagat caacgttttcc ccgttcaaga tcggcaatat     660
ctctttgcta aatttaacgc caaagatatt cgtggtgata ttgacaaggc agaa           714

<210> SEQ ID NO 36
<211> LENGTH: 238
<212> TYPE: PRT
<213> ORGANISM: Streptococcus mutans

<400> SEQUENCE: 36

Met Glu Thr Asn Lys Leu Phe Gln Tyr Asn Thr Leu Gly Ala Leu Met
1               5                   10                  15

Ala Gly Leu Tyr Asp Gly Ser Leu Thr Val Gly Glu Leu Leu Glu Tyr
            20                  25                  30

Gly Asp Leu Gly Leu Gly Thr Leu Asp Ser Ile Asp Gly Glu Leu Ile
        35                  40                  45

```
Val Leu Asp Gly Lys Ala Tyr Gln Ala Lys Gly Gly Asp Lys Pro
 50                  55                  60
Glu Val Glu Val Pro Asp Met Lys Val Pro Tyr Ala Ala Val
 65                  70                  75                  80
Ile His His Glu Ala Glu Val Ile Phe Lys Gln Arg Phe Glu Met Thr
                 85                  90                  95
Asp Lys Glu Leu Gln Glu Arg Ile Glu Ser Tyr Tyr Asp Gly Glu Asn
            100                 105                 110
Leu Phe Arg Ser Ile Lys Ile His Gly Thr Phe Ala Lys Met His Val
        115                 120                 125
Arg Met Ile Pro Arg Ser Thr Pro Asp Glu Lys Phe Ala Glu Val Ala
130                 135                 140
Thr His Gln Pro Glu Tyr Arg Ala Glu Asn Ile Thr Gly Thr Ile Val
145                 150                 155                 160
Gly Ile Trp Thr Pro Glu Ile Phe His Gly Val Ser Val Ala Gly Tyr
                165                 170                 175
His Leu His Phe Ile Ser Asp Asp His Thr Phe Gly Gly His Val Met
            180                 185                 190
Asp Tyr Val Ile Ser Glu Gly Gln Val Glu Val Gly Ala Val Asp Gln
        195                 200                 205
Leu Asp Gln Arg Phe Pro Val Gln Asp Arg Gln Tyr Leu Phe Ala Lys
210                 215                 220
Phe Asn Ala Lys Asp Ile Arg Gly Asp Ile Asp Lys Ala Glu
225                 230                 235

<210> SEQ ID NO 37
<211> LENGTH: 708
<212> TYPE: DNA
<213> ORGANISM: Lactococcus lactis

<400> SEQUENCE: 37
atgtcagaaa tcacacaact ttttcaatat aatacccttg gggcattaat ggccggactt      60
tatgagggga caatgacgat tggtgagctc ttgaaacatg gtgacttagg aattggaact     120
ttagattcaa ttgatggcga attgattgtt ttagatggta aagcttatca agctaaggga     180
gataaaacga tcgtcgaatt aactgacgat atcaaagttc cttacgctgc agttgttcct     240
catcaggcag aagttgtttt caaacaaaaa tttacagtaa gcgataaaga attagaagac     300
cgaattgaaa gctattttga tggtcaaaac ttattccgct caatcaaaat tactggtgaa     360
tttccaaaaa tgcatgtacg aatgattccg cgtgctaaat caggaacaaa atttgtagaa     420
gtttcacaaa accaaccaga atataccgaa gaaaatgtca aggaacaat tgtcggaatt     480
tggactcctg aaatgttcca tggtgtcagc gttgctggtt atcatcttca ttttattagt     540
gaagatttca cttttggtgg acatattctt gattttatta ttgataatgg gactgttgaa     600
attggagcaa ttgaccaatt gaatcaatca ttccctgttc aagatcgcaa attttatttt     660
gccgaccttg catcgaggc tttgaaaaaa gatattgacg tagctgaa                   708

<210> SEQ ID NO 38
<211> LENGTH: 236
<212> TYPE: PRT
<213> ORGANISM: Lactococcus lactis

<400> SEQUENCE: 38

Met Ser Glu Ile Thr Gln Leu Phe Gln Tyr Asn Thr Leu Gly Ala Leu
 1               5                  10                  15
```

```
Met Ala Gly Leu Tyr Glu Gly Thr Met Thr Ile Gly Glu Leu Leu Lys
            20                  25                  30
His Gly Asp Leu Gly Ile Gly Thr Leu Asp Ser Ile Asp Gly Glu Leu
        35                  40                  45
Ile Val Leu Asp Gly Lys Ala Tyr Gln Ala Lys Gly Asp Lys Thr Ile
    50                  55                  60
Val Glu Leu Thr Asp Asp Ile Lys Val Pro Tyr Ala Ala Val Val Pro
65                  70                  75                  80
His Gln Ala Glu Val Val Phe Lys Gln Lys Phe Thr Val Ser Asp Lys
                85                  90                  95
Glu Leu Glu Asp Arg Ile Glu Ser Tyr Phe Asp Gly Gln Asn Leu Phe
            100                 105                 110
Arg Ser Ile Lys Ile Thr Gly Glu Phe Pro Lys Met His Val Arg Met
        115                 120                 125
Ile Pro Arg Ala Lys Ser Gly Thr Lys Phe Val Glu Val Ser Gln Asn
    130                 135                 140
Gln Pro Glu Tyr Thr Glu Glu Asn Val Lys Gly Thr Ile Val Gly Ile
145                 150                 155                 160
Trp Thr Pro Glu Met Phe His Gly Val Ser Val Ala Gly Tyr His Leu
                165                 170                 175
His Phe Ile Ser Glu Asp Phe Thr Phe Gly Gly His Ile Leu Asp Phe
            180                 185                 190
Ile Ile Asp Asn Gly Thr Val Glu Ile Gly Ala Ile Asp Gln Leu Asn
        195                 200                 205
Gln Ser Phe Pro Val Gln Asp Arg Lys Phe Leu Phe Ala Asp Leu Asp
    210                 215                 220
Ile Glu Ala Leu Lys Lys Asp Ile Asp Val Ala Glu
225                 230                 235

<210> SEQ ID NO 39
<211> LENGTH: 2442
<212> TYPE: DNA
<213> ORGANISM: Lactobacillus plantarum

<400> SEQUENCE: 39
atgatcatgt ctgaaacttt aactaaaaca acgacaacta ttaaccactt cggtaaattg      60
acgccaatga tggatcgctt acgcgatagc atcattgatg caaaacctta tgtcgatcca     120
gaacgggcga ttctcacaac cgaaacttat cgacaacacc aagacgaaca agtcgatata     180
ttacgggcta aaatgcttga acacgttctt gataaaatga gtatcttcat tgaagatgat     240
actttaattg ttggtaacca agcacgccaa atcgttggg caccagtatt ccctgagtat     300
tctatgaatt gggtcattga tgaattagat acatttgaga agcgtcctgg tgacgttttc     360
tatattacgg agaaatccaa ggaagaactt cgtgcgattg cgcctttctg gaaacataat     420
accttggaag accgcggcta cgctagtttt ccagaagcaa gtcgtatttt ttatgattta     480
ggtattattg gagccgatgg taatatcact tctggtgatg gtcacattgc ggtcgactat     540
aaaaacgttg ttaataaggg acttaaatgg tatgaagacc gcattaagac agcacttgct     600
aatcttgacc ttactgattt taaccagcaa aaacaatact atttctataa agcgggccta     660
attgtaattg atgccattca caattttgct aaacgttacg cccaattagc gtccaagcaa     720
gctcaaaaca cgacatccgc aactcgcaaa gcacaacttg aaaaaatcgc ccaaattcta     780
aacaaggttc cttacgaacc tgcaaattca ttttatgaag cgattcaagc tgtctggtta     840
gttcatctga ccttacaaat cgaatccaac ggtcattctg tctcatatgg tcgtctagat     900
```

```
cagtacctag ctccattcta tgagcacgat ttaaaaactg gtgctattga cgccaacggt    960
gcaaccgaat tactcacaaa cttatgtctt aagacgttaa cgattaataa agtacgctca   1020
tggcaacata ctgaattttc tgcagggagt ccctctacc aaaacattac gattggtggt    1080
caaacaccag atggtaaaga tgccgttaat ccgacgtcct atctgatttt acgagcaatt   1140
gcgcaagcac atttaccaca acccaactta acggtccgtt atcaccatgg cttaagcgat   1200
aagtttatgc gtgaatgtgt cgaagttatt aaacaaggct taggtatgcc tgcgtttaat   1260
aacgacgaaa ttattattcc gtcgtttatt cgtcgtggcg tcaagaaaga agacgcctat   1320
aattacagtg ccatcggttg tgtcgaaaca gcgatccctg aaaatgggg ctatcgttgc    1380 accgggatga gcttcattaa cttcccacgc gttctcttac tcattatgaa tggtggcatt   1440
gatcctgaat ctggcaaacg gttattaccc gattatggta agttcactga tatgacttct   1500
tttgatcaac ttatgactgc ttgggacaaa gcgctccgtg aaatgacacg acaaagtgtg   1560
attatcgaaa atagttgtga tttggctttg gaacaaaatt atcctgatat tctctgctcc   1620
gttttaaccg acgattgtat cggtcgtggt aagaccatta agaaggtgg cgcggtatac    1680 gactttatca gtggattaca agttggtatt gctaacctag cggactccct agctgcaatc   1740
aagaaacttg tctttgaaga aaagaagttg acaacaaccc aactttggca cgcacttacc   1800
actgattttg cggatgaaga tggtgaaaag attcggcaga tgctcattaa tgatgcccca   1860
aagtatggta acgatgatga ttatgttgat gatttgattg ttgaagctta taaaccatat   1920
attgatgaaa ttgccaagta caaaaacacg cgctacggtc gcggccctat tggtggcttg   1980
cgctacgcag gaacctcttc tatttcggcc aacgttggtc aagggcacag cactttggct   2040
acaccagatg tcggcacgc tcggacacca ttagccgaag gttgctcacc agaacatgca    2100
atggatactg atggcccaac tgctgtgttc aaatcagttt ccaaattatc cactaaggac   2160
atcactggtg gcgtattact gaaccaaaag atgtcaccac aaattctacg gagtgatgaa   2220
agctgcatga aattggttgc actactacgg accttcttca atcgacttca tggttaccat   2280
gtccaataca acattgtttc acgggatacc ttgattgatg cacagaacca tcctgacaag   2340
caccgtgact tgattgttcg ggttgctgga tattccgcct tcttcgtggg cctatccaaa   2400
gaaacccaag atgatattat cgaacggacg gagcagtctc ta                      2442
```

<210> SEQ ID NO 40
<211> LENGTH: 814
<212> TYPE: PRT
<213> ORGANISM: Lactobacillus plantarum

<400> SEQUENCE: 40

Met Ile Met Ser Glu Thr Leu Thr Lys Thr Thr Thr Ile Asn His
1               5                   10                  15

Phe Gly Lys Leu Thr Pro Met Met Asp Arg Leu Arg Asp Ser Ile Ile
            20                  25                  30

Asp Ala Lys Pro Tyr Val Asp Pro Glu Arg Ala Ile Leu Thr Thr Glu
        35                  40                  45

Thr Tyr Arg Gln His Gln Asp Glu Gln Val Asp Ile Leu Arg Ala Lys
    50                  55                  60

Met Leu Glu His Val Leu Asp Lys Met Ser Ile Phe Ile Glu Asp Asp
65                  70                  75                  80

Thr Leu Ile Val Gly Asn Gln Ala Arg Gln Asn Arg Trp Ala Pro Val
                85                  90                  95

-continued

```
Phe Pro Glu Tyr Ser Met Asn Trp Val Ile Asp Glu Leu Asp Thr Phe
                100                 105                 110

Glu Lys Arg Pro Gly Asp Val Phe Tyr Ile Thr Glu Lys Ser Lys Glu
            115                 120                 125

Glu Leu Arg Ala Ile Ala Pro Phe Trp Lys His Asn Thr Leu Glu Asp
        130                 135                 140

Arg Gly Tyr Ala Ser Phe Pro Glu Ala Ser Arg Ile Phe Tyr Asp Leu
145                 150                 155                 160

Gly Ile Ile Gly Ala Asp Gly Asn Ile Thr Ser Gly Asp Gly His Ile
                165                 170                 175

Ala Val Asp Tyr Lys Asn Val Val Asn Lys Gly Leu Lys Trp Tyr Glu
            180                 185                 190

Asp Arg Ile Lys Thr Ala Leu Ala Asn Leu Asp Leu Thr Asp Phe Asn
        195                 200                 205

Gln Gln Lys Gln Tyr Tyr Phe Tyr Lys Ala Gly Leu Ile Val Ile Asp
    210                 215                 220

Ala Ile His Asn Phe Ala Lys Arg Tyr Ala Gln Leu Ala Ser Lys Gln
225                 230                 235                 240

Ala Gln Asn Thr Thr Ser Ala Thr Arg Lys Ala Gln Leu Glu Lys Ile
                245                 250                 255

Ala Gln Ile Leu Asn Lys Val Pro Tyr Glu Pro Ala Asn Ser Phe Tyr
            260                 265                 270

Glu Ala Ile Gln Ala Val Trp Leu Val His Leu Thr Leu Gln Ile Glu
        275                 280                 285

Ser Asn Gly His Ser Val Ser Tyr Gly Arg Leu Asp Gln Tyr Leu Ala
    290                 295                 300

Pro Phe Tyr Glu His Asp Leu Lys Thr Gly Ala Ile Asp Ala Asn Gly
305                 310                 315                 320

Ala Thr Glu Leu Leu Thr Asn Leu Cys Leu Lys Thr Leu Thr Ile Asn
                325                 330                 335

Lys Val Arg Ser Trp Gln His Thr Glu Phe Ser Ala Gly Ser Pro Leu
            340                 345                 350

Tyr Gln Asn Ile Thr Ile Gly Gly Gln Thr Pro Asp Gly Lys Asp Ala
        355                 360                 365

Val Asn Pro Thr Ser Tyr Leu Ile Leu Arg Ala Ile Ala Gln Ala His
370                 375                 380

Leu Pro Gln Pro Asn Leu Thr Val Arg Tyr His His Gly Leu Ser Asp
385                 390                 395                 400

Lys Phe Met Arg Glu Cys Val Glu Val Ile Lys Gln Gly Leu Gly Met
                405                 410                 415

Pro Ala Phe Asn Asn Asp Glu Ile Ile Pro Ser Phe Ile Arg Arg
            420                 425                 430

Gly Val Lys Lys Glu Asp Ala Tyr Asn Tyr Ser Ala Ile Gly Cys Val
        435                 440                 445

Glu Thr Ala Ile Pro Gly Lys Trp Gly Tyr Arg Cys Thr Gly Met Ser
    450                 455                 460

Phe Ile Asn Phe Pro Arg Val Leu Leu Ile Met Asn Gly Gly Ile
465                 470                 475                 480

Asp Pro Glu Ser Gly Lys Arg Leu Leu Pro Asp Tyr Gly Lys Phe Thr
                485                 490                 495

Asp Met Thr Ser Phe Asp Gln Leu Met Thr Ala Trp Asp Lys Ala Leu
            500                 505                 510

Arg Glu Met Thr Arg Gln Ser Val Ile Ile Glu Asn Ser Cys Asp Leu
```

|     |     | 515 |     |     | 520 |     |     | 525 |     |     |     |
| --- | --- | --- | --- | --- | --- | --- | --- | --- | --- | --- | --- |
| Ala | Leu | Glu | Gln | Asn | Tyr | Pro | Asp | Ile | Leu | Cys | Ser | Val | Leu | Thr | Asp |

Ala Leu Glu Gln Asn Tyr Pro Asp Ile Leu Cys Ser Val Leu Thr Asp
                530                 535                 540

Asp Cys Ile Gly Arg Gly Lys Thr Ile Lys Glu Gly Gly Ala Val Tyr
545                 550                 555                 560

Asp Phe Ile Ser Gly Leu Gln Val Gly Ile Ala Asn Leu Ala Asp Ser
                565                 570                 575

Leu Ala Ala Ile Lys Lys Leu Val Phe Glu Glu Lys Lys Leu Thr Thr
                580                 585                 590

Thr Gln Leu Trp His Ala Leu Thr Thr Asp Phe Ala Asp Glu Asp Gly
                595                 600                 605

Glu Lys Ile Arg Gln Met Leu Ile Asn Asp Ala Pro Lys Tyr Gly Asn
610                 615                 620

Asp Asp Asp Tyr Val Asp Asp Leu Ile Val Glu Ala Tyr Lys Pro Tyr
625                 630                 635                 640

Ile Asp Glu Ile Ala Lys Tyr Lys Asn Thr Arg Tyr Gly Arg Gly Pro
                645                 650                 655

Ile Gly Gly Leu Arg Tyr Ala Gly Thr Ser Ser Ile Ser Ala Asn Val
                660                 665                 670

Gly Gln Gly His Ser Thr Leu Ala Thr Pro Asp Gly Arg His Ala Arg
                675                 680                 685

Thr Pro Leu Ala Glu Gly Cys Ser Pro Glu His Ala Met Asp Thr Asp
                690                 695                 700

Gly Pro Thr Ala Val Phe Lys Ser Val Ser Lys Leu Ser Thr Lys Asp
705                 710                 715                 720

Ile Thr Gly Gly Val Leu Leu Asn Gln Lys Met Ser Pro Gln Ile Leu
                725                 730                 735

Arg Ser Asp Glu Ser Cys Met Lys Leu Val Ala Leu Leu Arg Thr Phe
                740                 745                 750

Phe Asn Arg Leu His Gly Tyr His Val Gln Tyr Asn Ile Val Ser Arg
                755                 760                 765

Asp Thr Leu Ile Asp Ala Gln Asn His Pro Asp Lys His Arg Asp Leu
                770                 775                 780

Ile Val Arg Val Ala Gly Tyr Ser Ala Phe Phe Val Gly Leu Ser Lys
785                 790                 795                 800

Glu Thr Gln Asp Asp Ile Ile Glu Arg Thr Glu Gln Ser Leu
                805                 810

<210> SEQ ID NO 41
<211> LENGTH: 2256
<212> TYPE: DNA
<213> ORGANISM: Lactobacillus plantarum

<400> SEQUENCE: 41

```
atgattacat cagaaaagac aacaaaacca gcagcttgga aaggtttcaa aggcgggcac      60
tggcaggaag aaatcaacat tcgtgatttt attcaaaata acttcacaca gtacaatggc     120
gacgaaagct tcctggccgg accaacagcc gctactaaga ccttgaatga caaagtctta     180
gaattaaaga acaagaacg tgccgctggt ggtgtgttgg atgctgatac taaagtcgtt      240
gcaacgatta cttcacacgg ccctggttat attcaaaaag atctcgaaaa gattgttggt     300
ctccagactg acaagccttt gaagcgggcc ttcatgccat tggtggtat  tcgaatggct     360 gatgacgctt tgaaatcata cggttatacc cctgatgaag aaaacgacaa gattttcact     420
gaatatcgca agactcataa ccaaggcgtc ttcgatgttt atactcctga catgcggaaa     480
```

-continued

```
gcacgtcact acaagatcat caccggacta ccagatgcat acgcacgtgg ccgtctcatt    540
cctgatcttc cacgggtcgc tgtttatggg atcgatcgtt taatggaaga caaagctaat    600
gactttgccc acattggtga tggtgaattg actgatgatg ttattcgcct ccgtgaagaa    660
gttcaagatc aataccgtgc tttagcagat atgaagaaga tggctgccag ttatggctac    720
gatattagca agcctgcaac taatgctcaa gaagctattc aatggatgta cttcgcttac    780
ttagctgcta tcaagaccca aaacggcgct gcaatgtccg ttggccggat tgatacaacg    840
atggacatct tcatccaacg tgacttggac aatggtgttc tggacgaaag ccaagctcaa    900
gaattaattg atcaattcgt catgaaaacta cggatggttc ggttcatccg tactgaagaa    960
tacaattctc tcttctctgg tgacccaatc tgggcaacct tatcaatgtg tggtttaggc   1020
gtcgacggtc aacaccatgt gactaagact gctttccgga ttttaaagac tttgacaac    1080
atgggcgccg caccagaacc aaacatcacg atttttatggt cagaccgctt accagaagac   1140
ttcaaacgtt acgcaactga agtttcaatc gacagttcaa ccattcagta tgaaaatgat   1200
gacttgatgc gggtacaatg gggtaccgat tattatggca ttgcttgctg tgtttccgca   1260
caaccaattg ctgatggaat ccagtacttc ggtgcccggg caaacttagc caaagcgatt   1320
ctttatgcca tcaatggtgg ccgcgacgaa attgctggag atcaagttgg ccctgcttac   1380
gaaccaatta cttcagaata catcgattac gacgaattca tgaagaaatt agacaagcaa   1440
atggattggt tagctgacac ttacgttaac tcactgaatg caattcatta tatgcatgat   1500
aagtactact atgaagctgc ccaattagct ttgaagaata ctgatcttga tcggacccttt   1560
gcaactggga tttctggctt atcacatgcc gcggattcaa tctcagctat caagtatggt   1620
cacgttaaag taattcgtga cgaacgtggt atcgccgttg acttcaaagc cgacaatgac   1680
tacccacgtt atgggaacaa tgacgatcgc gctgatgaca ttgctaaatg gttagtcaaa   1740
gaattataca gcaagatgaa cacgcatcac ctctatcgga atgccaaact ttcaacttct   1800
gttttgacga ttacctccaa cgttgtttat ggtaagaaca ctggtaccac gccaaatggc   1860
cgtcaaaaag cgaaccatt ctcaccaggt gctaaccctg catacggtgc tgaaaagagt   1920
ggtgcattag cttcacttct ttcaactgcc aaattaccat accgttacgc aactgacggg   1980
atttccaaca cgttcggcgt tacccctaac acgttaggcc atgacctcga atcacggaaa   2040
gacacgttag taaacatgtt agacggttac atgaagaacg atgggatgca cttgaacatc   2100
aacgtcttca ataaagacac tttgattgat gctcagaaac accctgaaga atacccaaca   2160
ttaacggttc gggtttctgg ctattgtgtc tacttcgcag atttaaccaa ggaacaacaa   2220
gatgacgtta tttcacggac attcttcgaa tcaatg                              2256
```

```
<210> SEQ ID NO 42
<211> LENGTH: 752
<212> TYPE: PRT
<213> ORGANISM: Lactobacillus plantarum

<400> SEQUENCE: 42

Met Ile Thr Ser Glu Lys Thr Thr Lys Pro Ala Ala Trp Lys Gly Phe
1               5                   10                  15

Lys Gly Gly His Trp Gln Glu Glu Ile Asn Ile Arg Asp Phe Ile Gln
            20                  25                  30

Asn Asn Phe Thr Gln Tyr Asn Gly Asp Glu Ser Phe Leu Ala Gly Pro
        35                  40                  45

Thr Ala Ala Thr Lys Thr Leu Asn Asp Lys Val Leu Glu Leu Lys Lys
```

```
                50                  55                  60
Gln Glu Arg Ala Ala Gly Gly Val Leu Asp Ala Asp Thr Lys Val Val
 65                  70                  75                  80

Ala Thr Ile Thr Ser His Gly Pro Gly Tyr Ile Gln Lys Asp Leu Glu
                 85                  90                  95

Lys Ile Val Gly Leu Gln Thr Asp Lys Pro Leu Lys Arg Ala Phe Met
            100                 105                 110

Pro Phe Gly Gly Ile Arg Met Ala Asp Asp Ala Leu Lys Ser Tyr Gly
            115                 120                 125

Tyr Thr Pro Asp Glu Glu Asn Asp Lys Ile Phe Thr Glu Tyr Arg Lys
        130                 135                 140

Thr His Asn Gln Gly Val Phe Asp Val Tyr Thr Pro Asp Met Arg Lys
145                 150                 155                 160

Ala Arg His Tyr Lys Ile Ile Thr Gly Leu Pro Asp Ala Tyr Ala Arg
                165                 170                 175

Gly Arg Leu Ile Pro Asp Leu Pro Arg Val Ala Val Tyr Gly Ile Asp
            180                 185                 190

Arg Leu Met Glu Asp Lys Ala Asn Asp Phe Ala His Ile Gly Asp Gly
        195                 200                 205

Glu Leu Thr Asp Asp Val Ile Arg Leu Arg Glu Glu Val Gln Asp Gln
210                 215                 220

Tyr Arg Ala Leu Ala Asp Met Lys Lys Met Ala Ala Ser Tyr Gly Tyr
225                 230                 235                 240

Asp Ile Ser Lys Pro Ala Thr Asn Ala Gln Glu Ala Ile Gln Trp Met
                245                 250                 255

Tyr Phe Ala Tyr Leu Ala Ala Ile Lys Thr Gln Asn Gly Ala Ala Met
            260                 265                 270

Ser Val Gly Arg Ile Asp Thr Thr Met Asp Ile Phe Ile Gln Arg Asp
        275                 280                 285

Leu Asp Asn Gly Val Leu Asp Glu Ser Gln Ala Gln Glu Leu Ile Asp
    290                 295                 300

Gln Phe Val Met Lys Leu Arg Met Val Arg Phe Ile Arg Thr Glu Glu
305                 310                 315                 320

Tyr Asn Ser Leu Phe Ser Gly Asp Pro Ile Trp Ala Thr Leu Ser Met
                325                 330                 335

Cys Gly Leu Gly Val Asp Gly Gln His His Val Thr Lys Thr Ala Phe
            340                 345                 350

Arg Ile Leu Lys Thr Leu Asp Asn Met Gly Ala Ala Pro Glu Pro Asn
        355                 360                 365

Ile Thr Ile Leu Trp Ser Asp Arg Leu Pro Glu Asp Phe Lys Arg Tyr
    370                 375                 380

Ala Thr Glu Val Ser Ile Asp Ser Ser Thr Ile Gln Tyr Glu Asn Asp
385                 390                 395                 400

Asp Leu Met Arg Val Gln Trp Gly Thr Asp Tyr Tyr Gly Ile Ala Cys
                405                 410                 415

Cys Val Ser Ala Gln Pro Ile Ala Asp Gly Ile Gln Tyr Phe Gly Ala
            420                 425                 430

Arg Ala Asn Leu Ala Lys Ala Ile Leu Tyr Ala Ile Asn Gly Gly Arg
        435                 440                 445

Asp Glu Ile Ala Gly Asp Gln Val Gly Pro Ala Tyr Glu Pro Ile Thr
    450                 455                 460

Ser Glu Tyr Ile Asp Tyr Asp Glu Phe Met Lys Lys Leu Asp Lys Gln
465                 470                 475                 480
```

```
Met Asp Trp Leu Ala Asp Thr Tyr Val Asn Ser Leu Asn Ala Ile His
                485                 490                 495

Tyr Met His Asp Lys Tyr Tyr Glu Ala Ala Gln Leu Ala Leu Lys
            500                 505                 510

Asn Thr Asp Leu Asp Arg Thr Phe Ala Thr Gly Ile Ser Gly Leu Ser
                515                 520                 525

His Ala Ala Asp Ser Ile Ser Ala Ile Lys Tyr Gly His Val Lys Val
                530                 535                 540

Ile Arg Asp Glu Arg Gly Ile Ala Val Asp Phe Lys Ala Asp Asn Asp
545                 550                 555                 560

Tyr Pro Arg Tyr Gly Asn Asn Asp Asp Arg Ala Asp Asp Ile Ala Lys
                565                 570                 575

Trp Leu Val Lys Glu Leu Tyr Ser Lys Met Asn Thr His His Leu Tyr
                580                 585                 590

Arg Asn Ala Lys Leu Ser Thr Ser Val Leu Thr Ile Thr Ser Asn Val
                595                 600                 605

Val Tyr Gly Lys Asn Thr Gly Thr Pro Asn Gly Arg Gln Lys Gly
                610                 615                 620

Glu Pro Phe Ser Pro Gly Ala Asn Pro Ala Tyr Gly Ala Glu Lys Ser
625                 630                 635                 640

Gly Ala Leu Ala Ser Leu Leu Ser Thr Ala Lys Leu Pro Tyr Arg Tyr
                645                 650                 655

Ala Thr Asp Gly Ile Ser Asn Thr Phe Gly Val Thr Pro Asn Thr Leu
                660                 665                 670

Gly His Asp Leu Glu Ser Arg Lys Asp Thr Leu Val Asn Met Leu Asp
                675                 680                 685

Gly Tyr Met Lys Asn Asp Gly Met His Leu Asn Ile Asn Val Phe Asn
                690                 695                 700

Lys Asp Thr Leu Ile Asp Ala Gln Lys His Pro Glu Glu Tyr Pro Thr
705                 710                 715                 720

Leu Thr Val Arg Val Ser Gly Tyr Cys Val Tyr Phe Ala Asp Leu Thr
                725                 730                 735

Lys Glu Gln Gln Asp Asp Val Ile Ser Arg Thr Phe Phe Glu Ser Met
                740                 745                 750

<210> SEQ ID NO 43
<211> LENGTH: 801
<212> TYPE: DNA
<213> ORGANISM: Lactobacillus plantarum

<400> SEQUENCE: 43
atgccaacga tcacaactaa gacgcccgta aaaggactaa tatttaacat tcaaaaattt      60
agtatcaatg atggaccagg tattcgaaca gtagttttct ttaaagggtg cccgttacgc     120
tgcaagtggt gttctaatcc agaatcacaa tcaggtgagc aagaatcaat gtatgatgaa     180
cagaccgcca agcaaaccat cgtcggtgat tatatgacgg ttgatgatat tatgaaagtt     240
attctacaag ataaagactt ctatgaagag tctggcggtg gggtaacctt ctctggtggt     300
gaagttcttt ttcaagcttc ctttgcgatt gagcttgcta aggcagttaa agcagctggc     360
attaatttag cctgtgagac aactggttac gcacggccta aggttttaa tgaattcatg     420 tcttatatgg acttcatgta ttatgactgt aaacaatggg acccagccca acatcgaatc     480
ggaacgggtg ccgataacgg ggtaatttta cgtaacttag caactgcagt gcaagctcat     540
caaaagatga tggttcggat tccggttatt ccaggtttta attatacatt gaatgacgcg     600
```

```
gatcattttg  dacaactatt  taatcagatt  ggcgtaaccg  aagttgaatt  attgccattt    660
caccagtttg  ggttgaaaaa  gtatcaagat  ttgggccgaa  aatatgcgct  agttaatgtt    720
aaacagttac  aagcggatga  cttaattgat  tatgctgaac  atattcgtgc  acatggtgtt    780
aaagtacggg  tgaatgggtg  g                                                 801
```

<210> SEQ ID NO 44
<211> LENGTH: 267
<212> TYPE: PRT
<213> ORGANISM: Lactobacillus plantarum

<400> SEQUENCE: 44

```
Met Pro Thr Ile Thr Thr Lys Thr Pro Val Lys Gly Leu Ile Phe Asn
1               5                   10                  15

Ile Gln Lys Phe Ser Ile Asn Asp Gly Pro Gly Ile Arg Thr Val Val
            20                  25                  30

Phe Phe Lys Gly Cys Pro Leu Arg Cys Lys Trp Cys Ser Asn Pro Glu
        35                  40                  45

Ser Gln Ser Gly Glu Gln Glu Ser Met Tyr Asp Glu Gln Thr Ala Lys
    50                  55                  60

Gln Thr Ile Val Gly Asp Tyr Met Thr Val Asp Asp Ile Met Lys Val
65                  70                  75                  80

Ile Leu Gln Asp Lys Asp Phe Tyr Glu Glu Ser Gly Gly Gly Val Thr
                85                  90                  95

Phe Ser Gly Gly Glu Val Leu Phe Gln Ala Ser Phe Ala Ile Glu Leu
            100                 105                 110

Ala Lys Ala Val Lys Ala Ala Gly Ile Asn Leu Ala Cys Glu Thr Thr
        115                 120                 125

Gly Tyr Ala Arg Pro Lys Val Phe Asn Glu Phe Met Ser Tyr Met Asp
    130                 135                 140

Phe Met Tyr Tyr Asp Cys Lys Gln Trp Asp Pro Ala Gln His Arg Ile
145                 150                 155                 160

Gly Thr Gly Ala Asp Asn Gly Val Ile Leu Arg Asn Leu Ala Thr Ala
                165                 170                 175

Val Gln Ala His Gln Lys Met Met Val Arg Ile Pro Val Ile Pro Gly
            180                 185                 190

Phe Asn Tyr Thr Leu Asn Asp Ala Asp His Phe Gly Gln Leu Phe Asn
        195                 200                 205

Gln Ile Gly Val Thr Glu Val Glu Leu Leu Pro Phe His Gln Phe Gly
    210                 215                 220

Leu Lys Lys Tyr Gln Asp Leu Gly Arg Lys Tyr Ala Leu Val Asn Val
225                 230                 235                 240

Lys Gln Leu Gln Ala Asp Asp Leu Ile Asp Tyr Ala Glu His Ile Arg
                245                 250                 255

Ala His Gly Val Lys Val Arg Val Asn Gly Trp
            260                 265
```

<210> SEQ ID NO 45
<211> LENGTH: 819
<212> TYPE: DNA
<213> ORGANISM: Lactobacillus plantarum

<400> SEQUENCE: 45

```
atggaaaaca  aacagttttc  aacaacgcaa  gcggcggcaa  aggagccttt  gataggctac     60
gttcactcca  tcgaaacgtt  tggctccgtt  gacggaccag  gtatccgtta  cgtggcattc    120
```

```
cttcaaggat gccacatgcg ttgccaatac tgtcacaacc ctgatacttg gaaactcaac      180
gttggcgatc aaatgacggc cgacgagatt ctcgaagacg cggctaaata ccgggctttc      240
tggggcaaga cgggtggcat cacagtcagt ggtggtgaat cactggtaca aatcgacttc      300
atcttagact tattcgaaaa agccaaggcg atgaatatca gtacttgtct ggatacctct      360
ggacagcctt ttacccgaga acaacctttc tttgacaagt tcgaacgtct aatgaaggtc      420
acggacattt cgttggtcga cattaagcac atcgattctg ccaaacacaa gcagttgacc      480
cagtatggga acgaaaatat cttggatatg attcagtaca tggcccaaca ccacgatgat      540
atgtggattc gtcacgtcct ggttccccaa cggactgatt acgatgaaga cttgaagaaa      600
ctcggcgatt acattgctaa aattccaaac gacgtcgttc aaaaagtcga agtattgccg      660
taccatactt tgggcgttaa aaaatatcat gaaatgaaga tcaagtaccg gcttgaagga      720
atcgagtctc aacccaaga tcgggtggca aatgccgaaa agctactgca cactgctgat      780
tacaacgggt acaagacatg gatgccattg ccaaaactt                            819
```

<210> SEQ ID NO 46
<211> LENGTH: 273
<212> TYPE: PRT
<213> ORGANISM: Lactobacillus plantarum

<400> SEQUENCE: 46

```
Met Glu Asn Lys Gln Val Ser Thr Thr Gln Ala Ala Lys Glu Pro
1               5                   10                  15

Leu Ile Gly Tyr Val His Ser Ile Glu Thr Phe Gly Ser Val Asp Gly
                20                  25                  30

Pro Gly Ile Arg Tyr Val Ala Phe Leu Gln Gly Cys His Met Arg Cys
            35                  40                  45

Gln Tyr Cys His Asn Pro Asp Thr Trp Lys Leu Asn Val Gly Asp Gln
        50                  55                  60

Met Thr Ala Asp Glu Ile Leu Glu Asp Ala Ala Lys Tyr Arg Ala Phe
65                  70                  75                  80

Trp Gly Lys Thr Gly Gly Ile Thr Val Ser Gly Gly Glu Ser Leu Val
                85                  90                  95

Gln Ile Asp Phe Ile Leu Asp Leu Phe Glu Lys Ala Lys Ala Met Asn
            100                 105                 110

Ile Ser Thr Cys Leu Asp Thr Ser Gly Gln Pro Phe Thr Arg Glu Gln
        115                 120                 125

Pro Phe Phe Asp Lys Phe Glu Arg Leu Met Lys Val Thr Asp Ile Ser
    130                 135                 140

Leu Val Asp Ile Lys His Ile Asp Ser Ala Lys His Lys Gln Leu Thr
145                 150                 155                 160

Gln Tyr Gly Asn Glu Asn Ile Leu Asp Met Ile Gln Tyr Met Ala Gln
                165                 170                 175

His His Asp Asp Met Trp Ile Arg His Val Leu Val Pro Gln Arg Thr
            180                 185                 190

Asp Tyr Asp Glu Asp Leu Lys Lys Leu Gly Asp Tyr Ile Ala Lys Ile
        195                 200                 205

Pro Asn Asp Val Val Gln Lys Val Glu Val Leu Pro Tyr His Thr Leu
    210                 215                 220

Gly Val Lys Lys Tyr His Glu Met Lys Ile Lys Tyr Arg Leu Glu Gly
225                 230                 235                 240

Ile Glu Ser Pro Thr Gln Asp Arg Val Ala Asn Ala Glu Lys Leu Leu
```

|  |  | 245 |  |  |  | 250 |  |  |  | 255 |  |
| --- | --- | --- | --- | --- | --- | --- | --- | --- | --- | --- | --- |
| His | Thr | Ala | Asp | Tyr | Asn | Gly | Tyr | Lys | Thr | Trp | Met Pro Leu Pro Lys |
|  |  | 260 |  |  |  | 265 |  |  |  | 270 |  |

Leu

<210> SEQ ID NO 47
<211> LENGTH: 2361
<212> TYPE: DNA
<213> ORGANISM: Lactococcus lactis

<400> SEQUENCE: 47

```
atgaaaaccg aagttacgga aaatatcttt gaacaagctt gggatggttt taaaggaacc      60
aactggcgcg ataaagcaag cgttactcgc tttgtacaag aaaactacaa accatatgat     120
ggtgatgaaa gctttcttgc tgggccaaca gaacgtacac ttaaagtaaa gaaaattatt     180
gaagatacaa aaatcactac gaagaagta ggatttccct tcgatactga ccgcgtaacc     240
tctattgata aatccctgc tggatatatc gatgctaatg ataaagaact tgaactcatc     300
tatgggatgc aaaatagcga acttttccgc ttgaatttca tgccaagagg tggacttcgt     360
gttgctgaaa agattttgac agaacacggt ctctcagttg acccaggctt gcatgatgtt     420
ttgtcacaaa caatgacttc tgtaaatgat ggaatctttc gtgcttatac ttcagcaatt     480
cgtaaagcac gtcatgctca tactgtaaca ggtttgccag atgcttactc tcgtggacgt     540
atcattggtg tctatgcacg tcttgccctt tacggtgctg attaccttat gaaggaaaaa     600
gcaaaagaat gggatgcaat cactgaaatt aacgaagaaa acattcgtct taaagaagaa     660
attaatatgc aataccaagc tttgcaagaa gttgtaaact ttggtgcttt atatggtctt     720
gatgtttcac gtccagctat gaacgtaaaa gaagcaatcc aatgggttaa catcgcttat     780
atggcagtat gtcgtgtcat taatggagct gcaacttcac ttgacgtgt tccaatcgtt     840
cttgatatct ttgcagaacg tgaccttgct cgtggaacat ttactgaaca gaaaattcaa     900
gaatttgttg atgatttcgt tttgaagctt cgtacaatga atttgcgcg tgcagctgct     960
tatgatgaac tttattctgg tgacccaaca ttcatcacaa catctatggc tggtatgggt    1020
aatgacggac gtcaccgtgt cactaaaatg gactaccgtt tcttgaacac acttgataca    1080
atcggaaatg ctccagaacc aaacttgaca gtcctttggg attctaaact tccttactca    1140
ttcaaacgtt attcaatgtc tatgagccac aagcattctt ctattcaata tgaaggtgtt    1200
gaaacaatgg ctaaagatgg atatggcgaa atgtcatgta tctcttgttg tgtctcacca    1260
cttgatccag aaaatgaaga aggacgtcat aacctccaat actttggtgc gcgtgtaaac    1320
gtcttgaaag caatgttgac tggtttgaac ggtggttatg atgacgttca taaagattat    1380
aaagtattcg acatcgaacc tgttcgtgac gaaattcttg actatgatac agttatggaa    1440
aactttgaca atctctcga ctggttgact gatacttatg ttgatgcaat gaatatcatt    1500
cattacatga ctgataaata taactatgaa gcagttcaaa tggccttctt gcctactaaa    1560
gttcgtgcta acatgggatt tggtatctgt ggattcgcaa atacagttga ttcactttca    1620
gcaattaaat atgctaaagt taaaacattg cgtgatgaaa atggctatat ctacgattac    1680
gaagtagaag gtgatttccc tcgttatggt aaagatgatg atcgtgctga tgatattgct    1740
aaacttgtca tgaaaatgta ccatgaaaaa ttagcttcac acaaacttta caaaaatgct    1800
gaagctactg tttcactttt gacaattaca tctaacgttg cttactctaa acaaactggt    1860
aattctccag tacataaagg agtattcctc aatgaagatg gtacagtaaa taatctaaa    1920
```

```
cttgaattct tctcaccagg tgctaaccca tctaataaag ctaagggtgg ttggttgcaa    1980
aatcttcgct cattggctaa gttggaattc aaagatgcaa atgatggtat ttcattgact    2040
actcaagttt cacctcgtgc acttggtaaa actcgtgatg aacaagtgga taacttggtt    2100
caaattcttg atggatactt cacaccaggt gctttgatta atggtactga atttgcaggt    2160
caacacgtta acttgaacgt aatggacctt aaagatgttt acgataaaat catgcgtggt    2220
gaagatgtta tcgttcgtat ctctggttac tgtgtcaata ctaaatacct cacaccagaa    2280
caaaaacaag aattaactga acgtgtcttc catgaagttc tttcaaacga tgatgaagaa    2340
gtaatgcata cttcaaacat c                                              2361
```

<210> SEQ ID NO 48
<211> LENGTH: 787
<212> TYPE: PRT
<213> ORGANISM: Lactococcus lactis
<400> SEQUENCE: 48

```
Met Lys Thr Glu Val Thr Glu Asn Ile Phe Glu Gln Ala Trp Asp Gly
1               5                   10                  15

Phe Lys Gly Thr Asn Trp Arg Asp Lys Ala Ser Val Thr Arg Phe Val
            20                  25                  30

Gln Glu Asn Tyr Lys Pro Tyr Asp Gly Asp Glu Ser Phe Leu Ala Gly
        35                  40                  45

Pro Thr Glu Arg Thr Leu Lys Val Lys Ile Ile Glu Asp Thr Lys
    50                  55                  60

Asn His Tyr Glu Val Gly Phe Pro Phe Asp Thr Asp Arg Val Thr
65                  70                  75                  80

Ser Ile Asp Lys Ile Pro Ala Gly Tyr Ile Asp Ala Asn Asp Lys Glu
                85                  90                  95

Leu Glu Leu Ile Tyr Gly Met Gln Asn Ser Glu Leu Phe Arg Leu Asn
            100                 105                 110

Phe Met Pro Arg Gly Gly Leu Arg Val Ala Glu Lys Ile Leu Thr Glu
        115                 120                 125

His Gly Leu Ser Val Asp Pro Gly Leu His Asp Val Leu Ser Gln Thr
    130                 135                 140

Met Thr Ser Val Asn Asp Gly Ile Phe Arg Ala Tyr Thr Ser Ala Ile
145                 150                 155                 160

Arg Lys Ala Arg His Ala His Thr Val Thr Gly Leu Pro Asp Ala Tyr
                165                 170                 175

Ser Arg Gly Arg Ile Ile Gly Val Tyr Ala Arg Leu Ala Leu Tyr Gly
            180                 185                 190

Ala Asp Tyr Leu Met Lys Glu Lys Ala Lys Glu Trp Asp Ala Ile Thr
        195                 200                 205

Glu Ile Asn Glu Glu Asn Ile Arg Leu Lys Glu Glu Ile Asn Met Gln
    210                 215                 220

Tyr Gln Ala Leu Gln Glu Val Val Asn Phe Gly Ala Leu Tyr Gly Leu
225                 230                 235                 240

Asp Val Ser Arg Pro Ala Met Asn Val Lys Glu Ala Ile Gln Trp Val
                245                 250                 255

Asn Ile Ala Tyr Met Ala Val Cys Arg Val Ile Asn Gly Ala Ala Thr
            260                 265                 270

Ser Leu Gly Arg Val Pro Ile Val Leu Asp Ile Phe Ala Glu Arg Asp
        275                 280                 285

Leu Ala Arg Gly Thr Phe Thr Glu Gln Glu Ile Gln Glu Phe Val Asp
```

```
              290                 295                 300

Asp Phe Val Leu Lys Leu Arg Thr Met Lys Phe Ala Arg Ala Ala
305                 310                 315                 320

Tyr Asp Glu Leu Tyr Ser Gly Asp Pro Thr Phe Ile Thr Thr Ser Met
                    325                 330                 335

Ala Gly Met Gly Asn Asp Gly Arg His Arg Val Thr Lys Met Asp Tyr
                340                 345                 350

Arg Phe Leu Asn Thr Leu Asp Thr Ile Gly Asn Ala Pro Glu Pro Asn
            355                 360                 365

Leu Thr Val Leu Trp Asp Ser Lys Leu Pro Tyr Ser Phe Lys Arg Tyr
        370                 375                 380

Ser Met Ser Met Ser His Lys His Ser Ser Ile Gln Tyr Glu Gly Val
385                 390                 395                 400

Glu Thr Met Ala Lys Asp Gly Tyr Gly Glu Met Ser Cys Ile Ser Cys
                405                 410                 415

Cys Val Ser Pro Leu Asp Pro Glu Asn Glu Glu Gly Arg His Asn Leu
            420                 425                 430

Gln Tyr Phe Gly Ala Arg Val Asn Val Leu Lys Ala Met Leu Thr Gly
        435                 440                 445

Leu Asn Gly Gly Tyr Asp Asp Val His Lys Asp Tyr Lys Val Phe Asp
450                 455                 460

Ile Glu Pro Val Arg Asp Glu Ile Leu Asp Tyr Asp Thr Val Met Glu
465                 470                 475                 480

Asn Phe Asp Lys Ser Leu Asp Trp Leu Thr Asp Thr Tyr Val Asp Ala
                485                 490                 495

Met Asn Ile Ile His Tyr Met Thr Asp Lys Tyr Asn Tyr Glu Ala Val
                500                 505                 510

Gln Met Ala Phe Leu Pro Thr Lys Val Arg Ala Asn Met Gly Phe Gly
            515                 520                 525

Ile Cys Gly Phe Ala Asn Thr Val Asp Ser Leu Ser Ala Ile Lys Tyr
        530                 535                 540

Ala Lys Val Lys Thr Leu Arg Asp Glu Asn Gly Tyr Ile Tyr Asp Tyr
545                 550                 555                 560

Glu Val Glu Gly Asp Phe Pro Arg Tyr Gly Glu Asp Asp Arg Ala
                565                 570                 575

Asp Asp Ile Ala Lys Leu Val Met Lys Met Tyr His Glu Lys Leu Ala
            580                 585                 590

Ser His Lys Leu Tyr Lys Asn Ala Glu Ala Thr Val Ser Leu Leu Thr
        595                 600                 605

Ile Thr Ser Asn Val Ala Tyr Ser Lys Gln Thr Gly Asn Ser Pro Val
    610                 615                 620

His Lys Gly Val Phe Leu Asn Glu Asp Gly Thr Val Asn Lys Ser Lys
625                 630                 635                 640

Leu Glu Phe Phe Ser Pro Gly Ala Asn Pro Ser Asn Lys Ala Lys Gly
                645                 650                 655

Gly Trp Leu Gln Asn Leu Arg Ser Leu Ala Lys Leu Glu Phe Lys Asp
            660                 665                 670

Ala Asn Asp Gly Ile Ser Leu Thr Thr Gln Val Ser Pro Arg Ala Leu
        675                 680                 685

Gly Lys Thr Arg Asp Glu Gln Val Asp Asn Leu Val Gln Ile Leu Asp
    690                 695                 700

Gly Tyr Phe Thr Pro Gly Ala Leu Ile Asn Gly Thr Glu Phe Ala Gly
705                 710                 715                 720
```

Gln His Val Asn Leu Asn Val Met Asp Leu Lys Asp Val Tyr Asp Lys
            725                 730                 735

Ile Met Arg Gly Glu Asp Val Ile Val Arg Ile Ser Gly Tyr Cys Val
            740                 745                 750

Asn Thr Lys Tyr Leu Thr Pro Glu Gln Lys Gln Glu Leu Thr Glu Arg
            755                 760                 765

Val Phe His Glu Val Leu Ser Asn Asp Asp Glu Glu Val Met His Thr
    770                 775                 780

Ser Asn Ile
785

<210> SEQ ID NO 49
<211> LENGTH: 792
<212> TYPE: DNA
<213> ORGANISM: Lactococcus lactis

<400> SEQUENCE: 49

```
atgatgtcag agaatataga tgaacttaaa aaagttactg gactgattca ttcaactgaa      60
tcttttggtt ctgttgatgg ccctggggtc gtttttatta ttttcatgca aggctgtcgg     120
atgcgttgca atattgtca caaccctgat acttgggcat aaagtcaga taaagcgaca       180
gagcgtaccg tagaagatgt catggatgag gcacttcgtt ttagaggttt ttggggagag     240
aaaggtggaa ttaccgtttc tggtggtgag gcgctccttc aaattgactt tgtattagct     300
cttttcaaat atgcaaaatc tctcggtatt catacaacac ttgatacagc ggctcaacca     360
tatttgactg ataaatatgt aaccgaaaaa attgatgagt actagatta taccgactta     420
gtattattag acattaaaga ataaatcca gaacgacaca agaattgac agctaataaa       480
aacgataata tttagctttt tgcacagtat ttatcagacc gtggtaatgc aatgtgggtt     540
cgtcacgttc ttgttcctgg tgaaagtgat tttgatgaag atttagttca attaggtgaa     600
tttgtaaaaa ctttaaaaaa tgtcttgaaa tttgaaattt taccctacca tacaatgggt     660
gaatttaaat ggcgtgaatt aggttggaaa tatccgcttg aaggtgtgaa acctccaaca     720
aaagatcgtg ttcataatgc taaagaaatc atgaatacag aatcttatca agattactta     780
gaacgtataa ga                                                        792
```

<210> SEQ ID NO 50
<211> LENGTH: 264
<212> TYPE: PRT
<213> ORGANISM: Lactococcus lactis

<400> SEQUENCE: 50

Met Met Ser Glu Asn Ile Asp Glu Leu Lys Lys Val Thr Gly Leu Ile
1               5                   10                  15

His Ser Thr Glu Ser Phe Gly Ser Val Asp Gly Pro Gly Val Arg Phe
            20                  25                  30

Ile Ile Phe Met Gln Gly Cys Arg Met Arg Cys Lys Tyr Cys His Asn
        35                  40                  45

Pro Asp Thr Trp Ala Leu Lys Ser Asp Lys Ala Thr Glu Arg Thr Val
    50                  55                  60

Glu Asp Val Met Asp Glu Ala Leu Arg Phe Arg Gly Phe Trp Gly Glu
65                  70                  75                  80

Lys Gly Gly Ile Thr Val Ser Gly Gly Glu Ala Leu Leu Gln Ile Asp
            85                  90                  95

Phe Val Leu Ala Leu Phe Lys Tyr Ala Lys Ser Leu Gly Ile His Thr

```
              100                 105                 110
Thr Leu Asp Thr Ala Ala Gln Pro Tyr Leu Thr Asp Lys Tyr Val Thr
            115                 120                 125

Glu Lys Ile Asp Glu Leu Leu Asp Tyr Thr Asp Leu Val Leu Leu Asp
            130                 135                 140

Ile Lys Glu Ile Asn Pro Glu Arg His Lys Glu Leu Thr Ala Asn Lys
145                 150                 155                 160

Asn Asp Asn Ile Leu Ala Phe Ala Gln Tyr Leu Ser Asp Arg Gly Asn
                165                 170                 175

Ala Met Trp Val Arg His Val Leu Val Pro Gly Glu Ser Asp Phe Asp
            180                 185                 190

Glu Asp Leu Val Gln Leu Gly Glu Phe Val Lys Thr Leu Lys Asn Val
            195                 200                 205

Leu Lys Phe Glu Ile Leu Pro Tyr His Thr Met Gly Glu Phe Lys Trp
            210                 215                 220

Arg Glu Leu Gly Trp Lys Tyr Pro Leu Glu Gly Val Lys Pro Pro Thr
225                 230                 235                 240

Lys Asp Arg Val His Asn Ala Lys Glu Ile Met Asn Thr Glu Ser Tyr
                245                 250                 255

Gln Asp Tyr Leu Glu Arg Ile Arg
            260
```

<210> SEQ ID NO 51
<211> LENGTH: 2307
<212> TYPE: DNA
<213> ORGANISM: Streptococcus thermophilus

<400> SEQUENCE: 51

```
atggcaacgg ttaaaactaa cacagatgtt tttgaaaaag cgtgggaagg ctttaaagga    60
actgactgga agaaaaagc aagtgtgtct cgcttcgtac aagcaaacta cacaccatat    120
gatggtgatg aaagcttcct tgcaggacca actgaacgct cacttaaaat caaaaaaatc   180
attgaagaaa ctaaagctca ctacgaagaa actcgtttcc aatggatac tcgtccgaca    240
tcaatcgcag atattcctgc cggctatatt tcaaaagacg acgaactaat ctacggtatt    300
caaaatgatg agttattcaa attgaatttc atgccaaaag gcggaattcg tatggcagaa    360
acagctctca aggaacatgg ctatgaacct gatccagctg ttcacgaaat ttttacaaaa    420
catgtaacta cagtaaatga cggtatcttc cgtgcttata catcaaatat ccgtcgtgca    480
cgtcacgcac acactataac tggacttcca gatgcttact ctcgtggacg tatcatcggt    540
gtttatgctc gccttgctct ttacggtgct gacttcttga tgcaagaaaa agtaaacgac    600
tggaactcta tcgaagaaat caacgaagaa actattcgtc ttcgtgaaga gttaaccttt    660
caataccaag cacttcaaga tgttgttcgc cttggtgacc tttacggtgt agatgttcgt    720
cgtccagcct tcgatactaa agaagctatc aatggacaa acattgcttt tatggctgta    780
tgtcgtgtta tcaatggtgc ggctacttca cttggtcgtg tgccaatcgt ccttgacata    840
tatgcagaac gtgaccttgc tcgtggtact tacactgaat cagaaatcca agaattcgtt    900
gatgattttg tcttgaaact tcgtactgta aaattcgcac gtacaaaagc ttacgacgaa    960
ctttactcag gtgacccaac attcatcaca acttctatgg ctggtatggg tgctgacgga   1020
cgtcaccgtg ttactaaaat ggactaccgt tcttgaaca cacttgataa tattggtaat   1080
gctccagaac caaacttgac agttctttgg tctgacaaat tgcctactc attccgtcgc   1140
tactgtatgc acatgagtca caagcactct tctattcaat acgaaggtgt gactactatg   1200
```

-continued

```
gctaaagacg gatacggtga aatgagctgt atctcatgtt gtgtatcacc acttgaccca    1260
gaaaacgaag aacaacgcca caacatccaa tacttcggtg ctcgtgttaa cgtacttaaa    1320
gcccttctta ctggtttgaa cggtggttac gacgatgttc ataaagacta caaagtattt    1380
gacatcgatc cagtccgtga tgaagttctt gactttgaca ctgttaaagc taacttcgaa    1440
aaatctcttg actggttgac tgacacttat gtagatgccc ttaacatcat ccactacatg    1500
actgataagt acaactacga agctgttcaa atggccttct tgccaactaa caacgtgct     1560 aacatgggat tcggtatctg tggtttcgca atactgttg atacattgtc agctatcaag    1620
tacgctacag ttaaaccaat ccgtgacgaa gatggctaca tctacgacta cgaaacaatc    1680
ggtgaatacc cacgttgggg tgaagatgac ccacgttcaa acgaattggc agaatggttg    1740
attgaagctt acactactcg tcttcgtagc cataaactct acaaagatgc agaagctaca    1800
gtttcacttc ttacaatcac ttcgaacgtt gcttactcta acaaactgg taactctcca     1860 gttcacaaag gggtatacct caacgaagat ggttcagtga acttgtctaa attggaattc    1920
ttctcaccag gtgctaaccc atctaacaaa gctaaggtg atggttgca aaacttgaac     1980 tcacttgcaa gccttgactt cggttatgca gctgacggta tctcacttac tactcaagta    2040
tcacctcgtg cccttggtaa gactcgcgac gaacaagttg ataacctcgt aactatcctt    2100
gacggatact tcgaaaacgg tggacaacac cttaacttga acgttatgga cttgtcagct    2160
gtttacaaaa agatcatgag cggtgaagat gttatcgtac gtatctctgg atactgtgta    2220
aacactaaat acctcactcc agaacaaaaa actgaattga cacaacgtgt cttccacgaa    2280
gttctttcaa cggacgatgc tatggga                                        2307
```

<210> SEQ ID NO 52
<211> LENGTH: 769
<212> TYPE: PRT
<213> ORGANISM: Streptococcus thermophilus

<400> SEQUENCE: 52

```
Met Ala Thr Val Lys Thr Asn Thr Asp Val Phe Glu Lys Ala Trp Glu
1               5                   10                  15

Gly Phe Lys Gly Thr Asp Trp Lys Glu Lys Ala Ser Val Ser Arg Phe
            20                  25                  30

Val Gln Ala Asn Tyr Thr Pro Tyr Asp Gly Asp Glu Ser Phe Leu Ala
        35                  40                  45

Gly Pro Thr Glu Arg Ser Leu Lys Ile Lys Lys Ile Glu Glu Thr
    50                  55                  60

Lys Ala His Tyr Glu Glu Thr Arg Phe Pro Met Asp Thr Arg Pro Thr
65                  70                  75                  80

Ser Ile Ala Asp Ile Pro Ala Gly Tyr Ile Ser Lys Asp Asp Glu Leu
                85                  90                  95

Ile Tyr Gly Ile Gln Asn Asp Glu Leu Phe Lys Leu Asn Phe Met Pro
            100                 105                 110

Lys Gly Gly Ile Arg Met Ala Glu Thr Ala Leu Lys Glu His Gly Tyr
        115                 120                 125

Glu Pro Asp Pro Ala Val His Glu Ile Phe Thr Lys His Val Thr Thr
    130                 135                 140

Val Asn Asp Gly Ile Phe Arg Ala Tyr Thr Ser Asn Ile Arg Arg Ala
145                 150                 155                 160

Arg His Ala His Thr Ile Thr Gly Leu Pro Asp Ala Tyr Ser Arg Gly
                165                 170                 175
```

```
Arg Ile Ile Gly Val Tyr Ala Arg Leu Ala Leu Tyr Gly Ala Asp Phe
            180                 185                 190

Leu Met Gln Glu Lys Val Asn Asp Trp Asn Ser Ile Glu Glu Ile Asn
        195                 200                 205

Glu Glu Thr Ile Arg Leu Arg Glu Val Asn Leu Gln Tyr Gln Ala
        210                 215                 220

Leu Gln Asp Val Val Arg Leu Gly Asp Leu Tyr Gly Val Asp Val Arg
225                 230                 235                 240

Arg Pro Ala Phe Asp Thr Lys Glu Ala Ile Gln Trp Thr Asn Ile Ala
                245                 250                 255

Phe Met Ala Val Cys Arg Val Ile Asn Gly Ala Ala Thr Ser Leu Gly
            260                 265                 270

Arg Val Pro Ile Val Leu Asp Ile Tyr Ala Glu Arg Asp Leu Ala Arg
        275                 280                 285

Gly Thr Tyr Thr Glu Ser Glu Ile Gln Glu Phe Val Asp Asp Phe Val
        290                 295                 300

Leu Lys Leu Arg Thr Val Lys Phe Ala Arg Thr Lys Ala Tyr Asp Glu
305                 310                 315                 320

Leu Tyr Ser Gly Asp Pro Thr Phe Ile Thr Thr Ser Met Ala Gly Met
                325                 330                 335

Gly Ala Asp Gly Arg His Arg Val Thr Lys Met Asp Tyr Arg Phe Leu
            340                 345                 350

Asn Thr Leu Asp Asn Ile Gly Asn Ala Pro Glu Pro Asn Leu Thr Val
        355                 360                 365

Leu Trp Ser Asp Lys Leu Pro Tyr Ser Phe Arg Arg Tyr Cys Met His
        370                 375                 380

Met Ser His Lys His Ser Ser Ile Gln Tyr Glu Gly Val Thr Thr Met
385                 390                 395                 400

Ala Lys Asp Gly Tyr Gly Glu Met Ser Cys Ile Ser Cys Cys Val Ser
                405                 410                 415

Pro Leu Asp Pro Glu Asn Glu Glu Gln Arg His Asn Ile Gln Tyr Phe
            420                 425                 430

Gly Ala Arg Val Asn Val Leu Lys Ala Leu Leu Thr Gly Leu Asn Gly
        435                 440                 445

Gly Tyr Asp Asp Val His Lys Asp Tyr Lys Val Phe Asp Ile Asp Pro
        450                 455                 460

Val Arg Asp Glu Val Leu Asp Phe Asp Thr Val Lys Ala Asn Phe Glu
465                 470                 475                 480

Lys Ser Leu Asp Trp Leu Thr Asp Thr Tyr Val Asp Ala Leu Asn Ile
                485                 490                 495

Ile His Tyr Met Thr Asp Lys Tyr Asn Tyr Glu Ala Val Gln Met Ala
            500                 505                 510

Phe Leu Pro Thr Lys Gln Arg Ala Asn Met Gly Phe Gly Ile Cys Gly
        515                 520                 525

Phe Ala Asn Thr Val Asp Thr Leu Ser Ala Ile Lys Tyr Ala Thr Val
        530                 535                 540

Lys Pro Ile Arg Asp Glu Asp Gly Tyr Ile Tyr Asp Tyr Glu Thr Ile
545                 550                 555                 560

Gly Glu Tyr Pro Arg Trp Gly Glu Asp Pro Arg Ser Asn Glu Leu
                565                 570                 575

Ala Glu Trp Leu Ile Glu Ala Tyr Thr Thr Arg Leu Arg Ser His Lys
            580                 585                 590
```

```
Leu Tyr Lys Asp Ala Glu Ala Thr Val Ser Leu Leu Thr Ile Thr Ser
            595                 600                 605

Asn Val Ala Tyr Ser Lys Gln Thr Gly Asn Ser Pro Val His Lys Gly
        610                 615                 620

Val Tyr Leu Asn Glu Asp Gly Ser Val Asn Leu Ser Lys Leu Glu Phe
625                 630                 635                 640

Phe Ser Pro Gly Ala Asn Pro Ser Asn Lys Ala Lys Gly Gly Trp Leu
                645                 650                 655

Gln Asn Leu Asn Ser Leu Ala Ser Leu Asp Phe Gly Tyr Ala Ala Asp
            660                 665                 670

Gly Ile Ser Leu Thr Thr Gln Val Ser Pro Arg Ala Leu Gly Lys Thr
        675                 680                 685

Arg Asp Glu Gln Val Asp Asn Leu Val Thr Ile Leu Asp Gly Tyr Phe
690                 695                 700

Glu Asn Gly Gly Gln His Leu Asn Leu Asn Val Met Asp Leu Ser Ala
705                 710                 715                 720

Val Tyr Lys Lys Ile Met Ser Gly Glu Asp Val Ile Val Arg Ile Ser
                725                 730                 735

Gly Tyr Cys Val Asn Thr Lys Tyr Leu Thr Pro Glu Gln Lys Thr Glu
            740                 745                 750

Leu Thr Gln Arg Val Phe His Glu Val Leu Ser Thr Asp Asp Ala Met
        755                 760                 765

Gly

<210> SEQ ID NO 53
<211> LENGTH: 798
<212> TYPE: DNA
<213> ORGANISM: Streptococcus thermophilus

<400> SEQUENCE: 53
atggcagaaa ttgattacag tcaggtgact ggacttgttc attcaaccga aagtttcgga      60
tccgtagatg gtcctggtat ccgttttatt gtgtttatgc aaggctgtaa gctgcgttgc     120
caatattgtc ataacccaga tacttgggcc atgaagtcaa ataaggctgt tgaacgtaca     180
gttgaagatg tcttagaaga ggctcttcgc ttccgtcatt tctggggtga gcatggtgga     240
atcactgtat caggtggtga agccatgctt cagattgatt ttgtcactgc cctctttaca     300
gaggctaaga gttagggat tcactgtacg cttgatacgt gtggcttgtc ttatcgtaat     360
actccagagt atcatgaagt tgtcgacaaa cttttggctg taactgactt ggttctactg     420
gatatcaaag agattgaccc cgaacaacac aagtttgtga cccgtcaacc taataagaat     480
atcttggaat tgctcaata tctgtctgat aaacaagttc cggtctggat tcgtcatgtc     540
ttggtacctg gtttgacaga ttttgacgaa cacttggtta agctcggcga gtttgtaaag     600
accttgaaaa atgtcgataa atttgaaatt cttccatatc atacgatggg ggaattcaag     660
tggcgtgaac ttggcatccc ttatccattg aaggtgtca accaccaac tgcagatcgt     720
gttaaaaatg ctaaggctct tatgcatacg gaaacttatc aagagtataa gaatcgtatc     780
ggggttaaaa ccttggat                                                     798

<210> SEQ ID NO 54
<211> LENGTH: 266
<212> TYPE: PRT
<213> ORGANISM: Streptococcus thermophilus

<400> SEQUENCE: 54
```

Met Ala Glu Ile Asp Tyr Ser Gln Val Thr Gly Leu Val His Ser Thr
1               5                   10                  15
Glu Ser Phe Gly Ser Val Asp Gly Pro Gly Ile Arg Phe Ile Val Phe
            20                  25                  30
Met Gln Gly Cys Lys Leu Arg Cys Gln Tyr Cys His Asn Pro Asp Thr
        35                  40                  45
Trp Ala Met Lys Ser Asn Lys Ala Val Glu Arg Thr Val Glu Asp Val
50                  55                  60
Leu Glu Glu Ala Leu Arg Phe Arg His Phe Trp Gly Glu His Gly Gly
65                  70                  75                  80
Ile Thr Val Ser Gly Gly Glu Ala Met Leu Gln Ile Asp Phe Val Thr
                85                  90                  95
Ala Leu Phe Thr Glu Ala Lys Lys Leu Gly Ile His Cys Thr Leu Asp
                100                 105                 110
Thr Cys Gly Leu Ser Tyr Arg Asn Thr Pro Glu Tyr His Glu Val Val
            115                 120                 125
Asp Lys Leu Leu Ala Val Thr Asp Leu Val Leu Asp Ile Lys Glu
    130                 135                 140
Ile Asp Pro Glu Gln His Lys Phe Val Thr Arg Gln Pro Asn Lys Asn
145                 150                 155                 160
Ile Leu Glu Phe Ala Gln Tyr Leu Ser Asp Lys Gln Val Pro Val Trp
                165                 170                 175
Ile Arg His Val Leu Val Pro Gly Leu Thr Asp Phe Asp Glu His Leu
            180                 185                 190
Val Lys Leu Gly Glu Phe Val Lys Thr Leu Lys Asn Val Asp Lys Phe
        195                 200                 205
Glu Ile Leu Pro Tyr His Thr Met Gly Glu Phe Lys Trp Arg Glu Leu
        210                 215                 220
Gly Ile Pro Tyr Pro Leu Glu Gly Val Lys Pro Pro Thr Ala Asp Arg
225                 230                 235                 240
Val Lys Asn Ala Lys Ala Leu Met His Thr Glu Thr Tyr Gln Glu Tyr
                245                 250                 255
Lys Asn Arg Ile Gly Val Lys Thr Leu Asp
                260                 265

<210> SEQ ID NO 55
<211> LENGTH: 1716
<212> TYPE: DNA
<213> ORGANISM: Bacillus subtilis

<400> SEQUENCE: 55
atgttgacaa agcaacaaa agaacaaaaa tcccttgtga aaaacagagg ggcggagctt 60
gttgttgatt gcttagtgga gcaaggtgtc acacatgtat ttggcattcc aggtgcaaaa 120
attgatgcgg tatttgacgc tttacaagat aaaggacctg aaattatcgt tgcccggcac 180
gaacaaaacg cagcattcat ggcccaagca gtcggccgtt taactggaaa accgggagtc 240
gtgttagtca catcaggacc gggtgcctct aacttggcaa caggcctgct gacagcgaac 300
actgaaggag accctgtcgt tgcgcttgct ggaaacgtga tccgtgcaga tcgtttaaaa 360
cggacacatc aatctttgga taatgcgcgc ctattccagc cgattacaaa atacagtgta 420
gaagttcaag atgtaaaaaa tataccggaa gctgttacaa atgcatttag atagcgtca 480
gcagggcagg ctggggccgc ttttgtgagc tttccgcaag atgttgtgaa tgaagtcaca 540
aatacgaaaa acgtgcgtgc tgttgcagcg ccaaaactcg gtcctgcagc agatgatgca 600

-continued

```
atcagtgcgg ccatagcaaa atccaaaca gcaaaacttc ctgtcgtttt ggtcggcatg      660
aaaggcggaa gaccggaagc aattaaagcg gttcgcaagc ttttgaaaaa ggttcagctt      720
ccatttgttg aaacatatca agctgccggt acccttteta gagatttaga ggatcaatat      780
tttggccgta tcggtttgtt ccgcaaccag cctggcgatt tactgctaga gcaggcagat      840
gttgttctga cgatcggcta tgacccgatt gaatatgatc cgaaattctg gaatatcaat      900
ggagaccgga caattatcca tttagacgag attatcgctg acattgatca tgcttaccag      960
cctgatcttg aattgatcgg tgacattccg tccacgatca atcatatcga acacgatgct     1020
gtgaaagtgg aatttgcaga gcgtgagcag aaaatccttt ctgatttaaa acaatatatg     1080
catgaaggtg agcaggtgcc tgcagattgg aaatcagaca gagcgcaccc tcttgaaatc     1140
gttaaagagt tgcgtaatgc agtcgatgat catgttacag taacttgcga tatcggttcg     1200
cacgccattt ggatgtcacg ttatttccgc agctacgagc cgttaacatt aatgatcagt     1260
aacggtatgc aaacactcgg cgttgcgctt ccttgggcaa tcggcgcttc attggtgaaa     1320
ccgggagaaa aagtggtttc tgtctctggt gacggcggtt tcttattctc agcaatggaa     1380
ttagagacag cagttcgact aaaagcacca attgtacaca ttgtatggaa cgacagcaca     1440
tatgacatgg ttgcattcca gcaattgaaa aaatataacc gtacatctgc ggtcgatttc     1500
ggaaatatcg atatcgtgaa atatgcggaa agcttcggag caactggctt gcgcgtagaa     1560
tcaccagacc agctggcaga tgttctgcgt caaggcatga acgctgaagg tcctgtcatc     1620
atcgatgtcc cggttgacta cagtgataac attaatttag caagtgacaa gcttccgaaa     1680
gaattcgggg aactcatgaa aacgaaagct ctctag                              1716
```

<210> SEQ ID NO 56
<211> LENGTH: 571
<212> TYPE: PRT
<213> ORGANISM: Bacillus subtilis

<400> SEQUENCE: 56

```
Met Leu Thr Lys Ala Thr Lys Glu Gln Lys Ser Leu Val Lys Asn Arg
1               5                   10                  15

Gly Ala Glu Leu Val Val Asp Cys Leu Val Gln Gly Val Thr His
            20                  25                  30

Val Phe Gly Ile Pro Gly Ala Lys Ile Asp Ala Val Phe Asp Ala Leu
        35                  40                  45

Gln Asp Lys Gly Pro Glu Ile Ile Val Ala Arg His Glu Gln Asn Ala
    50                  55                  60

Ala Phe Met Ala Gln Ala Val Gly Arg Leu Thr Gly Lys Pro Gly Val
65                  70                  75                  80

Val Leu Val Thr Ser Gly Pro Gly Ala Ser Asn Leu Ala Thr Gly Leu
                85                  90                  95

Leu Thr Ala Asn Thr Glu Gly Asp Pro Val Val Ala Leu Ala Gly Asn
            100                 105                 110

Val Ile Arg Ala Asp Arg Leu Lys Arg Thr His Gln Ser Leu Asp Asn
        115                 120                 125

Ala Ala Leu Phe Gln Pro Ile Thr Lys Tyr Ser Val Glu Val Gln Asp
    130                 135                 140

Val Lys Asn Ile Pro Glu Ala Val Thr Asn Ala Phe Arg Ile Ala Ser
145                 150                 155                 160

Ala Gly Gln Ala Gly Ala Ala Phe Val Ser Phe Pro Gln Asp Val Val
                165                 170                 175
```

Asn Glu Val Thr Asn Thr Lys Asn Val Arg Ala Val Ala Ala Pro Lys
            180                 185                 190

Leu Gly Pro Ala Ala Asp Asp Ala Ile Ser Ala Ile Ala Lys Ile
        195                 200                 205

Gln Thr Ala Lys Leu Pro Val Val Leu Val Gly Met Lys Gly Gly Arg
210                 215                 220

Pro Glu Ala Ile Lys Ala Val Arg Lys Leu Leu Lys Lys Val Gln Leu
225                 230                 235                 240

Pro Phe Val Glu Thr Tyr Gln Ala Ala Gly Thr Leu Ser Arg Asp Leu
            245                 250                 255

Glu Asp Gln Tyr Phe Gly Arg Ile Gly Leu Phe Arg Asn Gln Pro Gly
        260                 265                 270

Asp Leu Leu Leu Glu Gln Ala Asp Val Val Leu Thr Ile Gly Tyr Asp
    275                 280                 285

Pro Ile Glu Tyr Asp Pro Lys Phe Trp Asn Ile Asn Gly Asp Arg Thr
290                 295                 300

Ile Ile His Leu Asp Glu Ile Ala Asp Ile Asp His Ala Tyr Gln
305                 310                 315                 320

Pro Asp Leu Glu Leu Ile Gly Asp Ile Pro Ser Thr Ile Asn His Ile
            325                 330                 335

Glu His Asp Ala Val Lys Val Glu Phe Ala Glu Arg Glu Gln Lys Ile
        340                 345                 350

Leu Ser Asp Leu Lys Gln Tyr Met His Glu Gly Glu Gln Val Pro Ala
    355                 360                 365

Asp Trp Lys Ser Asp Arg Ala His Pro Leu Glu Ile Val Lys Glu Leu
370                 375                 380

Arg Asn Ala Val Asp Asp His Val Thr Val Thr Cys Asp Ile Gly Ser
385                 390                 395                 400

His Ala Ile Trp Met Ser Arg Tyr Phe Arg Ser Tyr Glu Pro Leu Thr
            405                 410                 415

Leu Met Ile Ser Asn Gly Met Gln Thr Leu Gly Val Ala Leu Pro Trp
        420                 425                 430

Ala Ile Gly Ala Ser Leu Val Lys Pro Gly Glu Lys Val Val Ser Val
    435                 440                 445

Ser Gly Asp Gly Gly Phe Leu Phe Ser Ala Met Glu Leu Glu Thr Ala
450                 455                 460

Val Arg Leu Lys Ala Pro Ile Val His Ile Val Trp Asn Asp Ser Thr
465                 470                 475                 480

Tyr Asp Met Val Ala Phe Gln Gln Leu Lys Lys Tyr Asn Arg Thr Ser
            485                 490                 495

Ala Val Asp Phe Gly Asn Ile Asp Ile Val Lys Tyr Ala Glu Ser Phe
        500                 505                 510

Gly Ala Thr Gly Leu Arg Val Glu Ser Pro Asp Gln Leu Ala Asp Val
    515                 520                 525

Leu Arg Gln Gly Met Asn Ala Glu Gly Pro Val Ile Ile Asp Val Pro
530                 535                 540

Val Asp Tyr Ser Asp Asn Ile Asn Leu Ala Ser Asp Lys Leu Pro Lys
545                 550                 555                 560

Glu Phe Gly Glu Leu Met Lys Thr Lys Ala Leu
            565                 570

<210> SEQ ID NO 57
<211> LENGTH: 1713
<212> TYPE: DNA

<213> ORGANISM: artificial sequence
<220> FEATURE:
<223> OTHER INFORMATION: codon optimized coding region for expression in
      Lactobacillus plantarum

<400> SEQUENCE: 57

```
atgttgacca aggctaccaa agaacaaaag agtttagtca aaaaccgtgg tgctgaatta      60
gtcgtggatt gtttggttga acaaggtgtg acgcatgttt ttggtattcc aggagctaaa     120
attgatgccg tttttgatgc gttacaagat aagggtccag aaattattgt ggcacgtcat     180
gaacaaaatg cagcgtttat ggctcaagca gttggtcggt tgactggcaa accaggtgtg     240
gttttagtga cgtcaggtcc aggtgcgagt aatttagcga ctggcttgtt aacggcgaat     300
actgaaggtg atccagtcgt tgctttggca ggcaatgtca ttcgtgccga tcgtttaaag     360
cggacccatc agagtttgga taatgcagcc ttgtttcaac cgattacgaa atattcagtt     420
gaagtccaag atgtcaagaa tattccagaa gcggttacga atgcgtttcg tattgcatca     480
gctggccaag caggcgcagc gtttgtgagt tttccacaag atgtcgtgaa tgaagttact     540
aacaccaaga atgtccgtgc agtcgcagct ccaaagttag gtccagcagc tgacgatgcc     600
attagtgcag ctattgccaa aattcagact gcaaaattgc cggttgtgtt agttggcatg     660
aaaggtggtc gtccagaagc cattaaagcg gttcgtaagt tattgaaaaa ggttcaatta     720
ccatttgttg aaacgtatca agctgcaggt acgttaagtc gtgacttaga agatcaatat     780
tttggtcgga ttggttttgtt cgtaatcaa ccaggtgatt tgttattaga acaagctgat     840
gtggttttaa ctattggcta tgatccgatt gaatatgatc aaagttttg gaatattaat     900
ggtgatcgta ccatcattca tttggatgaa atcattgctg atattgatca cgcttatcaa     960
ccggatttgg aattaattgg tgacattcca agtacgatta tcacattga acatgatgct    1020
gtgaaggttg agtttgcgga acgggaacag aaaatttat cagatttgaa gcaatatatg    1080
catgaaggtg aacaagtgcc agcagattgg aagtcagatc gggcccatcc attagaaatt    1140
gttaaagaat acggaatgc agtggacgat catgtgaccg tgacttgtga tattggtagt    1200
catgctattt ggatgagtcg ttactttcgg tcatatgaac cgttaacttt aatgatttca    1260
aacggtatgc aaactttagg tgttgccttg ccatgggcca ttggtgcgtc attggtcaaa    1320
ccaggtgaaa aggtcgtgtc agtcagtgga gatggtggct tcttattcag tgctatggaa    1380
ttagaaaccg ctgtgcggtt gaaggcaccg attgtgcata ttgtgtggaa cgatagtact    1440
tatgatatgg tcgcatttca acagttgaag aaatataatc gtacctcagc agtggatttt    1500
ggtaatatcg atattgtcaa gtatgccgaa agttttggtg ccaccggttt gcgtgtcgaa    1560
tcaccagatc aattagctga tgtcttgcgt caaggtatga atgcggaagg cccagttatt    1620
attgatgtgc cagttgatta cagtgataac attaatttag ctagtgataa gttgccgaaa    1680
gaatttggtg aattaatgaa gacgaaagcg tta                                 1713
```

<210> SEQ ID NO 58
<211> LENGTH: 1680
<212> TYPE: DNA
<213> ORGANISM: K. pneumoniae

<400> SEQUENCE: 58

```
atggacaaac agtatccggt acgccagtgg gcgcacggcg ccgatctcgt cgtcagtcag      60
ctggaagctc agggagtacg ccaggtgttc ggcatcccg cgccaaaat cgacaaggtc     120
tttgattcac tgctggattc ctccattcgc attattccgg tacgccacga agccaacgcc     180
```

```
gcatttatgg ccgccgccgt cggacgcatt accggcaaag cgggcgtggc gctggtcacc      240
tccggtccgg gctgttccaa cctgatcacc ggcatggcca ccgcgaacag cgaaggcgac      300
ccggtggtgg ccctgggcgg cgcggtaaaa cgcgccgata aagcgaagca ggtccaccag      360
agtatggata cggtggcgat gttcagcccg gtcaccaaat acgccatcga ggtgacggcg      420
ccggatgcgc tggcggaagt ggtctccaac gccttccgcg ccgccgagca gggccggccg      480
ggcagcgcgt tcgttagcct gccgcaggat gtggtcgatg cccgtcag cggcaaagtg       540
ctgccggcca gcggggcccc gcagatgggc gccgcgccgg atgatgccat cgaccaggtg      600
gcgaagctta tcgcccaggc gaagaacccg atcttcctgc tcggcctgat ggccagccag      660
ccggaaaaca gcaaggcgct cgccgtttg ctggagacca gccatattcc agtcaccagc      720
acctatcagg ccgccggagc ggtgaatcag gataacttct ctcgcttcgc cggccgggtt      780
gggctgttta caaccaggc cggggaccgt ctgctgcagc tcgccgacct ggtgatctgc      840
atcggctaca gcccggtgga atacgaaccg gcgatgtgga acagcggcaa cgcgacgctg      900
gtgcacatcg acgtgctgcc cgcctatgaa gagcgcaact acaccccgga tgtcgagctg      960
gtgggcgata tcgccggcac tctcaacaag ctggcgcaaa atatcgatca tcggctggtg     1020
ctctccccgc aggcggcgga gatcctccgc gaccgccagc accagcgcga gctgctggac     1080
cgccgcggcg cgcagctcaa ccagtttgcc ctgcatcccc tgcgcatcgt tcgcgccatg     1140
caggatatcg tcaacagcga cgtcacgttg accgtggaca tgggcagctt ccatatctgg     1200
attgcccgct acctgtacac gttccgcgcc cgtcaggtga tgatctccaa cggccagcag     1260
accatgggcg tcgccctgcc ctgggctatc ggcgcctggc tggtcaatcc tgagcgcaaa     1320
gtggtctccg tctccggcga cggcggcttc ctgcagtcga gcatggagct ggagaccgcc     1380
gtccgcctga agccaacgt gctgcatctt atctgggtcg ataacggcta caacatggtc     1440
gctatccagg aagagaaaaa atatcagcgc ctgtccggcg tcgagtttgg ccgatggat     1500
tttaaagcct atgccgaatc cttcggcgcg aaagggtttg ccgtggaaag cgccgaggcg     1560
ctggagccga ccctgcgcgc ggcgatggac gtcgacggcc cggcggtagt ggccatcccg     1620
gtggattatc gcgataaccc gctgctgatg ggccagctgc atctgagtca gattctgtaa     1680
```

<210> SEQ ID NO 59
<211> LENGTH: 559
<212> TYPE: PRT
<213> ORGANISM: K. pneumoniae

<400> SEQUENCE: 59

```
Met Asp Lys Gln Tyr Pro Val Arg Gln Trp Ala His Gly Ala Asp Leu
1               5                   10                  15

Val Val Ser Gln Leu Glu Ala Gln Gly Val Arg Gln Val Phe Gly Ile
            20                  25                  30

Pro Gly Ala Lys Ile Asp Lys Val Phe Asp Ser Leu Leu Asp Ser Ser
        35                  40                  45

Ile Arg Ile Ile Pro Val Arg His Glu Ala Asn Ala Ala Phe Met Ala
    50                  55                  60

Ala Ala Val Gly Arg Ile Thr Gly Lys Ala Gly Val Ala Leu Val Thr
65                  70                  75                  80

Ser Gly Pro Gly Cys Ser Asn Leu Ile Thr Gly Met Ala Thr Ala Asn
                85                  90                  95

Ser Glu Gly Asp Pro Val Val Ala Leu Gly Gly Ala Val Lys Arg Ala
            100                 105                 110
```

```
Asp Lys Ala Lys Gln Val His Gln Ser Met Asp Thr Val Ala Met Phe
        115                 120                 125
Ser Pro Val Thr Lys Tyr Ala Ile Glu Val Thr Ala Pro Asp Ala Leu
130                 135                 140
Ala Glu Val Val Ser Asn Ala Phe Arg Ala Ala Glu Gln Gly Arg Pro
145                 150                 155                 160
Gly Ser Ala Phe Val Ser Leu Pro Gln Asp Val Val Asp Gly Pro Val
                165                 170                 175
Ser Gly Lys Val Leu Pro Ala Ser Gly Ala Pro Gln Met Gly Ala Ala
                180                 185                 190
Pro Asp Asp Ala Ile Asp Gln Val Ala Lys Leu Ile Ala Gln Ala Lys
                195                 200                 205
Asn Pro Ile Phe Leu Leu Gly Leu Met Ala Ser Gln Pro Glu Asn Ser
210                 215                 220
Lys Ala Leu Arg Arg Leu Leu Glu Thr Ser His Ile Pro Val Thr Ser
225                 230                 235                 240
Thr Tyr Gln Ala Ala Gly Ala Val Asn Gln Asp Asn Phe Ser Arg Phe
                245                 250                 255
Ala Gly Arg Val Gly Leu Phe Asn Asn Gln Ala Gly Asp Arg Leu Leu
                260                 265                 270
Gln Leu Ala Asp Leu Val Ile Cys Ile Gly Tyr Ser Pro Val Glu Tyr
                275                 280                 285
Glu Pro Ala Met Trp Asn Ser Gly Asn Ala Thr Leu Val His Ile Asp
                290                 295                 300
Val Leu Pro Ala Tyr Glu Glu Arg Asn Tyr Thr Pro Asp Val Glu Leu
305                 310                 315                 320
Val Gly Asp Ile Ala Gly Thr Leu Asn Lys Leu Ala Gln Asn Ile Asp
                325                 330                 335
His Arg Leu Val Leu Ser Pro Gln Ala Ala Glu Ile Leu Arg Asp Arg
                340                 345                 350
Gln His Gln Arg Glu Leu Leu Asp Arg Arg Gly Ala Gln Leu Asn Gln
                355                 360                 365
Phe Ala Leu His Pro Leu Arg Ile Val Arg Ala Met Gln Asp Ile Val
                370                 375                 380
Asn Ser Asp Val Thr Leu Thr Val Asp Met Gly Ser Phe His Ile Trp
385                 390                 395                 400
Ile Ala Arg Tyr Leu Tyr Thr Phe Arg Ala Arg Gln Val Met Ile Ser
                405                 410                 415
Asn Gly Gln Gln Thr Met Gly Val Ala Leu Pro Trp Ala Ile Gly Ala
                420                 425                 430
Trp Leu Val Asn Pro Glu Arg Lys Val Val Ser Val Ser Gly Asp Gly
                435                 440                 445
Gly Phe Leu Gln Ser Ser Met Glu Leu Glu Thr Ala Val Arg Leu Lys
                450                 455                 460
Ala Asn Val Leu His Leu Ile Trp Val Asp Asn Gly Tyr Asn Met Val
465                 470                 475                 480
Ala Ile Gln Glu Glu Lys Lys Tyr Gln Arg Leu Ser Gly Val Glu Phe
                485                 490                 495
Gly Pro Met Asp Phe Lys Ala Tyr Ala Glu Ser Phe Gly Ala Lys Gly
                500                 505                 510
Phe Ala Val Glu Ser Ala Glu Ala Leu Glu Pro Thr Leu Arg Ala Ala
                515                 520                 525
Met Asp Val Asp Gly Pro Ala Val Val Ala Ile Pro Val Asp Tyr Arg
```

Asp Asn Pro Leu Leu Met Gly Gln Leu His Leu Ser Gln Ile Leu
545                 550                 555

<210> SEQ ID NO 60
<211> LENGTH: 1665
<212> TYPE: DNA
<213> ORGANISM: Lactococcus lactis

<400> SEQUENCE: 60

| | |
|---|---:|
| atgtctgaga aacaatttgg ggcgaacttg gttgtcgata gtttgattaa ccataaagtg | 60 |
| aagtatgtat ttgggattcc aggagcaaaa attgaccggg ttttgattt attagaaaat | 120 |
| gaagaaggcc ctcaaatggt cgtgactcgt catgagcaag gagctgcttt catggctcaa | 180 |
| gctgtcggtc gtttaactgg cgaacctggt gtagtagttg ttacgagtgg gcctggtgta | 240 |
| tcaaaccttg cgactccgct tttgaccgcg acatcagaag gtgatgctat tttggctatc | 300 |
| ggtggacaag ttaaacgaag tgaccgtctt aaacgtgcgc accaatcaat ggataatgct | 360 |
| ggaatgatgc aatcagcaac aaaatattca gcagaagttc ttgaccctaa tacactttct | 420 |
| gaatcaattg ccaacgctta tcgtattgca aaatcaggac atccaggtgc aactttctta | 480 |
| tcaatccccc aagatgtaac ggatgccgaa gtatcaatca aagccattca accactttca | 540 |
| gaccctaaaa tggggaatgc ctctattgat gacattaatt attagcaca gcaattaaa | 600 |
| aatgctgtat tgccagtaat tttggttgga gctggtgctt cagatgctaa agtcgcttca | 660 |
| tccttgcgta atctattgac tcatgttaat attcctgtcg ttgaaacatt ccaaggtgca | 720 |
| ggggttattt cacatgattt agaacatact ttttatggac gtatcggtct tttccgcaat | 780 |
| caaccaggcg atatgcttct gaaacgttct gaccttgtta ttgctgttgg ttatgaccca | 840 |
| attgaatatg aagctcgtaa ctggaatgca gaaattgata gtcgaattat cgttattgat | 900 |
| aatgccattg ctgaaattga tacttactac caaccagagc gtgaattaat tggtgatatc | 960 |
| gcagcaacat tggataatct tttaccagct gttcgtggct acaaaattcc aaaaggaaca | 1020 |
| aaagattatc tcgatggcct tcatgaagtt gctgagcaac acgaatttga tactgaaaat | 1080 |
| actgaagaag gtagaatgca ccctcttgat ttggtcagca ctttccaaga aatcgtcaag | 1140 |
| gatgatgaaa cagtaaccgt tgacgtaggt tcactctaca tttggatggc acgtcatttc | 1200 |
| aaatcatacg aaccacgtca tctcctcttc tcaaacggaa tgcaaacact cggagttgca | 1260 |
| cttccttggg caattacagc cgcattgttg cgcccaggta aaaagtttta ttcacactct | 1320 |
| ggtgatggag gcttcctttt cacagggcaa gaattggaaa cagctgtacg tttgaatctt | 1380 |
| ccaatcgttc aaattatctg gaatgacggc cattatgata tggttaaatt ccaagaagaa | 1440 |
| atgaaatatg gtcgttcagc agccgttgat tttggctatg ttgattacgt aaaatatgct | 1500 |
| gaagcaatga gagcaaaagg ttaccgtgca cacagcaaag aagaacttgc tgaaattctc | 1560 |
| aaatcaatcc cagatactac tggaccggtg gtaattgacg ttcctttgga ctattctgat | 1620 |
| aacattaaat tagcagaaaa attattgcct gaagagtttt attga | 1665 |

<210> SEQ ID NO 61
<211> LENGTH: 554
<212> TYPE: PRT
<213> ORGANISM: Lactococcus lactis

<400> SEQUENCE: 61

Met Ser Glu Lys Gln Phe Gly Ala Asn Leu Val Val Asp Ser Leu Ile
1                 5                  10                  15

```
Asn His Lys Val Lys Tyr Val Phe Gly Ile Pro Gly Ala Lys Ile Asp
            20                  25                  30

Arg Val Phe Asp Leu Leu Glu Asn Glu Glu Gly Pro Gln Met Val Val
            35                  40                  45

Thr Arg His Glu Gln Gly Ala Ala Phe Met Ala Gln Ala Val Gly Arg
 50                  55                  60

Leu Thr Gly Glu Pro Gly Val Val Val Thr Ser Gly Pro Gly Val
 65                  70                  75                  80

Ser Asn Leu Ala Thr Pro Leu Leu Thr Ala Thr Ser Glu Gly Asp Ala
                    85                  90                  95

Ile Leu Ala Ile Gly Gly Gln Val Lys Arg Ser Asp Arg Leu Lys Arg
                100                 105                 110

Ala His Gln Ser Met Asp Asn Ala Gly Met Met Gln Ser Ala Thr Lys
        115                 120                 125

Tyr Ser Ala Glu Val Leu Asp Pro Asn Thr Leu Ser Glu Ser Ile Ala
130                 135                 140

Asn Ala Tyr Arg Ile Ala Lys Ser Gly His Pro Gly Ala Thr Phe Leu
145                 150                 155                 160

Ser Ile Pro Gln Asp Val Thr Asp Ala Glu Val Ser Ile Lys Ala Ile
                165                 170                 175

Gln Pro Leu Ser Asp Pro Lys Met Gly Asn Ala Ser Ile Asp Asp Ile
                180                 185                 190

Asn Tyr Leu Ala Gln Ala Ile Lys Asn Ala Val Leu Pro Val Ile Leu
            195                 200                 205

Val Gly Ala Gly Ala Ser Asp Ala Lys Val Ala Ser Ser Leu Arg Asn
210                 215                 220

Leu Leu Thr His Val Asn Ile Pro Val Val Glu Thr Phe Gln Gly Ala
225                 230                 235                 240

Gly Val Ile Ser His Asp Leu Glu His Thr Phe Tyr Gly Arg Ile Gly
                245                 250                 255

Leu Phe Arg Asn Gln Pro Gly Asp Met Leu Leu Lys Arg Ser Asp Leu
            260                 265                 270

Val Ile Ala Val Gly Tyr Asp Pro Ile Glu Tyr Glu Ala Arg Asn Trp
            275                 280                 285

Asn Ala Glu Ile Asp Ser Arg Ile Ile Val Ile Asp Asn Ala Ile Ala
290                 295                 300

Glu Ile Asp Thr Tyr Tyr Gln Pro Glu Arg Glu Leu Ile Gly Asp Ile
305                 310                 315                 320

Ala Ala Thr Leu Asp Asn Leu Leu Pro Ala Val Arg Gly Tyr Lys Ile
                325                 330                 335

Pro Lys Gly Thr Lys Asp Tyr Leu Asp Gly Leu His Glu Val Ala Glu
            340                 345                 350

Gln His Glu Phe Asp Thr Glu Asn Thr Glu Glu Gly Arg Met His Pro
        355                 360                 365

Leu Asp Leu Val Ser Thr Phe Gln Glu Ile Val Lys Asp Asp Glu Thr
370                 375                 380

Val Thr Val Asp Val Gly Ser Leu Tyr Ile Trp Met Ala Arg His Phe
385                 390                 395                 400

Lys Ser Tyr Glu Pro Arg His Leu Leu Phe Ser Asn Gly Met Gln Thr
                405                 410                 415

Leu Gly Val Ala Leu Pro Trp Ala Ile Thr Ala Ala Leu Leu Arg Pro
            420                 425                 430
```

```
Gly Lys Lys Val Tyr Ser His Ser Gly Asp Gly Phe Leu Phe Thr
            435                 440                 445

Gly Gln Glu Leu Glu Thr Ala Val Arg Leu Asn Leu Pro Ile Val Gln
    450                 455                 460

Ile Ile Trp Asn Asp Gly His Tyr Asp Met Val Lys Phe Gln Glu Glu
465                 470                 475                 480

Met Lys Tyr Gly Arg Ser Ala Ala Val Asp Phe Gly Tyr Val Asp Tyr
                485                 490                 495

Val Lys Tyr Ala Glu Ala Met Arg Ala Lys Gly Tyr Arg Ala His Ser
            500                 505                 510

Lys Glu Glu Leu Ala Glu Ile Leu Lys Ser Ile Pro Asp Thr Thr Gly
            515                 520                 525

Pro Val Val Ile Asp Val Pro Leu Asp Tyr Ser Asp Asn Ile Lys Leu
            530                 535                 540

Ala Glu Lys Leu Leu Pro Glu Glu Phe Tyr
545                 550

<210> SEQ ID NO 62
<211> LENGTH: 1665
<212> TYPE: DNA
<213> ORGANISM: Staphylococcus aureus
<220> FEATURE:
<221> NAME/KEY: CDS
<222> LOCATION: (1)..(1665)

<400> SEQUENCE: 62 atg act gat aaa aag tac act gca gcc gat atg gtt att gat act ttg      48
Met Thr Asp Lys Lys Tyr Thr Ala Ala Asp Met Val Ile Asp Thr Leu
1               5                   10                  15 aaa aat aat ggg gta gaa tat gtt ttt ggt att ccg ggt gca aag ata      96
Lys Asn Asn Gly Val Glu Tyr Val Phe Gly Ile Pro Gly Ala Lys Ile
                20                  25                  30 gac tat cta ttt aat gct tta att gat gat ggt cct gaa ctt att gtc     144
Asp Tyr Leu Phe Asn Ala Leu Ile Asp Asp Gly Pro Glu Leu Ile Val
            35                  40                  45 act cgt cat gaa caa aat gct gca atg atg gca caa ggt att gga aga     192
Thr Arg His Glu Gln Asn Ala Ala Met Met Ala Gln Gly Ile Gly Arg
        50                  55                  60 tta aca ggt aaa ccg ggt gta gta ctt gtt aca agt ggc cct ggt gta     240
Leu Thr Gly Lys Pro Gly Val Val Leu Val Thr Ser Gly Pro Gly Val
65                  70                  75                  80 agt aat tta acg act gga cta tta aca gct aca tct gaa ggg gat cct     288
Ser Asn Leu Thr Thr Gly Leu Leu Thr Ala Thr Ser Glu Gly Asp Pro
                85                  90                  95 gta tta gcg tta ggt ggc caa gtg aaa cgt aat gat tta tta cga tta     336
Val Leu Ala Leu Gly Gly Gln Val Lys Arg Asn Asp Leu Leu Arg Leu
            100                 105                 110 acg cat caa agt att gat aat gct gcg cta tta aaa tat tca tca aaa     384
Thr His Gln Ser Ile Asp Asn Ala Ala Leu Leu Lys Tyr Ser Ser Lys
        115                 120                 125 tac agt gaa gaa gta caa gat cct gaa tca tta tca gaa gtt atg aca     432
Tyr Ser Glu Glu Val Gln Asp Pro Glu Ser Leu Ser Glu Val Met Thr
    130                 135                 140 aat gca att cga att gct act tca gga aaa aat ggc gca agt ttt att     480
Asn Ala Ile Arg Ile Ala Thr Ser Gly Lys Asn Gly Ala Ser Phe Ile
145                 150                 155                 160 agt att ccg caa gac gtt att tct tca cca gtt gaa tct aaa gct ata     528
Ser Ile Pro Gln Asp Val Ile Ser Ser Pro Val Glu Ser Lys Ala Ile
                165                 170                 175
```

```
                                                       -continued tca ctt tgc caa aaa cca aat tta gga gta ccg agt gaa caa gat att        576
Ser Leu Cys Gln Lys Pro Asn Leu Gly Val Pro Ser Glu Gln Asp Ile
            180                 185                 190 aat gat gtc att gaa gcg att aaa aat gca tca ttt cct gtt tta tta        624
Asn Asp Val Ile Glu Ala Ile Lys Asn Ala Ser Phe Pro Val Leu Leu
        195                 200                 205 gct ggt atg aga agt tca agt gca gaa gaa aca aat gcc att cgc aaa        672
Ala Gly Met Arg Ser Ser Ser Ala Glu Glu Thr Asn Ala Ile Arg Lys
    210                 215                 220 tta gtt gag cgc acg aat tta cca gtt gta gaa aca ttc caa ggt gca        720
Leu Val Glu Arg Thr Asn Leu Pro Val Val Glu Thr Phe Gln Gly Ala
225                 230                 235                 240 ggt gta att agt cgt gaa tta gaa aat cat ttc ttc ggt cgt gtg ggc        768
Gly Val Ile Ser Arg Glu Leu Glu Asn His Phe Phe Gly Arg Val Gly
                245                 250                 255 tta ttc cgc aat caa gtt ggt gat gaa tta tta cgt aaa agt gat tta        816
Leu Phe Arg Asn Gln Val Gly Asp Glu Leu Leu Arg Lys Ser Asp Leu
            260                 265                 270 gtt gtt aca atc ggt tat gat cca att gaa tac gaa gct agt aac tgg        864
Val Val Thr Ile Gly Tyr Asp Pro Ile Glu Tyr Glu Ala Ser Asn Trp
        275                 280                 285 aat aaa gaa tta gaa aca caa att atc aat att gac gaa gtt caa gct        912
Asn Lys Glu Leu Glu Thr Gln Ile Ile Asn Ile Asp Glu Val Gln Ala
    290                 295                 300 gaa att act aat tat atg caa ccg aaa aaa gag ttg att ggt aat att        960
Glu Ile Thr Asn Tyr Met Gln Pro Lys Lys Glu Leu Ile Gly Asn Ile
305                 310                 315                 320 gct aaa acg att gaa atg att tct gaa aaa gtg gat gag cca ttt ata       1008
Ala Lys Thr Ile Glu Met Ile Ser Glu Lys Val Asp Glu Pro Phe Ile
                325                 330                 335 aat caa caa cat tta gac gaa tta gaa caa tta aga aca cat att gat       1056
Asn Gln Gln His Leu Asp Glu Leu Glu Gln Leu Arg Thr His Ile Asp
            340                 345                 350 gaa gaa act ggt att aaa gcg acg cat gaa gaa gga att cta cat cca       1104
Glu Glu Thr Gly Ile Lys Ala Thr His Glu Glu Gly Ile Leu His Pro
        355                 360                 365 gtg gaa att att gaa tct atg caa aag gta tta act gat gat act act       1152
Val Glu Ile Ile Glu Ser Met Gln Lys Val Leu Thr Asp Asp Thr Thr
    370                 375                 380 gta aca gtt gat gtt gga agt cac tat att tgg atg gca cgt aat ttc       1200
Val Thr Val Asp Val Gly Ser His Tyr Ile Trp Met Ala Arg Asn Phe
385                 390                 395                 400 aga agt tac aat cca aga cat tta tta ttt agc aat ggt atg caa acg       1248
Arg Ser Tyr Asn Pro Arg His Leu Leu Phe Ser Asn Gly Met Gln Thr
                405                 410                 415 ctt ggt gta gca tta ccg tgg gca att tca gct gca ctt gtg cgc cct       1296
Leu Gly Val Ala Leu Pro Trp Ala Ile Ser Ala Ala Leu Val Arg Pro
            420                 425                 430 aat acg caa gtt gtg tcc gtt gct ggc gat ggt ggc ttt tta ttt tca       1344
Asn Thr Gln Val Val Ser Val Ala Gly Asp Gly Gly Phe Leu Phe Ser
        435                 440                 445 tca caa gat tta gaa acg gcc gta cgt aaa aat tta aat atc atc cag       1392
Ser Gln Asp Leu Glu Thr Ala Val Arg Lys Asn Leu Asn Ile Ile Gln
    450                 455                 460 ctt att tgg aat gat gga aaa tat aac atg gtt gaa ttc caa gaa gaa       1440
Leu Ile Trp Asn Asp Gly Lys Tyr Asn Met Val Glu Phe Gln Glu Glu
465                 470                 475                 480 atg aaa tat aaa cgt tcg tca ggt gta gac ttc ggt cct gta gat ttt       1488
Met Lys Tyr Lys Arg Ser Ser Gly Val Asp Phe Gly Pro Val Asp Phe
                485                 490                 495
```

```
gta aaa tat gca gaa tca ttt ggc gcg aaa ggt tta cga gtt act aat    1536
Val Lys Tyr Ala Glu Ser Phe Gly Ala Lys Gly Leu Arg Val Thr Asn
        500                 505                 510 caa gaa gaa tta gaa gcg gca att aaa gag ggc tat gaa aca gat ggt    1584
Gln Glu Glu Leu Glu Ala Ala Ile Lys Glu Gly Tyr Glu Thr Asp Gly
        515                 520                 525 cca gta tta att gat ata cct gta aat tac aaa gat aat atc aaa ctt    1632
Pro Val Leu Ile Asp Ile Pro Val Asn Tyr Lys Asp Asn Ile Lys Leu
        530                 535                 540 tca aca aat atg tta cct gac gta ttt aac taa                        1665
Ser Thr Asn Met Leu Pro Asp Val Phe Asn
545                 550

<210> SEQ ID NO 63
<211> LENGTH: 554
<212> TYPE: PRT
<213> ORGANISM: Staphylococcus aureus

<400> SEQUENCE: 63

Met Thr Asp Lys Lys Tyr Thr Ala Ala Asp Met Val Ile Asp Thr Leu
1               5                   10                  15

Lys Asn Asn Gly Val Glu Tyr Val Phe Gly Ile Pro Gly Ala Lys Ile
            20                  25                  30

Asp Tyr Leu Phe Asn Ala Leu Ile Asp Asp Gly Pro Glu Leu Ile Val
        35                  40                  45

Thr Arg His Glu Gln Asn Ala Ala Met Met Ala Gln Gly Ile Gly Arg
    50                  55                  60

Leu Thr Gly Lys Pro Gly Val Val Leu Val Thr Ser Gly Pro Gly Val
65                  70                  75                  80

Ser Asn Leu Thr Thr Gly Leu Leu Thr Ala Thr Ser Glu Gly Asp Pro
                85                  90                  95

Val Leu Ala Leu Gly Gly Gln Val Lys Arg Asn Asp Leu Leu Arg Leu
            100                 105                 110

Thr His Gln Ser Ile Asp Asn Ala Ala Leu Leu Lys Tyr Ser Ser Lys
        115                 120                 125

Tyr Ser Glu Glu Val Gln Asp Pro Glu Ser Leu Ser Glu Val Met Thr
    130                 135                 140

Asn Ala Ile Arg Ile Ala Thr Ser Gly Lys Asn Gly Ala Ser Phe Ile
145                 150                 155                 160

Ser Ile Pro Gln Asp Val Ile Ser Ser Pro Val Glu Ser Lys Ala Ile
                165                 170                 175

Ser Leu Cys Gln Lys Pro Asn Leu Gly Val Pro Ser Glu Gln Asp Ile
            180                 185                 190

Asn Asp Val Ile Glu Ala Ile Lys Asn Ala Ser Phe Pro Val Leu Leu
        195                 200                 205

Ala Gly Met Arg Ser Ser Ser Ala Glu Glu Thr Asn Ala Ile Arg Lys
    210                 215                 220

Leu Val Glu Arg Thr Asn Leu Pro Val Val Glu Thr Phe Gln Gly Ala
225                 230                 235                 240

Gly Val Ile Ser Arg Glu Leu Glu Asn His Phe Phe Gly Arg Val Gly
                245                 250                 255

Leu Phe Arg Asn Gln Val Gly Asp Glu Leu Leu Arg Lys Ser Asp Leu
            260                 265                 270

Val Val Thr Ile Gly Tyr Asp Pro Ile Glu Tyr Glu Ala Ser Asn Trp
        275                 280                 285
```

```
Asn Lys Glu Leu Glu Thr Gln Ile Ile Asn Ile Asp Glu Val Gln Ala
    290                 295                 300

Glu Ile Thr Asn Tyr Met Gln Pro Lys Lys Glu Leu Ile Gly Asn Ile
305                 310                 315                 320

Ala Lys Thr Ile Glu Met Ile Ser Glu Lys Val Asp Glu Pro Phe Ile
                325                 330                 335

Asn Gln Gln His Leu Asp Glu Leu Glu Gln Leu Arg Thr His Ile Asp
            340                 345                 350

Glu Glu Thr Gly Ile Lys Ala Thr His Glu Glu Gly Ile Leu His Pro
        355                 360                 365

Val Glu Ile Ile Glu Ser Met Gln Lys Val Leu Thr Asp Asp Thr Thr
370                 375                 380

Val Thr Val Asp Val Gly Ser His Tyr Ile Trp Met Ala Arg Asn Phe
385                 390                 395                 400

Arg Ser Tyr Asn Pro Arg His Leu Leu Phe Ser Asn Gly Met Gln Thr
                405                 410                 415

Leu Gly Val Ala Leu Pro Trp Ala Ile Ser Ala Ala Leu Val Arg Pro
            420                 425                 430

Asn Thr Gln Val Val Ser Val Ala Gly Asp Gly Gly Phe Leu Phe Ser
        435                 440                 445

Ser Gln Asp Leu Glu Thr Ala Val Arg Lys Asn Leu Asn Ile Ile Gln
450                 455                 460

Leu Ile Trp Asn Asp Gly Lys Tyr Asn Met Val Glu Phe Gln Glu Glu
465                 470                 475                 480

Met Lys Tyr Lys Arg Ser Ser Gly Val Asp Phe Gly Pro Val Asp Phe
                485                 490                 495

Val Lys Tyr Ala Glu Ser Phe Gly Ala Lys Gly Leu Arg Val Thr Asn
            500                 505                 510

Gln Glu Glu Leu Glu Ala Ala Ile Lys Glu Gly Tyr Glu Thr Asp Gly
        515                 520                 525

Pro Val Leu Ile Asp Ile Pro Val Asn Tyr Lys Asp Asn Ile Lys Leu
530                 535                 540

Ser Thr Asn Met Leu Pro Asp Val Phe Asn
545                 550

<210> SEQ ID NO 64
<211> LENGTH: 1698
<212> TYPE: DNA
<213> ORGANISM: Listeria monocytogenes
<220> FEATURE:
<221> NAME/KEY: CDS
<222> LOCATION: (1)..(1698)

<400> SEQUENCE: 64 atg gcg aaa cta gaa aaa gac caa gaa aaa gta ata aca caa ggg aaa      48
Met Ala Lys Leu Glu Lys Asp Gln Glu Lys Val Ile Thr Gln Gly Lys
1               5                   10                  15 tca gga gcg gat tta gtt gta gac agc tta att aat caa ggt gtt acg      96
Ser Gly Ala Asp Leu Val Val Asp Ser Leu Ile Asn Gln Gly Val Thr
            20                  25                  30 cat gta ttc ggg att ccg gga gcg aaa att gat aaa gtt ttt gat gtg     144
His Val Phe Gly Ile Pro Gly Ala Lys Ile Asp Lys Val Phe Asp Val
        35                  40                  45 atg gaa gaa cgt gga cca gaa tta att gtc agt cgt cat gaa caa aat     192
Met Glu Glu Arg Gly Pro Glu Leu Ile Val Ser Arg His Glu Gln Asn
50                  55                  60 gcg gcg ttt atg gct gct gct atc ggt cgt cta acc ggg aaa cct ggt     240
```

```
Ala Ala Phe Met Ala Ala Ile Gly Arg Leu Thr Gly Lys Pro Gly
 65              70                  75                  80 gtt gta ctt gta act agt gga cct ggc gca tcg aat ctt gca aca ggg    288
Val Val Leu Val Thr Ser Gly Pro Gly Ala Ser Asn Leu Ala Thr Gly
                     85                  90                  95 ctt gta acc gca act gca gaa gga gat cca gtc gtt gcg att gct ggt    336
Leu Val Thr Ala Thr Ala Glu Gly Asp Pro Val Val Ala Ile Ala Gly
                100                 105                 110 aac gta aca agg caa gac cgc tta aaa aga acc cac caa tca atg gat    384
Asn Val Thr Arg Gln Asp Arg Leu Lys Arg Thr His Gln Ser Met Asp
            115                 120                 125 aat gca gca ctt ttc cgt ccg att aca aaa tac agc gaa gaa gta gtt    432
Asn Ala Ala Leu Phe Arg Pro Ile Thr Lys Tyr Ser Glu Glu Val Val
        130                 135                 140 cac gcc gaa agt att cca gaa gca atc act aac gct ttt cgc tcg gca    480
His Ala Glu Ser Ile Pro Glu Ala Ile Thr Asn Ala Phe Arg Ser Ala
145                 150                 155                 160 aca gaa cca aac caa ggc gct gct ttt gtc agt ttg cca caa gat atc    528
Thr Glu Pro Asn Gln Gly Ala Ala Phe Val Ser Leu Pro Gln Asp Ile
                165                 170                 175 gtg aac gaa cca aac gta cca gta aaa gcg att cgc cca ctt gct aaa    576
Val Asn Glu Pro Asn Val Pro Val Lys Ala Ile Arg Pro Leu Ala Lys
            180                 185                 190 cca gaa aat ggt cct gct tcc aaa gaa caa gtt gca aaa ctt gtt aca    624
Pro Glu Asn Gly Pro Ala Ser Lys Glu Gln Val Ala Lys Leu Val Thr
        195                 200                 205 cgt ttg aaa aaa gcg aaa tta ccg gta ttg cta ttg ggt atg cga gca    672
Arg Leu Lys Lys Ala Lys Leu Pro Val Leu Leu Leu Gly Met Arg Ala
210                 215                 220 tct agt cca gaa gta act ggt gca att cgt cgc tta ctc caa aaa aca    720
Ser Ser Pro Glu Val Thr Gly Ala Ile Arg Arg Leu Leu Gln Lys Thr
225                 230                 235                 240 agt atc cca gta gta gaa act ttc caa gca gct ggc gtc att tca cgc    768
Ser Ile Pro Val Val Glu Thr Phe Gln Ala Ala Gly Val Ile Ser Arg
                245                 250                 255 gac tta gaa gat aac ttc ttt gga cgt gtt ggt ctg ttc cgc aac caa    816
Asp Leu Glu Asp Asn Phe Phe Gly Arg Val Gly Leu Phe Arg Asn Gln
            260                 265                 270 cca ggg gat att ttg tta aat aaa gct gat tta gtt att aca gtg ggt    864
Pro Gly Asp Ile Leu Leu Asn Lys Ala Asp Leu Val Ile Thr Val Gly
        275                 280                 285 tat gat cca att gaa tac gat cca aaa gct tgg aat gcc tct ggt gat    912
Tyr Asp Pro Ile Glu Tyr Asp Pro Lys Ala Trp Asn Ala Ser Gly Asp
290                 295                 300 aga acg att gtc cat tta gac gac att cgc gct gat att gat cat tat    960
Arg Thr Ile Val His Leu Asp Asp Ile Arg Ala Asp Ile Asp His Tyr
305                 310                 315                 320 tac caa cca gtg aca gag cta gtc gga aac atc gcg ctt act tta gac   1008
Tyr Gln Pro Val Thr Glu Leu Val Gly Asn Ile Ala Leu Thr Leu Asp
                325                 330                 335 cga gtg aat gcg aaa ttc agc ggt tta gaa tta gcg gaa aaa gaa ctt   1056
Arg Val Asn Ala Lys Phe Ser Gly Leu Glu Leu Ala Glu Lys Glu Leu
            340                 345                 350 gaa aca tta aaa gaa ctt cat gct caa tta gag cga gat gtt ccg       1104
Glu Thr Leu Lys Glu Leu His Ala Gln Leu Glu Arg Asp Val Pro
        355                 360                 365 cca gaa agt gat gaa act aac cga gta cat cca ttg tcg gtc att caa   1152
Pro Glu Ser Asp Glu Thr Asn Arg Val His Pro Leu Ser Val Ile Gln
370                 375                 380
```

| | | | | | | | | | | | | | | | | |
|---|---|---|---|---|---|---|---|---|---|---|---|---|---|---|---|---|
| aca | cta | cgt | tcg | gca | att | gat | gac | aac | gta | act | gtg | aca | gtc | gac | gtt | 1200 |
| Thr | Leu | Arg | Ser | Ala | Ile | Asp | Asp | Asn | Val | Thr | Val | Thr | Val | Asp | Val | |
| 385 | | | | 390 | | | | | 395 | | | | | 400 | | |

| | | | | | | | | | | | | | | | | |
|---|---|---|---|---|---|---|---|---|---|---|---|---|---|---|---|---|
| ggt | tca | cat | tat | att | tgg | atg | gca | cgt | cat | ttc | cgc | tcc | tat | gaa | cca | 1248 |
| Gly | Ser | His | Tyr | Ile | Trp | Met | Ala | Arg | His | Phe | Arg | Ser | Tyr | Glu | Pro | |
| | | | | 405 | | | | | 410 | | | | | 415 | | |

| | | | | | | | | | | | | | | | | |
|---|---|---|---|---|---|---|---|---|---|---|---|---|---|---|---|---|
| cgc | cgt | ctg | ctt | ttc | agt | aac | ggt | atg | caa | acg | ctt | ggt | gtt | gcg | ctt | 1296 |
| Arg | Arg | Leu | Leu | Phe | Ser | Asn | Gly | Met | Gln | Thr | Leu | Gly | Val | Ala | Leu | |
| | | | | 420 | | | | | 425 | | | | | 430 | | |

| | | | | | | | | | | | | | | | | |
|---|---|---|---|---|---|---|---|---|---|---|---|---|---|---|---|---|
| cct | tgg | gga | att | gct | gca | aca | ctt | gta | cat | ccg | ggt | gaa | aaa | gtg | gtt | 1344 |
| Pro | Trp | Gly | Ile | Ala | Ala | Thr | Leu | Val | His | Pro | Gly | Glu | Lys | Val | Val | |
| | | 435 | | | | | 440 | | | | | 445 | | | | |

| | | | | | | | | | | | | | | | | |
|---|---|---|---|---|---|---|---|---|---|---|---|---|---|---|---|---|
| tcg | att | tct | ggt | gac | ggt | ggt | ttc | tta | ttt | tcc | gcg | atg | gaa | tta | gaa | 1392 |
| Ser | Ile | Ser | Gly | Asp | Gly | Gly | Phe | Leu | Phe | Ser | Ala | Met | Glu | Leu | Glu | |
| | 450 | | | | | 455 | | | | | 460 | | | | | |

| | | | | | | | | | | | | | | | | |
|---|---|---|---|---|---|---|---|---|---|---|---|---|---|---|---|---|
| aca | gct | gtc | cgc | ttg | cgt | gcg | cca | ctt | gta | cac | cta | gta | tgg | aat | gac | 1440 |
| Thr | Ala | Val | Arg | Leu | Arg | Ala | Pro | Leu | Val | His | Leu | Val | Trp | Asn | Asp | |
| 465 | | | | 470 | | | | | 475 | | | | |

```
Asn Ala Ala Leu Phe Arg Pro Ile Thr Lys Tyr Ser Glu Val Val
    130                 135                 140

His Ala Glu Ser Ile Pro Glu Ala Ile Thr Asn Ala Phe Arg Ser Ala
145                 150                 155                 160

Thr Glu Pro Asn Gln Gly Ala Ala Phe Val Ser Leu Pro Gln Asp Ile
                165                 170                 175

Val Asn Glu Pro Asn Val Pro Val Lys Ala Ile Arg Pro Leu Ala Lys
                180                 185                 190

Pro Glu Asn Gly Pro Ala Ser Lys Glu Gln Val Ala Lys Leu Val Thr
                195                 200                 205

Arg Leu Lys Lys Ala Lys Leu Pro Val Leu Leu Gly Met Arg Ala
    210                 215                 220

Ser Ser Pro Glu Val Thr Gly Ala Ile Arg Arg Leu Leu Gln Lys Thr
225                 230                 235                 240

Ser Ile Pro Val Val Glu Thr Phe Gln Ala Ala Gly Val Ile Ser Arg
                245                 250                 255

Asp Leu Glu Asp Asn Phe Phe Gly Arg Val Gly Leu Phe Arg Asn Gln
                260                 265                 270

Pro Gly Asp Ile Leu Leu Asn Lys Ala Asp Leu Val Ile Thr Val Gly
                275                 280                 285

Tyr Asp Pro Ile Glu Tyr Asp Pro Lys Ala Trp Asn Ala Ser Gly Asp
290                 295                 300

Arg Thr Ile Val His Leu Asp Asp Ile Arg Ala Asp Ile Asp His Tyr
305                 310                 315                 320

Tyr Gln Pro Val Thr Glu Leu Val Gly Asn Ile Ala Leu Thr Leu Asp
                325                 330                 335

Arg Val Asn Ala Lys Phe Ser Gly Leu Glu Leu Ala Glu Lys Glu Leu
                340                 345                 350

Glu Thr Leu Lys Glu Leu His Ala Gln Leu Glu Glu Arg Asp Val Pro
            355                 360                 365

Pro Glu Ser Asp Glu Thr Asn Arg Val His Pro Leu Ser Val Ile Gln
    370                 375                 380

Thr Leu Arg Ser Ala Ile Asp Asp Asn Val Thr Val Thr Val Asp Val
385                 390                 395                 400

Gly Ser His Tyr Ile Trp Met Ala Arg His Phe Arg Ser Tyr Glu Pro
                405                 410                 415

Arg Arg Leu Leu Phe Ser Asn Gly Met Gln Thr Leu Gly Val Ala Leu
                420                 425                 430

Pro Trp Gly Ile Ala Ala Thr Leu Val His Pro Gly Glu Lys Val Val
        435                 440                 445

Ser Ile Ser Gly Asp Gly Gly Phe Leu Phe Ser Ala Met Glu Leu Glu
    450                 455                 460

Thr Ala Val Arg Leu Arg Ala Pro Leu Val His Leu Val Trp Asn Asp
465                 470                 475                 480

Gly Ser Tyr Asp Met Val Ala Phe Gln Gln Lys Met Lys Tyr Gly Lys
                485                 490                 495

Glu Ala Ala Val Arg Phe Gly Asp Val Asp Ile Val Lys Phe Ala Glu
                500                 505                 510

Ser Phe Gly Ala Lys Gly Leu Arg Val Thr Asn Pro Ala Glu Leu Ser
            515                 520                 525

Asp Val Leu Lys Glu Ala Leu Glu Thr Glu Gly Pro Val Val Val Asp
    530                 535                 540
```

```
Ile Pro Ile Asp Tyr Arg Asp Asn Ile Lys Leu Gly Glu Thr Leu Leu
545                 550                 555                 560

Pro Asp Gln Phe Tyr
            565
```

<210> SEQ ID NO 66
<211> LENGTH: 1680
<212> TYPE: DNA
<213> ORGANISM: Streptococcus mutans
<220> FEATURE:
<221> NAME/KEY: CDS
<222> LOCATION: (1)..(1680)

<400> SEQUENCE: 66

```
atg acc gaa ata aat aag gaa ggc tat ggg gct gac ctg att gta gac      48
Met Thr Glu Ile Asn Lys Glu Gly Tyr Gly Ala Asp Leu Ile Val Asp
1               5                   10                  15 agc ctc att aat cat gat gtc aac tat gtt ttt gga atc cct ggt gca      96
Ser Leu Ile Asn His Asp Val Asn Tyr Val Phe Gly Ile Pro Gly Ala
                20                  25                  30 aaa att gat cgt gtc ttt gat acc tta gaa gat aag ggg cca gaa ctt     144
Lys Ile Asp Arg Val Phe Asp Thr Leu Glu Asp Lys Gly Pro Glu Leu
            35                  40                  45 att gta gca cgc cat gag caa aat gct gct ttt atg gct caa gga att     192
Ile Val Ala Arg His Glu Gln Asn Ala Ala Phe Met Ala Gln Gly Ile
        50                  55                  60 ggc cgt att act ggt gag cct ggt gtt gtg att aca acc agc ggt ccc     240
Gly Arg Ile Thr Gly Glu Pro Gly Val Val Ile Thr Thr Ser Gly Pro
65                  70                  75                  80 ggt gtt tcc aat ctg gtg act ggt ctt gtt act gcg aca gct gag gga     288
Gly Val Ser Asn Leu Val Thr Gly Leu Val Thr Ala Thr Ala Glu Gly
                85                  90                  95 gat cct gtc ctt gct att ggt ggt cag gtt aaa cgt gct gat ttg ctc     336
Asp Pro Val Leu Ala Ile Gly Gly Gln Val Lys Arg Ala Asp Leu Leu
                100                 105                 110 aaa cgg gct cac cag tca atg aat aat gtt gct atg ctc gat ccc att     384
Lys Arg Ala His Gln Ser Met Asn Asn Val Ala Met Leu Asp Pro Ile
            115                 120                 125 acc aaa tat tca gca gaa att cag gat ccc gca aca ctt tca gaa aat     432
Thr Lys Tyr Ser Ala Glu Ile Gln Asp Pro Ala Thr Leu Ser Glu Asn
        130                 135                 140 att gct aat gcc tat cgt ttg gct aaa gca gga aag ccg gga gct agt     480
Ile Ala Asn Ala Tyr Arg Leu Ala Lys Ala Gly Lys Pro Gly Ala Ser
145                 150                 155                 160 ttc tta tct att cct caa gat ata act gat agt cct gtt act gtc aag     528
Phe Leu Ser Ile Pro Gln Asp Ile Thr Asp Ser Pro Val Thr Val Lys
                165                 170                 175 gcg att aag ccc ttg aca gat cct aaa cta ggt tca gcg tca gtt gct     576
Ala Ile Lys Pro Leu Thr Asp Pro Lys Leu Gly Ser Ala Ser Val Ala
                180                 185                 190 gat att aat tat ttg gca cag gcc ata aaa aat gcg gtc ctt cct gtc     624
Asp Ile Asn Tyr Leu Ala Gln Ala Ile Lys Asn Ala Val Leu Pro Val
            195                 200                 205 tta ctt tta gga aat ggt gcg tca acg gct gca gtt aca gct tct att     672
Leu Leu Leu Gly Asn Gly Ala Ser Thr Ala Ala Val Thr Ala Ser Ile
        210                 215                 220 cgc cgt ttg tta gga gct gtc aag ctg cca gtc gtt gaa act ttc caa     720
Arg Arg Leu Leu Gly Ala Val Lys Leu Pro Val Val Glu Thr Phe Gln
225                 230                 235                 240 gga gct ggt att gtt tca aga gat tta gaa gag gac act ttt ttt ggt     768
Gly Ala Gly Ile Val Ser Arg Asp Leu Glu Glu Asp Thr Phe Phe Gly
```

|     |     |     |     |     |     |     |     |     |     |     |     |     |     |     |     |      |
|---|---|---|---|---|---|---|---|---|---|---|---|---|---|---|---|---|
|     |     |     | 245 |     |     |     |     | 250 |     |     |     |     | 255 |     |     |      |
| cgt | gtg | ggg | ctt | ttt | cgt | aat | cag | ccc | gga | gat | atg | ttg | ctg | aag | cgt | 816  |
| Arg | Val | Gly | Leu | Phe | Arg | Asn | Gln | Pro | Gly | Asp | Met | Leu | Leu | Lys | Arg |      |
|     |     | 260 |     |     |     |     | 265 |     |     |     |     | 270 |     |     |     |      |
| tct | gac | tta | gtt | atc | gct | att | ggc | tat | gat | cct | att | gaa | tat | gaa | gcg | 864  |
| Ser | Asp | Leu | Val | Ile | Ala | Ile | Gly | Tyr | Asp | Pro | Ile | Glu | Tyr | Glu | Ala |      |
|     |     | 275 |     |     |     |     | 280 |     |     |     |     | 285 |     |     |     |      |
| cgc | aat | tgg | aat | gct | gaa | att | tcg | gct | cgc | att | atc | gtt | att | gat | gtt | 912  |
| Arg | Asn | Trp | Asn | Ala | Glu | Ile | Ser | Ala | Arg | Ile | Ile | Val | Ile | Asp | Val |      |
|     | 290 |     |     |     |     | 295 |     |     |     |     | 300 |     |     |     |     |      |
| gct | cca | gct | gaa | att | gat | act | tat | ttc | caa | cct | gaa | cgt | gaa | tta | att | 960  |
| Ala | Pro | Ala | Glu | Ile | Asp | Thr | Tyr | Phe | Gln | Pro | Glu | Arg | Glu | Leu | Ile |      |
| 305 |     |     |     |     | 310 |     |     |     |     | 315 |     |     |     |     | 320 |      |
| ggt | gat | ata | gct | gaa | aca | ctt | gat | tta | ctc | cta | cct | gct | att | agt | ggc | 1008 |
| Gly | Asp | Ile | Ala | Glu | Thr | Leu | Asp | Leu | Leu | Leu | Pro | Ala | Ile | Ser | Gly |      |
|     |     |     |     | 325 |     |     |     |     | 330 |     |     |     |     | 335 |     |      |
| tac | tca | ctt | cca | aaa | ggt | tct | ctt | gac | tat | ctc | aaa | ggc | ctt | cgt | gat | 1056 |
| Tyr | Ser | Leu | Pro | Lys | Gly | Ser | Leu | Asp | Tyr | Leu | Lys | Gly | Leu | Arg | Asp |      |
|     |     |     | 340 |     |     |     |     | 345 |     |     |     |     | 350 |     |     |      |
| aat | gta | gta | gaa | gat | gtc | aaa | ttt | gat | aag | aca | gtc | aaa | tcc | ggt | ctg | 1104 |
| Asn | Val | Val | Glu | Asp | Val | Lys | Phe | Asp | Lys | Thr | Val | Lys | Ser | Gly | Leu |      |
|     |     | 355 |     |     |     |     | 360 |     |     |     |     | 365 |     |     |     |      |
| gtt | cat | ccg | ctt | gat | gtg | att | gat | gtc | ctt | caa | aag | caa | acg | act | gat | 1152 |
| Val | His | Pro | Leu | Asp | Val | Ile | Asp | Val | Leu | Gln | Lys | Gln | Thr | Thr | Asp |      |
|     | 370 |     |     |     |     | 375 |     |     |     |     | 380 |     |     |     |     |      |
| gat | atg | aca | gta | acg | gtt | gat | gtt | ggc | agc | cat | tat | att | tgg | atg | gct | 1200 |
| Asp | Met | Thr | Val | Thr | Val | Asp | Val | Gly | Ser | His | Tyr | Ile | Trp | Met | Ala |      |
| 385 |     |     |     |     | 390 |     |     |     |     | 395 |     |     |     |     | 400 |      |
| cgt | tat | ttt | aaa | agc | tat | gaa | gca | cgg | cac | tta | ctt | ttc | tca | aat | ggt | 1248 |
| Arg | Tyr | Phe | Lys | Ser | Tyr | Glu | Ala | Arg | His | Leu | Leu | Phe | Ser | Asn | Gly |      |
|     |     |     |     | 405 |     |     |     |     | 410 |     |     |     |     | 415 |     |      |
| atg | caa | acc | tta | ggt | gtt | gct | ttg | cct | tgg | gca | att | tcg | gca | gct | ctt | 1296 |
| Met | Gln | Thr | Leu | Gly | Val | Ala | Leu | Pro | Trp | Ala | Ile | Ser | Ala | Ala | Leu |      |
|     |     |     | 420 |     |     |     |     | 425 |     |     |     |     | 430 |     |     |      |
| gta | cgg | cca | aat | gag | aag | att | att | tct | att | tca | ggt | gat | ggt | ggt | ttc | 1344 |
| Val | Arg | Pro | Asn | Glu | Lys | Ile | Ile | Ser | Ile | Ser | Gly | Asp | Gly | Gly | Phe |      |
|     |     | 435 |     |     |     |     | 440 |     |     |     |     | 445 |     |     |     |      |
| ctc | ttt | tct | ggc | caa | gaa | ttg | gaa | aca | gct | gtt | cgt | tta | cat | tta | cca | 1392 |
| Leu | Phe | Ser | Gly | Gln | Glu | Leu | Glu | Thr | Ala | Val | Arg | Leu | His | Leu | Pro |      |
|     | 450 |     |     |     |     | 455 |     |     |     |     | 460 |     |     |     |     |      |
| att | gtt | cat | atc | att | tgg | aat | gat | ggt | aaa | tat | aat | atg | gtt | gaa | ttc | 1440 |
| Ile | Val | His | Ile | Ile | Trp | Asn | Asp | Gly | Lys | Tyr | Asn | Met | Val | Glu | Phe |      |
| 465 |     |     |     |     | 470 |     |     |     |     | 475 |     |     |     |     | 480 |      |
| caa | gaa | gaa | atg | aaa | tac | ggc | cgt | tca | gca | ggt | gtt | gat | ttt | ggt | cct | 1488 |
| Gln | Glu | Glu | Met | Lys | Tyr | Gly | Arg | Ser | Ala | Gly | Val | Asp | Phe | Gly | Pro |      |
|     |     |     |     | 485 |     |     |     |     | 490 |     |     |     |     | 495 |     |      |
| gtt | gat | ttt | gtc | aag | tat | gct | gat | agt | ttc | ggt | gct | aaa | ggt | tac | cgt | 1536 |
| Val | Asp | Phe | Val | Lys | Tyr | Ala | Asp | Ser | Phe | Gly | Ala | Lys | Gly | Tyr | Arg |      |
|     |     |     | 500 |     |     |     |     | 505 |     |     |     |     | 510 |     |     |      |
| gct | gat | agt | aaa | gaa | aag | ttt | gat | caa | gtt | ctt | caa | aca | gca | ctc | aag | 1584 |
| Ala | Asp | Ser | Lys | Glu | Lys | Phe | Asp | Gln | Val | Leu | Gln | Thr | Ala | Leu | Lys |      |
|     |     | 515 |     |     |     |     | 520 |     |     |     |     | 525 |     |     |     |      |
| gaa | gct | gca | aat | ggc | cca | gtt | ctc | att | gat | gtt | cca | atg | gac | tat | aaa | 1632 |
| Glu | Ala | Ala | Asn | Gly | Pro | Val | Leu | Ile | Asp | Val | Pro | Met | Asp | Tyr | Lys |      |
|     | 530 |     |     |     |     | 535 |     |     |     |     | 540 |     |     |     |     |      |
| gat | aat | gta | aaa | ttg | ggt | gaa | act | att | ttg | cct | gat | gaa | ttc | tac | taa | 1680 |
| Asp | Asn | Val | Lys | Leu | Gly | Glu | Thr | Ile | Leu | Pro | Asp | Glu | Phe | Tyr |     |      |
| 545 |     |     |     |     | 550 |     |     |     |     | 555 |     |     |     |     |     |      |

```
<210> SEQ ID NO 67
<211> LENGTH: 559
<212> TYPE: PRT
<213> ORGANISM: Streptococcus mutans

<400> SEQUENCE: 67

Met Thr Glu Ile Asn Lys Glu Gly Tyr Gly Ala Asp Leu Ile Val Asp
1               5                   10                  15

Ser Leu Ile Asn His Asp Val Asn Tyr Val Phe Gly Ile Pro Gly Ala
                20                  25                  30

Lys Ile Asp Arg Val Phe Asp Thr Leu Glu Asp Lys Gly Pro Glu Leu
            35                  40                  45

Ile Val Ala Arg His Glu Gln Asn Ala Ala Phe Met Ala Gln Gly Ile
        50                  55                  60

Gly Arg Ile Thr Gly Glu Pro Gly Val Val Ile Thr Thr Ser Gly Pro
65                  70                  75                  80

Gly Val Ser Asn Leu Val Thr Gly Leu Val Thr Ala Thr Ala Glu Gly
                85                  90                  95

Asp Pro Val Leu Ala Ile Gly Gly Gln Val Lys Arg Ala Asp Leu Leu
            100                 105                 110

Lys Arg Ala His Gln Ser Met Asn Asn Val Ala Met Leu Asp Pro Ile
        115                 120                 125

Thr Lys Tyr Ser Ala Glu Ile Gln Asp Pro Ala Thr Leu Ser Glu Asn
130                 135                 140

Ile Ala Asn Ala Tyr Arg Leu Ala Lys Ala Gly Lys Pro Gly Ala Ser
145                 150                 155                 160

Phe Leu Ser Ile Pro Gln Asp Ile Thr Asp Ser Pro Val Thr Val Lys
                165                 170                 175

Ala Ile Lys Pro Leu Thr Asp Pro Lys Leu Gly Ser Ala Ser Val Ala
            180                 185                 190

Asp Ile Asn Tyr Leu Ala Gln Ala Ile Lys Asn Ala Val Leu Pro Val
        195                 200                 205

Leu Leu Leu Gly Asn Gly Ala Ser Thr Ala Ala Val Thr Ala Ser Ile
210                 215                 220

Arg Arg Leu Leu Gly Ala Val Lys Leu Pro Val Val Glu Thr Phe Gln
225                 230                 235                 240

Gly Ala Gly Ile Val Ser Arg Asp Leu Glu Glu Asp Thr Phe Phe Gly
                245                 250                 255

Arg Val Gly Leu Phe Arg Asn Gln Pro Gly Asp Met Leu Leu Lys Arg
            260                 265                 270

Ser Asp Leu Val Ile Ala Ile Gly Tyr Asp Pro Ile Glu Tyr Glu Ala
        275                 280                 285

Arg Asn Trp Asn Ala Glu Ile Ser Ala Arg Ile Ile Val Ile Asp Val
290                 295                 300

Ala Pro Ala Glu Ile Asp Thr Tyr Phe Gln Pro Glu Arg Glu Leu Ile
305                 310                 315                 320

Gly Asp Ile Ala Glu Thr Leu Asp Leu Leu Pro Ala Ile Ser Gly
                325                 330                 335

Tyr Ser Leu Pro Lys Gly Ser Leu Asp Tyr Leu Lys Gly Leu Arg Asp
            340                 345                 350

Asn Val Val Glu Asp Val Lys Phe Asp Lys Thr Val Lys Ser Gly Leu
        355                 360                 365

Val His Pro Leu Asp Val Ile Asp Val Leu Gln Lys Gln Thr Thr Asp
370                 375                 380
```

```
Asp Met Thr Val Thr Val Asp Val Gly Ser His Tyr Ile Trp Met Ala
385                 390                 395                 400

Arg Tyr Phe Lys Ser Tyr Glu Ala Arg His Leu Leu Phe Ser Asn Gly
            405                 410                 415

Met Gln Thr Leu Gly Val Ala Leu Pro Trp Ala Ile Ser Ala Ala Leu
        420                 425                 430

Val Arg Pro Asn Glu Lys Ile Ile Ser Ile Ser Gly Asp Gly Gly Phe
    435                 440                 445

Leu Phe Ser Gly Gln Glu Leu Glu Thr Ala Val Arg Leu His Leu Pro
450                 455                 460

Ile Val His Ile Ile Trp Asn Asp Gly Lys Tyr Asn Met Val Glu Phe
465                 470                 475                 480

Gln Glu Glu Met Lys Tyr Gly Arg Ser Ala Gly Val Asp Phe Gly Pro
            485                 490                 495

Val Asp Phe Val Lys Tyr Ala Asp Ser Phe Gly Ala Lys Gly Tyr Arg
        500                 505                 510

Ala Asp Ser Lys Glu Lys Phe Asp Gln Val Leu Gln Thr Ala Leu Lys
    515                 520                 525

Glu Ala Ala Asn Gly Pro Val Leu Ile Asp Val Pro Met Asp Tyr Lys
530                 535                 540

Asp Asn Val Lys Leu Gly Glu Thr Ile Leu Pro Asp Glu Phe Tyr
545                 550                 555

<210> SEQ ID NO 68
<211> LENGTH: 1683
<212> TYPE: DNA
<213> ORGANISM: Streptococcus thermophilus
<220> FEATURE:
<221> NAME/KEY: CDS
<222> LOCATION: (1)..(1683)

<400> SEQUENCE: 68 gtg ttc atg tca gaa gaa aag caa ttg tat ggt gca gat tta gtg gtt      48
Val Phe Met Ser Glu Glu Lys Gln Leu Tyr Gly Ala Asp Leu Val Val
1               5                   10                  15 gat agt ttg atc aac cat gat gtt gag tat gtc ttt ggg att cca ggc      96
Asp Ser Leu Ile Asn His Asp Val Glu Tyr Val Phe Gly Ile Pro Gly
            20                  25                  30 gca aaa atc gat agg gtt ttt gat acc ttg gaa gat aag gga cct gaa     144
Ala Lys Ile Asp Arg Val Phe Asp Thr Leu Glu Asp Lys Gly Pro Glu
        35                  40                  45 ttg att gtt gcc cgt cat gag caa aat gct gct ttt atg gct caa ggt     192
Leu Ile Val Ala Arg His Glu Gln Asn Ala Ala Phe Met Ala Gln Gly
    50                  55                  60 gtt gga cgt att act ggg aaa cca ggt gta gta ttg gta aca tct ggt     240
Val Gly Arg Ile Thr Gly Lys Pro Gly Val Val Leu Val Thr Ser Gly
65                  70                  75                  80 cca ggt gtc tcc aat ttg gct act ggt ttg gta aca gcg acg gat gaa     288
Pro Gly Val Ser Asn Leu Ala Thr Gly Leu Val Thr Ala Thr Asp Glu
                85                  90                  95 gga gac cct gtt ctt gct att ggt ggt cag gtt aag cgt gca gat ctc     336
Gly Asp Pro Val Leu Ala Ile Gly Gly Gln Val Lys Arg Ala Asp Leu
            100                 105                 110 ttg aaa cgt gcc cac caa tca atg aat aac gtt gct atg ctt gag cca     384
Leu Lys Arg Ala His Gln Ser Met Asn Asn Val Ala Met Leu Glu Pro
        115                 120                 125 att acc aaa tat gct gct gaa gta cat gat gct aac acc ctt tct gaa     432
Ile Thr Lys Tyr Ala Ala Glu Val His Asp Ala Asn Thr Leu Ser Glu
    130                 135                 140
```

```
acg gtt gct aat gcc tat cgt cac gct aag tca ggg aaa cca ggt gca      480
Thr Val Ala Asn Ala Tyr Arg His Ala Lys Ser Gly Lys Pro Gly Ala
145                 150                 155                 160 agc ttc att tca att cct caa gac gtg acg gat gct ccg gtc agt gtt      528
Ser Phe Ile Ser Ile Pro Gln Asp Val Thr Asp Ala Pro Val Ser Val
                165                 170                 175 aag gct att aag cct atg aca gat cca aaa ctt ggt tca gca tct gtt      576
Lys Ala Ile Lys Pro Met Thr Asp Pro Lys Leu Gly Ser Ala Ser Val
            180                 185                 190 tct gat att aac tat cta gca caa gcc att aaa aat gca gtg ttg cca      624
Ser Asp Ile Asn Tyr Leu Ala Gln Ala Ile Lys Asn Ala Val Leu Pro
        195                 200                 205 gtc ttt ctt ttg ggg aat ggt gcc tca tca gaa gcc gta act tac tct      672
Val Phe Leu Leu Gly Asn Gly Ala Ser Ser Glu Ala Val Thr Tyr Ser
    210                 215                 220 att cgc caa att ttg aag cat gtt aaa ttg cca gtt gtt gaa act ttc      720
Ile Arg Gln Ile Leu Lys His Val Lys Leu Pro Val Val Glu Thr Phe
225                 230                 235                 240 caa ggt gcc ggt atc gtg tca cgt gac ctt gaa gaa gat act ttc ttt      768
Gln Gly Ala Gly Ile Val Ser Arg Asp Leu Glu Glu Asp Thr Phe Phe
                245                 250                 255 ggt cgt gta ggt ctt ttc cgt aac caa ccc gga gac atg ttg ctt aaa      816
Gly Arg Val Gly Leu Phe Arg Asn Gln Pro Gly Asp Met Leu Leu Lys
            260                 265                 270 aaa tcc gac tta gtt att gcc att ggt tat gat cca atc gaa tat gaa      864
Lys Ser Asp Leu Val Ile Ala Ile Gly Tyr Asp Pro Ile Glu Tyr Glu
        275                 280                 285 gca cgt aac tgg aat gct gaa att tca gca cgt atc atc gtt att gat      912
Ala Arg Asn Trp Asn Ala Glu Ile Ser Ala Arg Ile Ile Val Ile Asp
    290                 295                 300 gtc gag ccg gcc gag gtg gac act tac ttc caa ccg gaa cgt gaa ttg      960
Val Glu Pro Ala Glu Val Asp Thr Tyr Phe Gln Pro Glu Arg Glu Leu
305                 310                 315                 320 att ggt aat gta gaa gcg agc tta gac ttg ctt ttg ccc gct att caa     1008
Ile Gly Asn Val Glu Ala Ser Leu Asp Leu Leu Leu Pro Ala Ile Gln
                325                 330                 335 ggt tat aaa ttg cct gaa ggt gcg gtt gaa tat ctt aaa ggt ttg aaa     1056
Gly Tyr Lys Leu Pro Glu Gly Ala Val Glu Tyr Leu Lys Gly Leu Lys
            340                 345                 350 aac aat gtt gtt gag gat gtt aag ttt gac cgt cag cct gat gaa ggt     1104
Asn Asn Val Val Glu Asp Val Lys Phe Asp Arg Gln Pro Asp Glu Gly
        355                 360                 365 acg gtg cat ccg cta gat ttc atc gaa aat ttg caa gaa cac aca gat     1152
Thr Val His Pro Leu Asp Phe Ile Glu Asn Leu Gln Glu His Thr Asp
    370                 375                 380 gat gat atg act gtt acg ttt gat gtt ggt agt cac tat att tgg atg     1200
Asp Asp Met Thr Val Thr Phe Asp Val Gly Ser His Tyr Ile Trp Met
385                 390                 395                 400 gca cgt tat ctc aaa tcg tat gaa cca cgt cat ttg ctt ttc tca aat     1248
Ala Arg Tyr Leu Lys Ser Tyr Glu Pro Arg His Leu Leu Phe Ser Asn
                405                 410                 415 ggg atg caa acg ata ggt att gct att aca tgg gct atc tct gca gca     1296
Gly Met Gln Thr Ile Gly Ile Ala Ile Thr Trp Ala Ile Ser Ala Ala
            420                 425                 430 ttg gtt cgt cct aag aca aaa gtg att tct gta tct ggt gat ggt ggt     1344
Leu Val Arg Pro Lys Thr Lys Val Ile Ser Val Ser Gly Asp Gly Gly
        435                 440                 445 ttc ctc ttc tca gca caa gaa ttg gaa aca gca gtt cgt ttg aaa ttg     1392
Phe Leu Phe Ser Ala Gln Glu Leu Glu Thr Ala Val Arg Leu Lys Leu
```

```
                450                 455                 460
cca att gtc cat att atc tgg aac gat ggt cat tac aat atg gtg gaa    1440
Pro Ile Val His Ile Ile Trp Asn Asp Gly His Tyr Asn Met Val Glu
465                 470                 475                 480 ttc cag gaa gaa atg aag tac ggt cgt tca tct ggg gtt gac ttt ggt    1488
Phe Gln Glu Glu Met Lys Tyr Gly Arg Ser Ser Gly Val Asp Phe Gly
                485                 490                 495 cct gta gat ttt gta aaa tat gct gag agc ttt gga gcc aaa ggt tat    1536
Pro Val Asp Phe Val Lys Tyr Ala Glu Ser Phe Gly Ala Lys Gly Tyr
            500                 505                 510 cgt gca aca agt aaa gca gcg ttt gct agc ttg ctt caa gag gct ttg    1584
Arg Ala Thr Ser Lys Ala Ala Phe Ala Ser Leu Leu Gln Glu Ala Leu
        515                 520                 525 act cag gct gta gat gga cca gtc ctt att gat gtt cca att gac tat    1632
Thr Gln Ala Val Asp Gly Pro Val Leu Ile Asp Val Pro Ile Asp Tyr
    530                 535                 540 aaa gat aac att aaa ctc ggc gaa act att ttg cca gat gaa ttt tac    1680
Lys Asp Asn Ile Lys Leu Gly Glu Thr Ile Leu Pro Asp Glu Phe Tyr
545                 550                 555                 560 taa                                                                1683
```

<210> SEQ ID NO 69
<211> LENGTH: 560
<212> TYPE: PRT
<213> ORGANISM: Streptococcus thermophilus

<400> SEQUENCE: 69

Val Phe Met Ser Glu Glu Lys Gln Leu Tyr Gly Ala Asp Leu Val Val
1               5                   10                  15

Asp Ser Leu Ile Asn His Asp Val Glu Tyr Val Phe Gly Ile Pro Gly
            20                  25                  30

Ala Lys Ile Asp Arg Val Phe Asp Thr Leu Glu Asp Lys Gly Pro Glu
        35                  40                  45

Leu Ile Val Ala Arg His Glu Gln Asn Ala Ala Phe Met Ala Gln Gly
    50                  55                  60

Val Gly Arg Ile Thr Gly Lys Pro Gly Val Val Leu Val Thr Ser Gly
65                  70                  75                  80

Pro Gly Val Ser Asn Leu Ala Thr Gly Leu Val Thr Ala Thr Asp Glu
                85                  90                  95

Gly Asp Pro Val Leu Ala Ile Gly Gly Gln Val Lys Arg Ala Asp Leu
            100                 105                 110

Leu Lys Arg Ala His Gln Ser Met Asn Asn Val Ala Met Leu Glu Pro
        115                 120                 125

Ile Thr Lys Tyr Ala Ala Glu Val His Asp Ala Asn Thr Leu Ser Glu
    130                 135                 140

Thr Val Ala Asn Ala Tyr Arg His Ala Lys Ser Gly Lys Pro Gly Ala
145                 150                 155                 160

Ser Phe Ile Ser Ile Pro Gln Asp Val Thr Asp Ala Pro Val Ser Val
                165                 170                 175

Lys Ala Ile Lys Pro Met Thr Asp Pro Lys Leu Gly Ser Ala Ser Val
            180                 185                 190

Ser Asp Ile Asn Tyr Leu Ala Gln Ala Ile Lys Asn Ala Val Leu Pro
        195                 200                 205

Val Phe Leu Leu Gly Asn Gly Ala Ser Ser Glu Ala Val Thr Tyr Ser
    210                 215                 220

Ile Arg Gln Ile Leu Lys His Val Lys Leu Pro Val Val Glu Thr Phe

```
            225                 230                 235                 240
        Gln Gly Ala Gly Ile Val Ser Arg Asp Leu Glu Glu Asp Thr Phe Phe
                        245                 250                 255

Gly Arg Val Gly Leu Phe Arg Asn Gln Pro Gly Asp Met Leu Leu Lys
                        260                 265                 270

Lys Ser Asp Leu Val Ile Ala Ile Gly Tyr Asp Pro Ile Glu Tyr Glu
                        275                 280                 285

Ala Arg Asn Trp Asn Ala Glu Ile Ser Ala Arg Ile Ile Val Ile Asp
                        290                 295                 300

Val Glu Pro Ala Glu Val Asp Thr Tyr Phe Gln Pro Glu Arg Glu Leu
        305                 310                 315                 320

Ile Gly Asn Val Glu Ala Ser Leu Asp Leu Leu Pro Ala Ile Gln
                        325                 330                 335

Gly Tyr Lys Leu Pro Glu Gly Ala Val Glu Tyr Leu Lys Gly Leu Lys
                        340                 345                 350

Asn Asn Val Val Glu Asp Val Lys Phe Asp Arg Gln Pro Asp Glu Gly
                        355                 360                 365

Thr Val His Pro Leu Asp Phe Ile Glu Asn Leu Gln Glu His Thr Asp
                        370                 375                 380

Asp Asp Met Thr Val Thr Phe Asp Val Gly Ser His Tyr Ile Trp Met
        385                 390                 395                 400

Ala Arg Tyr Leu Lys Ser Tyr Glu Pro Arg His Leu Leu Phe Ser Asn
                        405                 410                 415

Gly Met Gln Thr Ile Gly Ile Ala Ile Thr Trp Ala Ile Ser Ala Ala
                        420                 425                 430

Leu Val Arg Pro Lys Thr Lys Val Ile Ser Val Ser Gly Asp Gly Gly
                        435                 440                 445

Phe Leu Phe Ser Ala Gln Glu Leu Glu Thr Ala Val Arg Leu Lys Leu
                        450                 455                 460

Pro Ile Val His Ile Ile Trp Asn Asp Gly His Tyr Asn Met Val Glu
        465                 470                 475                 480

Phe Gln Glu Glu Met Lys Tyr Gly Arg Ser Ser Gly Val Asp Phe Gly
                        485                 490                 495

Pro Val Asp Phe Val Lys Tyr Ala Glu Ser Phe Gly Ala Lys Gly Tyr
                        500                 505                 510

Arg Ala Thr Ser Lys Ala Ala Phe Ala Ser Leu Leu Gln Glu Ala Leu
                        515                 520                 525

Thr Gln Ala Val Asp Gly Pro Val Leu Ile Asp Val Pro Ile Asp Tyr
                        530                 535                 540

Lys Asp Asn Ile Lys Leu Gly Glu Thr Ile Leu Pro Asp Glu Phe Tyr
        545                 550                 555                 560

<210> SEQ ID NO 70
<211> LENGTH: 1665
<212> TYPE: DNA
<213> ORGANISM: Vibrio angustum
<220> FEATURE:
<221> NAME/KEY: CDS
<222> LOCATION: (1)..(1665)

<400> SEQUENCE: 70 atg tcg gat aaa acc gtc tct ggt gct gaa ctg gtt gtt gaa act tta      48
Met Ser Asp Lys Thr Val Ser Gly Ala Glu Leu Val Val Glu Thr Leu
1               5                   10                  15 aat gca cat aac gtt cca cac att ttt ggt att cct gga gca aag gtg      96
Asn Ala His Asn Val Pro His Ile Phe Gly Ile Pro Gly Ala Lys Val
```

-continued

```
              20                  25                  30
gat gct gtt ttc gat gct gtt tgt gat aac gga cca gaa atc att att      144
Asp Ala Val Phe Asp Ala Val Cys Asp Asn Gly Pro Glu Ile Ile Ile
         35                  40                  45 tgt cat cat gaa caa aat gca gcg ttt atg gca gca act ggg cgt          192
Cys His His Glu Gln Asn Ala Ala Phe Met Ala Ala Thr Gly Arg
 50                  55                  60 tta acg ggt aaa gca ggc att tgt tta gca acc tct gga cca ggc gca      240
Leu Thr Gly Lys Ala Gly Ile Cys Leu Ala Thr Ser Gly Pro Gly Ala
 65                  70                  75                  80 tca aac ctt gtc aca ggc gtt gca aca gcg aat agt gaa ggt gat cct      288
Ser Asn Leu Val Thr Gly Val Ala Thr Ala Asn Ser Glu Gly Asp Pro
             85                  90                  95 gtg gtt gca ctt gca ggt gct gta cct ctt tct atg tat tct cac aat      336
Val Val Ala Leu Ala Gly Ala Val Pro Leu Ser Met Tyr Ser His Asn
            100                 105                 110 act cat caa tcc atg gat acc cgt tca ctg ttt act cct atc acc aag      384
Thr His Gln Ser Met Asp Thr Arg Ser Leu Phe Thr Pro Ile Thr Lys
            115                 120                 125 ttt tca gca gaa gtg atg gat agc agc tcg gta tct gat gtt gta cat      432
Phe Ser Ala Glu Val Met Asp Ser Ser Ser Val Ser Asp Val Val His
130                 135                 140 aaa gct ttt cgt att gca gag caa cct acc caa ggt gct agc ttt gtt      480
Lys Ala Phe Arg Ile Ala Glu Gln Pro Thr Gln Gly Ala Ser Phe Val
145                 150                 155                 160 agt cta ccg caa gat att cta act aac cgt att cct tac cag cca gta      528
Ser Leu Pro Gln Asp Ile Leu Thr Asn Arg Ile Pro Tyr Gln Pro Val
             165                 170                 175 caa cag cct aat cca att ttg ttc ggt ggt gca cac cca caa gct att      576
Gln Gln Pro Asn Pro Ile Leu Phe Gly Gly Ala His Pro Gln Ala Ile
            180                 185                 190 cgt cag gct gct gat cgc att aat gct gca aaa aat ccg gtg tta tta      624
Arg Gln Ala Ala Asp Arg Ile Asn Ala Ala Lys Asn Pro Val Leu Leu
            195                 200                 205 ctg ggc atg gat gca agc cag cct ttt gtt gct gat gct att cgc caa      672
Leu Gly Met Asp Ala Ser Gln Pro Phe Val Ala Asp Ala Ile Arg Gln
            210                 215                 220 cta ctc aaa caa aca cca att gcc gtt gtg aat acg ttt gcc gca gct      720
Leu Leu Lys Gln Thr Pro Ile Ala Val Val Asn Thr Phe Ala Ala Ala
225                 230                 235                 240 ggg gtt att tct cat gat tta tac aac tgc ttt tta ggt cgt gtt ggc      768
Gly Val Ile Ser His Asp Leu Tyr Asn Cys Phe Leu Gly Arg Val Gly
             245                 250                 255 tta ttt aaa aat caa ccc ggt gat att gca tta aac agt gca gat tta      816
Leu Phe Lys Asn Gln Pro Gly Asp Ile Ala Leu Asn Ser Ala Asp Leu
            260                 265                 270 atc att acc att ggc tac agc cca att gaa tac gat ccg att ctt tgg      864
Ile Ile Thr Ile Gly Tyr Ser Pro Ile Glu Tyr Asp Pro Ile Leu Trp
            275                 280                 285 aat aaa gat gca aac aca cca att att cat att ggt tat caa caa gca      912
Asn Lys Asp Ala Asn Thr Pro Ile Ile His Ile Gly Tyr Gln Gln Ala
            290                 295                 300 gat tta gaa att agc tat aac cct gtt tgt gaa gtt gtg ggt gac tta      960
Asp Leu Glu Ile Ser Tyr Asn Pro Val Cys Glu Val Val Gly Asp Leu
305                 310                 315                 320 gcg gtg tct gtc acg tct att gct tct gaa tta gat aag cga gaa tca      1008
Ala Val Ser Val Thr Ser Ile Ala Ser Glu Leu Asp Lys Arg Glu Ser
            325                 330                 335 tta gaa aat aac caa caa atc caa tta tta cgc cac gat tta caa cat      1056
```

-continued

```
Leu Glu Asn Asn Gln Gln Ile Gln Leu Leu Arg His Asp Leu Gln His
            340                 345                 350 att atg cag atg ggg gta aat aaa acc tca aca aac ggc gtt cac ccg      1104
Ile Met Gln Met Gly Val Asn Lys Thr Ser Thr Asn Gly Val His Pro
        355                 360                 365 ctt cgt ttt gtt cat gag tta cgt cgc ttt gtt agt gac gac acc act      1152
Leu Arg Phe Val His Glu Leu Arg Arg Phe Val Ser Asp Asp Thr Thr
370                 375                 380 gta tgt tgt gat gta ggc tct att tat att tgg atg gca cgt tac ttc      1200
Val Cys Cys Asp Val Gly Ser Ile Tyr Ile Trp Met Ala Arg Tyr Phe
385                 390                 395                 400 cac agc ttt gaa cct cgt cgt tta ttg ttc agc aat ggc caa caa aca      1248
His Ser Phe Glu Pro Arg Arg Leu Leu Phe Ser Asn Gly Gln Gln Thr
                405                 410                 415 ttg ggc gta gct tta cct tgg gca att gca gct tcc ctt ctt cac cct      1296
Leu Gly Val Ala Leu Pro Trp Ala Ile Ala Ala Ser Leu Leu His Pro
            420                 425                 430 aat gaa aaa gta att tcc atg tct ggt gat ggt ggc ttc cta ttc tca      1344
Asn Glu Lys Val Ile Ser Met Ser Gly Asp Gly Gly Phe Leu Phe Ser
        435                 440                 445 tca atg gaa tta gcc acg gcc gtt cgc cat aaa tgt aat atc gtt cac      1392
Ser Met Glu Leu Ala Thr Ala Val Arg His Lys Cys Asn Ile Val His
450                 455                 460 ttt gtt tgg aca gat cac agt tat gac atg gtt aag atc caa cag ctt      1440
Phe Val Trp Thr Asp His Ser Tyr Asp Met Val Lys Ile Gln Gln Leu
465                 470                 475                 480 aaa aag tat ggt cga gag agt gcc gtc agc ttt ata ggt cct gat att      1488
Lys Lys Tyr Gly Arg Glu Ser Ala Val Ser Phe Ile Gly Pro Asp Ile
                485                 490                 495 gtt aag tac gca gaa agc ttc ggc gca cat ggt tta gcg atc aat act      1536
Val Lys Tyr Ala Glu Ser Phe Gly Ala His Gly Leu Ala Ile Asn Thr
            500                 505                 510 gcc gat gat att gag cct gtt atg cga aaa gct atg agc tta agt ggc      1584
Ala Asp Asp Ile Glu Pro Val Met Arg Lys Ala Met Ser Leu Ser Gly
        515                 520                 525 cca gta ttg gtc aac gtc aat gtt gat tat agc gat aac agt cgc cta      1632
Pro Val Leu Val Asn Val Asn Val Asp Tyr Ser Asp Asn Ser Arg Leu
530                 535                 540 ctt gat caa ctt cat cca tgc caa caa gat taa                          1665
Leu Asp Gln Leu His Pro Cys Gln Gln Asp
545                 550
```

<210> SEQ ID NO 71
<211> LENGTH: 554
<212> TYPE: PRT
<213> ORGANISM: Vibrio angustum

<400> SEQUENCE: 71

```
Met Ser Asp Lys Thr Val Ser Gly Ala Glu Leu Val Val Glu Thr Leu
1               5                   10                  15

Asn Ala His Asn Val Pro His Ile Phe Gly Ile Pro Gly Ala Lys Val
            20                  25                  30

Asp Ala Val Phe Asp Ala Val Cys Asp Asn Gly Pro Glu Ile Ile Ile
        35                  40                  45

Cys His His Glu Gln Asn Ala Ala Phe Met Ala Ala Ala Thr Gly Arg
    50                  55                  60

Leu Thr Gly Lys Ala Gly Ile Cys Leu Ala Thr Ser Gly Pro Gly Ala
65                  70                  75                  80

Ser Asn Leu Val Thr Gly Val Ala Thr Ala Asn Ser Glu Gly Asp Pro
```

-continued

```
                85                  90                  95
Val Val Ala Leu Ala Gly Ala Val Pro Leu Ser Met Tyr Ser His Asn
            100                 105                 110
Thr His Gln Ser Met Asp Thr Arg Ser Leu Phe Thr Pro Ile Thr Lys
            115                 120                 125
Phe Ser Ala Glu Val Met Asp Ser Ser Ser Val Ser Asp Val Val His
            130                 135                 140
Lys Ala Phe Arg Ile Ala Glu Gln Pro Thr Gln Gly Ala Ser Phe Val
145                 150                 155                 160
Ser Leu Pro Gln Asp Ile Leu Thr Asn Arg Ile Pro Tyr Gln Pro Val
                165                 170                 175
Gln Gln Pro Asn Pro Ile Leu Phe Gly Gly Ala His Pro Gln Ala Ile
                180                 185                 190
Arg Gln Ala Ala Asp Arg Ile Asn Ala Ala Lys Asn Pro Val Leu Leu
                195                 200                 205
Leu Gly Met Asp Ala Ser Gln Pro Phe Val Ala Asp Ala Ile Arg Gln
            210                 215                 220
Leu Leu Lys Gln Thr Pro Ile Ala Val Val Asn Thr Phe Ala Ala Ala
225                 230                 235                 240
Gly Val Ile Ser His Asp Leu Tyr Asn Cys Phe Leu Gly Arg Val Gly
                245                 250                 255
Leu Phe Lys Asn Gln Pro Gly Asp Ile Ala Leu Asn Ser Ala Asp Leu
            260                 265                 270
Ile Ile Thr Ile Gly Tyr Ser Pro Ile Glu Tyr Asp Pro Ile Leu Trp
            275                 280                 285
Asn Lys Asp Ala Asn Thr Pro Ile Ile His Ile Gly Tyr Gln Gln Ala
290                 295                 300
Asp Leu Glu Ile Ser Tyr Asn Pro Val Cys Glu Val Val Gly Asp Leu
305                 310                 315                 320
Ala Val Ser Val Thr Ser Ile Ala Ser Glu Leu Asp Lys Arg Glu Ser
            325                 330                 335
Leu Glu Asn Asn Gln Gln Ile Gln Leu Leu Arg His Asp Leu Gln His
            340                 345                 350
Ile Met Gln Met Gly Val Asn Lys Thr Ser Thr Asn Gly Val His Pro
        355                 360                 365
Leu Arg Phe Val His Glu Leu Arg Arg Phe Val Ser Asp Asp Thr Thr
    370                 375                 380
Val Cys Cys Asp Val Gly Ser Ile Tyr Ile Trp Met Ala Arg Tyr Phe
385                 390                 395                 400
His Ser Phe Glu Pro Arg Arg Leu Leu Phe Ser Asn Gly Gln Gln Thr
                405                 410                 415
Leu Gly Val Ala Leu Pro Trp Ala Ile Ala Ala Ser Leu Leu His Pro
            420                 425                 430
Asn Glu Lys Val Ile Ser Met Ser Gly Asp Gly Gly Phe Leu Phe Ser
            435                 440                 445
Ser Met Glu Leu Ala Thr Ala Val Arg His Lys Cys Asn Ile Val His
    450                 455                 460
Phe Val Trp Thr Asp His Ser Tyr Asp Met Val Lys Ile Gln Gln Leu
465                 470                 475                 480
Lys Lys Tyr Gly Arg Glu Ser Ala Val Ser Phe Ile Gly Pro Asp Ile
                485                 490                 495
Val Lys Tyr Ala Glu Ser Phe Gly Ala His Gly Leu Ala Ile Asn Thr
            500                 505                 510
```

```
Ala Asp Asp Ile Glu Pro Val Met Arg Lys Ala Met Ser Leu Ser Gly
        515                 520                 525

Pro Val Leu Val Asn Val Asn Val Asp Tyr Ser Asp Asn Ser Arg Leu
    530                 535                 540

Leu Asp Gln Leu His Pro Cys Gln Gln Asp
545                 550
```

<210> SEQ ID NO 72
<211> LENGTH: 1689
<212> TYPE: DNA
<213> ORGANISM: Bacillus cereus

<400> SEQUENCE: 72

```
ttgagtacag gtgtaaaagc aaacgacgtg aagacaaaaa caaaaggagc agatcttgtt     60
gttgattgtt taattaaaca aggtgttaca catgttttcg gtattccagg agcaaagatt    120
gactctgtat ttgatgtact gcaagaaaga ggaccagagt taattgtttg tcgtcatgaa    180
caaaatgcag catttatggc agctgctatt ggtagattaa caggaaaacc gggcgtatgt    240
cttgtaactt caggaccagg gacatcaaat ttagcgacag gtcttgttac tgcgaatgcg    300
gagagtgatc ccgttgttgc tttagctggt gcagttccgc gtacggatcg attaaaacgt    360
acacatcaat ctatggataa tgctgcacta ttcgaaccaa tcacaaaata tagcgtagaa    420
gtagagcatc ctgataatgt gccagaagca ttatcaaatg cattccgaag tgcgacttct    480
acaaatccag gagcaacttt agtaagtttg ccgcaagacg ttatgactgc ggaaacgact    540
gtagagtcta tcggtgcgct ttctaagcca cagcttggaa tcgctcccac acatgatatt    600
acatatgtag tagataaaat aaaagcagcg aaattaccag ttattttact cggtatgaga    660
gcgagcacaa atgaagtgac gaaagccgtt cgtaaattaa ttgcggatac agaacttcct    720
gtcgttgaaa catatcaagc ggctggtgcc atttcacgtg agttagaaga tcatttcttc    780
ggccgtgttg gactattccg taaccaacca ggtgatattt tactagaaga ggcagatctt    840
gttatttcta tcggttatga tccaattgag tatgatccaa agttctggaa taaacttgga    900
gacagaacga ttattcatct tgatgaccat caagcagata tagatcatga ttaccaacca    960
gagcgtgaat taattggtga tattgcctta acagtaaata gcatcgcaga aaagttaccg   1020
aaacttgtgt taagtacgaa atcagaagca gtgttagaac gattacgcgc gaaattatca   1080
gaacaagcag aagttccaaa tcgtccttca gaaggtgtta cacatccgct tcaagtgatt   1140
cgtacacttc gttctttaat tagtgacgac acaaccgtta catgtgacat cggttcccat   1200
tctatttgga tggcgagatg tttccgttct tatgaaccac gtagattatt atttagtaac   1260
ggtatgcaga cgttaggtgt tgcacttcct tgggcaattg ctgctacttt agtagaacca   1320
ggtaaaaaag tagtttccgt atcaggtgac ggtggtttct tattctcagc gatggagtta   1380
gaaacggcgg tacgtttaaa ttctccaatc gtccatcttg tttggagaga cggcacatat   1440
gatatggttg cattccaaca aatgatgaaa tacggcagaa catcagctac agagtttggt   1500
gatgttgatc ttgttaaata tgcggaaagt ttcggggcgt taggtcttcg tgttaacacg   1560
cctgatgaat tagaaggggt attgaaagaa gcactagcag cagacggccc tgtcattatt   1620
gatattccaa ttgactatcg tgacaacatt aaattaagcg aaaaattatt accaaaccaa   1680
ttaaactaa                                                           1689
```

<210> SEQ ID NO 73
<211> LENGTH: 562

<212> TYPE: PRT
<213> ORGANISM: Bacillus cereus

<400> SEQUENCE: 73

```
Met Ser Thr Gly Val Lys Ala Asn Asp Val Lys Thr Lys Thr Lys Gly
1               5                   10                  15

Ala Asp Leu Val Val Asp Cys Leu Ile Lys Gln Gly Val Thr His Val
            20                  25                  30

Phe Gly Ile Pro Gly Ala Lys Ile Asp Ser Val Phe Asp Val Leu Gln
        35                  40                  45

Glu Arg Gly Pro Glu Leu Ile Val Cys Arg His Glu Gln Asn Ala Ala
    50                  55                  60

Phe Met Ala Ala Ala Ile Gly Arg Leu Thr Gly Lys Pro Gly Val Cys
65                  70                  75                  80

Leu Val Thr Ser Gly Pro Gly Thr Ser Asn Leu Ala Thr Gly Leu Val
                85                  90                  95

Thr Ala Asn Ala Glu Ser Asp Pro Val Val Ala Leu Ala Gly Ala Val
            100                 105                 110

Pro Arg Thr Asp Arg Leu Lys Arg Thr His Gln Ser Met Asp Asn Ala
        115                 120                 125

Ala Leu Phe Glu Pro Ile Thr Lys Tyr Ser Val Glu Val Glu His Pro
    130                 135                 140

Asp Asn Val Pro Glu Ala Leu Ser Asn Ala Phe Arg Ser Ala Thr Ser
145                 150                 155                 160

Thr Asn Pro Gly Ala Thr Leu Val Ser Leu Pro Gln Asp Val Met Thr
                165                 170                 175

Ala Glu Thr Thr Val Glu Ser Ile Gly Ala Leu Ser Lys Pro Gln Leu
            180                 185                 190

Gly Ile Ala Pro Thr His Asp Ile Thr Tyr Val Val Asp Lys Ile Lys
        195                 200                 205

Ala Ala Lys Leu Pro Val Ile Leu Leu Gly Met Arg Ala Ser Thr Asn
    210                 215                 220

Glu Val Thr Lys Ala Val Arg Lys Leu Ile Ala Asp Thr Glu Leu Pro
225                 230                 235                 240

Val Val Glu Thr Tyr Gln Ala Ala Gly Ala Ile Ser Arg Glu Leu Glu
                245                 250                 255

Asp His Phe Phe Gly Arg Val Gly Leu Phe Arg Asn Gln Pro Gly Asp
            260                 265                 270

Ile Leu Leu Glu Glu Ala Asp Leu Val Ile Ser Ile Gly Tyr Asp Pro
        275                 280                 285

Ile Glu Tyr Asp Pro Lys Phe Trp Asn Lys Leu Gly Asp Arg Thr Ile
    290                 295                 300

Ile His Leu Asp Asp His Gln Ala Asp Ile Asp His Asp Tyr Gln Pro
305                 310                 315                 320

Glu Arg Glu Leu Ile Gly Asp Ile Ala Leu Thr Val Asn Ser Ile Ala
                325                 330                 335

Glu Lys Leu Pro Lys Leu Val Leu Ser Thr Lys Ser Glu Ala Val Leu
            340                 345                 350

Glu Arg Leu Arg Ala Lys Leu Ser Glu Gln Ala Glu Val Pro Asn Arg
        355                 360                 365

Pro Ser Glu Gly Val Thr His Pro Leu Gln Val Ile Arg Thr Leu Arg
    370                 375                 380

Ser Leu Ile Ser Asp Asp Thr Thr Val Thr Cys Asp Ile Gly Ser His
385                 390                 395                 400
```

Ser Ile Trp Met Ala Arg Cys Phe Arg Ser Tyr Glu Pro Arg Arg Leu
            405                 410                 415

Leu Phe Ser Asn Gly Met Gln Thr Leu Gly Val Ala Leu Pro Trp Ala
            420                 425                 430

Ile Ala Ala Thr Leu Val Glu Pro Gly Lys Lys Val Val Ser Val Ser
            435                 440                 445

Gly Asp Gly Gly Phe Leu Phe Ser Ala Met Glu Leu Glu Thr Ala Val
        450                 455                 460

Arg Leu Asn Ser Pro Ile Val His Leu Val Trp Arg Asp Gly Thr Tyr
465                 470                 475                 480

Asp Met Val Ala Phe Gln Gln Met Met Lys Tyr Gly Arg Thr Ser Ala
            485                 490                 495

Thr Glu Phe Gly Asp Val Asp Leu Val Lys Tyr Ala Glu Ser Phe Gly
            500                 505                 510

Ala Leu Gly Leu Arg Val Asn Thr Pro Asp Glu Leu Glu Gly Val Leu
        515                 520                 525

Lys Glu Ala Leu Ala Ala Asp Gly Pro Val Ile Ile Asp Ile Pro Ile
            530                 535                 540

Asp Tyr Arg Asp Asn Ile Lys Leu Ser Glu Lys Leu Leu Pro Asn Gln
545                 550                 555                 560

Leu Asn

<210> SEQ ID NO 74
<211> LENGTH: 1020
<212> TYPE: DNA
<213> ORGANISM: Lactococcus lactis

<400> SEQUENCE: 74
atggcagtta caatgtatta tgaagatgat gtagaagtat cagcacttgc tggaaagcaa      60
attgcagtaa tcggttatgg ttcacaagga catgctcacg cacagaattt gcgtgattct     120
ggtcacaacg ttatcattgg tgtgcgccac ggaaaatctt ttgataaagc aaaagaagat     180
ggctttgaaa catttgaagt aggagaagca gtagctaaag ctgatgttat tatggttttg     240
gcaccagatg aacttcaaca atccatttat gaagaggaca tcaaaccaaa cttgaaagca     300
ggttcagcac ttggttttgc tcacggattt aatatccatt ttggctatat taaagtacca     360
gaagacgttg acgtctttat ggttgcgcct aaggctccag tcaccttgtc cgtcggact      420 tatactgaag gttttggtac accagctttg tttgtttcac accaaaatgc aagtggtcat     480
gcgcgtgaaa tcgcaatgga ttgggccaaa ggaattggtt gtgctcgagt gggaattatt     540
gaaacaactt ttaaagaaga aacagaagaa gatttgtttg agaacaagc tgttctatgt     600 ggaggtttga cagcacttgt tgaagccggt tttgaaacac tgacagaagc tggatacgct     660
ggcgaattgg cttactttga agttttgcac gaaatgaaat tgattgttga cctcatgtat     720
gaaggtggtt ttactaaaat gcgtcaatcc atctcaaata ctgctgagtt tggcgattat     780
gtgactggtc cacggattat tactgacgaa gttaaaaaga atatgaagct tgtttttggct     840 gatattcaat ctggaaaatt tgctcaagat ttcgttgatg acttcaaagc ggggcgtcca     900
aaattaatag cctatcgcga agctgcaaaa atcttgaaa ttgaaaaaat tggggcagag     960
ctacgtcaag caatgccatt cacacaatct ggtgatgacg atgcctttaa aatctatcag    1020

<210> SEQ ID NO 75
<211> LENGTH: 340
<212> TYPE: PRT

<213> ORGANISM: Lactococcus lactis

<400> SEQUENCE: 75

| | | | | | | | | | | | | | | |
|---|---|---|---|---|---|---|---|---|---|---|---|---|---|---|
| Met | Ala | Val | Thr | Met | Tyr | Tyr | Glu | Asp | Asp | Val | Glu | Val | Ser | Ala | Leu |
| 1 | | | | 5 | | | | | 10 | | | | | 15 | |
| Ala | Gly | Lys | Gln | Ile | Ala | Val | Ile | Gly | Tyr | Gly | Ser | Gln | Gly | His | Ala |
| | | | 20 | | | | | 25 | | | | | 30 | | |
| His | Ala | Gln | Asn | Leu | Arg | Asp | Ser | Gly | His | Asn | Val | Ile | Ile | Gly | Val |
| | | 35 | | | | | 40 | | | | | 45 | | | |
| Arg | His | Gly | Lys | Ser | Phe | Asp | Lys | Ala | Lys | Glu | Asp | Gly | Phe | Glu | Thr |
| | 50 | | | | | 55 | | | | | 60 | | | | |
| Phe | Glu | Val | Gly | Glu | Ala | Val | Ala | Lys | Ala | Asp | Val | Ile | Met | Val | Leu |
| 65 | | | | | 70 | | | | | 75 | | | | | 80 |
| Ala | Pro | Asp | Glu | Leu | Gln | Gln | Ser | Ile | Tyr | Glu | Glu | Asp | Ile | Lys | Pro |
| | | | | 85 | | | | | 90 | | | | | 95 | |
| Asn | Leu | Lys | Ala | Gly | Ser | Ala | Leu | Gly | Phe | Ala | His | Gly | Phe | Asn | Ile |
| | | | 100 | | | | | 105 | | | | | 110 | | |
| His | Phe | Gly | Tyr | Ile | Lys | Val | Pro | Glu | Asp | Val | Asp | Val | Phe | Met | Val |
| | | 115 | | | | | 120 | | | | | 125 | | | |
| Ala | Pro | Lys | Ala | Pro | Gly | His | Leu | Val | Arg | Arg | Thr | Tyr | Thr | Glu | Gly |
| | 130 | | | | | 135 | | | | | 140 | | | | |
| Phe | Gly | Thr | Pro | Ala | Leu | Phe | Val | Ser | His | Gln | Asn | Ala | Ser | Gly | His |
| 145 | | | | | 150 | | | | | 155 | | | | | 160 |
| Ala | Arg | Glu | Ile | Ala | Met | Asp | Trp | Ala | Lys | Gly | Ile | Gly | Cys | Ala | Arg |
| | | | | 165 | | | | | 170 | | | | | 175 | |
| Val | Gly | Ile | Ile | Glu | Thr | Thr | Phe | Lys | Glu | Glu | Thr | Glu | Glu | Asp | Leu |
| | | | 180 | | | | | 185 | | | | | 190 | | |
| Phe | Gly | Glu | Gln | Ala | Val | Leu | Cys | Gly | Gly | Leu | Thr | Ala | Leu | Val | Glu |
| | | 195 | | | | | 200 | | | | | 205 | | | |
| Ala | Gly | Phe | Glu | Thr | Leu | Thr | Glu | Ala | Gly | Tyr | Ala | Gly | Glu | Leu | Ala |
| | 210 | | | | | 215 | | | | | 220 | | | | |
| Tyr | Phe | Glu | Val | Leu | His | Glu | Met | Lys | Leu | Ile | Val | Asp | Leu | Met | Tyr |
| 225 | | | | | 230 | | | | | 235 | | | | | 240 |
| Glu | Gly | Gly | Phe | Thr | Lys | Met | Arg | Gln | Ser | Ile | Ser | Asn | Thr | Ala | Glu |
| | | | | 245 | | | | | 250 | | | | | 255 | |
| Phe | Gly | Asp | Tyr | Val | Thr | Gly | Pro | Arg | Ile | Ile | Thr | Asp | Glu | Val | Lys |
| | | | 260 | | | | | 265 | | | | | 270 | | |
| Lys | Asn | Met | Lys | Leu | Val | Leu | Ala | Asp | Ile | Gln | Ser | Gly | Lys | Phe | Ala |
| | | 275 | | | | | 280 | | | | | 285 | | | |
| Gln | Asp | Phe | Val | Asp | Asp | Phe | Lys | Ala | Gly | Arg | Pro | Lys | Leu | Ile | Ala |
| | 290 | | | | | 295 | | | | | 300 | | | | |
| Tyr | Arg | Glu | Ala | Ala | Lys | Asn | Leu | Glu | Ile | Glu | Lys | Ile | Gly | Ala | Glu |
| 305 | | | | | 310 | | | | | 315 | | | | | 320 |
| Leu | Arg | Gln | Ala | Met | Pro | Phe | Thr | Gln | Ser | Gly | Asp | Asp | Ala | Phe |
| | | | | 325 | | | | | 330 | | | | | 335 |
| Lys | Ile | Tyr | Gln | | | | | | | | | | | |
| | | | 340 | | | | | | | | | | | |

<210> SEQ ID NO 76
<211> LENGTH: 1485
<212> TYPE: DNA
<213> ORGANISM: Vibrio cholerae

<400> SEQUENCE: 76

```
atggcgaatt atttcaatac gctgaatctg cgtgaacagt tggatcaact tggtcgttgc    60
```

```
cgttttatgg cgcgagaaga gtttgcaacc gaagctgatt acctaaaagg taagaaagtg      120
gtgatcgtag gttgtggggc tcaaggccta aaccaaggcc tcaatatgcg tgattcaggt      180
ttggatgttt cttacgctct gcgtcaggct gcgattgatg aacagcgtca gtcatttaag      240
aatgccaaga taatggctt caacgtgggt agttatgaac aactcatccc aaccgcagat       300
ttggtgatta acttgacgcc agacaagcag cacaccagtg tggtcaatgc ggtgatgcct      360
ctgatgaagc aaggtgctgc cttgggttac tcacacggtt ttaatatcgt tgaagagggc      420
atgcagatcc gtaaagacat cacggttgtg atggtggcac caaatgtccc gggtacggaa      480
gttcgtgaag agtataagcg cggtttcggc gttcctactc ttatcgcggt acaccctgaa      540
aacgatccac aaggtgaagg ttgggaaatt gctaaagcgt gggctgcggc aacgggtggc      600
catcgtgcgg gctgtttagc ttcttctttt gtggcggaag tgaaatccga tttgatgggt      660
gagcaaacca ttctctgcgg tatgctgcaa gcgggctcta tcgtttgtta cgagaaaatg      720
gttgctgatg gcatcgaccc tggttatgcg ggcaagcttt tgcaatttgg ttgggaaacc      780
attaccgaag cactcaagtt tggcggtatt actcatatga tggatcgcct gtctaaccct      840
gcaaaaatca aagcgtttga gctgtctgaa gagttgaaag atctgatgcg cccactgtac      900
aacaagcata tggatgacat catttctggc cacttctcta gcaccatgat ggcggattgg      960
gcgaatgatg ataaagactt attcggctgg cgtgcagaaa ccgctgagac gacctttgaa     1020
aactatccaa caaccgacgt aaaaattgct gagcaagaat actttgataa cggtattttg     1080
atgattgcca tggtgcgtgc tggggttgag ttggcgtttg aagcgatgac ggcttcaggc     1140
atcatcgatg agtcggctta ctatgaatca ctgcacgaac tcccactgat tgccaatacg     1200
gtagcgcgta agcgtctgta tgaaatgaac gtggtaatct ctgacactgc tgagtacggt     1260
aactatctgt ttgccaatgt ggcggtacca ctattgcgtg aaaagtttat gccgaaagtg     1320
ggcactgatg tgattggtaa aggattaggc gtggtctcta atcaagttga taacgcaacg     1380
cttatcgaag taaacagcat catccgtaac catccggttg agtatatcgg tgaagagcta     1440
cgcggttaca tgaaagacat gaagcgcatc gccgtgggtg attaa                     1485
```

<210> SEQ ID NO 77
<211> LENGTH: 494
<212> TYPE: PRT
<213> ORGANISM: Vibrio cholerae

<400> SEQUENCE: 77

Met Ala Asn Tyr Phe Asn Thr Leu Asn Leu Arg Glu Gln Leu Asp Gln
1               5                   10                  15

Leu Gly Arg Cys Arg Phe Met Ala Arg Glu Glu Phe Ala Thr Glu Ala
            20                  25                  30

Asp Tyr Leu Lys Gly Lys Lys Val Ile Val Gly Cys Gly Ala Gln
        35                  40                  45

Gly Leu Asn Gln Gly Leu Asn Met Arg Asp Ser Gly Leu Asp Val Ser
    50                  55                  60

Tyr Ala Leu Arg Gln Ala Ala Ile Asp Glu Gln Arg Gln Ser Phe Lys
65                  70                  75                  80

Asn Ala Lys Asn Asn Gly Phe Asn Val Gly Ser Tyr Glu Gln Leu Ile
                85                  90                  95

Pro Thr Ala Asp Leu Val Ile Asn Leu Thr Pro Asp Lys Gln His Thr
            100                 105                 110

Ser Val Val Asn Ala Val Met Pro Leu Met Lys Gln Gly Ala Ala Leu

```
            115                 120                 125
Gly Tyr Ser His Gly Phe Asn Ile Val Glu Glu Gly Met Gln Ile Arg
    130                 135                 140
Lys Asp Ile Thr Val Val Met Val Ala Pro Lys Cys Pro Gly Thr Glu
145                 150                 155                 160
Val Arg Glu Glu Tyr Lys Arg Gly Phe Gly Val Pro Thr Leu Ile Ala
                165                 170                 175
Val His Pro Glu Asn Asp Pro Gln Gly Glu Gly Trp Glu Ile Ala Lys
            180                 185                 190
Ala Trp Ala Ala Thr Gly Gly His Arg Ala Gly Cys Leu Ala Ser
        195                 200                 205
Ser Phe Val Ala Glu Val Lys Ser Asp Leu Met Gly Glu Gln Thr Ile
    210                 215                 220
Leu Cys Gly Met Leu Gln Ala Gly Ser Ile Val Cys Tyr Glu Lys Met
225                 230                 235                 240
Val Ala Asp Gly Ile Asp Pro Gly Tyr Ala Gly Lys Leu Leu Gln Phe
                245                 250                 255
Gly Trp Glu Thr Ile Thr Glu Ala Leu Lys Phe Gly Gly Ile Thr His
            260                 265                 270
Met Met Asp Arg Leu Ser Asn Pro Ala Lys Ile Lys Ala Phe Glu Leu
        275                 280                 285
Ser Glu Glu Leu Lys Asp Leu Met Arg Pro Leu Tyr Asn Lys His Met
    290                 295                 300
Asp Asp Ile Ile Ser Gly His Phe Ser Ser Thr Met Met Ala Asp Trp
305                 310                 315                 320
Ala Asn Asp Asp Lys Asp Leu Phe Gly Trp Arg Ala Glu Thr Ala Glu
                325                 330                 335
Thr Thr Phe Glu Asn Tyr Pro Thr Thr Asp Val Lys Ile Ala Glu Gln
            340                 345                 350
Glu Tyr Phe Asp Asn Gly Ile Leu Met Ile Ala Met Val Arg Ala Gly
        355                 360                 365
Val Glu Leu Ala Phe Glu Ala Met Thr Ala Ser Gly Ile Ile Asp Glu
    370                 375                 380
Ser Ala Tyr Tyr Glu Ser Leu His Glu Leu Pro Leu Ile Ala Asn Thr
385                 390                 395                 400
Val Ala Arg Lys Arg Leu Tyr Glu Met Asn Val Val Ile Ser Asp Thr
                405                 410                 415
Ala Glu Tyr Gly Asn Tyr Leu Phe Ala Asn Val Ala Val Pro Leu Leu
            420                 425                 430
Arg Glu Lys Phe Met Pro Lys Val Gly Thr Asp Val Ile Gly Lys Gly
        435                 440                 445
Leu Gly Val Val Ser Asn Gln Val Asp Asn Ala Thr Leu Ile Glu Val
    450                 455                 460
Asn Ser Ile Ile Arg Asn His Pro Val Glu Tyr Ile Gly Glu Glu Leu
465                 470                 475                 480
Arg Gly Tyr Met Lys Asp Met Lys Arg Ile Ala Val Gly Asp
                485                 490
```

<210> SEQ ID NO 78
<211> LENGTH: 1014
<212> TYPE: DNA
<213> ORGANISM: Pseudomonas aeruginosa

<400> SEQUENCE: 78

-continued

```
atgcgcgttt tctacgataa agactgtgac ctctcgatca tccagggcaa gaaagttgcc      60
atcatcggct acggctccca gggccacgcc catgcctgca acctgaagga ctccggcgtc     120
gacgtcaccg tgggcctgcg tagcggctcc gccaccgtgg ccaaggccga agcgcacggt     180
ctgaaggttg ccgacgtgaa gaccgccgtc gccgcagccg acgtggtcat gatcctcacc     240
ccggacgagt tccagggccg cctgtacaag gaagagatcg agccgaacct gaagaagggc     300
gccaccctgg ccttcgctca cggcttctcc atccactaca accaggtcgt cccgcgcgcc     360
gacctcgacg tgatcatgat cgcgccgaag gcaccgggtc acaccgtgcg ttccgagttc     420
gtcaagggcg gtggcatccc tgacctgatc gccatctacc aggacgcttc cggcaacgcc     480
aagaacgtcg ccctgtccta cgcctgcggc gtcggcggcg gtcgtaccgg tatcatcgaa     540
accaccttca aggacgagac cgaaaccgac ctgttcggtg agcaggccgt tctctgcggt     600
ggttgcgtcg agctggtcaa ggccggtttc gaaaccctgg tcgaagccgg ttacgcgccg     660
gaaatggcct acttcgagtg cctgcacgag ctgaagctga tcgtcgacct gatgtacgaa     720
ggcggcatcg ccaacatgaa ctactccatc tccaacaatg ccgaatacgg tgagtacgta     780
accggtccgg aggtgatcaa cgccgagtcc cgtgctgcca tgcgcaacgc cctgaagcgc     840
atccaggacg gcgagtacgc gaaaatgttc attaccgaag gtgcggccaa ctacccgtcg     900
atgactgcct accgccgcaa caacgccgct cacccgatcg agcagatcgg cgagaagctg     960
cgcgcgatga tgccgtggat cgcagccaac aagatcgtcg acaagagcaa gaac         1014
```

<210> SEQ ID NO 79
<211> LENGTH: 338
<212> TYPE: PRT
<213> ORGANISM: Pseudomonas aeruginosa

<400> SEQUENCE: 79

Met Arg Val Phe Tyr Asp Lys Asp Cys Asp Leu Ser Ile Ile Gln Gly
1               5                   10                  15

Lys Lys Val Ala Ile Ile Gly Tyr Gly Ser Gln Gly His Ala His Ala
            20                  25                  30

Cys Asn Leu Lys Asp Ser Gly Val Asp Val Thr Val Gly Leu Arg Ser
        35                  40                  45

Gly Ser Ala Thr Val Ala Lys Ala Glu Ala His Gly Leu Lys Val Ala
    50                  55                  60

Asp Val Lys Thr Ala Val Ala Ala Asp Val Val Met Ile Leu Thr
65                  70                  75                  80

Pro Asp Glu Phe Gln Gly Arg Leu Tyr Lys Glu Glu Ile Glu Pro Asn
                85                  90                  95

Leu Lys Lys Gly Ala Thr Leu Ala Phe Ala His Gly Phe Ser Ile His
            100                 105                 110

Tyr Asn Gln Val Val Pro Arg Ala Asp Leu Asp Val Ile Met Ile Ala
        115                 120                 125

Pro Lys Ala Pro Gly His Thr Val Arg Ser Glu Phe Val Lys Gly Gly
    130                 135                 140

Gly Ile Pro Asp Leu Ile Ala Ile Tyr Gln Asp Ala Ser Gly Asn Ala
145                 150                 155                 160

Lys Asn Val Ala Leu Ser Tyr Ala Cys Gly Val Gly Gly Gly Arg Thr
                165                 170                 175

Gly Ile Ile Glu Thr Thr Phe Lys Asp Glu Thr Glu Thr Asp Leu Phe
            180                 185                 190

Gly Glu Gln Ala Val Leu Cys Gly Gly Cys Val Glu Leu Val Lys Ala

```
              195                 200                 205
Gly Phe Glu Thr Leu Val Glu Ala Gly Tyr Ala Pro Glu Met Ala Tyr
    210                 215                 220

Phe Glu Cys Leu His Glu Leu Lys Leu Ile Val Asp Leu Met Tyr Glu
225                 230                 235                 240

Gly Gly Ile Ala Asn Met Asn Tyr Ser Ile Ser Asn Asn Ala Glu Tyr
                245                 250                 255

Gly Glu Tyr Val Thr Gly Pro Glu Val Ile Asn Ala Glu Ser Arg Ala
            260                 265                 270

Ala Met Arg Asn Ala Leu Lys Arg Ile Gln Asp Gly Glu Tyr Ala Lys
        275                 280                 285

Met Phe Ile Thr Glu Gly Ala Ala Asn Tyr Pro Ser Met Thr Ala Tyr
    290                 295                 300

Arg Arg Asn Asn Ala Ala His Pro Ile Glu Gln Ile Gly Glu Lys Leu
305                 310                 315                 320

Arg Ala Met Met Pro Trp Ile Ala Ala Asn Lys Ile Val Asp Lys Ser
                325                 330                 335

Lys Asn

<210> SEQ ID NO 80
<211> LENGTH: 1014
<212> TYPE: DNA
<213> ORGANISM: Pseudomonas fluorescens

<400> SEQUENCE: 80
atgaaagttt tctacgataa agactgcgac ctgtcgatca tccaaggtaa gaaagttgcc      60
atcatcggct acggttccca gggccacgct caagcatgca acctgaagga ttccggcgta     120
gacgtgactg ttggcctgcg taaaggctcg gctaccgttg ccaaggctga agcccacggc     180
ttgaaagtga ccgacgttgc tgcagccgtt gccggtgccg acttggtcat gatcctgacc     240
ccggacgagt ccagtccca gctgtacaag aacgaaatcg agccgaacat caagaagggc     300
gccactctgg ccttctccca cggcttcgcg atccactaca accaggttgt gcctcgtgcc     360
gacctcgacg tgatcatgat cgcgccgaag gctccaggcc acaccgtacg ttccgagttc     420
gtcaagggcg gtggtattcc tgacctgatc gcgatctacc aggacgcttc cggcaacgcc     480
aagaacgttg ccctgtccta cgccgcaggc gtgggcggcg ccgtaccgg catcatcgaa      540 accaccttca aggacgagac tgaaaccgac ctgttcggtg agcaggctgt tctgtgtggc     600
ggtaccgtcg agctggtcaa agccggtttc gaaaccctgg ttgaagctgg ctacgctcca     660
gaaatggcct acttcgagtg cctgcacgaa ctgaagctga tcgttgacct catgtacgaa     720
ggcggtatcg ccaacatgaa ctactcgatc tccaacaacg ctgaatacgg cgagtacgtg     780
actggtccag aagtcatcaa cgccgaatcc cgtcaggcca tgcgcaatgc tctgaagcgc     840
atccaggacg gcgaatacgc gaagatgttc atcagcgaag cgctaccgg ctacccatcg      900 atgaccgcca agcgtcgtaa caacgctgct cacggtatcg aaatcatcgg cgagcaactg     960
cgctcgatga tgccttggat cggtgccaac aaaatcgtcg acaaagccaa gaac          1014

<210> SEQ ID NO 81
<211> LENGTH: 338
<212> TYPE: PRT
<213> ORGANISM: Pseudomonas fluorescens

<400> SEQUENCE: 81

Met Lys Val Phe Tyr Asp Lys Asp Cys Asp Leu Ser Ile Ile Gln Gly
```

```
  1               5                  10                 15
Lys Lys Val Ala Ile Ile Gly Tyr Gly Ser Gln Gly His Ala Gln Ala
                    20                 25                 30

Cys Asn Leu Lys Asp Ser Gly Val Asp Val Thr Val Gly Leu Arg Lys
                35                 40                 45

Gly Ser Ala Thr Val Ala Lys Ala Glu Ala His Gly Leu Lys Val Thr
            50                 55                 60

Asp Val Ala Ala Val Ala Gly Ala Asp Leu Val Met Ile Leu Thr
65                 70                 75                 80

Pro Asp Glu Phe Gln Ser Gln Leu Tyr Lys Asn Glu Ile Glu Pro Asn
                    85                 90                 95

Ile Lys Lys Gly Ala Thr Leu Ala Phe Ser His Gly Phe Ala Ile His
                100                105                110

Tyr Asn Gln Val Val Pro Arg Ala Asp Leu Asp Val Ile Met Ile Ala
                115                120                125

Pro Lys Ala Pro Gly His Thr Val Arg Ser Glu Phe Val Lys Gly Gly
            130                135                140

Gly Ile Pro Asp Leu Ile Ala Ile Tyr Gln Asp Ala Ser Gly Asn Ala
145                150                155                160

Lys Asn Val Ala Leu Ser Tyr Ala Ala Gly Val Gly Gly Arg Thr
                    165                170                175

Gly Ile Ile Glu Thr Thr Phe Lys Asp Glu Thr Glu Thr Asp Leu Phe
                180                185                190

Gly Glu Gln Ala Val Leu Cys Gly Gly Thr Val Glu Leu Val Lys Ala
                195                200                205

Gly Phe Glu Thr Leu Val Glu Ala Gly Tyr Ala Pro Glu Met Ala Tyr
            210                215                220

Phe Glu Cys Leu His Glu Leu Lys Leu Ile Val Asp Leu Met Tyr Glu
225                230                235                240

Gly Gly Ile Ala Asn Met Asn Tyr Ser Ile Ser Asn Ala Glu Tyr
                    245                250                255

Gly Glu Tyr Val Thr Gly Pro Glu Val Ile Asn Ala Glu Ser Arg Gln
                260                265                270

Ala Met Arg Asn Ala Leu Lys Arg Ile Gln Asp Gly Glu Tyr Ala Lys
                275                280                285

Met Phe Ile Ser Glu Gly Ala Thr Gly Tyr Pro Ser Met Thr Ala Lys
            290                295                300

Arg Arg Asn Asn Ala Ala His Gly Ile Glu Ile Ile Gly Glu Gln Leu
305                310                315                320

Arg Ser Met Met Pro Trp Ile Gly Ala Asn Lys Ile Val Asp Lys Ala
                    325                330                335

Lys Asn

<210> SEQ ID NO 82
<211> LENGTH: 1713
<212> TYPE: DNA
<213> ORGANISM: Lactococcus lactis

<400> SEQUENCE: 82
atggaattca aatataacgg aaaagttgaa tcaatagagc tcaataagta ttcaaaaaca      60
ttgacacaag acccaacaca gccagcgacc caagccatgc actatggcat tggttttaaa     120
gatgaggact tcaaaaagc tcaggtcgga atcgtcagca tggattggga cggaaatccc      180
tgtaacatgc acttgggcac actcggtagt aaaatcaaaa attctgtcaa tcaaactgac     240
```

```
ggactgattg ggcttcaatt tcacacgatt ggggtttctg acggaattgc caacggaaag      300
cttggcatga gatattcctt ggtcagtcgt gaagttattg ctgacagtat tgaaaccaac      360
gctggcgccg aatattacga tgcaattgtc gctgttccg gttgtgacaa aaatatgcca       420
ggctcaatca ttggcatggc tcggctcaat cgtccgtcaa ttatggttta tggtggaacg      480
attgaacatg gcgaatacaa aggcgaaaag ttaaatattg tttcggcttt tgaagcgctt      540
ggacaaaaaa tcactggaaa tatttccgag aagattatc acggcgtcat ttgtaatgcc       600
attccgggac agggtgcttg tggggcatg tatacagcaa atacactggc ttcggcaatt       660
gaaactttgg gaatgagttt gccttattcg gcttcaaatc cagcggtcag tcaagaaaaa      720
gaagacgaat gtgatgaaat tggtctggca atcaaaaatt tgctagaaaa agacatcaaa      780
ccaagcgata tcatgaccaa ggaagctttt gaaaatgcca taacgatcgt catggttctc      840
ggtggttcaa ctaatgctgt gcttcatatc attgccatgg ctaatgccat cggtgtcgaa      900
attacgcaag atgattttca acgtatttcc gatgtcacgc ctgtgcttgg cgacttcaag      960
ccaagtggca agtacatgat ggaagatttg cacaaaattg gtggcgtgcc tgctgttttg     1020
aaatatttgc tcaaagaggg caagcttcat ggcgactgtt tgacagttac tggtaaaact     1080
ctagctgaaa atgttgaaac agcactggat ttggactttg acagccaaga cattattcga     1140
ccacttgaaa atcctatcaa agcaacaggt catttgcaaa ttctctatgg caatcttgct     1200
gaaggtggtt ctgtggcaaa aatttctgga aaagaagggg aattttttcaa aggaacagct     1260
cgtgtctttg atggcgaaca acatttttatt gacggaattg agtcaggtcg tttgcacgca     1320
ggagatgtcg ctgtcattcg taatatcggt ccagtcggag gcccaggaat gccagaaatg     1380
ttaaaaccga cctcagcctt gattggagca ggtcttggaa atcttgtgc tttgattact      1440
gacggacgtt tctctggtgg cacacatggc tttgtggttg gccacattgt ccccgaagcg     1500
gttgagggtg gattgattgg cttggtcgaa gatgatgata ttatcgagat tgatgcggtc     1560
aataacagca ttagtttgaa agttgctgac gatgagattg ctagacgacg tgccaattat     1620
caaaaacctg ctcctaaagc aacgcgtggg gttcttgcta aatttgctaa actcacgcgc     1680
ccagccagtg aaggctgtgt gactgattta tag                                  1713
```

<210> SEQ ID NO 83
<211> LENGTH: 570
<212> TYPE: PRT
<213> ORGANISM: Lactococcus lactis

<400> SEQUENCE: 83

Met Glu Phe Lys Tyr Asn Gly Lys Val Glu Ser Ile Glu Leu Asn Lys
1               5                   10                  15

Tyr Ser Lys Thr Leu Thr Gln Asp Pro Thr Gln Pro Ala Thr Gln Ala
            20                  25                  30

Met His Tyr Gly Ile Gly Phe Lys Asp Glu Asp Phe Lys Lys Ala Gln
        35                  40                  45

Val Gly Ile Val Ser Met Asp Trp Asp Gly Asn Pro Cys Asn Met His
    50                  55                  60

Leu Gly Thr Leu Gly Ser Lys Ile Lys Asn Ser Val Asn Gln Thr Asp
65                  70                  75                  80

Gly Leu Ile Gly Leu Gln Phe His Thr Ile Gly Val Ser Asp Gly Ile
                85                  90                  95

Ala Asn Gly Lys Leu Gly Met Arg Tyr Ser Leu Val Ser Arg Glu Val
            100                 105                 110

```
Ile Ala Asp Ser Ile Glu Thr Asn Ala Gly Ala Glu Tyr Tyr Asp Ala
            115                 120                 125
Ile Val Ala Val Pro Gly Cys Asp Lys Asn Met Pro Gly Ser Ile Ile
130                 135                 140
Gly Met Ala Arg Leu Asn Arg Pro Ser Ile Met Val Tyr Gly Gly Thr
145                 150                 155                 160
Ile Glu His Gly Glu Tyr Lys Gly Glu Lys Leu Asn Ile Val Ser Ala
            165                 170                 175
Phe Glu Ala Leu Gly Gln Lys Ile Thr Gly Asn Ile Ser Glu Glu Asp
            180                 185                 190
Tyr His Gly Val Ile Cys Asn Ala Ile Pro Gly Gln Gly Ala Cys Gly
            195                 200                 205
Gly Met Tyr Thr Ala Asn Thr Leu Ala Ser Ala Ile Glu Thr Leu Gly
210                 215                 220
Met Ser Leu Pro Tyr Ser Ala Ser Asn Pro Ala Val Ser Gln Glu Lys
225                 230                 235                 240
Glu Asp Glu Cys Asp Glu Ile Gly Leu Ala Ile Lys Asn Leu Leu Glu
            245                 250                 255
Lys Asp Ile Lys Pro Ser Asp Ile Met Thr Lys Glu Ala Phe Glu Asn
            260                 265                 270
Ala Ile Thr Ile Val Met Val Leu Gly Gly Ser Thr Asn Ala Val Leu
            275                 280                 285
His Ile Ile Ala Met Ala Asn Ala Ile Gly Val Glu Ile Thr Gln Asp
            290                 295                 300
Asp Phe Gln Arg Ile Ser Asp Val Thr Pro Val Leu Gly Asp Phe Lys
305                 310                 315                 320
Pro Ser Gly Lys Tyr Met Met Glu Asp Leu His Lys Ile Gly Gly Val
            325                 330                 335
Pro Ala Val Leu Lys Tyr Leu Leu Lys Glu Gly Lys Leu His Gly Asp
            340                 345                 350
Cys Leu Thr Val Thr Gly Lys Thr Leu Ala Glu Asn Val Glu Thr Ala
            355                 360                 365
Leu Asp Leu Asp Phe Asp Ser Gln Asp Ile Ile Arg Pro Leu Glu Asn
            370                 375                 380
Pro Ile Lys Ala Thr Gly His Leu Gln Ile Leu Tyr Gly Asn Leu Ala
385                 390                 395                 400
Glu Gly Gly Ser Val Ala Lys Ile Ser Gly Lys Glu Gly Glu Phe Phe
            405                 410                 415
Lys Gly Thr Ala Arg Val Phe Asp Gly Glu Gln His Phe Ile Asp Gly
            420                 425                 430
Ile Glu Ser Gly Arg Leu His Ala Gly Asp Val Ala Val Ile Arg Asn
            435                 440                 445
Ile Gly Pro Val Gly Gly Pro Gly Met Pro Glu Met Leu Lys Pro Thr
            450                 455                 460
Ser Ala Leu Ile Gly Ala Gly Leu Gly Lys Ser Cys Ala Leu Ile Thr
465                 470                 475                 480
Asp Gly Arg Phe Ser Gly Gly Thr His Gly Phe Val Val Gly His Ile
            485                 490                 495
Val Pro Glu Ala Val Glu Gly Gly Leu Ile Gly Leu Val Glu Asp Asp
            500                 505                 510
Asp Ile Ile Glu Ile Asp Ala Val Asn Asn Ser Ile Ser Leu Lys Val
            515                 520                 525
```

Ala Asp Asp Glu Ile Ala Arg Arg Arg Ala Asn Tyr Gln Lys Pro Ala
        530                 535                 540

Pro Lys Ala Thr Arg Gly Val Leu Ala Lys Phe Ala Lys Leu Thr Arg
545                 550                 555                 560

Pro Ala Ser Glu Gly Cys Val Thr Asp Leu
                565                 570

<210> SEQ ID NO 84
<211> LENGTH: 1713
<212> TYPE: DNA
<213> ORGANISM: Streptococcus mutans

<400> SEQUENCE: 84

```
atgactgaca aaaaaactct taaagactta agaaatcgta gttctgttta cgattcaatg      60
gttaaatcac ctaatcgtgc tatgttgcgt gcaactggta tgcaagatga agactttgaa     120
aaacctatcg tcggtgtcat ttcaacttgg gctgaaaaca caccttgtaa tatccactta     180
catgactttg gtaaactagc caaagtcggt gttaaggaag ctggtgcttg gccagttcag     240
ttcggaacaa tcacggtttc tgatggaatc gccatgggaa cccaaggaat gcgtttctcc     300
ttgacatctc gtgatattat tgcagattct attgaagcag ccatggggag tcataatgcg     360
gatgcttttg tagccattgg cggttgtgat aaaaacatgc ccggttctgt tatcgctatg     420
gctaacatgg atatcccagc cattttttgct tacggcggaa caattgcacc tggtaattta     480
gacggcaaag atatcgattt agtctctgtc tttgaaggtg tcggccattg gaaccacggc     540
gatatgacca agaagaagt taagctttg gaatgtaatg cttgtcccgg tcctggaggc     600
tgcggtggta tgtatactgc taacacaatg gcgacagcta ttgaagtttt gggacttagc     660
cttccgggtt catcttctca cccggctgaa tccgcagaaa agaaagcaga tattgaagaa     720
gctggtcgcg ctgttgtcaa aatgctcgaa atgggcttaa aaccttctga cattttaacg     780
cgtgaagctt ttgaagatgc tattactgta actatggctc tgggaggttc aaccaactca     840
acccttcacc tcttagctat tgcccatgct gctaatgtgg aattgacact tgatgatttc     900
aatactttcc aagaaaaagt tcctcatttg gctgatttga accttctgg tcaatatgta     960
ttccaagacc tttacaaggt cggaggggta ccagcagtta tgaaatatct ccttaaaaat    1020
ggcttccttc atggtgaccg tatcacttgt actggcaaaa cagtcgctga aaatttgaag    1080
gcttttgatg atttaacacc tggtcaaaag gttattatgc cgcttgaaaa tcctaaacgt    1140
gaagatggtc cgctcattat tctccatggt aacttggctc cagacggtgc cgttgccaaa    1200
gtttctggtg taaaagtgcg tcgtcatgtc ggtcctgcta aggtctttaa ttctgaagaa    1260
gaagccattg aagctgtctt gaatgatgat attgttgatg gtgatgttgt tgtcgtacgt    1320
tttgtaggac caaagggcgg tcctggtatg cctgaaatgc tttccctttc atcaatgatt    1380
gttggtaaag ggcaaggtga aaagttgcc cttctgacag atggccgctt ctcaggtggt    1440
acttatggtc ttgtcgtggg tcatatcgct cctgaagcac aagatggcgg tccaatcgcc    1500
tacctgcaaa caggagacat agtcactatt gaccaagaca ctaaggaatt acactttgat    1560
atctccgatg aagagttaaa acatcgtcaa gagaccattg aattgccacc gctctattca    1620
cgcggtatcc ttggtaaata tgctcacatc gtttcgtctg cttctagggg agccgtaaca    1680
gacttttgga gcctgaagaa actggcaaa aaa                                  1713
```

<210> SEQ ID NO 85
<211> LENGTH: 571
<212> TYPE: PRT

<213> ORGANISM: Streptococcus mutans

<400> SEQUENCE: 85

```
Met Thr Asp Lys Lys Thr Leu Lys Asp Leu Arg Asn Arg Ser Ser Val
1               5                   10                  15

Tyr Asp Ser Met Val Lys Ser Pro Asn Arg Ala Met Leu Arg Ala Thr
            20                  25                  30

Gly Met Gln Asp Glu Asp Phe Glu Lys Pro Ile Val Gly Val Ile Ser
        35                  40                  45

Thr Trp Ala Glu Asn Thr Pro Cys Asn Ile His Leu His Asp Phe Gly
    50                  55                  60

Lys Leu Ala Lys Val Gly Val Lys Glu Ala Gly Ala Trp Pro Val Gln
65                  70                  75                  80

Phe Gly Thr Ile Thr Val Ser Asp Gly Ile Ala Met Gly Thr Gln Gly
                85                  90                  95

Met Arg Phe Ser Leu Thr Ser Arg Asp Ile Ile Ala Asp Ser Ile Glu
            100                 105                 110

Ala Ala Met Gly Gly His Asn Ala Asp Ala Phe Val Ala Ile Gly Gly
        115                 120                 125

Cys Asp Lys Asn Met Pro Gly Ser Val Ile Ala Met Ala Asn Met Asp
130                 135                 140

Ile Pro Ala Ile Phe Ala Tyr Gly Gly Thr Ile Ala Pro Gly Asn Leu
145                 150                 155                 160

Asp Gly Lys Asp Ile Asp Leu Val Ser Val Phe Glu Gly Val Gly His
                165                 170                 175

Trp Asn His Gly Asp Met Thr Lys Glu Glu Val Lys Ala Leu Glu Cys
            180                 185                 190

Asn Ala Cys Pro Gly Pro Gly Gly Cys Gly Gly Met Tyr Thr Ala Asn
        195                 200                 205

Thr Met Ala Thr Ala Ile Glu Val Leu Gly Leu Ser Leu Pro Gly Ser
210                 215                 220

Ser Ser His Pro Ala Glu Ser Ala Glu Lys Lys Ala Asp Ile Glu Glu
225                 230                 235                 240

Ala Gly Arg Ala Val Val Lys Met Leu Glu Met Gly Leu Lys Pro Ser
                245                 250                 255

Asp Ile Leu Thr Arg Glu Ala Phe Glu Asp Ala Ile Thr Val Thr Met
            260                 265                 270

Ala Leu Gly Gly Ser Thr Asn Ser Thr Leu His Leu Leu Ala Ile Ala
        275                 280                 285

His Ala Ala Asn Val Glu Leu Thr Leu Asp Asp Phe Asn Thr Phe Gln
290                 295                 300

Glu Lys Val Pro His Leu Ala Asp Leu Lys Pro Ser Gly Gln Tyr Val
305                 310                 315                 320

Phe Gln Asp Leu Tyr Lys Val Gly Gly Val Pro Ala Val Met Lys Tyr
                325                 330                 335

Leu Leu Lys Asn Gly Phe Leu His Gly Asp Arg Ile Thr Cys Thr Gly
            340                 345                 350

Lys Thr Val Ala Glu Asn Leu Lys Ala Phe Asp Asp Leu Thr Pro Gly
        355                 360                 365

Gln Lys Val Ile Met Pro Leu Glu Asn Pro Lys Arg Glu Asp Gly Pro
370                 375                 380

Leu Ile Ile Leu His Gly Asn Leu Ala Pro Asp Gly Ala Val Ala Lys
385                 390                 395                 400
```

```
Val Ser Gly Val Lys Val Arg Arg His Val Gly Pro Ala Lys Val Phe
            405                 410                 415

Asn Ser Glu Glu Glu Ala Ile Glu Ala Val Leu Asn Asp Asp Ile Val
            420                 425                 430

Asp Gly Asp Val Val Val Arg Phe Val Gly Pro Lys Gly Gly Pro
            435                 440             445

Gly Met Pro Glu Met Leu Ser Leu Ser Ser Met Ile Val Gly Lys Gly
            450                 455                 460

Gln Gly Glu Lys Val Ala Leu Leu Thr Asp Gly Arg Phe Ser Gly Gly
465                 470                 475                 480

Thr Tyr Gly Leu Val Val Gly His Ile Ala Pro Glu Ala Gln Asp Gly
            485                 490                 495

Gly Pro Ile Ala Tyr Leu Gln Thr Gly Asp Ile Val Thr Ile Asp Gln
            500                 505                 510

Asp Thr Lys Glu Leu His Phe Asp Ile Ser Asp Glu Glu Leu Lys His
            515                 520                 525

Arg Gln Glu Thr Ile Glu Leu Pro Pro Leu Tyr Ser Arg Gly Ile Leu
            530                 535                 540

Gly Lys Tyr Ala His Ile Val Ser Ser Ala Ser Arg Gly Ala Val Thr
545                 550                 555                 560

Asp Phe Trp Lys Pro Glu Glu Thr Gly Lys Lys
            565                 570

<210> SEQ ID NO 86
<211> LENGTH: 1647
<212> TYPE: DNA
<213> ORGANISM: Lactococcus lactis

<400> SEQUENCE: 86
atgtatacag taggagatta cctattagac cgattacacg agttaggaat tgaagaaatt        60
tttggagtcc ctggagacta aacttacaa ttttttagatc aaattatttc ccacaaggat       120
atgaaatggg tcggaaatgc taatgaatta atgcttcat atatggctga tggctatgct       180
cgtactaaaa aagctgccgc atttcttaca acctttggag taggtgaatt gagtgcagtt       240
aatggattag caggaagtta cgccgaaaat ttaccagtag tagaaatagt gggatcacct       300
acatcaaaag ttcaaaatga aggaaaattt gttcatcata cgctggctga cggtgatttt       360
aaacacttta tgaaatgca cgaacctgtt acagcagctc gaactttact acagcagaa        420 aatgcaaccg ttgaaattga ccgagtactt tctgcactat aaaagaaag aaaacctgtc       480 tatatcaact taccagttga tgttgctgct gcaaaagcag agaaaccctc actcccttg       540 aaaaaggaaa actcaacttc aaatacaagt gaccaagaaa ttttgaacaa aattcaagaa       600
agcttgaaaa atgccaaaaa accaatcgtg attacaggac atgaaataat tagttttggc       660
ttagaaaaaa cagtcactca atttatttca aagacaaaac tacctattac gacattaaac       720
tttggtaaaa gttcagttga tgaagccctc ccttcatttt taggaatcta taatggtaca       780
ctctcagagc ctaatcttaa agaattcgtg gaatcagccg acttcatctt gatgcttgga       840
gttaaactca cagactcttc aacaggagcc ttcactcatc atttaaatga aaataaaatg       900
atttcactga atatgatga aggaaaaata tttaacgaaa gaatccaaaa ttttgatttt        960
gaatccctca tctcctctct cttagaccta agcgaaatag aatacaaagg aaaatatatc      1020
gataaaaagc aagaagactt tgttccatca aatgcgcttt tatcacaaga ccgcctatgg      1080
caagcagttg aaaacctaac tcaaagcaat gaaacaatcg ttgctgaaca agggacatca      1140
```

```
ttctttggcg cttcatcaat tttcttaaaa tcaaagagtc attttattgg tcaacccctta    1200 tggggatcaa ttggatatac attcccagca gcattaggaa gccaaattgc agataaagaa    1260
agcagacacc ttttatttat tggtgatggt tcacttcaac ttacagtgca agaattagga    1320
ttagcaatca gagaaaaaat taatccaatt tgctttatta tcaataatga tggttataca    1380
gtcgaaagag aaattcatgg accaaatcaa agctacaatg atattccaat gtggaattac    1440
tcaaaattac cagaatcgtt tggagcaaca gaagatcgag tagtctcaaa aatcgttaga    1500
actgaaaatg aatttgtgtc tgtcatgaaa gaagctcaag cagatccaaa tagaatgtac    1560
tggattgagt taattttggc aaaagaaggt gcaccaaaag tactgaaaaa aatgggcaaa    1620
ctatttgctg aacaaaataa atcataa                                        1647

<210> SEQ ID NO 87
<211> LENGTH: 548
<212> TYPE: PRT
<213> ORGANISM: Lactococcus lactis

<400> SEQUENCE: 87

Met Tyr Thr Val Gly Asp Tyr Leu Leu Asp Arg Leu His Glu Leu Gly
1               5                   10                  15

Ile Glu Glu Ile Phe Gly Val Pro Gly Asp Tyr Asn Leu Gln Phe Leu
            20                  25                  30

Asp Gln Ile Ile Ser His Lys Asp Met Lys Trp Val Gly Asn Ala Asn
        35                  40                  45

Glu Leu Asn Ala Ser Tyr Met Ala Asp Gly Tyr Ala Arg Thr Lys Lys
    50                  55                  60

Ala Ala Ala Phe Leu Thr Thr Phe Gly Val Gly Glu Leu Ser Ala Val
65                  70                  75                  80

Asn Gly Leu Ala Gly Ser Tyr Ala Glu Asn Leu Pro Val Val Glu Ile
                85                  90                  95

Val Gly Ser Pro Thr Ser Lys Val Gln Asn Glu Gly Lys Phe Val His
            100                 105                 110

His Thr Leu Ala Asp Gly Asp Phe Lys His Phe Met Lys Met His Glu
        115                 120                 125

Pro Val Thr Ala Ala Arg Thr Leu Leu Thr Ala Glu Asn Ala Thr Val
    130                 135                 140

Glu Ile Asp Arg Val Leu Ser Ala Leu Leu Lys Glu Arg Lys Pro Val
145                 150                 155                 160

Tyr Ile Asn Leu Pro Val Asp Val Ala Ala Ala Lys Ala Glu Lys Pro
                165                 170                 175

Ser Leu Pro Leu Lys Lys Glu Asn Ser Thr Ser Asn Thr Ser Asp Gln
            180                 185                 190

Glu Ile Leu Asn Lys Ile Gln Glu Ser Leu Lys Asn Ala Lys Lys Pro
        195                 200                 205

Ile Val Ile Thr Gly His Glu Ile Ile Ser Phe Gly Leu Glu Lys Thr
    210                 215                 220

Val Thr Gln Phe Ile Ser Lys Thr Lys Leu Pro Ile Thr Thr Leu Asn
225                 230                 235                 240

Phe Gly Lys Ser Ser Val Asp Glu Ala Leu Pro Ser Phe Leu Gly Ile
                245                 250                 255

Tyr Asn Gly Thr Leu Ser Glu Pro Asn Leu Lys Glu Phe Val Glu Ser
            260                 265                 270

Ala Asp Phe Ile Leu Met Leu Gly Val Lys Leu Thr Asp Ser Ser Thr
        275                 280                 285
```

```
Gly Ala Phe Thr His His Leu Asn Glu Asn Lys Met Ile Ser Leu Asn
    290                 295                 300

Ile Asp Glu Gly Lys Ile Phe Asn Glu Arg Ile Gln Asn Phe Asp Phe
305                 310                 315                 320

Glu Ser Leu Ile Ser Ser Leu Leu Asp Leu Ser Glu Ile Glu Tyr Lys
                325                 330                 335

Gly Lys Tyr Ile Asp Lys Lys Gln Glu Asp Phe Val Pro Ser Asn Ala
            340                 345                 350

Leu Leu Ser Gln Asp Arg Leu Trp Gln Ala Val Glu Asn Leu Thr Gln
        355                 360                 365

Ser Asn Glu Thr Ile Val Ala Glu Gln Gly Thr Ser Phe Phe Gly Ala
    370                 375                 380

Ser Ser Ile Phe Leu Lys Ser Lys Ser His Phe Ile Gly Gln Pro Leu
385                 390                 395                 400

Trp Gly Ser Ile Gly Tyr Thr Phe Pro Ala Ala Leu Gly Ser Gln Ile
                405                 410                 415

Ala Asp Lys Glu Ser Arg His Leu Leu Phe Ile Gly Asp Gly Ser Leu
            420                 425                 430

Gln Leu Thr Val Gln Glu Leu Gly Leu Ala Ile Arg Glu Lys Ile Asn
        435                 440                 445

Pro Ile Cys Phe Ile Ile Asn Asn Asp Gly Tyr Thr Val Glu Arg Glu
    450                 455                 460

Ile His Gly Pro Asn Gln Ser Tyr Asn Asp Ile Pro Met Trp Asn Tyr
465                 470                 475                 480

Ser Lys Leu Pro Glu Ser Phe Gly Ala Thr Asp Arg Val Val Ser
                485                 490                 495

Lys Ile Val Arg Thr Glu Asn Glu Phe Val Ser Val Met Lys Glu Ala
            500                 505                 510

Gln Ala Asp Pro Asn Arg Met Tyr Trp Ile Glu Leu Ile Leu Ala Lys
        515                 520                 525

Glu Gly Ala Pro Lys Val Leu Lys Lys Met Gly Lys Leu Phe Ala Glu
    530                 535                 540

Gln Asn Lys Ser
545
```

<210> SEQ ID NO 88
<211> LENGTH: 1644
<212> TYPE: DNA
<213> ORGANISM: artificial sequence
<220> FEATURE:
<223> OTHER INFORMATION: codon optimized coding region for expression in
      L. plantarum

<400> SEQUENCE: 88

```
atgtataccg ttggtgacta tttgttggat cggttacacg aattaggcat cgaagaaatc      60
ttcggtgttc caggcgatta caatttacaa ttttttggacc aaatcatcag tcacaaagac     120
atgaaatggg tcggtaacgc aaatgaatta atgcgagtt acatggctga cggttatgct      180
cggactaaga agctgcagc ctttttgacg acttttggtg ttggtgaatt atcagccgtt      240
aatggtttgg ccgtagttta cgccgaaaat ttaccggtcg ttgaaattgt tggcagtcca     300
acgagtaagg ttcaaaacga aggtaaattt gtccatcata ccttggcaga tggtgatttt     360
aaacacttta tgaagatgca tgaaccggtc actgctgcac ggactttatt aactgcggaa     420
aatgccaccg tcgaaattga ccgcgtttta tcagccttgt taaagaacg caaaccggtt     480
```

```
tacattaatt taccggtcga tgtggcagcg gccaaagctg aaaaaccgag tttgccgtta    540
aagaaggaaa atagtacctc aaatacctca gatcaagaaa tcttgaacaa gatccaagaa    600
tcattaaaaa atgctaaaaa accaatcgtt attaccggtc atgaaattat tagttttggt    660
ttggaaaaaa cggtgacgca atttatttca aagacgaaat taccaattac gaccttgaat    720
tttggtaaat caagtgttga cgaagcgttg ccaagtttct tgggtatcta taatggtact    780
ttaagtgaac cgaatttaaa agaatttgtg gaaagtgcag attttatttt aatgttgggt    840
gtcaagttaa ctgattcatc aactggcgcg ttcacgcatc atttaaatga aaataaaatg    900
atttcattga atattgatga aggcaaaatc ttcaacgaac ggattcaaaa ttttgatttt    960
gaatcattga ttagtagttt gttagattta tcagaaatcg aatacaaagg caagtatatt    1020
gataagaagc aggaagattt tgttccgagt aatgcattgt taagtcaaga tcgcttatgg    1080
caggcggttg aaaacttaac tcaatcaaac gaaaccattg ttgctgaaca aggtacttca    1140
ttcttcggcg catcaagtat cttttttaaaa tcaaaaagtc atttcatcgg tcaaccatta    1200
tggggtagta ttggttacac cttcccagcg gcgttaggta gtcaaattgc tgacaaagaa    1260
tcacgacact tattattcat tggtgacggt agtttacaat tgacggtcca ggaattaggt    1320
ttggccattc gcgaaaagat caacccaatt tgtttcatta tcaataatga cggttatact    1380
gttgaacggg aaattcacgg tccgaaccaa agttacaatg atattccaat gtggaactac    1440
tcaaaattgc cggaaagttt tggcgccacc gaagatcggg tcgttagtaa aattgtgcgg    1500
accgaaaatg aattcgtgtc agtgatgaag gaagcacaag ccgatccgaa ccggatgtat    1560
tggattgaat taatccttggc taaggaaggt gccccgaagg ttttaaagaa gatgggcaag    1620
ttatttgcag aacaaaataa aagt                                          1644
```

<210> SEQ ID NO 89
<211> LENGTH: 21
<212> TYPE: DNA
<213> ORGANISM: artificial sequence
<220> FEATURE:
<223> OTHER INFORMATION: primer

<400> SEQUENCE: 89

```
ttgttacttg attgcgactc g                                               21
```

<210> SEQ ID NO 90
<211> LENGTH: 22
<212> TYPE: DNA
<213> ORGANISM: artificial sequence
<220> FEATURE:
<223> OTHER INFORMATION: primer

<400> SEQUENCE: 90

```
taccgatgct aggtcataaa tc                                              22
```

<210> SEQ ID NO 91
<211> LENGTH: 1047
<212> TYPE: DNA
<213> ORGANISM: Achromobacter xylosoxidans

<400> SEQUENCE: 91

```
atgaaagctc tggtttatca cggtgaccac aagatctcgc ttgaagacaa gcccaagccc    60
acccttcaaa agcccacgga tgtagtagta cgggttttga agaccacgat ctgcggcacg    120
gatctcggca tctacaaagg caagaatcca gaggtcgccg acgggcgcat cctgggccat    180
gaaggggtag gcgtcatcga ggaagtgggc gagagtgtca cgcagttcaa gaaaggcgac    240
```

```
aaggtcctga tttcctgcgt cacttcttgc ggctcgtgcg actactgcaa gaagcagctt    300
tactcccatt gccgcgacgg cgggtggatc ctgggttaca tgatcgatgg cgtgcaggcc    360
gaatacgtcc gcatcccgca tgccgacaac agcctctaca agatccccca gacaattgac    420
gacgaaatcg ccgtcctgct gagcgacatc ctgcccaccg ccacgaaat cggcgtccag     480
tatgggaatg tccagccggg cgatgcggtg gctattgtcg gcgcgggccc cgtcggcatg    540
tccgtactgt tgaccgccca gttctactcc ccctcgacca tcatcgtgat cgacatggac    600
gagaatcgcc tccagctcgc caaggagctc ggggcaacgc acaccatcaa ctccggcacg    660
gagaacgttg tcgaagccgt gcataggatt gcggcagagg gagtcgatgt tgcgatcgag    720
gcggtgggca taccggcgac ttgggacatc tgccaggaga tcgtcaagcc cggcgcgcac    780
atcgccaacg tcggcgtgca tggcgtcaag gttgacttcg agattcagaa gctctggatc    840
aagaacctga cgatcaccac gggactggtg aacacgaaca cgacgcccat gctgatgaag    900
gtcgcctcga ccgacaagct tccgttgaag aagatgatta cccatcgctt cgagctggcc    960
gagatcgagc acgcctatca ggtattcctc aatggcgcca aggagaaggc gatgaagatc   1020
atcctctcga acgcaggcgc tgcctga                                       1047
```

<210> SEQ ID NO 92  
<211> LENGTH: 348  
<212> TYPE: PRT  
<213> ORGANISM: Achromobacter xylosoxidans

<400> SEQUENCE: 92

```
Met Lys Ala Leu Val Tyr His Gly Asp His Lys Ile Ser Leu Glu Asp
 1               5                  10                  15

Lys Pro Lys Pro Thr Leu Gln Lys Pro Thr Asp Val Val Arg Val
             20                  25                  30

Leu Lys Thr Thr Ile Cys Gly Thr Asp Leu Gly Ile Tyr Lys Gly Lys
         35                  40                  45

Asn Pro Glu Val Ala Asp Gly Arg Ile Leu Gly His Glu Gly Val Gly
     50                  55                  60

Val Ile Glu Glu Val Gly Glu Ser Val Thr Gln Phe Lys Lys Gly Asp
 65                  70                  75                  80

Lys Val Leu Ile Ser Cys Val Thr Ser Cys Gly Ser Cys Asp Tyr Cys
                 85                  90                  95

Lys Lys Gln Leu Tyr Ser His Cys Arg Asp Gly Gly Trp Ile Leu Gly
            100                 105                 110

Tyr Met Ile Asp Gly Val Gln Ala Glu Tyr Val Arg Ile Pro His Ala
        115                 120                 125

Asp Asn Ser Leu Tyr Lys Ile Pro Gln Thr Ile Asp Asp Glu Ile Ala
    130                 135                 140

Val Leu Leu Ser Asp Ile Leu Pro Thr Gly His Glu Ile Gly Val Gln
145                 150                 155                 160

Tyr Gly Asn Val Gln Pro Gly Asp Ala Val Ala Ile Val Gly Ala Gly
                165                 170                 175

Pro Val Gly Met Ser Val Leu Leu Thr Ala Gln Phe Tyr Ser Pro Ser
            180                 185                 190

Thr Ile Ile Val Ile Asp Met Asp Glu Asn Arg Leu Gln Leu Ala Lys
        195                 200                 205

Glu Leu Gly Ala Thr His Thr Ile Asn Ser Gly Thr Glu Asn Val Val
    210                 215                 220
```

```
Glu Ala Val His Arg Ile Ala Ala Glu Gly Val Asp Val Ala Ile Glu
225                 230                 235                 240

Ala Val Gly Ile Pro Ala Thr Trp Asp Ile Cys Gln Glu Ile Val Lys
            245                 250                 255

Pro Gly Ala His Ile Ala Asn Val Gly Val His Gly Val Lys Val Asp
        260                 265                 270

Phe Glu Ile Gln Lys Leu Trp Ile Lys Asn Leu Thr Ile Thr Thr Gly
    275                 280                 285

Leu Val Asn Thr Asn Thr Thr Pro Met Leu Met Lys Val Ala Ser Thr
290                 295                 300

Asp Lys Leu Pro Leu Lys Lys Met Ile Thr His Arg Phe Glu Leu Ala
305                 310                 315                 320

Glu Ile Glu His Ala Tyr Gln Val Phe Leu Asn Gly Ala Lys Glu Lys
                325                 330                 335

Ala Met Lys Ile Ile Leu Ser Asn Ala Gly Ala Ala
            340                 345

<210> SEQ ID NO 93
<211> LENGTH: 1440
<212> TYPE: DNA
<213> ORGANISM: Escherichia coli

<400> SEQUENCE: 93
```

| | | | | |
|---|---|---|---|---|
| atggtaacgt tcatgataac ttctgctctt catcgtgcgg ccgactgggc taaatctgtg | 60 |
| ttctcttcgg cggcgctggg tgatcctcgc cgtactgccc gcttggttaa cgtcgccgcc | 120 |
| caattggcaa atattctgg taaatcaata accatctcat cagagggtag tgaagccatg | 180 |
| caggaaggcg cttaccgatt tatccgcaat cccaacgttt ctgccgaggc gatcagaaag | 240 |
| gctggcgcca tgcaaacagt caagttggct caggagtttc ccgaactgct ggccattgag | 300 |
| gacaccacct ctttgagtta tcgccaccag gtcgccgaag agcttggcaa gctgggctct | 360 |
| attcaggata atcccgcgg atggtgggtt cactccgttc tcttgctcga ggccaccaca | 420 |
| ttccgcaccg taggattact gcatcaggag tggtggatgc gcccggatga ccctgccgat | 480 |
| gcggatgaaa aggagagtgg caaatggctg cagccgccg caactagccg gttacgcatg | 540 |
| ggcagcatga tgagcaacgt gattgcggtc tgtgaccgcg aagccgatat tcatgcttat | 600 |
| ctgcaggaca aactggcgca taacgagcgc ttcgtggtgc gctccaagca cccacgcaag | 660 |
| gacgtagagt ctgggttgta tctgtacgac catctgaaga accaaccgga gttgggtggc | 720 |
| tatcagatca gcattccgca aagggcgtg gtggataaac gcggtaaacg taaaaatcga | 780 |
| ccagcccgca aggcgagctt gagcctgcgc agtgggcgca tcacgctaaa acaggggaat | 840 |
| atcacgctca acgcggtgct ggccgaggag attaacccgc caagggtga ccccgttg | 900 |
| aaatggttgt tgctgaccag cgaaccggtc gagtcgctag cccaagcctt gcgcgtcatc | 960 |
| gacatttata cccatcgctg gcggatcgag gagttccata aggcatggaa accggagca | 1020 |
| ggagccgaga ggcaacgcat ggaggagccg ataatctgg agcggatggt ctcgatcctc | 1080 |
| tcgtttgttg cggtcaggct gttacagctc agagaaagct tcacgctgcc gcaagcactc | 1140 |
| agggcgcaag gctgctaaa ggaagcggaa cacgtagaaa gccagtccgc agaaacggtg | 1200 |
| ctgaccccgg atgaatgtca gctactgggc tatctggaca agggaaaacg caagcgcaaa | 1260 |
| gagaaagcag gtagcttgca gtgggcttac atggcgatag ctagactggg cggttttatg | 1320 |
| gacagcaagc gaaccggaat tgccagctgg ggcgccctct gggaaggttg ggaagccctg | 1380 |
| caaagtaaac tggatggctt tcttgccgcc aaggatctga tggcgcaggg gatcaagatc | 1440 |

<210> SEQ ID NO 94
<211> LENGTH: 480
<212> TYPE: PRT
<213> ORGANISM: Escherichia coli

<400> SEQUENCE: 94

```
Met Val Thr Phe Met Ile Thr Ser Ala Leu His Arg Ala Asp Trp
1               5                   10                  15

Ala Lys Ser Val Phe Ser Ala Ala Leu Gly Asp Pro Arg Arg Thr
            20                  25                  30

Ala Arg Leu Val Asn Val Ala Ala Gln Leu Ala Lys Tyr Ser Gly Lys
        35                  40                  45

Ser Ile Thr Ile Ser Ser Glu Gly Ser Glu Ala Met Gln Glu Gly Ala
    50                  55                  60

Tyr Arg Phe Ile Arg Asn Pro Asn Val Ser Ala Glu Ala Ile Arg Lys
65                  70                  75                  80

Ala Gly Ala Met Gln Thr Val Lys Leu Ala Gln Glu Phe Pro Glu Leu
                85                  90                  95

Leu Ala Ile Glu Asp Thr Thr Ser Leu Ser Tyr Arg His Gln Val Ala
            100                 105                 110

Glu Glu Leu Gly Lys Leu Gly Ser Ile Gln Asp Lys Ser Arg Gly Trp
        115                 120                 125

Trp Val His Ser Val Leu Leu Leu Glu Ala Thr Thr Phe Arg Thr Val
    130                 135                 140

Gly Leu Leu His Gln Glu Trp Trp Met Arg Pro Asp Asp Pro Ala Asp
145                 150                 155                 160

Ala Asp Glu Lys Glu Ser Gly Lys Trp Leu Ala Ala Ala Thr Ser
                165                 170                 175

Arg Leu Arg Met Gly Ser Met Met Ser Asn Val Ile Ala Val Cys Asp
            180                 185                 190

Arg Glu Ala Asp Ile His Ala Tyr Leu Gln Asp Lys Leu Ala His Asn
        195                 200                 205

Glu Arg Phe Val Val Arg Ser Lys His Pro Arg Lys Asp Val Glu Ser
    210                 215                 220

Gly Leu Tyr Leu Tyr Asp His Leu Lys Asn Gln Pro Glu Leu Gly Gly
225                 230                 235                 240

Tyr Gln Ile Ser Ile Pro Gln Lys Gly Val Asp Lys Arg Gly Lys
                245                 250                 255

Arg Lys Asn Arg Pro Ala Arg Lys Ala Ser Leu Ser Leu Arg Ser Gly
            260                 265                 270

Arg Ile Thr Leu Lys Gln Gly Asn Ile Thr Leu Asn Ala Val Leu Ala
        275                 280                 285

Glu Glu Ile Asn Pro Pro Lys Gly Glu Thr Pro Leu Lys Trp Leu Leu
    290                 295                 300

Leu Thr Ser Glu Pro Val Glu Ser Leu Ala Gln Ala Leu Arg Val Ile
305                 310                 315                 320

Asp Ile Tyr Thr His Arg Trp Arg Ile Glu Glu Phe His Lys Ala Trp
                325                 330                 335

Lys Thr Gly Ala Gly Ala Glu Arg Gln Arg Met Glu Pro Asp Asn
            340                 345                 350

Leu Glu Arg Met Val Ser Ile Leu Ser Phe Val Ala Val Arg Leu Leu
        355                 360                 365

Gln Leu Arg Glu Ser Phe Thr Leu Pro Gln Ala Leu Arg Ala Gln Gly
```

```
                370             375             380
Leu Leu Lys Glu Ala Glu His Val Glu Ser Gln Ser Ala Glu Thr Val
385                 390                 395                 400

Leu Thr Pro Asp Glu Cys Gln Leu Leu Gly Tyr Leu Asp Lys Gly Lys
                405                 410                 415

Arg Lys Arg Lys Glu Lys Ala Gly Ser Leu Gln Trp Ala Tyr Met Ala
            420                 425                 430

Ile Ala Arg Leu Gly Gly Phe Met Asp Ser Lys Arg Thr Gly Ile Ala
        435                 440                 445

Ser Trp Gly Ala Leu Trp Glu Gly Trp Glu Ala Leu Gln Ser Lys Leu
    450                 455                 460

Asp Gly Phe Leu Ala Ala Lys Asp Leu Met Ala Gln Gly Ile Lys Ile
465                 470                 475                 480

<210> SEQ ID NO 95
<211> LENGTH: 19
<212> TYPE: DNA
<213> ORGANISM: artificial sequence
<220> FEATURE:
<223> OTHER INFORMATION: synthesized transposase recognition sequence

<400> SEQUENCE: 95
ctgtctcttg atcagatct                                               19

<210> SEQ ID NO 96
<211> LENGTH: 19
<212> TYPE: DNA
<213> ORGANISM: artificial sequence
<220> FEATURE:
<223> OTHER INFORMATION: synthesized transposase recognition sequence

<400> SEQUENCE: 96
acttgtgtat aagagtcag                                               19

<210> SEQ ID NO 97
<211> LENGTH: 5323
<212> TYPE: DNA
<213> ORGANISM: artificial sequence
<220> FEATURE:
<223> OTHER INFORMATION: vector

<400> SEQUENCE: 97
gaattcagat ctctcgagcc cgggatcgat ggtacctcgc gaaagcttgg atgttgtaca    60
ggataatgtc cagaaggtcg atagaaagcg tgagaaacag cgtacagacg atttagagat   120
gtagaggtac ttttatgccg agaaaacttt ttgcgtgtga cagtccttaa aatatactta   180
gagcgtaagc gaaagtagta gcgacagcta ttaactttcg gttgcaaagc tctaggattt   240
ttaatggacg cagcgcatca cacgcaaaaa ggaaattgga ataaatgcga aatttgagat   300
gttaattaaa gacctttttg aggtcttttt tcttagatt ttttggggtta tttaggggag    360 aaaacatagg ggggtactac gacctccccc ctaggtgtcc attgtccatt gtccaaacaa   420
ataaataaat attgggtttt taatgttaaa aggttgtttt ttatgttaaa gtgaaaaaaa   480
cagatgttgg gaggtacagt gatagttgta gatagaaaag aagagaaaaa agttgctgtt   540
actttaagac ttacaacaga agaaaatgag atattaaata gaatcaaaga aaaatataat   600
attagcaaat cagatgcaac cggtattcta ataaaaaaat atgcaaagga ggaatacggt   660
gcattttaaa caaaaaaaga tagacagcac tggcatgctg cctatctatg actaaatttt   720
gttaagtgta ttagcaccgt tattatatca tgagcgaaaa tgtaataaaa gaaactgaaa   780
```

```
acaagaaaaa ttcaagagga cgtaattgga catttgtttt atatccagaa tcagcaaaag    840
ccgagtggtt agagtattta aaagagttac acattcaatt tgtagtgtct ccattacatg    900
atagggatac tgatacagaa ggtaggatga aaaagagca ttatcatatt ctagtgatgt    960
atgagggtaa taaatcttat gaacagataa aaataattaa cagaagaatt gaatgcgact   1020
attccgcaga ttgcaggaag tgtgaaaggt cttgtgagat atatgcttca catggacgat   1080
cctaataaat ttaaatatca aaagaagat atgatagttt atggcggtgt agatgttgat   1140
gaattattaa agaaaacaac aacagataga tataaattaa ttaaagaaat gattgagttt   1200
attgatgaac aaggaatcgt agaatttaag agtttaatgg attatgcaat gaagtttaaa   1260
tttgatgatt ggttcccgct tttatgtgat aactcggcgt atgttattca agaatatata   1320
aaatcaaatc ggtataaatc tgaccgatag attttgaatt taggtgtcac aagacactct   1380
tttttcgcac cagcgaaaac tggtttaagc cgactgcgca aaagacataa tcgattcaca   1440
aaaaataggc acacgaaaaa caagttaagg gatgcagttt atgcatccct taacttactt   1500
attaaataat ttatagctat tgaaaagaga taagaattgt tcaaagctaa tattgtttaa   1560
atcgtcaatt cctgcatgtt ttaaggaatt gttaaattga tttttttgtaa atattttctt   1620 gtattctttg ttaacccatt tcataacgaa ataattatac ttttgtttat ctttgtgtga   1680
tattcttgat tttttctac ttaatctgat aagtgagcta ttcactttag gtttaggatg   1740
aaaatattct cttggaacca tacttaatat agaaatatca acttctgcca ttaaaagtaa   1800
tgccaatgag cgttttgtat ttaataatct tttagcaaac ccgtattcca cgattaaata   1860
aatctcatta gctatactat caaaaacaat tttgcgtatt atatccgtac ttatgttata   1920
aggtatatta ccatatattt tataggattg gtttttagga aatttaaact gcaatatatc   1980
cttgtttaaa acttggaaat tatcgtgatc aacaagttta ttttctgtag ttttgcataa   2040
tttatggtct atttcaatgg cagttacgaa attcacacctc tttactaatt caagggtaaa   2100 atggccttt cctgagccga tttcaaagat attatcatgt tcatttaatc ttatatttgt   2160
cattatttta tctatattat gttttgaagt aataaagttt tgactgtgtt ttatatttt   2220 ctcgttcatt ataaccctct ttaatttggt tatatgaatt ttgcttatta acgattcatt   2280
ataaccactt attttttgtt tggttgataa tgaactgtgc tgattacaaa aatactaaaa   2340
atgcccatat tttttcctcc ttataaaatt agtataatta tagcacgagc tctgataaat   2400
atgaacatga tgagtgatcg ttaaatttat actgcaatcg gatgcgatta ttgaataaaa   2460
gatatgagag atttatctaa tttcttttt cttgtaaaaa aagaaagttc ttaaaggttt   2520
tatagttttg gtcgtagagc acacggttta acgacttaat tacgaagtaa ataagtctag   2580
tgtgttagac tttatgaaat ctatatacgt ttatatatat ttattatccg gatctgcatc   2640
gcaggatgct gctggctacc ctgtggaaca cctacatctg tattaacgaa gcgctggcat   2700
tgaccctgag tgattttct ctggtcccgc cgcatccata ccgccagttg tttaccctca   2760
caacgttcca gtaaccgggc atgttcatca tcagtaaccc gtatcgtgag catcctctct   2820
cgtttcatcg gtatcattac ccccatgaac agaaattccc ccttacacgg aggcatcaag   2880
tgaccaaaca ggaaaaaacc gcccttaaca tggcccgctt tatcagaagc cagacattaa   2940
cgcttctgga gaaactcaac gagctggacg cggatgaaca ggcagacatc tgtgaatcgc   3000
ttcacgacca cgctgatgag ctttaccgca gctgcctcgc gcgtttcggt gatgacggtg   3060
aaaacctctg acacatgcag ctcccggaga cggtcacagc ttgtctgtaa gcggatgccg   3120
```

```
ggagcagaca agcccgtcag ggcgcgtcag cgggtgttgg cgggtgtcgg ggcgcagcca   3180
tgacccagtc acgtagcgat agcggagtgt atactggctt aactatgcgg catcagagca   3240
gattgtactg agagtgcacc atatgcggtg tgaaataccg cacagatgcg taaggagaaa   3300
ataccgcatc aggcgctctt ccgcttcctc gctcactgac tcgctgcgct cggtcgttcg   3360
gctgcggcga gcggtatcag ctcactcaaa ggcggtaata cggttatcca cagaatcagg   3420
ggataacgca ggaaagaaca tgtgagcaaa aggccagcaa aaggccagga accgtaaaaa   3480
ggccgcgttg ctggcgtttt tccataggct ccgcccccct gacgagcatc acaaaaatcg   3540
acgctcaagt cagaggtggc gaaacccgac aggactataa agataccagg cgtttccccc   3600
tggaagctcc ctcgtgcgct ctcctgttcc gaccctgccg cttaccggat acctgtccgc   3660
ctttctccct tcgggaagcg tggcgctttc tcaatgctca cgctgtaggt atctcagttc   3720
ggtgtaggtc gttcgctcca agctgggctg tgtgcacgaa ccccccgttc agcccgaccg   3780
ctgcgcctta tccggtaact atcgtcttga gtccaacccg gtaagacacg acttatcgcc   3840
actggcagca gccactggta acaggattag cagagcgagg tatgtaggcg gtgctacaga   3900
gttcttgaag tggtggccta actacggcta cactagaagg acagtatttg gtatctgcgc   3960
tctgctgaag ccagttacct tcggaaaaag agttggtagc tcttgatccg gcaaacaaac   4020
caccgctggt agcggtggtt tttttgtttg caagcagcag attacgcgca gaaaaaaagg   4080
atctcaagaa gatcctttga tcttttctac ggggtctgac gctcagtgga acgaaaactc   4140
acgttaaggg attttggtca tgagattatc aaaaaggatc ttcacctaga tccttttaaa   4200
ttaaaaatga agttttaaat caatctaaag tatatatgag taaacttggt ctgacagtta   4260
ccaatgctta atcagtgagg cacctatctc agcgatctgt ctatttcgtt catccatagt   4320
tgcctgactc cccgtcgtgt agataactac gatacgggag ggcttaccat ctggccccag   4380
tgctgcaatg ataccgcgag acccacgctc accggctcca gatttatcag caataaacca   4440
gccagccgga agggccgagc gcagaagtgg tcctgcaact ttatccgcct ccatccagtc   4500
tattaattgt tgccgggaag ctagagtaag tagttcgcca gttaatagtt tgcgcaacgt   4560
tgttgccatt gctgcaggca tcgtggtgtc acgctcgtcg tttggtatgg cttcattcag   4620
ctccggttcc caacgatcaa ggcgagttac atgatccccc atgttgtgca aaaaagcggt   4680
tagctccttc ggtcctccga tcgttgtcag aagtaagttg gccgcagtgt tatcactcat   4740
ggttatggca gcactgcata attctcttac tgtcatgcca tccgtaagat gcttttctgt   4800
gactggtgag tactcaacca agtcattctg agaatagtgt atgcggcgac cgagttgctc   4860
ttgcccggcg tcaacacggg ataataccgc gccacatagc agaactttaa aagtgctcat   4920
cattggaaaa cgttcttcgg ggcgaaaact ctcaaggatc ttaccgctgt tgagatccag   4980
ttcgatgtaa cccactcgtg cacccaactg atcttcagca tcttttactt tcaccagcgt   5040
ttctgggtga gcaaaaacag gaaggcaaaa tgccgcaaaa aagggaataa gggcgacacg   5100
gaaatgttga atactcatac tcttcctttt tcaatattat tgaagcattt atcagggtta   5160
ttgtctcatg agcggataca tatttgaatg tatttagaaa aataaacaaa tagggggttcc   5220 gcgcacattt ccccgaaaag tgccacctga cgtctaagaa accattatta tcatgacatt   5280
aacctataaa aataggcgta tcacgaggcc ctttcgtctt caa                       5323
```

<210> SEQ ID NO 98
<211> LENGTH: 31
<212> TYPE: DNA
<213> ORGANISM: artificial sequence

```
<220> FEATURE:
<223> OTHER INFORMATION: primer

<400> SEQUENCE: 98
catgaattcg tgctaagagc cagattgtgg a                              31

<210> SEQ ID NO 99
<211> LENGTH: 50
<212> TYPE: DNA
<213> ORGANISM: artificial sequence
<220> FEATURE:
<223> OTHER INFORMATION: primer

<400> SEQUENCE: 99
catgaagacc acgcgtaggc cttctagagc taaattttca catcgtgagc          50

<210> SEQ ID NO 100
<211> LENGTH: 49
<212> TYPE: DNA
<213> ORGANISM: artificial sequence
<220> FEATURE:
<223> OTHER INFORMATION: primer

<400> SEQUENCE: 100
atttagctct agaaggccta cgcgtggtct tcatgaactt gttcaaccg           49

<210> SEQ ID NO 101
<211> LENGTH: 31
<212> TYPE: DNA
<213> ORGANISM: artificial sequence
<220> FEATURE:
<223> OTHER INFORMATION: primer

<400> SEQUENCE: 101
catctcgagc caagctcagt cacgcattta a                              31

<210> SEQ ID NO 102
<211> LENGTH: 22
<212> TYPE: DNA
<213> ORGANISM: artificial sequence
<220> FEATURE:
<223> OTHER INFORMATION: primer

<400> SEQUENCE: 102
aagcacaacg ggaagcgaac at                                        22

<210> SEQ ID NO 103
<211> LENGTH: 23
<212> TYPE: DNA
<213> ORGANISM: artificial sequence
<220> FEATURE:
<223> OTHER INFORMATION: primer

<400> SEQUENCE: 103
atacaactat gacgctggaa gcg                                       23

<210> SEQ ID NO 104
<211> LENGTH: 23
<212> TYPE: DNA
<213> ORGANISM: artificial sequence
<220> FEATURE:
<223> OTHER INFORMATION: primer

<400> SEQUENCE: 104
gtaggttttc ccgtccttga tag                                       23
```

```
<210> SEQ ID NO 105
<211> LENGTH: 35
<212> TYPE: DNA
<213> ORGANISM: artificial sequence
<220> FEATURE:
<223> OTHER INFORMATION: primer

<400> SEQUENCE: 105
tataagatct tgactctggt gaacttgtcg caacc                              35

<210> SEQ ID NO 106
<211> LENGTH: 34
<212> TYPE: DNA
<213> ORGANISM: artificial sequence
<220> FEATURE:
<223> OTHER INFORMATION: primer

<400> SEQUENCE: 106
atatctcgag aataagtcat cctctcgtag tgaa                               34

<210> SEQ ID NO 107
<211> LENGTH: 34
<212> TYPE: DNA
<213> ORGANISM: artificial sequence
<220> FEATURE:
<223> OTHER INFORMATION: primer

<400> SEQUENCE: 107
tatactcgag taatcatttc atacgattaa atgt                               34

<210> SEQ ID NO 108
<211> LENGTH: 32
<212> TYPE: DNA
<213> ORGANISM: artificial sequence
<220> FEATURE:
<223> OTHER INFORMATION: primer

<400> SEQUENCE: 108
atatcccggg gtgagcgggt aaagtccttg cc                                 32

<210> SEQ ID NO 109
<211> LENGTH: 710
<212> TYPE: DNA
<213> ORGANISM: Lactobacillus plantarum

<400> SEQUENCE: 109
atgaagcgac caattatcat tgcgttagat tttcccaccg ccgaacgggc cttagctttt   60
ttagaccaat ttccggctga tttacatgtc actgtcaaaa tcggcatgga gttattttat  120
gcagcgggac cgagtattgt gacggacgtg caagctcgcg ccatgcggt tttcttagat    180 ttgaaactac atgatattcc caataccgtc gaatccgcaa tgcgggtgat cgggcggtta  240
ggggtaacct atacgacggt tcatgctgcg ggtgggcacg tgatgctttc agccgccaaa  300
cgaggattgg tcgcgggtgc aatggccgct ggagtcactg cccccaagtt attagcgatt  360
acgcagttaa cttcgactaa tcaagctatt ttgaatcagg accagcaaat catgggaacg  420
gttcgggcga gtgtcgtgca ttatgccaaa ctagcacggg cgagtgactg tgatggcgtc  480
atttgttccg cccaagaagt tcaggcgatt catacggccg tcggtgctga ttttctcgga  540
attacgccgg gaattcggcc agcgtcggcg cagtcagatg accagcaacg ggtgatgaca  600
ccggctgccg ctgctaaggc tgggagcaac ggtctcgtca tcgggcggcc aattacgcag  660
gctgcagaac cagttcaagc ttaccgagat attatgacag aatggagtaa              710
```

```
<210> SEQ ID NO 110
<211> LENGTH: 21
<212> TYPE: DNA
<213> ORGANISM: artificial sequence
<220> FEATURE:
<223> OTHER INFORMATION: primer

<400> SEQUENCE: 110
cgggcacctg caaccgaggt c                                              21

<210> SEQ ID NO 111
<211> LENGTH: 22
<212> TYPE: DNA
<213> ORGANISM: artificial sequence
<220> FEATURE:
<223> OTHER INFORMATION: primer

<400> SEQUENCE: 111
ctgtttctca cgctttctat cg                                             22

<210> SEQ ID NO 112
<211> LENGTH: 22
<212> TYPE: DNA
<213> ORGANISM: artificial sequence
<220> FEATURE:
<223> OTHER INFORMATION: primer

<400> SEQUENCE: 112
gattttcttt atcaacttcg ac                                             22

<210> SEQ ID NO 113
<211> LENGTH: 21
<212> TYPE: DNA
<213> ORGANISM: artificial sequence
<220> FEATURE:
<223> OTHER INFORMATION: primer

<400> SEQUENCE: 113
ttggaaaacg ttcttcgggg c                                              21

<210> SEQ ID NO 114
<211> LENGTH: 20
<212> TYPE: DNA
<213> ORGANISM: artificial sequence
<220> FEATURE:
<223> OTHER INFORMATION: ribosome binding site

<400> SEQUENCE: 114
atataggagg aatttttgta                                                20

<210> SEQ ID NO 115
<211> LENGTH: 5124
<212> TYPE: DNA
<213> ORGANISM: artificial sequence
<220> FEATURE:
<223> OTHER INFORMATION: constructed plasmid

<400> SEQUENCE: 115
gacgaaaggg ccttataact tacaaataac ccctcgaaaa cattgaaaga ataaccccca      60
agatctatat tatagatctt gggggttatt tgttttaata ttaagaaat gacttcttct     120 atttgtcatc aatactaaac aataatttgt acaaagtgat tatttcttct agttcttcac    180
gcgatacatg atcgacaata gtttcatcag tgacatgtct tgcccgtaaa tctaaggcta    240
```

```
tggtttgatc taataatact tttccatata ctgtttgact actagttagt cgatgataca    300
ttggaaaatt acgcttggta ctgctaattg gagccacaat cgtcatgtta cttgtctgac    360
agactagatc attgcttagc gcaatggctg gtcgcttatt catctgttca tgaccacggc    420
ttggattaaa gttaacataa aatatatcac cttggcttac cattgaagtt cattaccttc    480
tgactttccc caatcaagct cgtgatccct tttcccgtca tctttccaat ccttaaatag    540
ttcgtgaata ttggttgggt tctttttttat tggtgttaaa acaattgatc cattttcaat    600
ggttattgtc atatcttggt tatcatctaa tttcagttgt ttaataattt ggctaggaat    660
tctagcagct ttcgagtttc cccactttgc taagcgtgtt tgttctttaa taagttccat    720
attttcccct cctaaattat tattacaagt caagtatatc ccatgtagat acacaatgca    780
aatattctta ctgagaaaat aacaccttaa gtctagcacc acccgcacgc atagcggtgc    840
ttaaaccatc aagggtcaag cccttaggct ctctcaaaca gttatcctaa tcgtgaataa    900
ctgcgcttct tttgcagtat aaagagagaa ctctttatca gacaatttaa gctcaaccag    960
cccttgcact aactattatt agagttggtt ttagcagcaa cccgaataat ctgcgttaat   1020
agttagcctg tccgtatcat ttcctagtct tccagccacg tctttagtcg cgttgatctc   1080
gacaaggttt agcatacctc tgttgttaac tgcaagcggg gtcacgaacg acactcacgg   1140
gaggttttac tagctaagaa caggtttcca gcctttagtt gctttgatgg ttgctaacca   1200
ttgaataaca aaaaaacggt tgctatcagg tttctgttaa gattcccgat aacaaccgtt   1260
tactttaagt atcaatggtt gaaaaactta gcctacatgt tataatagta ccaagttaga   1320
tagcttgtat tggtagtact tgctatcgaa aatcttatca ggttgtgctg ataagtcgtg   1380
aatcctaact ctgctaagtt gagggttctt tttttttgcgt tcatttatta agttgagtac   1440
attataaccg taatataaga ttaatacaac ctttatcatt ttaacgtctc aaccagccga   1500
ataatcctta aaaaggatt gattctaatg aagaaagcag acaagtaagc ctcctaaatt   1560
cactttagat aaaaatttag gaggcatatc aaatgaactt taataaaatt gatttagaca   1620
attggaagag aaaagagata tttaatcatt atttgaacca acaaacgact tttagtataa   1680
ccacagaaat tgatattagt gtttttatacc gaaacataaa acaagaagga tataaatttt   1740
accctgcatt tattttctta gtgacaaggg tgataaactc aaatacagct tttagaactg   1800
gttacaatag cgacggagag ttaggttatt gggataagtt agagccactt tatacaattt   1860
ttgatggtgt atctaaaaca ttctctggta tttggactcc tgtaaagaat gacttcaaag   1920
agttttatga tttataccttt tctgatgtag agaaatataa tggttcgggg aaattgtttc   1980
ccaaaacacc tatacctgaa aatgcttttt ctctttctat tattccatgg acttcattta   2040
ctgggtttaa cttaaatatc aataataata gtaattaccct tctacccatt attacagcag   2100
gaaaattcat taataaaggt aattcaatat atttaccgct atctttacag gtacatcatt   2160
ctgtttgtga tggttatcat gcaggattgt ttatgaactc tattcaggaa ttgtcagata   2220
ggcctaatga ctggctttta aagggcccg cgctagcgga gtgtatactg gcttactatg   2280
ttggcactga tgagggtgtc agtgaagtgc ttcatgtggc aggagaaaaa aggctgcacc   2340
ggtgcgtcag cagaatatgt gatacaggat atattccgct tcctcgctca ctgactcgct   2400
acgctcggtc gttcgactgc ggcgagcgga aatggcttac gaacggggcg agatttcct   2460
ggaagatgcc aggaagatac ttaacaggga agtgagaggg ccgcggcaaa gccgttttc   2520
cataggctcc gccccctga caagcatcac gaaatctgac gctcaaatca gtggtggcga   2580
aacccgacag gactataaag ataccaggcg tttcccctg gcggctccct cgtgcgctct   2640
```

```
cctgttcctg cctttcggtt taccggtgtc attccgctgt tatggccgcg tttgtctcat    2700
tccacgcctg acactcagtt ccgggtaggc agttcgctcc aagctggact gtatgcacga    2760
accccccgtt cagtccgacc gctgcgcctt atccggtaac tatcgtcttg agtccaaccc    2820
ggaaagacat gcaaaagcac cactggcagc agccactggt aattgattta gaggagttag    2880
tcttgaagtc atgcgccggt taaggctaaa ctgaaaggac aagttttggt gactgcgctc    2940
ctccaagcca gttacctcgg ttcaaagagt tggtagctca gagaaccttc gaaaaccgc     3000
cctgcaaggc ggttttttcg ttttcagagc aagagattac gcgcagacca aaacgatctc    3060
aagaagatca tcttattaat cagataaaat atttctagat tcagtgcaa tttatctctt     3120
caaatgtagc acctgaagtc agccccatac gatataagtt gtctcgagga ccgagcgcag    3180
cgagtcagtg agcgaggaag cggaagagcg agggcggagt tgttgacagc cgaggtacca    3240
tgtggtataa tcccgagtgt ggaattgtga gcggataaca ggatccatat aggaggaatt    3300
tttgtaatgg aattcaaata taacggaaaa gttgaatcag tggaactcaa taaatattct    3360
aagacattga ctcaagatcc aacacaacca gcgactcaag cgatgtacta cggcattggt    3420
tttaaagatg aggatttcaa aaaagctcag gtcggaatcg tcagcatgga ttgggacgga    3480
aatccatgta atatgcactt gggaacactt gggagtaaaa tcaaaagttc tgtcaaccaa    3540
actgacggat tgattggact tcaatttcat actattggag tttctgatgg aattgctaac    3600
ggaaagcttg gcatgagata ttctttggtc agtcgtgaag ttattgctga cagcatcgaa    3660
accaacgctg gcgcagaata ttatgatgcc atcgttgcca ttcccggttg tgataaaaat    3720
atgcccgggt caattatcgg aatggctcgc ttaaatcgtc cgtcaattat ggtctatggt    3780
ggaacgattg aacatggcga atataaaggt gaaaaattaa atattgtttc ggcctttgaa    3840
gctctggggc aaaaaatcac tggaaatatt tctgatgaag attatcatgg cgttatttgc    3900
aatgccattc caggacaagg tgcttgcgga ggaatgtaca ctgccaatac cctggctgct    3960
gctattgaaa ctttgggaat gagtttacct tattcctctt ccaatccagc agtcagtcaa    4020
gaaaaacaag aagagtgtga tgacattggt ttagccatca aaaatttatt agaaaaagat    4080
attaaaccaa gtgatatcat gaccaaagaa gcttttgaaa atgccataac aattgtcatg    4140
gtccttggag gctcaaccaa tgctgtgctt catatcattg caatggcaaa tgccattggt    4200
gtagaaatta cgcaagatga tttccaacgt atttcagata ttaccccctgt tcttggcgat    4260
ttcaaaccga gcggaaaata tatgatggaa gatctgcaca aaattggtgg ccttcctgct    4320
gttttgaaat acctacttaa agaaggaaaa cttcacggtg attgtttgac cgtcacaggt    4380
aaaactttgg ctgaaaatgt tgaaacagca ttagatttgg actttgacag tcaagatatt    4440
atgcgaccac taaaaaatcc aattaaagct actggacatt tacaaatttt gtacggtaat    4500
cttgcccaag ggggttctgt tgcaaaaatt tctggtaaag aaggcgaatt tttcaaagga    4560
acagctcgtg ttttttgacgg agaacaacac tttatcgatg cattgagtc tggccgattg     4620
catgccggtg atgttgcggt cattagaaat attggcccag tcggaggtcc gggaatgcca    4680
gagatgttaa aaccaacctc agcattaatt ggagcaggac ttggaaaatc ttgtgcccta    4740
attactgacg gaagattttc tggtggcaca cacggctttg ttgtgggtca tatcgtccct    4800
gaagcagttg aaggtgggtt gattggttta gttgaagatg atgatattat cgaaattgat    4860
gcggtgaata atagtattag tttaaaagtt tctaatgaag aaattgctaa acgacgtgcc    4920
aattatcaaa aaccaacccc taaagcaacg cgtggtgttc ttgcaaaatt tgccaaactt    4980
```

```
acgcgccccg ctagtgaagg ttgcgttaca gatttactgc aggacgggct tgtctgctcc    5040
cggcatccgc ttacagacaa gctgtgaccg tctccgggag ctgcatgtgt cagaggtttt    5100
caccgtcatc accgaaacgc gcga                                           5124
```

<210> SEQ ID NO 116
<211> LENGTH: 3748
<212> TYPE: DNA
<213> ORGANISM: artificial sequence
<220> FEATURE:
<223> OTHER INFORMATION: vector

<400> SEQUENCE: 116

```
gacgaaaggg ccttataact tacaaataac ccctcgaaaa cattgaaaga ataaccccca      60
agatctatat tatagatctt gggggttatt tgttttaata ttaaagaaat gacttcttct     120
atttgtcatc aatactaaac aataatttgt acaaagtgat tatttcttct agttcttcac     180
gcgatacatg atcgacaata gtttcatcag tgacatgtct tgcccgtaaa tctaaggcta     240
tggtttgatc taataatact tttccatata ctgtttgact actagttagt cgatgataca     300
ttggaaaatt acgcttggta ctgctaattg gagccacaat cgtcatgtta cttgtctgac     360
agactagatc attgcttagc gcaatggctg gtcgcttatt catctgttca tgaccacggc     420
ttggattaaa gttaacataa aatatatcac cttggcttac cattgaagtt cattaccttc     480
tgactttccc caatcaagct cgtgatccct tttcccgtca tctttccaat ccttaaatag     540
ttcgtgaata ttggttgggt tcttttttat tggtgttaaa acaattgatc cattttcaat     600
ggttattgtc atatcttggt tatcatctaa tttcagttgt ttaataattt ggctaggaat     660
tctagcagct ttcgagtttc cccactttgc taagcgtgtt tgttctttaa taagttccat     720
attttcccct cctaaattat tattacaagt caagtatatc ccatgtagat acacaatgca     780
aatattctta ctggagaaat aacaccttaa gtctagcacc acccgcacgc atagcggtgc     840
ttaaaccatc aagggtcaag cccctaggct ctctcaaaca gttatcctaa tcgtgaataa     900
ctgcgcttct tttgcagtat aaagagagaa ctctttatca gacaatttaa gctcaaccag     960
cccttgcact aactattatt agagttggtt ttagcagcaa cccgaataat ctgcgttaat    1020
agttagcctg tccgtatcat ttcctagtct tccagccacg tctttagtcg cgttgatctc    1080
gacaaggttt agcataccta tgttgttaac tgcaagcggg gtcacgaacg acactcacgg    1140
gaggttttac tagctaagaa caggtttcca gcctttagtt gctttgatgg ttgctaacca    1200
ttgaataaca aaaaacggt tgctatcagg tttctgttaa gattcccgat aacaaccgtt    1260
tactttaagt atcaatggtt gaaaaactta gcctacatgt tataatagta ccaagttaga    1320
tagcttgtat tggtagtact tgctatcgaa aatcttatca ggttgtgctg ataagtcgtg    1380
aatcctaact ctgctaagtt gagggttctt tttttgcgt tcatttatta agttgagtac    1440
attataaccg taatataaga ttaatacaac ctttatcatt ttaacgtctc aaccagccga    1500
ataatcctta aaaaggatt gattctaatg aagaaagcag acaagtaagc ctcctaaatt    1560
cactttagat aaaaatttag gaggcatatc aaatgaactt taataaaatt gatttagaca    1620
attggaagag aaaagagata tttaatcatt atttgaacca acaacgact tttagtataa    1680 ccacagaaat tgatattagt gttttatacc gaaacataaa acaagaagga tataaatttt    1740
accctgcatt tattttctta gtgacaaggg tgataaactc aaatacagct tttagaactg    1800 gttacaaatag cgacggagag ttaggttatt gggataagt agagccactt tatacaattt    1860
ttgatggtgt atctaaaaca ttctctggta tttggactcc tgtaaagaat gacttcaaag    1920
```

```
agtttatga tttataccttt tctgatgtag agaaatataa tggttcgggg aaattgtttc    1980
ccaaaacacc tatacctgaa aatgcttttt ctctttctat tattccatgg acttcattta    2040
ctgggtttaa cttaaatatc aataataata gtaattacct tctacccatt attacagcag    2100
gaaaattcat taataaaggt aattcaatat atttaccgct atctttacag gtacatcatt    2160
ctgtttgtga tggttatcat gcaggattgt ttatgaactc tattcaggaa ttgtcagata    2220
ggcctaatga ctggctttta taagggcccg cgctagcgga gtgtatactg gcttactatg    2280
ttggcactga tgagggtgtc agtgaagtgc ttcatgtggc aggagaaaaa aggctgcacc    2340
ggtgcgtcag cagaatatgt gatacaggat atattccgct tcctcgctca ctgactcgct    2400
acgctcggtc gttcgactgc ggcgagcgga atggcttac gaacggggcg agatttcct    2460
ggaagatgcc aggaagatac ttaacaggga agtgagaggg ccgcggcaaa gccgtttttc    2520
cataggctcc gcccccctga caagcatcac gaaatctgac gctcaaatca gtggtggcga    2580
aacccgacag gactataaag ataccaggcg tttcccctg gcggctccct cgtgcgctct    2640
cctgttcctg cctttcggtt taccggtgtc attccgctgt tatggccgcg tttgtctcat    2700
tccacgcctg acactcagtt ccgggtaggc agttcgctcc aagctggact gtatgcacga    2760
accccccgtt cagtccgacc gctgcgcctt atccggtaac tatcgtcttg agtccaaccc    2820
ggaaagacat gcaaaagcac cactggcagc agccactggt aattgattta gaggagttag    2880
tcttgaagtc atgcgccggt taaggctaaa ctgaaaggac aagttttggt gactgcgctc    2940
ctccaagcca gttacctcgg ttcaaagagt tggtagctca gagaaccttc gaaaaaccgc    3000
cctgcaaggc ggttttttcg ttttcagagc aagagattac gcgcagacca aaacgatctc    3060
aagaagatca tcttattaat cagataaaat atttctagat ttcagtgcaa tttatctctt    3120
caaatgtagc acctgaagtc agccccatac gatataagtt gtctcgagga ccgagcgcag    3180
cgagtcagtg agcgaggaag cggaagagcg agggcggagt tgttgacagc cgaggtacca    3240
tgtggtataa tcccgagtgt ggaattgtga gcggataaca atttcacaca ggaaacagct    3300
atgaccatga ttacgccaag cttggctgca ggtcgacgga tccccgggaa ttcactggcc    3360
gtcgttttac aacgtcgtga ctgggaaaac cctggcgtta cccaacttaa tcgccttgca    3420
gcacatcccc ctttcgccag ctggcgtaat agcgaagagg cccgcaccga tcgcccttcc    3480
caacagttgc gcagcctgaa tggcgaatgg cgcctgatgc ggtattttct ccttacgcat    3540
ctgtgcggta tttcacaccg catatggtgc actctcagta caatctgctc tgatgccgca    3600
tagttaagcc agccccgaca cccgccaaca cccgctgacg cgccctgacg gcttgtctg    3660
ctcccggcat ccgcttacag acaagctgtg accgtctccg ggagctgcat gtgtcagagg    3720
ttttcaccgt catcaccgaa acgcgcga                                       3748
```

<210> SEQ ID NO 117
<211> LENGTH: 22
<212> TYPE: DNA
<213> ORGANISM: artificial sequence
<220> FEATURE:
<223> OTHER INFORMATION: primer

<400> SEQUENCE: 117
ttgtctcgag gaccgagcgc ag                                              22

<210> SEQ ID NO 118
<211> LENGTH: 60
<212> TYPE: DNA

<213> ORGANISM: artificial sequence
<220> FEATURE:
<223> OTHER INFORMATION: primer

<400> SEQUENCE: 118

```
tatagacaag cccgtcctgc agttaagctt ttggatcctg ttatccgctc acaattccac    60
```

<210> SEQ ID NO 119
<211> LENGTH: 1730
<212> TYPE: DNA
<213> ORGANISM: artificial sequence
<220> FEATURE:
<223> OTHER INFORMATION: PCR fragment with ribosome binding site and
      ilvD coding region from L. lactis

<400> SEQUENCE: 119

```
atataggagg aattttttgta atggaattca aatataacgg aaaagttgaa tcagtggaac    60
tcaataaata ttctaagaca ttgactcaag atccaacaca accagcgact caagcgatgt   120
actacggcat tggttttaaa gatgaggatt caaaaaagc tcaggtcgga atcgtcagca    180
tggattggga cggaaatcca tgtaatatgc acttgggaac acttgggagt aaaatcaaaa   240
gttctgtcaa ccaaactgac ggattgattg gacttcaatt tcatactatt ggagtttctg   300
atggaattgc taacggaaag cttggcatga gatattcttt ggtcagtcgt gaagttattg   360
ctgacagcat cgaaccaac gctggcgcag aatattatga tgccatcgtt gccattcccg    420
gttgtgataa aaatatgccc gggtcaatta tcggaatggc tcgcttaaat cgtccgtcaa   480
ttatggtcta tggtggaacg attgaacatg gcgaatataa aggtgaaaaa ttaaatattg   540
tttcggcctt tgaagctctg ggcaaaaaa tcactggaaa tatttctgat gaagattatc    600
atggcgttat ttgcaatgcc attccaggac aaggtgcttg cggaggaatg tacactgcca   660
ataccctggc tgctgctatt gaaactttgg gaatgagttt accttattcc tcttccaatc   720
cagcagtcag tcaagaaaaa caagaagagt gtgatgacat tggtttagcc atcaaaaatt   780
tattagaaaa agatattaaa ccaagtgata tcatgaccaa agaagctttt gaaaatgcca   840
taacaattgt catggtcctt ggaggctcaa ccaatgctgt gcttcatatc attgcaatgg   900
caaatgccat tggtgtagaa attacgcaag atgatttcca acgtatttca gatattaccc   960
ctgttcttgg cgatttcaaa ccgagcggaa aatatgatg ggaagatctg cacaaaattg   1020
gtggccttcc tgctgttttg aaatacctac ttaaagaagg aaaacttcac ggtgattgtt   1080
tgaccgtcac aggtaaaact ttggctgaaa atgttgaaac agcattagat ttggactttg   1140
acagtcaaga tattatgcga ccactaaaaa atccaattaa agctactgga catttacaaa   1200
ttttgtacgg taatcttgcc caaggggtt ctgttgcaaa aatttctggt aaagaaggcg    1260
aatttttcaa aggaacagct cgtgttttttg acgagaaca cactttatc gatggcattg    1320
agtctggccg attgcatgcc ggtgatgttg cggtcattag aaatattggc ccagtcggag    1380
gtccgggaat gccagagatg ttaaaaccaa cctcagcatt aattggagca ggacttggaa    1440
aatcttgtgc cctaattact gacggaagat tttctggtgg cacacacggc tttgttgtgg    1500
gtcatatcgt ccctgaagca gttgaaggtg ggttgattgg tttagttgaa gatgatgata    1560
ttatcgaaat tgatgcggtg aataatagta ttagtttaaa agtttctaat gaagaaattg    1620
ctaaacgacg tgccaattat caaaaaccaa cccctaaagc aacgcgtggt gttcttgcaa    1680
aatttgccaa acttacgcgc cccgctagtg aaggttgcgt tacagattta                1730
```

<210> SEQ ID NO 120

```
<211> LENGTH: 33
<212> TYPE: DNA
<213> ORGANISM: artificial sequence
<220> FEATURE:
<223> OTHER INFORMATION: primer

<400> SEQUENCE: 120
tattctcgag atataggagg aatttttgta atg                                      33

<210> SEQ ID NO 121
<211> LENGTH: 31
<212> TYPE: DNA
<213> ORGANISM: artificial sequence
<220> FEATURE:
<223> OTHER INFORMATION: primer

<400> SEQUENCE: 121
atatctcgag ctataaatct gtaacgcaac c                                        31

<210> SEQ ID NO 122
<211> LENGTH: 36
<212> TYPE: DNA
<213> ORGANISM: artificial sequence
<220> FEATURE:
<223> OTHER INFORMATION: primer

<400> SEQUENCE: 122
atatctcgag gtggcaacgg gtcaaaaatg gggcct                                   36

<210> SEQ ID NO 123
<211> LENGTH: 1014
<212> TYPE: DNA
<213> ORGANISM: artificial sequence
<220> FEATURE:
<223> OTHER INFORMATION: PCR fragment: restriction sites added to a 5'
      portion of sufoperon of L. plantarum

<400> SEQUENCE: 123
atggcaacct tggaagttaa agatttacac gttgaagtga cggatgatga gcaaaaaaag          60
tctcgtgaga ttttaaaagg cgtcaattta tctatgaaaa ctggtgaaat tcatgccatt        120
atgggaccaa atgggactgg taagtccact ttatcacaaa ctattatggg ccaaccggct        180
tatcacgtta ctcagggtga tatcttgttg aacggcgaaa gtatcgtaaa catgccagtt        240
gatgaacgtg cacgtaaggg actcttcctc ggcatgcagt atccagctga aattcaaggg        300
gtcaccaacg ctgaattttt acgggcagca atgaacgcac gccgaccagc cgatgatcaa        360
atctcagtga tggcctttct taaagaactc gacaagaact tggcactact taatatgagc        420
gaatccatga cggaacgtta cctaaacgaa ggtttctccg gtggtgaaaa gaagcgtaac        480
gaaattttgc aattattgat gatcaagcca tcattcgcct tattggacga aattgattcc        540
gggcttgata tcgatgcgtt acaagtggtt tctaagggtg ttaattcgat gcggggcgat        600
aatttcggct cattgattat cacgcattat caacggctgt taaactacat tgtgcccgat        660
gtcgttcacg tgatgatggg tggtcgaatc gtgaagactg gtaacgccga cttagcaaag        720
acccttgaaa agaaaggtta tgctggttta cgtgacgatt tgaacattga tgtcaaactt        780
gttgacgacg aagattaggg ggtggcagta atggaagcaa ctgctgatta tgaaactatc        840
aaaacaacgc tagctgcggc tgctaacgaa catggtgaac cgcactggct cgttgaacgc        900
cgtttagcgg ctttagatgc gatgcaaggc ctagcggttc ccaaagctga tcgctttagt        960
attcgcgact ggccactgac gcccaccgac caaccactaa agttcagtcg ttcg            1014
```

<210> SEQ ID NO 124
<211> LENGTH: 57
<212> TYPE: DNA
<213> ORGANISM: artificial sequence
<220> FEATURE:
<223> OTHER INFORMATION: primer

<400> SEQUENCE: 124
tagctagccc gggatatata ggaggaattt ttgtaatggc aaccttggaa gttaaag       57

<210> SEQ ID NO 125
<211> LENGTH: 39
<212> TYPE: DNA
<213> ORGANISM: artificial sequence
<220> FEATURE:
<223> OTHER INFORMATION: primer

<400> SEQUENCE: 125
attatgtcag gtacccgaac gactgaactt tagtggttg       39

<210> SEQ ID NO 126
<211> LENGTH: 93
<212> TYPE: DNA
<213> ORGANISM: artificial sequence
<220> FEATURE:
<223> OTHER INFORMATION: primer

<400> SEQUENCE: 126
tgtaggactc gagagatctc ggccgggagt tgttgacaca caaaaccaga catggtatta       60
taatctataa gcgagatctg ctcggggagt tgt       93

<210> SEQ ID NO 127
<211> LENGTH: 74
<212> TYPE: DNA
<213> ORGANISM: artificial sequence
<220> FEATURE:
<223> OTHER INFORMATION: primer

<400> SEQUENCE: 127
tagctagccc ggggcgctat accgagatta tatcatgcct tgctgcgcgt gtcaacaact       60
ccccgagcag atct       74

<210> SEQ ID NO 128
<211> LENGTH: 21
<212> TYPE: DNA
<213> ORGANISM: artificial sequence
<220> FEATURE:
<223> OTHER INFORMATION: primer

<400> SEQUENCE: 128
tgtaggactc gagagatctc g       21

<210> SEQ ID NO 129
<211> LENGTH: 16
<212> TYPE: DNA
<213> ORGANISM: artificial sequence
<220> FEATURE:
<223> OTHER INFORMATION: primer

<400> SEQUENCE: 129
tagctagccc ggggcg       16

<210> SEQ ID NO 130
<211> LENGTH: 1331

```
<212> TYPE: DNA
<213> ORGANISM: artificial sequence
<220> FEATURE:
<223> OTHER INFORMATION: PCR product; restriction sites and sufP

<400> SEQUENCE: 130
cgaagacggg tagccctaag aacggattgg tgacccactt gtcgatttta gcagtcatct      60
cgacgtggct ggtgcttgcc aagttttgac tagcgctggc taaggtttgc tcaataaagt     120
ctagtcgggt ttggaaaatc tgctcgtcga attttgagc gtcgtaataa gcggcttgac      180
tagtgagtgg tgtcaatccc atgtgtttcg cgtaggctcg aattggctta ttttgattaa     240
taaattgaat cgtcagccac cgtgcgaagt ctgctgtcaa atcaaatttt ttgatgagct     300
gttggctagc ctgacgaatg gcttgctcaa tcatgaaagg atagttgagt ttgagcggtg     360
tcgcggccgg atgggacct gccaataagt cttcgcgtag ctgatgcagc ccttctttat      420
tgcgggcgtt agtcgctttg atctgacagc caagttgttc agctagcgtg tcaaaatcat     480
aataatggcc cgtccgtttg aggtcatcaa tcatgttgag tgcgataatc accggtgcgc     540
caaattccaa cacttcgatc gacagtagta agttacgctt gagctgactc gcgttggtca     600
cgttcagaat tagatcaggg tggttatgta gcagatagtt ggtgacgact gcttcatctt     660
tggtgattgg attaagtgaa tagactccgg gtaaatcgac catttcaact tcagagtgcc     720
gaatccggcc catcttcttc tcaacggtca cgccggtcca gttaccgacg tacgcgtatt     780
tatccgtcag ttcattgaat agcgtggtct taccagtatt gggatttccg agcaatgcaa     840
ccgtcgtcat cttaatggcc tccaatcaac gtttgaaata cggtgtaccg aatcccaatc     900
cgttgttgat caatctgaac aattactggt ccgtgaaacg atagtagcg dacaacggcc      960
agcggactgc cgacatgtag ccctaagctg tgcaatcgtt gaacggtctg attatccaaa    1020
cctgtgaatt gttgaatatg tagttgtgat gtattagtaa cggattgact tagcataagg    1080
ctcagtcctt tctgaatatt ccaatagtga ataattcatc aaaaatatta tacctacatc    1140
atagcatgaa agggctttta ttaatatggg gaaaagcctt attttctttt gaaatgaaaa    1200
cggttatact ctaagtatag aatacaaaaa ggccgatgct acgctatttt tgttgaagcc    1260
gttgactaat cattatatac ggaaggaata acggcttggg taataaattc aattgttgga    1320
ggatgattta a                                                         1331

<210> SEQ ID NO 131
<211> LENGTH: 34
<212> TYPE: DNA
<213> ORGANISM: artificial sequence
<220> FEATURE:
<223> OTHER INFORMATION: primer

<400> SEQUENCE: 131
tgctgattga attccgaaga cgggtagccc taag                                  34

<210> SEQ ID NO 132
<211> LENGTH: 37
<212> TYPE: DNA
<213> ORGANISM: artificial sequence
<220> FEATURE:
<223> OTHER INFORMATION: primer

<400> SEQUENCE: 132
tgtaggactc gagttaaatc atcctccaac aattgaa                               37

<210> SEQ ID NO 133
```

```
<211> LENGTH: 22
<212> TYPE: DNA
<213> ORGANISM: artificial sequence
<220> FEATURE:
<223> OTHER INFORMATION: primer

<400> SEQUENCE: 133
gcatcaagcg gtccgtaact ag                                             22

<210> SEQ ID NO 134
<211> LENGTH: 25
<212> TYPE: DNA
<213> ORGANISM: artificial sequence
<220> FEATURE:
<223> OTHER INFORMATION: primer

<400> SEQUENCE: 134
gcgctatacc gagattatat catgc                                          25

<210> SEQ ID NO 135
<211> LENGTH: 28
<212> TYPE: DNA
<213> ORGANISM: artificial sequence
<220> FEATURE:
<223> OTHER INFORMATION: primer

<400> SEQUENCE: 135
ccagacatgg tattataatc tataagcg                                       28

<210> SEQ ID NO 136
<211> LENGTH: 22
<212> TYPE: DNA
<213> ORGANISM: artificial sequence
<220> FEATURE:
<223> OTHER INFORMATION: primer

<400> SEQUENCE: 136
tggtttatca atcccgcgac tc                                             22

<210> SEQ ID NO 137
<211> LENGTH: 6249
<212> TYPE: DNA
<213> ORGANISM: artificial sequence
<220> FEATURE:
<223> OTHER INFORMATION: constructed plasmid

<400> SEQUENCE: 137
cgaaagcttg tctaacacac tagacttatt tacttcgtaa ttaagtcgtt aaaccgtgtg    60
ctctacgacc aaaactataa aacctttaag aactttcttt ttttacaaga aaaagaaat   120 tagataaatc tctcatatct tttattcaat aatcgcatcc gattgcagta taaatttaac   180
gatcactcat catgttcata tttatcagag ctcgtgctat aattatacta atttttataag  240 gaggaaaaaa tatgggcatt tttagtattt ttgtaatcag cacagttcat tatcaaccaa   300
acaaaaaata agtggttata atgaatcgtt aataagcaaa attcatataa ccaaattaaa   360
gagggttata atgaacgaga aaaatataaa acacagtcaa aactttatta cttcaaaaca   420
taatatagat aaaataatga caaatataag attaaatgaa catgataata tctttgaaat   480
cggctcagga aaaggccatt ttaccccttga attagtaaag aggtgtaatt tcgtaactgc   540
cattgaaata gaccataaat tatgcaaaac tacagaaaat aaacttgttg atcacgataa   600
tttccaagtt ttaaacaagg atatattgca gtttaaattt cctaaaaacc aatcctataa   660
aatatatggt aatataccctt ataacataag tacggatata atacgcaaaa ttgttttttga   720
```

```
tagtatagct aatgagattt atttaatcgt ggaatacggg tttgctaaaa gattattaaa    780
tacaaaacgc tcattggcat tacttttaat ggcagaagtt gatatttcta tattaagtat    840
ggttccaaga gaatattttc atcctaaacc taaagtgaat agctcactta tcagattaag    900
tagaaaaaaa tcaagaatat cacacaaaga taaacaaaag tataattatt tcgttatgaa    960
atgggttaac aaagaataca agaaatatt  tacaaaaaat caatttaaca attccttaaa   1020
acatgcagga attgacgatt taaacaatat tagctttgaa caattcttat ctcttttcaa   1080
tagctataaa ttatttaata agtaagttaa gggatgcagt tcatcgatga agcttggatg   1140
ttgtacagga taatgtccag aaggtcgata gaaagcgtga gaaacagcgt acagacgatt   1200
tagagatgta gaggtacttt tatgccgaga aaactttttg cgtgtgacag tccttaaaat   1260
atacttagag cgtaagcgaa agtagtagcg acagctatta actttcggtt gcaaagctct   1320
aggatttta  atggacgcag cgcatcacac gcaaaaagga aattggaata aatgcgaaat   1380
ttgagatgtt aattaaagac cttttgagg  tctttttttc ttagattttt ggggttattt   1440
aggggagaaa acataggggg gtactacgac ctccccccta ggtgtccatt gtccattgtc   1500
caaacaaata aataaatatt gggttttaa  tgttaaaagg ttgttttta  tgttaaagtg   1560
aaaaaaacag atgttgggag gtacagtgat agttgtagat agaaagaag  agaaaaagt   1620
tgctgttact ttaagactta caacagaaga aaatgagata ttaaatagaa tcaaagaaaa   1680
atataatatt agcaaatcag atgcaaccgg tattctaata aaaaaatatg caaaggagga   1740
atacggtgca ttttaaacaa aaaaagatag acagcactgg catgctgcct atctatgact   1800
aaattttgtt aagtgtatta gcaccgttat tatatcatga gcgaaaatgt aataaaagaa   1860
actgaaaaca agaaaaattc aagaggacgt aattggacat ttgtttata  tccagaatca   1920
gcaaaagccg agtggttaga gtatttaaaa gagttacaca ttcaatttgt agtgtctcca   1980
ttacatgata gggatactga tacagaaggt aggatgaaaa aagagcatta tcatattcta   2040
gtgatgtatg agggtaataa atcttatgaa cagataaaaa taattaacag aagaattgaa   2100
tgcgactatt ccgcagattg caggaagtgt gaaaggtctt gtgagatata tgcttcacat   2160
ggacgatcct aataaattta atatcaaaa  agaagatatg atagtttatg gcggtgtaga   2220
tgttgatgaa ttattaaaga aaacaacaac agatagatat aaattaatta agaaatgat    2280
tgagtttatt gatgaacaag gaatcgtaga atttaagagt ttaatggatt atgcaatgaa   2340
gtttaaattt gatgattggt tcccgctttt atgtgataac tcggcgtatg ttattcaaga   2400
atatataaaa tcaaatcggt ataaatctga ccgatagatt ttgaatttag gtgtcacaag   2460
acactctttt ttcgcaccag cgaaaactgg tttaagccga ctgcgcaaaa gacataatcg   2520
attcacaaaa aataggcaca cgaaaaacaa gttaagggat gcagtttatg cattcagatc   2580
ttgatcccct gcgccatcag atccttggcg gcaagaaagc catccagttt actttgcagg   2640
gcttcccaac cttcccagag ggcgcccag  ctggcaattc cggttcgctt gctgtccata   2700
aaaccgccca gtctagctat cgccatgtaa gcccactgca agctacctgc tttctctttg   2760
cgcttgcgtt ttcccttgtc cagatagccc agtagctgac attcatccgg ggtcagcacc   2820
gtttctgcgg actggctttc tacgtgttcc gcttccttta gcagcccttg cgccctgagt   2880
gcttgcggca gcgtgaagct ttctctgagc tgtaacagcc tgaccgcaac aaacgagagg   2940
atcgagacca tccgctccag attatccggc tcctccatgc gttgcctctc ggctcctgct   3000
ccggttttcc atgccttatg gaactcctcg atccgccagc gatgggtata aatgtcgatg   3060
```

```
acgcgcaagg cttgggctag cgactcgacc ggttcgctgg tcagcaacaa ccatttcaac    3120
ggggtctcac ccttgggcgg gttaatctcc tcggccagca ccgcgttgag cgtgatattc    3180
ccctgtttta gcgtgatgcg cccactgcgc aggctcaagc tcgccttgcg ggctggtcga    3240
tttttacgtt taccgcgttt atccaccacg ccctttttgcg gaatgctgat ctgatagcca   3300
cccaactccg gttggttctt cagatggtcg tacagataca acccagactc tacgtccttg    3360
cgtgggtgct tggagcgcac cacgaagcgc tcgttatgcg ccagtttgtc ctgcagataa    3420
gcatgaatat cggcttcgcg gtcacagacc gcaatcacgt tgctcatcat gctgcccatg    3480
cgtaaccggc tagttgcggc ggctgccagc catttgccac tctccttttc atccgcatcg    3540
gcagggtcat ccgggcgcat ccaccactcc tgatgcagta atcctacggt gcggaatgtg    3600
gtggcctcga gcaagagaac ggagtgaacc caccatccgc gggatttatc ctgaatagag    3660
cccagcttgc caagctcttc ggcgacctgg tggcgataac tcaaagaggt ggtgtcctca    3720
atggccagca gttcgggaaa ctcctgagcc aacttgactg tttgcatggc gccagccttt    3780
ctgatcgcct cggcagaaac gttgggattg cggataaatc ggtaagcgcc ttcctgcatg    3840
gcttcactac cctctgatga gatggttatt gatttaccag aatattttgc caattgggcg    3900
gcgacgttaa ccaagcgggc agtacggcga ggatcaccca cgccgccga agagaacaca    3960 gatttagccc agtcgccgc acgatgaaga gcagaagtta tcatgaacgt taccataata    4020
aatccccctt tttgaaaata atgaagactt atattgttat aataaaccag caatctcgca    4080
ttctgcaata taaaactaga ctccgcggct gaattgatag aattgtccca tgcgggctgt    4140
cggcgggcgg tgtcagggga taagccgaga gacacgtgtt ggattagaca tgagtcgaat    4200
gacgcgattt tttctggaaa aaatgacaaa tgaagacggg aaaaatgata ggggaaaatg    4260
ttagatcatg catctgtctc ttgatcagat ctcacaccgt gaacgcgttg cttaagtgtt    4320
taaacgataa cttcgtataa tgtatgctat acgaagttat tctagattat aaaagccagt    4380
cattaggcct atctgacaat tcctgaatag agttcataaa caatcctgca tgataaccat    4440
cacaaacaga atgatgtacc tgtaaagata gcggtaaata tattgaatta cctttattaa    4500
tgaattttcc tgctgtaata atgggtagaa ggtaattact attattattg atatttaagt    4560
taaacccagt aaatgaagtc catggaataa tagaaagaga aaaagcattt tcaggtatag    4620
gtgtttgggg aaacaatttc cccgaaccat tatatttctc tacatcagaa aggtataaat    4680
cataaaactc tttgaagtca ttctttacag gagtccaaat accagagaat gttttagata    4740
caccatcaaa aattgtataa agtggctcta acttatccca ataacctaac tctccgtcgc    4800
tattgtaacc agttctaaaa gctgtatttg agtttatcac ccttgtcact aagaaaataa    4860
atgcagggta aaatttatat ccttcttgtt ttatgtttcg gtataaaaca ctaatatcaa    4920
tttctgtggt tatactaaaa gtcgtttgtt ggttcaaata atgattaaat atctcttttc    4980
tcttccaatt gtctaaatca attttattaa agttcatttg atatgcctcc taaataattg    5040
tgagcgctca caattccaca cattatgcca caccttgtag ataaagtcaa caacttttg    5100 caaattttt caggaatttt agcagaggtt gttctggatg tagaacaaaa catctttccg    5160
ctcttgtgct gttaggatat cttttcttgga agctaggtag gcaagggcta cctctagaat    5220
aacttcgtat aatgtatgct atacgaagtt attaggtccc tcgaagaggt tcactagtac    5280
tggccattgc ggccgcatag gatccatttg tcgactactt gtgtataaga gtcaggcgct    5340
agcggagtgt atactggctt actatgttgg cactgatgag ggtgtcagtg aagtgcttca    5400
tgtggcagga gaaaaaaggc tgcaccggtg cgtcagcaga atatgtgata caggatatat    5460
```

```
tccgcttcct cgctcactga ctcgctacgc tcggtcgttc gactgcggcg agcggaaatg    5520
gcttacgaac ggggcggaga tttcctggaa gatgccagga agatacttaa cagggaagtg    5580
agagggccgc ggcaaagccg ttttccata ggctccgccc ccctgacaag catcacgaaa    5640
tctgacgctc aaatcagtgg tggcgaaacc cgacaggact ataaagatac caggcgtttc    5700
cccctggcgg ctccctcgtg cgctctcctg ttcctgcctt tcggtttacc ggtgtcattc    5760
cgctgttatg gccgcgtttg tctcattcca cgcctgacac tcagttccgg gtaggcagtt    5820
cgctccaagc tggactgtat gcacgaaccc ccgttcagt ccgaccgctg cgccttatcc    5880
ggtaactatc gtcttgagtc caacccggaa agacatgcaa agcaccact ggcagcagcc    5940 actggtaatt gatttagagg agttagtctt gaagtcatgc gccggttaag gctaaactga    6000
aaggacaagt tttggtgact gcgctcctcc aagccagtta cctcggttca agagttggt    6060 agctcagaga accttcgaaa aaccgccctg caaggcggtt ttttcgtttt cagagcaaga    6120
gattacgcgc agaccaaaac gatctcaaga agatcatctt attaatcaga taaaatattt    6180
ctagatttca gtgcaattta tctcttcaaa tgtagcacct gaagtcagcc ccatacgata    6240
taagttgtg                                                           6249

<210> SEQ ID NO 138
<211> LENGTH: 979
<212> TYPE: DNA
<213> ORGANISM: artificial sequence
<220> FEATURE:
<223> OTHER INFORMATION: synthesized fragment: Tn5IE-loxP-cm-loxP
      cassette containing Tn5IE, loxP, chloramphenicol resistant gene
      (cm), and loxP

<400> SEQUENCE: 138
ctgtctcttg atcagatctc acaccgtgaa cgcgttgctt aagtgtttaa acgataactt     60
cgtataatgt atgctatacg aagttattct agattataaa agccagtcat taggcctatc    120
tgacaattcc tgaatagagt tcataaacaa tcctgcatga taaccatcac aaacagaatg    180
atgtacctgt aaagatagcg gtaaatatat tgaattacct ttattaatga attttcctgc    240
tgtaataatg ggtagaaggt aattactatt attattgata tttaagttaa acccagtaaa    300
tgaagtccat ggaataatag aaagagaaaa agcattttca ggtataggtg ttttgggaaa    360
caatttcccc gaaccattat atttctctac atcagaaagg tataaatcat aaaactcttt    420
gaagtcattc tttacaggag tccaaatacc agagaatgtt ttagatacac catcaaaaat    480
tgtataaagt ggctctaact tatcccaata acctaactct ccgtcgctat tgtaaccagt    540
tctaaaagct gtatttgagt ttatcaccct tgtcactaag aaaataaatg cagggtaaaa    600
tttatatcct tcttgttta tgtttcggta taaacacta atatcaattt ctgtggttat    660
actaaaagtc gtttgttggt tcaaataatg attaaatatc tcttttctct tccaattgtc    720
taaatcaatt ttattaaagt tcatttgata tgcctcctaa ataattgtga gcgctcacaa    780
ttccacacat tatgccacac cttgtagata aagtcaacaa cttttttgcaa aattttttcag    840 gaattttagc agaggttgtt ctggatgtag aacaaaacat ctttccgctc ttgtgctgtt    900
aggatatctt tcttggaagc taggtaggca agggctacct ctagaataac ttcgtataat    960
gtatgctata cgaagttat                                                979

<210> SEQ ID NO 139
<211> LENGTH: 57
<212> TYPE: DNA
```

```
<213> ORGANISM: artificial sequence
<220> FEATURE:
<223> OTHER INFORMATION: primer

<400> SEQUENCE: 139
cgatatttgt cgactacttg tgtataagag tcaggcgcta gcggagtgta tactggc        57

<210> SEQ ID NO 140
<211> LENGTH: 42
<212> TYPE: DNA
<213> ORGANISM: artificial sequence
<220> FEATURE:
<223> OTHER INFORMATION: primer

<400> SEQUENCE: 140
ctttatacga cgtcacaact tatatcgtat ggggctgact tc                        42

<210> SEQ ID NO 141
<211> LENGTH: 41
<212> TYPE: DNA
<213> ORGANISM: artificial sequence
<220> FEATURE:
<223> OTHER INFORMATION: primer

<400> SEQUENCE: 141
ttatactaag cttgtctaac acactagact tatttacttc g                         41

<210> SEQ ID NO 142
<211> LENGTH: 42
<212> TYPE: DNA
<213> ORGANISM: artificial sequence
<220> FEATURE:
<223> OTHER INFORMATION: primer

<400> SEQUENCE: 142
ctctagtaag cttcatcgat gaactgcatc ccttaactta ct                        42

<210> SEQ ID NO 143
<211> LENGTH: 251
<212> TYPE: DNA
<213> ORGANISM: artificial sequence
<220> FEATURE:
<223> OTHER INFORMATION: pPnpr promoter

<400> SEQUENCE: 143
gatctaacat ttttccctat catttttccc gtcttcattt gtcattttttt ccagaaaaaa    60 tcgcgtcatt cgactcatgt ctaatccaac acgtgtctct cggcttatcc cctgacaccg   120
cccgccgaca gcccgcatgg gacaattcta tcaattcagc cgcggagtct agttttatat   180
tgcagaatgc gagattgctg gtttattata acaatataag tcttcattat tttcaaaaag   240
ggggatttat t                                                         251

<210> SEQ ID NO 144
<211> LENGTH: 47
<212> TYPE: DNA
<213> ORGANISM: artificial sequence
<220> FEATURE:
<223> OTHER INFORMATION: primer

<400> SEQUENCE: 144
ggattacgat gcatgatcta acatttccc ctatcatttt tcccgtc                    47

<210> SEQ ID NO 145
<211> LENGTH: 49
```

<212> TYPE: DNA
<213> ORGANISM: artificial sequence
<220> FEATURE:
<223> OTHER INFORMATION: primer

<400> SEQUENCE: 145
atcatgaacg ttaccataat aaatccccct ttttgaaaat aatgaaaac           49

<210> SEQ ID NO 146
<211> LENGTH: 49
<212> TYPE: DNA
<213> ORGANISM: artificial sequence
<220> FEATURE:
<223> OTHER INFORMATION: primer

<400> SEQUENCE: 146
tttcaaaaag ggggatttat tatggtaacg ttcatgataa cttctgctc           49

<210> SEQ ID NO 147
<211> LENGTH: 46
<212> TYPE: DNA
<213> ORGANISM: artificial sequence
<220> FEATURE:
<223> OTHER INFORMATION: primer

<400> SEQUENCE: 147
actcatctta gatgcatcag atcttgatcc cctgcgccat cagatc             46

<210> SEQ ID NO 148
<211> LENGTH: 1694
<212> TYPE: DNA
<213> ORGANISM: artificial sequence
<220> FEATURE:
<223> OTHER INFORMATION: PCR fragment with Pnrp and thp coding region

<400> SEQUENCE: 148
gatctaacat tttccctat cattttttcc gtcttcattt gtcatttttt ccagaaaaaa        60
tcgcgtcatt cgactcatgt ctaatccaac acgtgtctct cggcttatcc cctgacaccg      120
cccgccgaca gcccgcatgg gacaattcta tcaattcagc cgcggagtct agttttatat      180
tgcagaatgc gagattgctg gtttattata acaatataag tcttcattat tttcaaaaag     240
ggggatttat tatggtaacg ttcatgataa cttctgctct tcatcgtgcg gccgactggg     300
ctaaatctgt gttctcttcg gcggcgctgg gtgatcctcg ccgtactgcc cgcttggtta     360
acgtcgccgc ccaattggca aaatattctg gtaaatcaat aaccatctca tcagagggta     420
gtgaagccat gcaggaaggc gcttaccgat ttatccgcaa tcccaacgtt tctgccgagg     480
cgatcagaaa ggctggcgcc atgcaaacag tcaagttggc tcaggagttt cccgaactgc     540
tggccattga ggacaccacc tctttgagtt atcgccacca ggtcgccgaa gagcttggca     600
agctgggctc tattcaggat aaatcccgcg atggtgggt tcactccgtt ctcttgctcg      660
aggccaccac attccgcacc gtaggattac tgcatcagga gtggtggatg cgccggatg      720 accctgccga tgcggatgaa aaggagagtg gcaaatggct ggcagccgcc gcaactagcc     780
ggttacgcat gggcagcatg atgagcaacg tgattgcggt ctgtgaccgc gaagccgata     840
ttcatgctta tctgcaggac aaactggcgc ataacgagcg cttcgtggtg cgctccaagc     900
acccacgcaa ggacgtagag tctgggttgt atctgtacga ccatctgaag aaccaaccgg     960
agttgggtgg ctatcagatc agcattccgc aaaaggcgt ggtggataaa cgcggtaaac    1020
gtaaaaatcg accagcccgc aaggcgagct tgagcctgcg cagtgggcgc atcacgctaa   1080

```
aacaggggaa tatcacgctc aacgcggtgc tggccgagga gattaacccg cccaagggtg   1140 agacccgtt  gaaatggttg ttgctgacca gcgaaccggt cgagtcgcta gcccaagcct   1200
tgcgcgtcat cgacatttat acccatcgct ggcggatcga ggagttccat aaggcatgga   1260
aaaccggagc aggagccgag aggcaacgca tggaggagcc ggataatctg gagcggatgg   1320
tctcgatcct ctcgtttgtt gcggtcaggc tgttacagct cagagaaagc ttcacgctgc   1380
cgcaagcact cagggcgcaa gggctgctaa aggaagcgga acacgtagaa agccagtccg   1440
cagaaacggt gctgaccccg gatgaatgtc agctactggg ctatctggac aagggaaaac   1500
gcaagcgcaa agagaaagca ggtagcttgc agtgggctta catggcgata gctagactgg   1560
gcggttttat ggacagcaag cgaaccggaa ttgccagctg gggcgccctc tgggaaggtt   1620
gggaagccct gcaaagtaaa ctggatggct ttcttgccgc caaggatctg atggcgcagg   1680
ggatcaagat ctga                                                    1694
```

<210> SEQ ID NO 149
<211> LENGTH: 29
<212> TYPE: DNA
<213> ORGANISM: artificial sequence
<220> FEATURE:
<223> OTHER INFORMATION: primer

<400> SEQUENCE: 149
ccaccacgcc cttttgcgga atgctgatc                                      29

<210> SEQ ID NO 150
<211> LENGTH: 29
<212> TYPE: DNA
<213> ORGANISM: artificial sequence
<220> FEATURE:
<223> OTHER INFORMATION: primer

<400> SEQUENCE: 150
cggccgcacg atgaagagca gaagttatc                                      29

<210> SEQ ID NO 151
<211> LENGTH: 29
<212> TYPE: DNA
<213> ORGANISM: artificial sequence
<220> FEATURE:
<223> OTHER INFORMATION: primer

<400> SEQUENCE: 151
ctgaccgata gattttgaat ttaggtgtc                                      29

<210> SEQ ID NO 152
<211> LENGTH: 114
<212> TYPE: DNA
<213> ORGANISM: artificial sequence
<220> FEATURE:
<223> OTHER INFORMATION: promoter fragment PgroE

<400> SEQUENCE: 152
aatgatgtaa gcgtgaaaaa ttttttatct tatcacttga aattggaagg gagattcttt   60
attataagaa ttgtggaatt gtgagcggat aacaattccc aattaaagga ggaa         114

<210> SEQ ID NO 153
<211> LENGTH: 42
<212> TYPE: DNA
<213> ORGANISM: artificial sequence
<220> FEATURE:
<223> OTHER INFORMATION: primer

<400> SEQUENCE: 153
acattgtcga cggtaccgct aacggaaaag ggagcggaaa ag        42

<210> SEQ ID NO 154
<211> LENGTH: 27
<212> TYPE: DNA
<213> ORGANISM: artificial sequence
<220> FEATURE:
<223> OTHER INFORMATION: primer

<400> SEQUENCE: 154
gacctccccg gatccttcct cctttaa        27

<210> SEQ ID NO 155
<211> LENGTH: 1681
<212> TYPE: DNA
<213> ORGANISM: artificial sequence
<220> FEATURE:
<223> OTHER INFORMATION: PCR fragment with ribosome binding site and
      kivD coding region optimized for L. plantarum

<400> SEQUENCE: 155

| ggatccgttt aaacataaaa tatggaggaa tgcgatgtat accgttggtg actatttgtt | 60 |
| ggatcggtta cacgaattag gcatcgaaga atcttcggt gttccaggcg attacaattt | 120 |
| acaattttg gaccaaatca tcagtcacaa agacatgaaa tgggtcggta acgcaaatga | 180 |
| attaaatgcg agttacatgg ctgacggtta tgctcggact aagaaagctg cagcctttt | 240 |
| gacgactttt ggtgttggtg aattatcagc cgttaatgtt ttggccggta gttacgccga | 300 |
| aaatttaccg gtcgttgaaa ttgttggcag tccaacgagt aaggttcaaa cgaaggtaa | 360 |
| atttgtccat cataccttgg cagatggtga ttttaaacac tttatgaaga tgcatgaacc | 420 |
| ggtcactgct gcacggactt tattaactgc ggaaaatgcc accgtcgaaa ttgaccgcgt | 480 |
| tttatcagcc ttgttaaaag aacgcaaacc ggtttacatt aatttaccgg tcgatgtggc | 540 |
| agcggccaaa gctgaaaaac cgagtttgcc gttaagaag gaaaatagta cctcaaatac | 600 |
| ctcagatcaa gaaatcttga caagatcca agaatcatta aaaaatgcta aaaaaccaat | 660 |
| cgttattacc ggtcatgaaa ttattagttt tggtttggaa aaaacggtga cgcaatttat | 720 |
| ttcaaagacg aaaattaccaa ttcgaccctt gaatttggt aaatcaagtg ttgacgaagc | 780 |
| gttgccaagt ttcttgggta tctataatgg tactttaagt gaaccgaatt taaaagaatt | 840 |
| tgtgaaagt gcagatttta ttttaatgtt gggtgtcaag ttaactgatt catcaactgg | 900 |
| cgcgttcacg catcatttaa atgaaaataa aatgatttca ttgaatattg atgaaggcaa | 960 |
| aatcttcaac gaacggattc aaaatttga tttgaatca ttgattagta gtttgttaga | 1020 |
| tttatcagaa atcgaataca aaggcaagta tattgataag aagcaggaag attttgttcc | 1080 |
| gagtaatgca ttgttaagtc aagatcgctt atggcaggcg gttgaaaact taactcaatc | 1140 |
| aaacgaaacc attgttgctg aacaaggtac ttcattcttc ggcgcatcaa gtatctttt | 1200 |
| aaaatcaaaa agtcatttca tcggtcaacc attatgggt agtattggtt acaccttccc | 1260 |
| agcggcgtta gtagtcaaa ttgctgacaa agaatcacga cacttattat tcattggtga | 1320 |
| cggtagttta caattgacgg tccaggaatt aggtttggcc attcgcgaaa agatcaaccc | 1380 |
| aatttgtttc attatcaata tgacggtta tactgttgaa cgggaaattc acggtccgaa | 1440 |
| ccaaagttac aatgatattc caatgtggaa ctactcaaaa ttgccggaaa gttttggcgc | 1500 |
| caccgaagat cgggtcgtta gtaaaattgt gcggaccgaa aatgaattcg tgtcagtgat | 1560 | gaaggaagca caagccgatc cgaaccggat gtattggatt gaattaatct tggctaagga    1620 aggtgccccg aaggttttaa agaagatggg caagttattt gcagaacaaa ataaaagtta    1680 a    1681

<210> SEQ ID NO 156
<211> LENGTH: 29
<212> TYPE: DNA
<213> ORGANISM: artificial sequence
<220> FEATURE:
<223> OTHER INFORMATION: primer

<400> SEQUENCE: 156
gacacccaac attaaaataa aatctgcac    29

<210> SEQ ID NO 157
<211> LENGTH: 1047
<212> TYPE: DNA
<213> ORGANISM: artificial sequence
<220> FEATURE:
<223> OTHER INFORMATION: codon optimized coding region of sadB for
      expression in L. plantarum

<400> SEQUENCE: 157
atgaaagctt tggtttacca tggtgaccac aaaattagtt tagaagataa gccaaaacca    60
actttgcaga agccaactga tgtcgtggtc cgtgtcttaa agacgaccat ttgtggcacg    120
gacttgggta tctataaggg caagaatcca gaagttgccg acggtcgtat cttaggtcat    180
gaaggcgtcg gtgttatcga agaagttggt gaaagtgtta cccaattcaa gaagggtgac    240
aaagttttaa tcagttgtgt tacgagttgt ggttcatgtg attactgtaa gaaacaattg    300
tacagtcatt gtcgtgacgg tggttggatc ttgggttaca tgattgatgg tgtccaagct    360
gaatacgtcc gtattccaca cgcagataat tcattgtata aaattccaca aactattgac    420
gacgaaattg ctgttttgtt atcagatatc ttaccaacgg gccatgaaat tggtgtccaa    480
tatggcaacg tccaaccagg cgatgccgtt gcaattgttg gcgccggtcc agtgggcatg    540
agtgttttat taacggctca attctattca ccatcaacta tcattgtcat cgacatggat    600
gaaaatcgtt tgcaattggc taaggaattg ggcgctacgc acactatcaa ttcaggtacg    660
gaaaatgttg ttgaagcagt ccatcgtatt gcagctgaag gcgtcgatgt ggcaattgaa    720
gccgtgggca ttccagcaac gtgggatatt tgtcaagaaa ttgttaagcc aggcgcccat    780
atcgccaatg tgggtgtgca tggtgtgaag gttgattttg aaattcaaaa attgtggatt    840
aaaaatttga cgattactac tggtttggtt aacacgaata cgactccaat gttaatgaag    900
gtcgcatcaa ccgataaatt accattgaag aagatgatta ctcaccgttt tgaattagca    960
gaaattgaac atgcctatca agttttctta aacggcgcca aggaaaaagc aatgaaaatt    1020
attttatcaa cgccggtgc agcttaa    1047

<210> SEQ ID NO 158
<211> LENGTH: 1067
<212> TYPE: DNA
<213> ORGANISM: artificial sequence
<220> FEATURE:
<223> OTHER INFORMATION: PCR fragment with ribosome binding site and
      optimized sadB coding region

<400> SEQUENCE: 158
atataggagg aatttttgta atgaaagctt tggtttacca tggtgaccac aaaattagtt    60

| | | |
|---|---|---|
| tagaagataa gccaaaacca actttgcaga agccaactga tgtcgtggtc cgtgtcttaa | 120 | |
| agacgaccat ttgtggcacg gacttgggta tctataaggg caagaatcca gaagttgccg | 180 | |
| acggtcgtat cttaggtcat gaaggcgtcg gtgttatcga agaagttggt gaaagtgtta | 240 | |
| cccaattcaa gaagggtgac aaagttttaa tcagttgtgt tacgagttgt ggttcatgtg | 300 | |
| attactgtaa gaaacaattg tacagtcatt gtcgtgacgg tggttggatc ttgggttaca | 360 | |
| tgattgatgg tgtccaagct gaatacgtcc gtattccaca cgcagataat tcattgtata | 420 | |
| aaattccaca aactattgac gacgaaattg ctgttttgtt atcagatatc ttaccaacgg | 480 | |
| gccatgaaat tggtgtccaa tatggcaacg tccaaccagg cgatgccgtt gcaattgttg | 540 | |
| gcgccggtcc agtgggcatg agtgttttat taacggctca attctattca ccatcaacta | 600 | |
| tcattgtcat cgacatggat gaaaatcgtt tgcaattggc taaggaattg ggcgctacgc | 660 | |
| acactatcaa ttcaggtacg gaaaatgttg ttgaagcagt ccatcgtatt gcagctgaag | 720 | |
| gcgtcgatgt ggcaattgaa gccgtgggca ttccagcaac gtgggatatt tgtcaagaaa | 780 | |
| ttgttaagcc aggcgcccat atcgccaatg tgggtgtgca tggtgtgaag gttgattttg | 840 | |
| aaattcaaaa attgtggatt aaaaatttga cgattactac tggtttggtt aacacgaata | 900 | |
| cgactccaat gttaatgaag gtcgcatcaa ccgataaatt accattgaag aagatgatta | 960 | |
| ctcaccgttt tgaattagca gaaattgaac atgcctatca agttttctta aacggcgcca | 1020 | |
| aggaaaaagc aatgaaaatt attttatcaa acgccggtgc agcttaa | 1067 | |

<210> SEQ ID NO 159
<211> LENGTH: 66
<212> TYPE: DNA
<213> ORGANISM: artificial sequence
<220> FEATURE:
<223> OTHER INFORMATION: primer

<400> SEQUENCE: 159

| | |
|---|---|
| acttgatatc gcggccgcat ataggaggaa tttttgtaat gaaagctttg gtttaccatg | 60 |
| gtgacc | 66 |

<210> SEQ ID NO 160
<211> LENGTH: 49
<212> TYPE: DNA
<213> ORGANISM: artificial sequence
<220> FEATURE:
<223> OTHER INFORMATION: primer

<400> SEQUENCE: 160

| | |
|---|---|
| gttatatgac tagcggccgc gagctcttaa gctgcaccgg cgtttgata | 49 |

<210> SEQ ID NO 161
<211> LENGTH: 28
<212> TYPE: DNA
<213> ORGANISM: artificial sequence
<220> FEATURE:
<223> OTHER INFORMATION: primer

<400> SEQUENCE: 161

| | |
|---|---|
| ggaagcacaa gccgatccga accggatg | 28 |

<210> SEQ ID NO 162
<211> LENGTH: 48
<212> TYPE: DNA
<213> ORGANISM: artificial sequence
<220> FEATURE:
<223> OTHER INFORMATION: primer

<400> SEQUENCE: 162

```
tcatttgata tgcctcctaa ataattgtga gcgctcacaa ttccacac          48
```

<210> SEQ ID NO 163
<211> LENGTH: 6639
<212> TYPE: DNA
<213> ORGANISM: artificial sequence
<220> FEATURE:
<223> OTHER INFORMATION: constructed plasmid

<400> SEQUENCE: 163

```
gaattcagat ctaattatag caatcattta cgcgttaatg gctaatcgcc atcttccagc      60
aggcgcacca ttgcccctgt ttcactatcc aggttacgga tatagttcat gacaatattt    120
acattggtcc agccaccagc ttgcatgatc tccggtattg aaactccagc gcgggccata    180
tctcgcgcgg ctccgacacg ggcactgtgt ccagaccagg ccaggtatct ctgaccagag    240
tcatccttag cgccgtaaat caatcgatga gttgcttcaa aaatcccttc cagggcgcga    300
gttgatagct ggctggtggc agatggcgcg gcaacaccat ttttctgac ccggcaaaac     360
aggtagttat tcggatcatc agctacacca gagacggaaa tccatcgctc gaccagttta    420
gttaccccca ggctaagtgc cttctctaca cctgcggtgc taaccagcgt tttcgttctg    480
ccaatatgga ttaacattct cccaccgtca gtacgtgaga tatctttaac cctgatcctg    540
gcaatttcgg ctatacgtaa cagggtgtta taagcaatcc ccagaaatgc agattacgt     600
atatcctggc agcgatcgct attttccatg agtgaacgaa cctggtcgaa atcagtgcgt    660
tcgaacgcta gagcctgttt tgcacgttca ccggcatcaa cgttttcttt tcggatccgc    720
cgcataacca gtgaaacagc attgctgtca cttggtcgtg gcagcccgga ccgacgatga    780
agcatgttta gctggcccaa atgttgctgg atagttttta ctgccagacc gcgcgcctga    840
agatatagaa gataatcgcg aacatcttca ggttctgcgg gaaaccattt ccggttattc    900
aacttgcacc atgccgccca cgaccggcaa acggacagaa gcatttccca ggtatgctca    960
gaaaacgcct ggcgatccct gaacatgtcc atcaggttct tgcgaacctc atcactcgtt   1020
gcatcgaccg gtaatgcagg caaattttgg tgtacggtca gtaaattgga caagtttcct   1080
ctccctctca ttttcgtagg aattgttatc cgctcacaat tcctataca aattatattt    1140
tacatatcag taaaataata acaaccccc tttattccta tttttacac agcggacagt     1200
ctggacagca taaaaatac cctgtctgat gacagacaag gtatttttat ggtcttcttc   1260
ttttctcaaa caatcgatcc acttcttcag ccaaatcatc agtcatcaaa ggctcaatgt   1320
tttcagccag tcttttcgta tgtgcgggta cctcgcgaaa gcttggatgt tgtacaggat   1380
aatgtccaga aggtcgatag aaagcgtgag aaacagcgta cagacgattt agagatgtag   1440
aggtactttt atgccgagaa aactttttgc gtgtgacagt ccttaaaata tacttagagc   1500
gtaagcgaaa gtagtagcga cagctattaa ctttcggttg caaagctcta ggattttaa    1560
tggacgcagc gcatcacacg caaaaaggaa attggaataa atgcgaaatt tgagatgtta   1620
attaaagacc ttttttgaggt ctttttttct tagatttttg gggttattta ggggagaaaa   1680
catagggggg tactacgacc tccccccctag gtgtccattg tccattgtcc aaacaaataa   1740
ataaatattg ggttttaat gttaaaggt tgttttttat gttaaagtga aaaaacaga      1800
tgttgggagg tacagtgata gttgtagata gaaaagaaga gaaaaagtt gctgttactt    1860
taagacttac aacagaagaa aatgagatat taaatagaat caaagaaaaa tataatatta   1920
```

```
gcaaatcaga tgcaaccggt attctaataa aaaaatatgc aaaggaggaa tacggtgcat    1980
tttaaacaaa aaaagataga cagcactggc atgctgccta tctatgacta aattttgtta    2040
agtgtattag caccgttatt atatcatgag cgaaaatgta ataaaagaaa ctgaaaacaa    2100
gaaaaattca agaggacgta attggacatt tgttttatat ccagaatcag caaaagccga    2160
gtggttagag tatttaaaag agttacacat tcaatttgta gtgtctccat tacatgatag    2220
ggatactgat acagaaggta ggatgaaaaa agagcattat catattctag tgatgtatga    2280
gggtaataaa tcttatgaac agataaaaat aattaacaga agaattgaat gcgactattc    2340
cgcagattgc aggaagtgtg aaaggtcttg tgagatatat gcttcacatg gacgatccta    2400
ataaatttaa atatcaaaaa gaagatatga tagtttatgg cggtgtagat gttgatgaat    2460
tattaaagaa aacaacaaca gatagatata aattaattaa agaaatgatt gagtttattg    2520
atgaacaagg aatcgtagaa tttaagagtt taatggatta tgcaatgaag tttaaatttg    2580
atgattggtt cccgctttta tgtgataact cggcgtatgt tattcaagaa tatataaaat    2640
caaatcggta taaatctgac cgatagattt tgaatttagg tgtcacaaga cactcttttt    2700
tcgcaccagc gaaaactggt ttaagccgac tgcgcaaaag acataatcga ttcacaaaaa    2760
ataggcacac gaaaaacaag ttaagggatg cagtttatgc atcccttaac ttacttatta    2820
aataatttat agctattgaa aagagataag aattgttcaa agctaatatt gtttaaatcg    2880
tcaattcctg catgttttaa ggaattgtta aattgatttt ttgtaaatat tttcttgtat    2940
tctttgttaa cccatttcat aacgaaataa ttatacttttt gtttatcttt gtgtgatatt    3000
cttgattttt ttctacttaa tctgataagt gagctattca ctttaggttt aggatgaaaa    3060
tattctcttg gaaccatact taatatagaa atatcaactt ctgccattaa agtaatgcc    3120 aatgagcgtt ttgtatttaa taatcttta gcaaacccgt attccacgat taaataaatc    3180
tcattagcta tactatcaaa acaattttg cgtattatat ccgtacttat gttataaggt    3240
atattaccat atatttata ggattggttt ttaggaaatt taaactgcaa tatatccttg    3300
tttaaaactt ggaaattatc gtgatcaaca agtttatttt ctgtagtttt gcataattta    3360
tggtctattt caatggcagt tacgaaatta caccctcttta ctaattcaag ggtaaaatgg    3420
ccttttcctg agccgatttc aaagatatta tcatgttcat ttaatcttat atttgtcatt    3480
attttatcta tattatgttt tgaagtaata agttttgac tgtgttttat attttttctcg    3540 ttcattataa ccctctttaa tttggttata tgaattttgc ttattaacga ttcattataa    3600
ccacttattt tttgtttggt tgataatgaa ctgtgctgat tacaaaaata ctaaaaatgc    3660
ccatattttt tcctccttat aaaattagta taattatagc acgagctctg ataaatatga    3720
acatgatgag tgatcgttaa atttatactg caatcggatg cgattattga ataaaagata    3780
tgagagattt atctaatttc ttttttcttg taaaaaaga agttcttaa aggttttata    3840 gttttggtcg tagagcacac ggtttaacga cttaattacg aagtaaataa gtctagtgtg    3900
ttagacttta tgaaatctat atacgtttat atatatttat tatccggatc tgcatcgcag    3960
gatgctgctg gctaccctgt ggaacaccta catctgtatt aacgaagcgc tggcattgac    4020
cctgagtgat ttttctctgg tcccgccgca tccataccgc cagttgttta ccctcacaac    4080
gttccagtaa ccgggcatgt tcatcatcag taacccgtat cgtgagcatc ctctctcgtt    4140
tcatcggtat cattaccccc atgaacagaa attcccccctt acacggaggc atcaagtgac    4200
caaacaggaa aaaccgcccc ttaacatggc ccgctttatc agaagccaga cattaacgct    4260
tctggagaaa ctcaacgagc tggacgcgga tgaacaggca gacatctgtg aatcgcttca    4320
```

```
cgaccacgct gatgagcttt accgcagctg cctcgcgcgt ttcgtgatg acggtgaaaa      4380 cctctgacac atgcagctcc cggagacggt cacagcttgt ctgtaagcgg atgccgggag     4440
cagacaagcc cgtcagggcg cgtcagcggg tgttggcggg tgtcggggcg cagccatgac     4500
ccagtcacgt agcgatagcg gagtgtatac tggcttaact atgcggcatc agagcagatt    4560
gtactgagag tgcaccatat gcggtgtgaa ataccgcaca gatgcgtaag gagaaaatac    4620
cgcatcaggc gctcttccgc ttcctcgctc actgactcgc tgcgctcggt cgttcggctg    4680
cggcgagcgg tatcagctca ctcaaaggcg gtaatacggt tatccacaga atcaggggat    4740
aacgcaggaa agaacatgtg agcaaaaggc cagcaaaagg ccaggaaccg taaaaaggcc    4800
gcgttgctgg cgttttttcca taggctccgc cccctgacg agcatcacaa aaatcgacgc    4860
tcaagtcaga ggtggcgaaa cccgacagga ctataaagat accaggcgtt tcccctgga    4920 agctccctcg tgcgctctcc tgttccgacc ctgccgctta ccggataccttt gtccgccttt   4980 ctcccttcgg gaagcgtggc gctttctcaa tgctcacgct gtaggtatct cagttcggtg    5040
taggtcgttc gctccaagct gggctgtgtg cacgaacccc ccgttcagcc cgaccgctgc    5100
gccttatccg gtaactatcg tcttgagtcc aacccggtaa gacacgactt atcgccactg    5160
gcagcagcca ctggtaacag gattagcaga gcgaggtatg taggcggtgc tacagagttc    5220
ttgaagtggt ggcctaacta cggctacact agaaggacag tatttggtat ctgcgctctg    5280
ctgaagccag ttaccttcgg aaaaagagtt ggtagctctt gatccggcaa acaaaccacc    5340
gctggtagcg gtggtttttt tgtttgcaag cagcagatta cgcgcagaaa aaaggatct    5400 caagaagatc ctttgatctt ttctacgggg tctgacgctc agtggaacga aaactcacgt    5460
taagggattt tggtcatgag attatcaaaa aggatcttca cctagatcct ttaaattaa    5520 aaatgaagtt ttaaatcaat ctaaagtata tatgagtaaa cttggtctga cagttaccaa    5580
tgcttaatca gtgaggcacc tatctcagcg atctgtctat ttcgttcatc catagttgcc    5640
tgactccccg tcgtgtagat aactacgata cgggagggct taccatctgg ccccagtgct    5700
gcaatgatac cgcgagaccc acgctcaccg gctccagatt tatcagcaat aaaccagcca    5760
gccggaaggg ccgagcgcag aagtggtcct gcaactttat ccgcctccat ccagtctatt    5820
aattgttgcc gggaagctag agtaagtagt tcgccagtta atagtttgcg caacgttgtt    5880
gccattgctg caggcatcgt ggtgtcacgc tcgtcgtttg gtatggcttc attcagctcc    5940
ggttcccaac gatcaaggcg agttacatga tcccccatgt tgtgcaaaaa agcggttagc    6000
tccttcggtc ctccgatcgt tgtcagaagt aagttggccg cagtgttatc actcatggtt    6060
atggcagcac tgcataattc tcttactgtc atgccatccg taagatgctt ttctgtgact    6120
ggtgagtact caaccaagtc attctgagaa tagtgtatgc ggcgaccgag ttgctcttgc    6180
ccggcgtcaa cacgggataa taccgcgcca catagcagaa ctttaaaagt gctcatcatt    6240
ggaaaacgtt cttcggggcg aaaactctca aggatcttac cgctgttgag atccagttcg    6300
atgtaaccca ctcgtgcacc caactgatct tcagcatctt ttactttcac cagcgtttct    6360
gggtgagcaa aaacaggaag gcaaaatgcc gcaaaaaagg gaataagggc gacacggaaa    6420
tgttgaatac tcatactctt cctttttcaa tattattgaa gcatttatca gggttattgt    6480
ctcatgagcg gatacatatt tgaatgtatt tagaaaaata aacaaatagg ggttccgcgc    6540
acatttcccc gaaaagtgcc acctgacgtc taagaaacca ttattatcat gacattaacc    6600
tataaaaata ggcgtatcac gaggcccttt cgtcttcaa                            6639
```

```
<210> SEQ ID NO 164
<211> LENGTH: 40
<212> TYPE: DNA
<213> ORGANISM: artificial sequence
<220> FEATURE:
<223> OTHER INFORMATION: primer

<400> SEQUENCE: 164
atatggtacc tcattgtgcc tccaaacgat ttgattgttg                    40

<210> SEQ ID NO 165
<211> LENGTH: 35
<212> TYPE: DNA
<213> ORGANISM: artificial sequence
<220> FEATURE:
<223> OTHER INFORMATION: primer

<400> SEQUENCE: 165
gataggtacc tgattacggc tggtgaactc ttaac                         35

<210> SEQ ID NO 166
<211> LENGTH: 29
<212> TYPE: DNA
<213> ORGANISM: artificial sequence
<220> FEATURE:
<223> OTHER INFORMATION: primer

<400> SEQUENCE: 166
atcctgtaca ttgccaacag acattctag                                29

<210> SEQ ID NO 167
<211> LENGTH: 21
<212> TYPE: DNA
<213> ORGANISM: artificial sequence
<220> FEATURE:
<223> OTHER INFORMATION: primer

<400> SEQUENCE: 167
ccacgtcgat gctggaacgg c                                        21

<210> SEQ ID NO 168
<211> LENGTH: 22
<212> TYPE: DNA
<213> ORGANISM: artificial sequence
<220> FEATURE:
<223> OTHER INFORMATION: primer

<400> SEQUENCE: 168
taattaaact gtagttcttc aa                                       22

<210> SEQ ID NO 169
<211> LENGTH: 22
<212> TYPE: DNA
<213> ORGANISM: artificial sequence
<220> FEATURE:
<223> OTHER INFORMATION: primer

<400> SEQUENCE: 169
ttggaggcac aatgaggtac ct                                       22

<210> SEQ ID NO 170
<211> LENGTH: 149
<212> TYPE: DNA
<213> ORGANISM: Lactococcus lactis

<400> SEQUENCE: 170
```

```
ccaaagctag tggtggcatg aaataaagcg aatacaggag agggaaaaag cgaacgtaag      60
ataaaaaaag gtataaaagt cacagttaat tcttgacaag tttagttagg tttgatagaa     120
tataatagaa ttgtgagcgg ataacaatt                                       149
```

<210> SEQ ID NO 171
<211> LENGTH: 57
<212> TYPE: DNA
<213> ORGANISM: artificial sequence
<220> FEATURE:
<223> OTHER INFORMATION: primer

<400> SEQUENCE: 171

```
acattgtcga cggtacccca aagctagtgg tggcatgaaa taaagcgaat acaggag        57
```

<210> SEQ ID NO 172
<211> LENGTH: 66
<212> TYPE: DNA
<213> ORGANISM: artificial sequence
<220> FEATURE:
<223> OTHER INFORMATION: primer

<400> SEQUENCE: 172

```
aattcggatc caattgttat ccgctcacaa ttctattata ttctatcaaa cctaactaaa     60
cttgtc                                                                66
```

<210> SEQ ID NO 173
<211> LENGTH: 56
<212> TYPE: DNA
<213> ORGANISM: artificial sequence
<220> FEATURE:
<223> OTHER INFORMATION: primer

<400> SEQUENCE: 173

```
atctagtgga tccaatgaga tagaaaagag aaatatcatg acagaaatca cacaac         56
```

<210> SEQ ID NO 174
<211> LENGTH: 56
<212> TYPE: DNA
<213> ORGANISM: artificial sequence
<220> FEATURE:
<223> OTHER INFORMATION: primer

<400> SEQUENCE: 174

```
gcattaacta gtgcggccgc tcattcagct acatcgatat cttttttag tgcttc          56
```

<210> SEQ ID NO 175
<211> LENGTH: 16
<212> TYPE: DNA
<213> ORGANISM: artificial sequence
<220> FEATURE:
<223> OTHER INFORMATION: primer

<400> SEQUENCE: 175

```
cggatgcgcg gtgaaa                                                     16
```

<210> SEQ ID NO 176
<211> LENGTH: 4895
<212> TYPE: DNA
<213> ORGANISM: artificial sequence
<220> FEATURE:
<223> OTHER INFORMATION: constructed plasmid

<400> SEQUENCE: 176

```
gacgaaaggg ccttataact tacaaataac ccctcgaaaa cattgaaaga ataaccccca    60
agatctatat tatagatctt gggggttatt tgttttaata ttaaagaaat gacttcttct   120
atttgtcatc aatactaaac aataatttgt acaaagtgat tatttcttct agttcttcac   180
gcgatacatg atcgcaaata gtttcatcag tgacatgtct tgcccgtaaa tctaaggcta   240
tggtttgatc taataatact tttccatata ctgtttgact actagttagt cgatgataca   300
ttggaaaatt acgcttggta ctgctaattg gagccacaat cgtcatgtta cttgtctgac   360
agactagatc attgcttagc gcaatggctg gtcgcttatt catctgttca tgaccacggc   420
ttggattaaa gttaacataa aatatatcac cttggcttac cattgaagtt cattaccttc   480
tgactttccc caatcaagct cgtgatccct tttcccgtca tctttccaat ccttaaatag   540
ttcgtgaata ttggttgggt tctttttttat tggtgttaaa acaattgatc cattttcaat   600
ggttattgtc atatcttggt tatcatctaa tttcagttgt ttaataattt ggctaggaat   660
tctagcagct ttcgagtttc cccactttgc taagcgtgtt tgttctttaa taagttccat   720
atttttcccct cctaaattat tattacaagt caagtatatc ccatgtagat acacaatgca   780
aatattctta ctggagaaat aacacccttaa gtctagcacc acccgcacgc atagcggtgc   840
ttaaaccatc aagggtcaag ccccttaggct ctctcaaaca gttatcctaa tcgtgaataa   900
ctgcgcttct tttgcagtat aaagagagaa ctctttatca gacaatttaa gctcaaccag   960
cccttgcact aactattatt agagttggtt ttagcagcaa cccgaataat ctgcgttaat  1020
agttagcctg tccgtatcat ttcctagtct tccagccacg tctttagtcg cgttgatctc  1080
gacaaggttt agcatacccta tgttgttaac tgcaagcggg gtcacgaacg acactcacgg  1140
gaggttttac tagctaagaa caggtttcca gcctttagtt gctttgatgg ttgctaacca  1200
ttgaataaca aaaaaacggt tgctatcagg tttctgttaa gattcccgat aacaaccgtt  1260
tactttaagt atcaatggtt gaaaaactta gcctacatgt tataatagta ccaagttaga  1320
tagcttgtat tggtagtact tgctatcgaa aatcttatca ggttgtgctg ataagtcgtg  1380
aatcctaact ctgctaagtt gagggttctt ttttttgcgt tcatttatta agttgagtac  1440
attataaccg taatataaga ttaatacaac ctttatcatt ttaacgtctc aaccagccga  1500
ataatcctta aaaaaggatt gattctaatg aagaaagcag acaagtaagc ctcctaaatt  1560
cactttagat aaaaatttag gaggcatatc aaatgaactt taataaaatt gatttagaca  1620
attggaagag aaaagagata tttaatcatt atttgaacca acaaacgact tttagtataa  1680
ccacagaaat tgatattagt gttttatacc gaaacataaa acaagaagga tataaatttt  1740
accctgcatt tattttctta gtgacaaggg tgataaactc aaatacagct tttagaactg  1800
gttacaatag cgacggagag ttaggttatt gggataagtt agagccactt tatacaattt  1860
ttgatggtgt atctaaaaca ttctctggta tttggactcc tgtaaagaat gacttcaaag  1920
agttttatga tttataccctt tctgatgtag agaaatataa tggttcgggg aaattgtttc  1980
ccaaaacacc tatacctgaa aatgcttttt ctctttctat tattccatgg acttcattta  2040
ctgggtttaa cttaaatatc aataataata gtaattaccct tctacccatt attacagcag  2100
gaaaattcat taataaaggt aattcaatat atttaccgct atctttacag gtacatcatt  2160
ctgtttgtga tggttatcat gcaggattgt ttatgaactc tattcaggaa ttgtcagata  2220
ggcctaatga ctggctttta taagggcccg cgctagcgga gtgtatactg gcttactatg  2280
ttggcactga tgagggtgtc agtgaagtgc ttcatgtggc aggagaaaaa aggctgcacc  2340
ggtgcgtcag cagaatatgt gatacaggat atattccgct tcctcgctca ctgactcgct  2400
```

```
acgctcggtc gttcgactgc ggcgagcgga atggcttac gaacgggcg gagatttcct      2460
ggaagatgcc aggaagatac ttaacaggga agtgagaggg ccgcggcaaa gccgttttc     2520
cataggctcc gcccccctga caagcatcac gaaatctgac gctcaaatca gtggtggcga     2580
aacccgacag gactataaag ataccaggcg tttccccctg gcggctccct cgtgcgctct     2640
cctgttcctg cctttcggtt taccggtgtc attccgctgt tatggccgcg tttgtctcat     2700
tccacgcctg acactcagtt ccgggtaggc agttcgctcc aagctggact gtatgcacga     2760
accccccgtt cagtccgacc gctgcgcctt atccggtaac tatcgtcttg agtccaaccc     2820
ggaaagacat gcaaaagcac cactggcagc agccactggt aattgattta gaggagttag     2880
tcttgaagtc atgcgccggt taaggctaaa ctgaaggac aagttttggt gactgcgctc      2940
ctccaagcca gttacctcgg ttcaaagagt tggtagctca gagaaccttc gaaaaaccgc     3000
cctgcaaggc ggttttttcg ttttcagagc aagagattac gcgcagacca aaacgatctc     3060
aagaagatca tcttattaat cagataaaat atttctagat ttcagtgcaa tttatctctt     3120
caaatgtagc acctgaagtc agccccatac gatataagtt gtctcgagga ccgagcgcag     3180
cgagtcagtg agcgaggaag cggaagagcg agggcggagt tgttgacagc cgagcaggcc     3240
ttaactcaca ttaattgcgt tgcgctcact gcccgctttc cagtcgggaa acctgtcgtg     3300
ccagctgcat taatgaatcg gccaacgcgc ggggagaggc ggtttgcgta ttgggcgcca     3360
gggtggtttt tcttttcacc agtgagacgg gcaacagctg attgcccttc accgcctggc     3420
cctgagagag ttgcagcaag cggtccacgc tggtttgccc cagcaggcga aaatcctgtt     3480
tgatggtggt tgacggcggg atataacatg agctgtcttc ggtatcgtcg tatcccacta     3540
ccgagatatc cgcaccaacg cgcagcccgg actcggtaat ggcgcgcatt gcgcccagcg     3600
ccatctgatc gttggcaacc agcatcgcag tgggaacgat gccctcattc agcatttgca     3660
tggtttgttg aaaaccggac atggcactcc agtcgcctttc ccgttccgct atcggctgaa    3720
tttgattgcg agtgagatat ttatgccagc cagccagacg cagacgcgcc gagacagaac     3780
ttaatgggcc cgctaacagc gcgatttgct ggtgacccaa tgcgaccaga tgctccacgc     3840
ccagtcgcgt accgtcttca tgggagaaaa taatactgtt gatgggtgtc tggtcagaga     3900
catcaagaaa taacgccgga acattagtgc aggcagcttc cacagcaatg gcatcctggt     3960
catccagcgg atagttaatg atcagcccac tgacgcgttg cgcgagaaga ttgtgcaccg     4020
ccgctttaca ggcttcgacg ccgcttcgtt ctaccatcga caccaccacg ctggcaccca     4080
gttgatcggc gcgagattta atcgccgcga caatttgcga cggcgcgtgc agggccagac     4140
tggaggtggc aacgccaatc agcaacgact gtttgcccgc cagttgttgt gccacgcggt     4200
tgggaatgta attcagctcc gccatcgccg cttccacttt ttcccgcgtt ttcgcagaaa     4260
cgtggctggc ctggttcacc acgcgggaaa cggtctgata agagacaccg gcatactctg     4320
cgacatcgta taacgttact ggtttcatca aaatcgtctc cctccgtttg aatatttgat     4380
tgatcgtaac cagatgaagc actctttcca ctatccctac agtgttatgg cttgaacaat     4440
cacgaaacaa taattggtac gtacgatctt tcagccgact caaacatcaa atcttacaaa     4500
tgtagtcttt gaaagtatta catatgtaag atttaaatgc aaccgttttt tcggaaggaa     4560
atgatgacct cgtttccacc ggaattagct tggtaccagc tattgtaaca taatcggtac     4620
gggggtgaaa aagctaacgg aaaagggagc ggaaaagaat gatgtaagcg tgaaaaattt     4680
tttatcttat cacttgaaat tggaagggag attctttatt ataagaattg tggaattgtg     4740
```

| | |
|---|---|
| agcggataac aattcccaat taaaggagga aggatccaaa agcttaactg caggacgggc | 4800 |
| ttgtctgctc ccggcatccg cttacagaca agctgtgacc gtctccggga gctgcatgtg | 4860 |
| tcagaggttt tcaccgtcat caccgaaacg cgcga | 4895 |

<210> SEQ ID NO 177
<211> LENGTH: 1548
<212> TYPE: DNA
<213> ORGANISM: artificial sequence
<220> FEATURE:
<223> OTHER INFORMATION: PCR fragment with B. subtilis groE promoter (PgroE) fused to a lacO operator sequence and a lacI repressor gene

<400> SEQUENCE: 177

| | |
|---|---|
| ccgagcaggc cttaactcac attaattgcg ttgcgctcac tgcccgcttt ccagtcggga | 60 |
| aacctgtcgt gccagctgca ttaatgaatc ggccaacgcg cggggagagg cggtttgcgt | 120 |
| attgggcgcc agggtggttt ttcttttcac cagtgagacg ggcaacagct gattgccctt | 180 |
| caccgcctgg ccctgagaga gttgcagcaa gcggtccacg ctggtttgcc ccagcaggcg | 240 |
| aaaatcctgt ttgatggtgg ttgacggcgg gatataacat gagctgtctt cggtatcgtc | 300 |
| gtatcccact accgagatat ccgcaccaac gcgcagcccg gactcggtaa tggcgcgcat | 360 |
| tgcgcccagc gccatctgat cgttggcaac cagcatcgca gtgggaacga tgccctcatt | 420 |
| cagcatttgc atggtttgtt gaaaaccgga catggcactc cagtcgcctt cccgttccgc | 480 |
| tatcggctga atttgattgc gagtgagata tttatgccag ccagccagac gcagacgcgc | 540 |
| cgagacagaa cttaatgggc ccgctaacag cgcgatttgc tggtgaccca atgcgaccag | 600 |
| atgctccacg cccagtcgcg taccgtcttc atgggagaaa ataatactgt tgatgggtgt | 660 |
| ctggtcagag acatcaagaa ataacgccgg aacattagtg caggcagctt ccacagcaat | 720 |
| ggcatcctgg tcatccagcg gatagttaat gatcagccca ctgacgcgtt gcgcgagaag | 780 |
| attgtgcacc gccgctttac aggcttcgac gccgcttcgt tctaccatcg acaccaccac | 840 |
| gctggcaccc agttgatcgg cgcgagattt aatcgccgcg acaatttgcg acggcgcgtg | 900 |
| cagggccaga ctggaggtgg caacgccaat cagcaacgac tgtttgcccg ccagttgttg | 960 |
| tgccacgcgg ttgggaatgt aattcagctc cgccatcgcc gcttccactt tttcccgcgt | 1020 |
| tttcgcagaa acgtggctgg cctggttcac cacgcgggaa acggtctgat aagagacacc | 1080 |
| ggcatactct gcgacatcgt ataacgttac tggtttcatc aaaatcgtct ccctccgttt | 1140 |
| gaatatttga ttgatcgtaa ccagatgaag cactctttcc actatcccta cagtgttatg | 1200 |
| gcttgaacaa tcacgaaaca ataattggta cgtacgatct ttcagccgac tcaaacatca | 1260 |
| aatcttacaa atgtagtctt tgaaagtatt acatatgtaa gatttaaatg caaccgtttt | 1320 |
| ttcggaagga aatgatgacc tcgtttccac cggaattagc ttggtaccag ctattgtaac | 1380 |
| ataatcggta cggggtgaa aaagctaacg gaaaagggag cggaaaagaa tgatgtaagc | 1440 |
| gtgaaaaatt ttttatctta tcacttgaaa ttggaaggga gattctttat tataagaatt | 1500 |
| gtggaattgt gagcggataa caattcccaa ttaaaggagg aaggatcc | 1548 |

<210> SEQ ID NO 178
<211> LENGTH: 32
<212> TYPE: DNA
<213> ORGANISM: artificial sequence
<220> FEATURE:
<223> OTHER INFORMATION: primer

<400> SEQUENCE: 178

```
gcgttacaga tttataggcg gccgctaagt cg                                    32
```

<210> SEQ ID NO 179
<211> LENGTH: 49
<212> TYPE: DNA
<213> ORGANISM: artificial sequence
<220> FEATURE:
<223> OTHER INFORMATION: primer

<400> SEQUENCE: 179

```
aatacattgt aactgccatt acaaaaattc ctcctatata tctcgaggc                  49
```

<210> SEQ ID NO 180
<211> LENGTH: 51
<212> TYPE: DNA
<213> ORGANISM: artificial sequence
<220> FEATURE:
<223> OTHER INFORMATION: primer

<400> SEQUENCE: 180

```
taggaggaat ttttgtaatg gcagttacaa tgtattatga agatgatgta g               51
```

<210> SEQ ID NO 181
<211> LENGTH: 47
<212> TYPE: DNA
<213> ORGANISM: artificial sequence
<220> FEATURE:
<223> OTHER INFORMATION: primer

<400> SEQUENCE: 181

```
cctacttcag acgatcgtta ctgatagatt ttaaaggcat cgtcatc                    47
```

<210> SEQ ID NO 182
<211> LENGTH: 26
<212> TYPE: DNA
<213> ORGANISM: artificial sequence
<220> FEATURE:
<223> OTHER INFORMATION: primer

<400> SEQUENCE: 182

```
tcgcgcgttt cggtgatgac ggtgaa                                           26
```

<210> SEQ ID NO 183
<211> LENGTH: 6207
<212> TYPE: DNA
<213> ORGANISM: artificial sequence
<220> FEATURE:
<223> OTHER INFORMATION: constructed plasmid

<400> SEQUENCE: 183

```
gacgaaaggg ccttataact tacaaataac ccctcgaaaa cattgaaaga ataaccccca      60
agatctatat tatagatctt gggggttatt tgttttaata ttaaagaaat gacttcttct     120
atttgtcatc aatactaaac aataatttgt acaaagtgat tatttcttct agttcttcac     180
gcgatacatg atcgacaata gtttcatcag tgacatgtct tgcccgtaaa tctaaggcta    240
tggtttgatc taataatact tttccatata ctgtttgact actagttagt cgatgataca    300
ttggaaaatt acgcttggta ctgctaattg gagccacaat cgtcatgtta cttgtctgac    360
agactagatc attgcttagc gcaatggctg gtcgcttatt catctgttca tgaccacggc    420
ttggattaaa gttaacataa aatatatcac cttggcttac cattgaagtt cattaccttc    480
tgactttccc caatcaagct cgtgatccct tttcccgtca tctttccaat ccttaaatag    540
```

```
ttcgtgaata ttggttgggt tctttttat tggtgttaaa acaattgatc cattttcaat      600
ggttattgtc atatcttggt tatcatctaa tttcagttgt ttaataattt ggctaggaat      660
tctagcagct ttcgagtttc cccactttgc taagcgtgtt tgttctttaa taagttccat      720
attttcccct cctaaattat tattacaagt caagtatatc ccatgtagat acacaatgca      780
aatattctta ctggagaaat aacaccttaa gtctagcacc acccgcacgc atagcggtgc      840
ttaaaccatc aagggtcaag cccttaggct ctctcaaaca gttatcctaa tcgtgaataa      900
ctgcgcttct tttgcagtat aaagagagaa ctctttatca gacaatttaa gctcaaccag      960
cccttgcact aactattatt agagttggtt ttagcagcaa cccgaataat ctgcgttaat     1020
agttagcctg tccgtatcat ttcctagtct tccagccacg tctttagtcg cgttgatctc     1080
gacaaggttt agcataccta tgttgttaac tgcaagcggg gtcacgaacg acactcacgg     1140
gaggttttac tagctaagaa caggtttcca gcctttagtt gctttgatgg ttgctaacca     1200
ttgaataaca aaaaacggt tgctatcagg tttctgttaa gattcccgat aacaaccgtt      1260
tactttaagt atcaatggtt gaaaaactta gcctacatgt tataatagta ccaagttaga     1320
tagcttgtat tggtagtact tgctatcgaa atcttatca ggttgtgctg ataagtcgtg      1380
aatcctaact ctgctaagtt gagggttctt ttttttgcgt tcatttatta agttgagtac     1440
attataaccg taatataaga ttaatacaac ctttatcatt ttaacgtctc aaccagccga     1500
ataatcctta aaaaggatt gattctaatg aagaaagcag acaagtaagc ctcctaaatt      1560
cactttagat aaaaattag gaggcatatc aaatgaactt taataaaatt gatttagaca      1620
attggaagag aaaagagata tttaatcatt atttgaacca acaaacgact tttagtataa     1680
ccacagaaat tgatattagt gttttatacc gaaacataaa acaagaagga tataaatttt     1740
accctgcatt tattttctta gtgacaaggg tgataaactc aaatacagct tttagaactg     1800
gttacaatag cgacggagag ttaggttatt gggataagtt agagccactt tatacaattt     1860
ttgatggtgt atctaaaaca ttctctggta tttggactcc tgtaaagaat gacttcaaag     1920
agttttatga tttataccctt tctgatgtag agaaatataa tggttcgggg aaattgtttc    1980
ccaaaacacc tatacctgaa aatgcttttt ctctttctat tattccatgg acttcattta     2040
ctgggtttaa cttaaatatc aataataata gtaattacct tctacccatt attacagcag     2100
gaaaattcat taataaaggt aattcaatat atttaccgct atctttacag gtacatcatt     2160
ctgtttgtga tggttatcat gcaggattgt ttatgaactc tattcaggaa ttgtcagata     2220
ggcctaatga ctggctttta taagggcccg cgctagcgga gtgtatactg gcttactatg     2280
ttggcactga tgagggtgtc agtgaagtgc ttcatgtggc aggagaaaaa aggctgcacc     2340
ggtgcgtcag cagaatatgt gatacaggat atattccgct tcctcgctca ctgactcgct     2400
acgctcggtc gttcgactgc ggcgagcgga atggcttac gaacggggcg agatttcct      2460 ggaagatgcc aggaagatac ttaacaggga agtgagaggg ccgcggcaaa gccgttttc     2520 cataggctcc gcccccctga caagcatcac gaaatctgac gctcaaatca gtggtggcga    2580
aacccgacag gactataaag ataccaggcg tttccccctg gcggctccct cgtgcgctct    2640
cctgttcctg cctttcggtt taccggtgtc attccgctgt tatggccgcg tttgtctcat    2700
tccacgcctg acactcagtt ccgggtaggc agttcgctcc aagctggact gtatgcacga    2760
accccccgtt cagtccgacc gctgcgcctt atccggtaac tatcgtcttg agtccaaccc    2820
ggaaagacat gcaaaagcac cactggcagc agccactggt aattgattta gaggagttag    2880
tcttgaagtc atgcgccggt taaggctaaa ctgaaaggac aagttttggt gactgcgctc    2940
```

```
ctccaagcca gttacctcgg ttcaaagagt tggtagctca gagaaccttc gaaaaaccgc    3000
cctgcaaggc ggttttttcg ttttcagagc aagagattac gcgcagacca aaacgatctc    3060
aagaagatca tcttattaat cagataaaat atttctagat ttcagtgcaa tttatctctt    3120
caaatgtagc acctgaagtc agccccatac gatataagtt gtctcgagga ccgagcgcag    3180
cgagtcagtg agcgaggaag cggaagagcg agggcggagt tgttgacagc cgagcaggcc    3240
ttaactcaca ttaattgcgt tgcgctcact gcccgctttc cagtcgggaa acctgtcgtg    3300
ccagctgcat taatgaatcg gccaacgcgc ggggagaggc ggtttgcgta ttgggcgcca    3360
gggtggtttt tcttttcacc agtgagacgg gcaacagctg attgcccttc accgcctggc    3420
cctgagagag ttgcagcaag cggtccacgc tggtttgccc cagcaggcga aaatcctgtt    3480
tgatggtggt taacgcggg atataacatg agctgtcttc ggtatcgtcg tatcccacta    3540
ccgagatatc cgcaccaacg cgcagcccgg actcggtaat ggcgcgcatt gcgcccagcg    3600
ccatctgatc gttggcaacc agcatcgcag tgggaacgat gccctcattc agcatttgca    3660
tggtttgttg aaaaccggac atggcactcc agtcgccttc ccgttccgct atcggctgaa    3720
tttgattgcg agtgagatat ttatgccagc cagccagacg cagacgcgcc gagacagaac    3780
ttaatgggcc cgctaacagc gcgatttgct ggtgacccaa tgcgaccaga tgctccacgc    3840
ccagtcgcgt accgtcttca tgggagaaaa taatactgtt gatgggtgtc tggtcagaga    3900
catcaagaaa taacgccgga acattagtgc aggcagcttc cacagcaatg gcatcctggt    3960
catccagcgg atagttaatg atcagcccac tgacgcgttg cgcgagaaga ttgtgcaccg    4020
ccgttttaca ggcttcgacg ccgcttcgtt ctaccatcga caccaccacg ctggcaccca    4080
gttgatcggc gcgagattta atcgccgcga caatttgcga cggcgcgtgc agggccagac    4140
tggaggtggc aacgccaatc agcaacgact gtttgcccgc cagttgttgt gccacgcggt    4200
tgggaatgta attcagctcc gccatcgccg cttccacttt ttcccgcgtt ttcgcagaaa    4260
cgtggctggc ctggttcacc acgcgggaaa cggtctgata agagacaccg gcatactctg    4320
cgacatcgta taacgttact ggtttcatca aaatcgtctc cctccgtttg aatatttgat    4380
tgatcgtaac cagatgaagc actctttcca ctatccctac agtgttatgg cttgaacaat    4440
cacgaaacaa taatcggtac gggggtgaaa aagctaacgg aaaagggagc ggaaaagaat    4500
gatgtaagcg tgaaaaattt tttatcttat cacttgaaat tggaagggag attctttatt    4560
ataagaattg tggaattgtg agcggataac aattcccaat taaggagga aggatcggcc    4620 gctaagtcgt attggcacca ctactcacac cgtgaccgac gcgcccgcca gtcaagtgtt    4680
caaaagttag cgtttattaa gtgcgataag tataccacaa agggcttatt gacgcccgcc    4740
aaagggtttt gcggacattg ttaataattg tattaaaagc atgctcaatc taacacttat    4800
tttgcacaaa catggtatac tttaaccgta aaaactaaat tttcactacg agaggatgac    4860
ttattttgtc aagcctcgag atatatagga ggaattttg taatggcagt tacaatgtat    4920
tatgaagatg atgtagaagt atcagcactt gctggaaagc aaattgcagt aatcggttat    4980
ggttcacaag gacatgctca cgcacagaat ttgcgtgatt ctggtcacaa cgttatcatt    5040
ggtgtgcgcc acggaaaatc tttttgataaa gcaaagaag atggctttga aacatttgaa    5100
gtaggagaag cagtagctaa agctgatgtt attatggttt tggcaccaga tgaacttcaa    5160
caatccattt atgaagagga catcaaacca aacttgaaag caggttcagc acttggtttt    5220
gctcacggat ttaatatcca ttttggctat attaaagtac cagaagacgt tgacgtcttt    5280
```

```
atggttgcgc ctaaggctcc aggtcacctt gtccgtcgga cttatactga aggttttggt    5340
acaccagctt tgtttgtttc acaccaaaat gcaagtggtc atgcgcgtga aatcgcaatg    5400
gattgggcca aaggaattgg ttgtgctcga gtgggaatta ttgaaacaac ttttaaagaa    5460
gaaacagaag aagatttgtt tggagaacaa gctgttctat gtggaggttt gacagcactt    5520
gttgaagccg ttttgaaac actgacagaa gctggatacg ctggcgaatt ggcttacttt    5580
```
(Note: line 5520→5580 shows `gttgaagccg ttttgaaac` — reading as image)

```
gaagttttgc acgaaatgaa attgattgtt gacctcatgt atgaaggtgg ttttactaaa    5640
atgcgtcaat ccatctcaaa tactgctgag tttggcgatt atgtgactgg tccacggatt    5700
attactgacg aagttaaaaa gaatatgaag cttgttttgg ctgatattca atctggaaaa    5760
tttgctcaag atttcgttga tgacttcaaa gcggggcgtc caaaattaat agcctatcgc    5820
gaagctgcaa aaatcttga aattgaaaaa attggggcag agctacgtca agcaatgcca    5880
ttcacacaat ctggtgatga cgatgccttt aaaatctatc agtaacgatc gcccttccca    5940
acagttgcgc agcctgaatg gcgaatggcg cctgatgcgg tattttctcc ttacgcatct    6000
gtgcggtatt tcacaccgca tatggtgcac tctcagtaca atctgctctg atgccgcata    6060
gttaagccag ccccgacacc cgccaacacc cgctgacgcg ccctgacggg cttgtctgct    6120
cccggcatcc gcttacagac aagctgtgac cgtctccggg agctgcatgt gtcagaggtt    6180
ttcaccgtca tcaccgaaac gcgcgaa                                         6207
```

<210> SEQ ID NO 184
<211> LENGTH: 32
<212> TYPE: DNA
<213> ORGANISM: artificial sequence
<220> FEATURE:
<223> OTHER INFORMATION: primer

<400> SEQUENCE: 184
atctctcgag attacatcag aaaagacaac aa                                   32

<210> SEQ ID NO 185
<211> LENGTH: 35
<212> TYPE: DNA
<213> ORGANISM: artificial sequence
<220> FEATURE:
<223> OTHER INFORMATION: primer

<400> SEQUENCE: 185
cgatcccggg ttagtcatca ttttcatact gaatg                                35

<210> SEQ ID NO 186
<211> LENGTH: 60
<212> TYPE: DNA
<213> ORGANISM: artificial sequence
<220> FEATURE:
<223> OTHER INFORMATION: primer

<400> SEQUENCE: 186
tcaaattatg gaggcgagaa acccgggatc gatggtacct aaatcggcat ttctagcatg    60

<210> SEQ ID NO 187
<211> LENGTH: 32
<212> TYPE: DNA
<213> ORGANISM: artificial sequence
<220> FEATURE:
<223> OTHER INFORMATION: primer

<400> SEQUENCE: 187
atcctgtaca actttgtaat acctgagtct ac                                   32

```
<210> SEQ ID NO 188
<211> LENGTH: 52
<212> TYPE: DNA
<213> ORGANISM: artificial sequence
<220> FEATURE:
<223> OTHER INFORMATION: primer

<400> SEQUENCE: 188
atagcccggg atataggagg aatttttgta atgttgacca aggctaccaa ag            52

<210> SEQ ID NO 189
<211> LENGTH: 33
<212> TYPE: DNA
<213> ORGANISM: artificial sequence
<220> FEATURE:
<223> OTHER INFORMATION: primer

<400> SEQUENCE: 189
tttaggtacc ttataacgct ttcgtcttca tta                                 33

<210> SEQ ID NO 190
<211> LENGTH: 21
<212> TYPE: DNA
<213> ORGANISM: artificial sequence
<220> FEATURE:
<223> OTHER INFORMATION: primer

<400> SEQUENCE: 190
gatccaaatc aaaagcaact g                                              21
```